(12) United States Patent
Xu et al.

(10) Patent No.: US 11,471,523 B2
(45) Date of Patent: Oct. 18, 2022

(54) UNIVERSAL VACCINES AGAINST IMMUNOGENS OF PATHOGENIC ORGANISMS THAT PROVIDE ORGANISM-SPECIFIC AND CROSS-GROUP PROTECTION

(71) Applicant: CN.USA BIOTECH HOLDINGS, INC., Englewood, NJ (US)

(72) Inventors: Jian Qing Xu, Shanghai (CN); Xiao Yan Zhang, Shanghai (CN); Jing Wang, Shanghai (CN); Ling Yan Zhu, Shanghai (CN); Beverly W. Lubit, Kinnelon, NJ (US)

(73) Assignee: CN.USA BIOTECH HOLDINGS, INC., Englewood, NJ (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 16/737,546

(22) Filed: Jan. 8, 2020

(65) Prior Publication Data

US 2021/0100892 A1    Apr. 8, 2021

Related U.S. Application Data

(63) Continuation-in-part of application No. PCT/CN2018/105020, filed on Sep. 11, 2018.

(51) Int. Cl.

| A61K 39/12 | (2006.01) |
|---|---|
| A61K 39/00 | (2006.01) |
| A61K 39/125 | (2006.01) |
| A61K 39/38 | (2006.01) |
| C07K 14/005 | (2006.01) |
| A61K 39/145 | (2006.01) |
| C12N 7/00 | (2006.01) |
| C12N 15/86 | (2006.01) |

(52) U.S. Cl.
CPC ............. *A61K 39/145* (2013.01); *C12N 7/00* (2013.01); *C12N 15/86* (2013.01); *C12N 2710/10043* (2013.01); *C12N 2800/00* (2013.01)

(58) Field of Classification Search
CPC .... A61K 39/00; A61K 2039/53; A61K 39/12; A61K 2039/545; A61P 37/04
See application file for complete search history.

(56) References Cited

U.S. PATENT DOCUMENTS

| 4,436,727 A | 3/1984 | Ribi |
|---|---|---|
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,800,159 A | 1/1989 | Mullis et al. |
| 4,844,893 A | 7/1989 | Honsik et al. |
| 4,866,034 A | 9/1989 | Ribi |
| 4,877,611 A | 10/1989 | Cantrell |
| 4,897,268 A | 1/1990 | Tice et al. |
| 4,912,094 A | 3/1990 | Myers et al. |
| 4,945,050 A | 7/1990 | Sanford et al. |
| 5,036,006 A | 7/1991 | Sanford et al. |
| 5,075,109 A | 12/1991 | Tice et al. |
| 5,135,855 A | 8/1992 | Moss et al. |
| 5,151,254 A | 9/1992 | Arai et al. |
| 5,185,146 A | 2/1993 | Altenburger |
| 5,580,859 A | 12/1996 | Felgner et al. |
| 5,589,466 A | 12/1996 | Felgner et al. |
| 5,593,972 A | 1/1997 | Weiner et al. |
| 5,622,856 A | 4/1997 | Natsoulis |
| 5,629,203 A | 5/1997 | Shuster |
| 5,658,776 A | 8/1997 | Flotte et al. |
| 5,676,594 A | 10/1997 | Joosten |
| 5,703,055 A | 12/1997 | Felgner et al. |
| RE35,749 E | 3/1998 | Rosenberg et al. |
| 5,739,118 A | 4/1998 | Carrano et al. |
| 5,811,128 A | 9/1998 | Tice et al. |
| 5,814,344 A | 9/1998 | Tice et al. |
| 5,817,637 A | 10/1998 | Weiner et al. |
| 5,820,883 A | 10/1998 | Tice et al. |
| 5,830,876 A | 11/1998 | Weiner et al. |
| 5,837,484 A | 11/1998 | Trempe et al. |
| 5,853,763 A | 12/1998 | Tice et al. |

(Continued)

FOREIGN PATENT DOCUMENTS

| GB | 2034323 A | 6/1980 |
|---|---|---|
| WO | 94/00153 A1 | 1/1994 |
| WO | 95/17210 A1 | 6/1995 |
| WO | 96/02555 A1 | 2/1996 |
| WO | 96/33739 A1 | 10/1996 |
| WO | 99/33488 A2 | 7/1999 |
| WO | 99/040934 A1 | 8/1999 |
| WO | 99/52549 A1 | 10/1999 |
| WO | 2007/024941 A2 | 3/2007 |

OTHER PUBLICATIONS

Xie et al., "Influenza vaccine with consensus internal antigens as immunogens provides cross-group protection against influenza a viruses", Frontiers in Microbiology, 2019, 10, Article 1630:1-13.*

(Continued)

*Primary Examiner* — Barry A Chestnut
(74) *Attorney, Agent, or Firm* — McCarter & English, LLP; Beverly W. Lubit

(57) ABSTRACT

The present disclosure provides, in part, a priming and boosting vector-based platform to develop vaccines against pathogens that is tailored to elicit a broad T cell response targeting conserved viral epitopes. The universal vaccines are prepared against an immunogen of an infectious pathogenic organism selected from a virus, a bacteria, a fungus or a protozoan comprising at least one ribonucleic acid (RNA) polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens. The effectiveness of the priming and boosting platform is tested in a humanized mouse model comprising a fully functional human immune system.

23 Claims, 29 Drawing Sheets

Specification includes a Sequence Listing.

(56) References Cited

U.S. PATENT DOCUMENTS

| | | | |
|---|---|---|---|
| 5,928,647 | A | 7/1999 | Rock |
| 5,942,252 | A | 8/1999 | Tice et al. |
| 5,962,428 | A | 10/1999 | Carrano et al. |
| 5,981,505 | A | 11/1999 | Weiner et al. |
| 6,113,918 | A | 9/2000 | Johnson et al. |
| 6,355,257 | B1 | 3/2002 | Johnson et al. |
| 6,365,403 | B1 | 4/2002 | Natsoulis et al. |
| 6,440,422 | B1 | 8/2002 | Sutter et al. |
| 6,475,769 | B1 | 11/2002 | Wilson et al. |
| 6,541,258 | B2 | 4/2003 | Allen et al. |
| 9,388,429 | B2 | 7/2016 | Gall et al. |
| 2003/0013190 | A1 | 1/2003 | Mayr |
| 2005/0186621 | A1 | 8/2005 | Galarza et al. |
| 2006/0263804 | A1 | 11/2006 | Robinson et al. |
| 2008/0003239 | A1 | 1/2008 | Duke et al. |
| 2008/0031895 | A1 | 2/2008 | Galarza et al. |
| 2009/0022762 | A1 | 1/2009 | Galarza et al. |
| 2015/0024002 | A1 | 1/2015 | Perri et al. |

OTHER PUBLICATIONS

Gorantla et al., "Human Immunodeficiency Virus Type 1 Pathobiology studied in Humanized BALB/c-Rag2-/-gamma-c-/-Mice", Journal ov Virology, 2007, 81(6):2700-2712.*

Drake et al., "Human CD34+ CD133+ Hematopoietic Stem Cells Cultured with Growth Factors Including Angptl5 Efficiently Engraft Adult NOD-SCID ll2rc2/2 (NSG) Mice", PLos One:6(4):1-9.*

James, S., "Malaria Vaccine Development Status Report" Foundation for the National Institute of Health (1999) available at www.researchgate.net/publication/266879756_Malaria_Vaccine_Development_Status_Report.

Janssen, EM et al. (2003) CD4+ T cells are required for secondary expansion and memory in CD8+ T lymphocytes. Nature 421: 852-856.

Janssen, EM. et al. CD4+ T-cell help controls CD8+ T-cell memory via TRAIL-mediated activation-induced cell death. Nature, 434 88-93 (2005).

Jay, E., et al. Chemical Synthesis of a Biologically ActiveG ene for Human Immune Interferon-y. (1984) J. Biol. Chem. 259:6311.

Jaye, A. et al. (1998) Ex vivo analysis of cytotoxic T lymphocytes to measles antigens during infection and after vaccination in Gambian children. J Clin. Investig., 102, 1969-1977.

Jaye, A.; et al.. (2003) Vigorous but short-term gamma interferon T-cell responses against a dominant HLA-A*02-restricted measles virus epitope in patients with measles. J. Virol., 77, 5014-5016.

Johnson NP, Mueller J. Updating the accounts: globalmortality of the 1918-1920 "Spanish" influenza pandemic. Bull Hist Med. 2002; 76(1): 105-115.

Jones Bg, et al. Sendai virus-based RSV vaccine protects against RSV challenge in an in vivo maternal antibody model. Vaccine (2014) 32:3264-3273.

Jones, C. "Herpes Simplex Virus Type 1 and Bovine Herpesvirus 1 Latency" Clinical Microbiology Reviews. (2003) 16 (1) 79-95.

Jun, Se-Ran, et al. Ebolavirus comparative genomics. (2015) FEMS Microbiology Reviews, vol. 39, Issue 5, pp. 764-778.

Kahn, Am, et al. A systematic bioinformatics approach for selection of epitopebased vaccine targets. Cell Immunol. 2006, 244(2):141-147.

Kalams, SA et al. (1999) Association between virus-specific cytotoxic T-lymphocyte and helper responses in human immunodeficiency virus type 1 infection. J Virol 73: 6715-6720.

Kamimura, D and Bevan, MJ (2007) Naive CD8+ T cells differentiate into protective memory-like cells after IL-2 anti IL-2 complex treatment in vivo. J Exp Med 204: 1803-1812.

Kaper, JB and Levine, MM. Recombinant attenuated Vibrio cholerae strains used as live oral vaccines. 1990, Res Microbiol. 1990;141:901-906.

Kapoor, S., et al., Equine Herpesviruses: A Brief Review. (2014)Advances in Animal and Veterinary Sciences 2(2S):46-54.

Karns, LR., et al, Manipulation of gene expression by an ecdysone-inducible gene switch in tumor xenografts. 2001 MBC Biotechnology 1:11.

Karrer, U., et al, Expansion of Protective CD8+ T-Cell Responses Driven by Recombinant Cytomegaloviruses. 2004 J. Virol. 78:2255-2264.

Katzelnick, LC, et al, Antibody-dependent enhancement of severe dengue disease in humans Science (2017) 358:929-932.

Kaufman, R. J., "Selection and coamplification of heterologous genes in mammalian cells," (1991) in Methods in Enzymology, vol. 185, pp. 537-566 Academic Press, Inc., San Diego Calif.

Kaufmann, B. et al., Neutralization of West Nile virus by cross-linking of its surface proteins with Fab fragments of the human monoclonal antibody CR4354. Proc. Natl Acad. Sci. USA (2010) 107: 18950-18955.

Keskin DB, et al. Physical detection of influenza A epitopes identifies a stealth subseton human lung epithelium evading natural CD8 immunity. Proc Natl Acad Sci US A 2015; 112(7): 2151-2156.

Kessler, J.R.et al. Interplay of measles virus with early induced cytokines reveals different wild type phenotypes. Virus Res. (2011) 155, 195-202.

Khan, A.M., et al., "A systematic bioinformatics approach for selection of epitope based vaccine targets." Cell Immunol. (2006) December; 244(2): 141-147.

Kiepiela, P., et al. (2007) "CD8+ T-cell responses to different HIV proteins have discordant associations with viral load." Nat Med 13: 46-53.

Kiermayr, S. et al., Impact of Quaternary Organization on the Antigenic Structure of the Tick-Borne Encephalitis Virus Envelope Glycoprotein E. J. Virol. (2009) 83: 8482-91.

Kimmel, A. R. Identification and characterization of specific clones: Strategy for confirming the validity of presumptive clones. Guide to Molecular Cloning, Methods Enzymol. 152:507-511 (1987).

Kirnbauer, R., et al.Efficient Self-Assembly of Human Papillomavirus Type 16 LI and L1-L2 into Virus-Like Particles. (1993) J. Virol. 67:6929-6936.

Kochetov, AV et al (1998) Eukaryotic mRNAs encoding abundant and scarce proteins are statistically dissimilar in many structural features. FEBS Letts. 440:351-355.

Kolybo, DV., et al. Immunobiology Of Diphtheria. Recent Approaches for the Prevention, Diagnosis, and Treatment of the Disease. Biotechnologia Acta,, V. 6, No. 4, 2013 43-62.

Komune, N., et al. Measles virus V protein inhibits NLRP3 inflammasome-mediated interieukin-1beta secretion. J. Virol. (2011) 85, 13019-13026.

Kostyuchenko, VA, et al., Structure of the thermally stable Zika virus. Nature. (2016) 533: 425-428.

Kowalzik F, et al. MMR and MMRV vaccines. Vaccine. Aug. 28, 2018;36(36):5402-5407. doi: 10.1016/j.vaccine.2017.07.051 Epub Jul. 27, 2017.

Kozak, M. The scanning model for translation: an update.J Cell Biol 108(2):229-241, 1989.

Kozak, M., and Shatkin, A. J., Characterization of translational initiation regions from eukaryotic messenger RNAs.. Methods Enzymol 60:360-375, 1979.

Kozak, M., Determinants of translational fidelity and efficiency in vertebrate mRNAs. 1994. Biochimie 76(9):815-821.

Kozak, M., Interpreting cDNA sequences: Some insights from studies on translation. Mamm. Genome 7(8):563-574, 1996.

Kristensen, T. and Belsham, GJ. Identification of a short, highly conserved, motif required for picornavirus capsid precursor processing at distal sites. PLoS Pathog 15(1): e1007509 (2019).

Krow-Lucal, ER et al., Zika Virus Infection in Patient with No Known Risk Factors, Utah, USA, 2016. Emerg. Infect. Dis. (2017)23: 1260-67.

Lafon, M. Evasive Strategies in Rabies Virus Infection, Chapter 3 in Advances in Virus Research, Research Advances in Rabies vol. 79, pp. 33-53, Alan C. Jackson, ed. 2011 Elsevier Inc.

Lalvani, A. et al. (1997) Rapid effector function in CD8+ memory T cells. J Exp Med 186: 859-865.

Lambert, N., "Rubella" Lancet. (2015) Jun. 6; 385(9984): 2297-2307.

(56) References Cited

OTHER PUBLICATIONS

Lamere MW, et al. Regulation of antinucleoprotein IgG by systemic vaccination and its effect on influenza virus clearance. J Virol. 2011; 85(10): 5027-5035.

Lanciotti, R.S, et al., Genetic and Serologic Properties of Zika Virus Associated with an Epidemic, Yap State, Micronesia, 2007. Emerg. Infect. Dis. (2008) 14: 1232-1239.

Lane, HC et al. (1985) "Qualitative analysis of immune function in patients with the acquired immunodeficiency syndrome; Evidence for a selective defect in soluble antigen recognition," N. Engl. J. Med. 313: 79-84.

Larena M., et al., Pivotal Role of Antibody and Subsidiary Contribution of CD8+ T Cells to Recovery from Infection in a Murine Model of Japanese Encephalitis. J. Virol. (2011); 85: 5446-5455.

Latham, T. and Galarza, JM. Formation of Wild-Type and Chimeric Influenza Virus-Like Particles following Simultaneous Expression of Only Four Structural Proteins. (2001) J. Virol. 75(13):6154 6165.

Lau, Y. F., et al., Amplification and expression of human alpha-globin genes in Chinese hamster ovary cells (1984) Mol. Cell. Biol. 4:1469-1475.

Lawrence CW, et al. Frequency, specificity, and sites of expansion of CD8+ T cells during primary pulmonary influenza virus infection. J Immunol. 2005; 174(9): 5332-40.

Lazo L, et al. A recombinant capsid protein from dengue-2 induces protection in mice against homologous virus. 2007 Vaccine 25:1064-1070.

Ledgerwood, JE et al. Chimpanzee Adenovirus Vector Ebola Vaccine. 2017 N Engl J Med.;376:928-938.

Sirohi, D. et al., The 3 8 Å resolution cryo-EM structure of Zika virus. Science. 2016;352:467-470.

Sitati E.M., Diamond M.S., CD4+ T-Cell Responses Are Required for Clearance of West Nile Virus from the Central Nervous System. J. Virol. (2006) 80: 12060-12069.

Skinner, M.A., et al. (2003) "Cytotoxic T-cell responses to Mycobacterium bovis during experimental infection of cattle with bovine tuberculosis." Immunology, vol. 110,2: 234-41.

Slon Campos, JL, et al, The immune response against flaviviruses. Nat. Immunol. (2018) 19: 1189-98.

Slutter B, et al. Dynamics of influenza-induced lung-resident memory T cells underlie waning heterosubtypic immunity. Sci Immunol. 2017; 2(7).

Smaill, F. etal., A Human Type 5 Adenovirus-Based Tuberculosis Vaccine Induces Robust T Cell Responses in Humans Despite Preexisting Anti-Adenovirus Immunity. Sci. Transl. Med. (2013) 5: 205ra134.

Smith, I. "Mycobacterium tuberculosis pathogenesis and molecular determinants of virulence." Clinical microbiology reviews vol. 16, 3 (2003): 463-96.

Smith, S., and Kotwa, G., "Immune Response to Poxvirus Infections in Various Animals." Critical Reviews in Microbiology. vol. 28, (3) 149-185 (2002).

Soria-Guerra, RE., et al., (2015) "An overview of bioinformatics tools for epitope prediction: Implications on vaccine development." Journal of Biomedical Informatics 53: 405-414.

Spranger, S, et al. NOD/scid IL-2Rgnull mice: a preclinical model system to evaluate human dendritic cell-based vaccine strategies in vivo Journal of Translational Medicine 2012, 10:30.

Sridhar S, et al. Cellular immune correlates of protection against symptomatic pandemic influenza. Nat Med. 2013; 19(10): 1305-12.

Srivastava, A., et al., Nucleotide Sequence and Organization of the Adeno-Associated Virus 2 Genome. (1983) J. Virol., 45: 555-564.

Stanekova Z and Varecykova E. Conserved epitopes of influenza A virus inducing protective immunity and their prospects for universal vaccine development. Viral J. 2010; 7: 351.

Stanley DA, et al. Chimpanzee adenovirus vaccine generates acute and durable protective immunity against ebolavirus challenge. Nat Med. 2014; 20(10): 1126-9.

Steel J, et al. Influenza virus vaccine based on the conserved hemagglutinin stalk domain. mBio. 2010; 1(1).

Steinman, R.M., The Dendritic Cell System and its Role in Immunogenicity. Ann. Rev. Immunol. 9:271-296 (1991).

Stettler, K. et al., Specificity, cross-reactivity, and function of antibodies elicited by Zika virus infection. Science (2016) 353 (6301): 823-827.

Stiasny, K. and Heinz, FX. Flavivirus membrane fusion. J Gen Virol. (2006) 87:2755-2766.

Sun, JC and Bevan, MJ (2003) Defective CD8 T cell memory following acute infection without CD4 T cell help. Science 300: 339-342.

Sztein, MB. (2007) Cell-Mediated Immunity and Antibody Responses Elicited by Attenuated *Salmonella enterica* Serovar Typhi Strains Used as Live Oral Vaccines in Humans, Clinical Infectious Diseases, vol. 45, Issue Supplement_1, pp. S15-S19.

Takahashi, H., et al. Detection and comparison of viral antigens in measles and rubella rashes. Clin. Infect. Dis. 1996, 22, 36-39.

Tatsis, N. and Ertl, HCJ. Adenoviruses as Vaccine Vectors. 2004 Mol Ther 10: 616-29.

Tatsis, N., et al., Adenoviral vectors persist in vivo and maintain activated CD8+ T cells: implications for their use as vaccines. 2007, Blood 110: 1916-23.

Tavel, J. A., et al., (2007) "Safety and Immunogenecity of a Gag-Pol candidate HIV-1 DNA vaccine administered by a need-free device in HIV-1-seronegative subjects." J. AIDS 44, 601-605.

Telford, E.A.R., et al. The DNA sequence of equine herpesvirus-4. Journal of General Virology (1998), 79, 1197-1203.

Teoh, EP etal., The Structural Basis for Serotype-Specific Neutralization of Dengue Virus by a Human Antibody. Sci. Trans. Med. (2012) 4: 139ra83.

Tiollais, P. et al., The hepatitis B virus. (1985) Nature 317:489-495.

Todryk, SM, and Walther, M.. (2005) "Building better T-cell-inducing malaria vaccines." Immunology, vol. 115,2: 163-9.

Tordo, N. & Kouknetzoff, A. (1993) The rabies virus genome: an overview. Onderstepoort Journal of Veterinary Research, 60:263-269.

Torti N, and Oxenius A. T cell memory in the context of persistent herpes viral infections. Viruses. (2012) 4(7):1116-1143.

Turnbull PCB. Bacillus. (1996) In: Baron S, editor. Medical Microbiology. 4th edition. Galveston (TX): University of Texas Medical Branch at Galveston; Chapter 15.

Turner SJ, et al. Differential tumor necrosis factor receptor 2-mediated editing of virus-specific CD8+ effector T cells. Proc Natl Acad Sci US A. 2004; 101(10): 3545-3550.

Tussey LG, et al. Different MHC class I alleles compete for presentation of overlapping viral epitopes. Immunity. 1995; 3(1): 65-77.

Tuthill, Tobias J et al. "Picornaviruses." (2010) Current Topics In Microbiology and Immunology vol. 343: 43-89. doi:10.1007/82_2010_37.

Uddback IE, et al. PB1 as a potential target for increasing the breadth of T-cell mediated immunity to Influenza A. Sci Rep. 2016; 6: 35033.

Valkenburg SA, et al. IL-15 adjuvanted multivalent vaccinia-based universal influenza vaccine requires CD4+ T cells for heterosubtypic protection. Proc Natl Acad Sci US A. 2014; 111(15): 5676- 81.

Vezys, V. et al. (2009) "Memory CD8 T cell comparlmnent grows in size with immunological experience," Nature 457: 196-199.

Vincent, KA et al., Analysis of Recombinant Adeno-Associated Virus Packaging and Requirements for rep and cap Gene Products. (1997)J Virol, 71:1897-1905.

Wachsman, M. et al., Protection of Guinea Pigs from Primary and Recurrent Herpes Simplex Virus (HSV) Type 2 Cutaneous Disease with Vaccinia Virus Recombinants Expressing HSV Glycoprotein D. J. of Inf. Dis. 155, 1188-1197 (1987).

Wahala, WMPB and De Silva, AM, The Human Antibody Response to Dengue Virus Infection. Viruses (2011) 3: 2374-95.

Wahl, G. M. et al. Molecular hybridization of immobilized nucleic acids : theoretical concepts and practical considerations. Guide to molecular cloning techniques. Methods Enzymol. 152:399-407 (1987).

Walker, B and McMichael, A. "The T-Cell Response to HIV. (Nov. 2012)"Cold Spring Harb Perspect Med. 2(11): a007054.

(56) References Cited

OTHER PUBLICATIONS

Walker, DH. Rickettsiae. In: Medical Microbiology. 4th edition. Baron S, editor. Galveston (TX): University of Texas Medical Branch at Galveston. Chapter 38.(1996) Available from: https://www.ncbi.nlm.nih.gov/books/NBK7624/.

Wang X, et al. Neutralizing antibody responses to enterovirus and adenovirus in healthy adults in China. Emerg Microbes Infec. 2014; 3(5): e30.

Wang, Q. et al., Molecular determinants of human neutralizing antibodies isolated from a patient infected with Zika virus. Sci. Trans. Med. (2016) 8: 3695a179.

Wang, Q., et al. Monoclonal Antibodies against Zika Virus: Therapeutics and Their Implications for Vaccine Design. J Virol 91:e01049-17. https://doi.org/10.1128/JVI.01049-17.

Wang, X-Y., et al. From therapeutic antibodies to immune complex vaccines. npj Vaccines (2019) 4:2.

Wang, Z, et al. Recovery from severe H7N9 disease is associated with diverse response mechanisms dominated by CD5+ T cells. Nat Commun. 2015; 6: 6833.

Ward, B.J. et al. (1990) Spontaneous proliferation of peripheral mononuclear cells in natural measles virus infection: Identification of dividing cells and correlation with mitogen responsiveness. Clin. Immunol. Immunopathol. 55, 315-326.

Ward, B.J., et al. Cytokine production in vitro and the lymphoproliferative defect of natural measles virus infection. Clin. Immunol. Immunopathol. (1991) 61, 236-248.

Lee, CYP, and NG, LFP, Zika virus: from an obscurity to a priority. (2018) Microbes and Infection 20 (2018) 635-645.

Lee, H.S., et al., (2019) "Structural and Physiological Exploration of *Salmonella* Typhi YfdX Uncovers Its Dual Function in Bacterial Antibiotic Stress and Virulence." Front. Microbiol., 9: 3329.

Lee, SF, Oral colonization and immune responses to *Streptococcus gordonii*: potential use as a vector to induce antibodies against respiratory pathogens. 2003 Curr Opin Infect Dis. 2003;16:231-235.

Leibiger, R. et al., Yersinia enterocolitica Yop mutants as oral live carrier vaccines. 2008, Vaccine 26:6664-6670.

Li, B., et al. (2008) "Interaction between Yersinia pestis and the Host Immune System." Infection and Immunity, vol. 76 (5) 1804-1811.

Li, B., et al. (2012) "Humoral and cellular immune responses to Yersinia pestis infection in long-term recovered plague patients." Clinical and Vaccine Immunology, vol. 19, 2: 228-34.

Li, G. et al, "Memory T Cells in Flavivirus Vaccination", Vaccines (2018) 6: 73.

Li, J., et al., Role for Highly Regulated rep Gene Expression in Adeno-Associated Virus Vector Production(1997) J Virol., 71:5236-5243.

Li, X. et al., A Novel Tuberculosis DNA Vaccine in an HIV-1 p24 Protein Backbone Confers Protection against Mycobacterium tuberculosis and Simultaneously Elicits Robust Humoral and Cellular Responses to HIV-1. Clin. Vaccine Immunol. 2012;19:723-730. doi: 10.1128/CVI.05700-11.

Li, Z, et al. Type II integral membrane protein, TM of J paramyxovirus promotes cell-to-cell fusion. (2015) Proc Natl Acad Sci U S A. 112:12504-12509.

Li, Z., et al. Adenosine deaminase acting on RNA 1 (ADAR1) suppresses the induction of interferon by measles virus. J. Virol. (2012), 86, 3787-3794.

Lightwood, R., et al. Epithelial giant cells in measles as an acid in diagnosis. J. Pediatr. 1970, 77, 59-64.

Lin, W.H., et al. Prolonged persistence of measles virus RNA is characteristic of primary infection dynamics. Proc. Natl. Acad. Sci. USA (2012) 109, 14989-14994.

Lin, W.H., et al. Vaccine-induced measles virus-specific T cells do not prevent infection or disease but facilitate subsequent clearance of viral RNA. mBio (2014) 5, e01047.

Lin, W.H., et al. Vaxfectin adjuvant improves antibody responses of juvenile rhesus macaques to a DNA vaccine encoding the measles virus hemagglutinin and fusion proteins. J. Virol. (2013) 87, 6560-6568.

Liu, L. et al. Vaccinia virus induces strong immunoregulatory cytokine production in healthy human epidermal keratinocytes: a novel strategy for immune evasion. J. Virol. 2005, 79:12, 7363-70.

Lloyd, ML.,et al, Immunocontraception Is Induced in BALB/c Mice Inoculated With Murine Cytomegalovirus Expressing Mouse Zona Pellucida 3. 2003 Biol. Reprod. 68:2024-2032.

Logan, G, et al. A universal protocol to generate consensus level genome sequences for foot-and-mouth disease virus and other positive-sense polyadenylated RNA viruses using the Illumina MiSeq. BMC Genomics 2014, 15:828.

Lowe, RS et al., Varicella-zoster virus as a live vector for the expression of foreign genes. (1987) Proc. Natl. Acad. Sci. USA, 84:3896-3900.

Lu, LL et al. Beyond binding: antibody effector functions in infectious diseases. Nat Rev Immunol. (2018) 18:46-61. doi: 10.1038/nri.2017.106.

Ludlow, M.,et al. Measles virus infection of epithelial cells in the macaque upper respiratory tract is mediated by subepithelial immune cells. J. Virol. 2013, 87, 4033-4042.

Lumley, Sheila F et al. (2018) "Hepatitis B Virus Adaptation to the CD8+ T Cell Response: Consequences for Host and Pathogen." Frontiers in Immunology vol. 9, 1561.

Lundstrom, K., Latest development on RNA-based drugs and vaccines. Future Sci. OA (2018) 4: FSO300 doi: 10.4155/fsoa-2017-0151.

Lunn, D.P., et al. Equine Herpesvirus-1 Consensus Statement. J Vet Intern Med 2009;23:450-461.

Lustig, Y. et al., Detection of Zika virus RNA in whole blood of imported Zika virus disease cases up to 2 months after symptom onset, Israel, Dec. 2015 to Apr. 2016. Euro Surveill. 2016;21(26):pii=30269. DOI: http://dx.doi.org/10.2807/1560-7917.ES.2016.21.26.30269.

Lyons, A., et al., A double-blind, placebo-controlled study of the safety and immunogenicity of live, oral type 4 and type 7 adenovirus vaccines in adults. 2008 Vaccine 26: 2890-98.

Lü, L. et al., Recombinant Mycobacterium smegmatis mc2155 vaccine expressing outer membrane protein 26 kDa antigen affords therapeutic protection against Helicobacter pylori infection. Vaccine. 2009;27:972-978.

MacGregor, R. et al. (2002) "T-cell responses induced in normal volunteers immunized with a DNA-based cavvine containing HIV-1 env and rev." AIDS 16, 2137-2143.

Mackay L.K.,et al. Long-lived epithelial immunity by tissue-resident memory T (TRM) cells in the absence of persisting local antigen presentation. Proc. Natl. Acad. Sci. USA. (2012) 109:7037-7042.

Mackenzie, J., Wrapping Things up about Virus RNA Replication. Traffic (2005) 6: 967-977.

Mackett, M., et al., Vaccinia virus: A selectable eukaryotic cloning and expression vector. (1982) Proc. Natl. Acad. Sci. USA, 79:7415 7419.

Maggioli MF, et al. (2015) Characterization of Effector and Memory T Cell Subsets in the Immune Response to Bovine Tuberculosis in Cattle. PLOS ONE 10(4): e0122571.

Mansfield, KL, et al., Flavivirus-induced antibody cross-reactivity. J. Gen. Virol. (2011) 92: 2821-29.

Marathe, S., et al. (2012) "Typhoid fever & vaccine development: a partially answered question." Indian J Med Res. Feb; 135(2): 161-169.

Martin, B., Filovirus proteins for antiviral drug discovery: Structure/function bases of the replication cycle. Antiviral Res. (2017) May;141:48-61.

Martin-Acebes, MA, et al., Antibody-Dependent Enhancement and Zika: Real Threat or Phantom Menace?. Front. Cell Infect. Microbiol. (2018) 8: 44.

Masopust, D., et al. Dynamic T cell migration program provides resident memory within intestinal epithelium. J Exp Med. 2010; 207(3): 553-64.

Mastroeni, P., et al., *Salmonella*: Immune Responses and Vaccines. 2001 Vet J 161:132-164.

Mathews J.H., et al., A Synthetic Peptide to the E Glycoprotein of Murray Valley Encephalitis Virus Defines Multiple Virus-Reactive T-and B-Cell Epitopes. J. Virol. (1992) 66: 6555-6562.

(56) References Cited

OTHER PUBLICATIONS

Matsuno, S. and Inouye, S. Purification of an Outer Capsid Glycoprotein of Neonatal Calf Diarrhea Virus and Preparation of Its Antisera (1983) Infection and Immunity 39:155-158.
Matsushita, T., et al. Adeno-associated virus vectors can be efficiently produced without helper virus. (1998) Gene Therapy, 5:938-945.
Mattapallil JJ, et al. (2005) Massive infection and loss of memory CD4+ T cells in multiple tissues during acute SIV infection. Nature 434: 1093-1097.
Mayr, A., et al., (1975) Creation of an attenuated strain of Ankara, MVA. Infection, 3:6-14.
McCaughan, KK et al. Translational termination efficiency in mammals is influenced by the base following the stop codon. (1995) PNAS USA 92:5431-5435.
McChesney, M.B., et al. Experimental measles. I. Pathogenesis in the normal and the immunized host. Virology 1997, 233, 74-84.
McCracken, MK et al, Impact of prior flavivirus immunity on Zika virus infection in rhesus macaques. PLoS Pathog. (2017) 13: e1006487.
Meeusen, E.N.T. et al., Current Status of Veterinary Vaccines. 2007, Clin Microbiol Rev 20:489-510.
Mesman, A.W., et al. A prominent role for DC-SIGN+ dendritic cells in initiation and dissemination of measles virus infection in non-human primates. PLoS ONE 2012, 7, e49573.
Mesman, A.W., et al. Measles virus suppresses RIG-I-like receptor activation in dendritic cells via DC-SIGN-mediated inhibition of PP1 phosphatases. Cell Host Microbe (2014) 16, 31-42.
Meyer, H. et al. Mapping of deletions in the genome of the highly attenuated vaccinia virus MVA and their influence an virulence [1991] J. Gen. Virol. 72, 1031-1038.
Dijkema, R., et al., Cloning and expression of the chromosomal immune interferon gene of the rat. EMBO J. (1985) 4:761-767.
Donnelly, JJ et al., Preclinical efficacy of a prototype DNA vaccine enhanced protection against antigenic drift in influenza virus. Nature Med. (1995) 1: 583-597 doi: 10.1038/nm0695-583.
Dos Santos, T. et al., Zika Virus and the Guillain-Barré Syndrome—Case Series from Seven Countries. N. Engl. J. Med. (2016) 375: 1598-1601.
Douam, R., et al. Selective expansion of myeloid and NK cells in humanized mice yields human-like vaccine responses. Nature Comm. (2018) 9-5031.
Douek DC, et al. (2002) HIV preferentially infects HIV-specific CD4+ T cells. Nature 417: 95-98.
Douek DC, et al. (2009) Emerging concepts in the immunopathogenesis of AIDS. Annu Rev Med 60: 471-484.
Dowd, KA and Pierson, TC, Antibody-mediated neutralization of flaviviruses: A reductionist view. (2011) Virology. 411: 306-315.
Draper SJ and Heeney JL. Viruses as vaccine vectors for infectious diseases and cancer. Nat Rev Microbiol. 2010; 8(1): 62-73.
Driggers, RW et al, Zika Virus Infection with Prolonged Maternal Viremia and Fetal Brain Abnormalities. N. Engl. J. Med. (2016) 374: 2142-2151.
Duc, LH et al., Bacterial Spores as Vaccine Vehicles. 2003, Infect Immun 71:2810-2818.
Duenas-Carrera S, et al. A truncated variant of the hepatitis C virus core induces a slow but potent immune response in mice following DNA immunization. 2000. Vaccine 19:992-997.https://doi.org/ 10.1016/S0264-410X(00)00209-7.
Duffy, MR et al., Zika Virus Outbreak on Yap Island, Federated States of Micronesia. N. Engl. J. Med. (2009) 360: 2536-2543.
Duvall, MG et al. (2008) Polyfunctional T cell responses are a hallmark of HIV-2 infection. Eur J Immunol 38: 350-363.
Dye C. 2014 After 2015: infectious diseases in a new era of health and development. Phil. Trans. R. Soc. B 369:Apr. 26, 2013. http://dx.doi.org/10.1098/rstb.2013.0426.
Díaz-San Segundo F, et al. (2009) Immunosuppression during Acute Infection with Foot-and-Mouth Disease Virus in Swine Is Mediated by IL-10. PLoS One 4(5): e5659.
Edge, MD., et al. Total synthesis of a human leukocyte interferon gene. (1981) Nature 292:756-762.
Edwards, BH et al. (2002) Magnitude of functional CD8+ T-cell responses to the gag protein of human immunodeficiency virus type 1 correlates inversely with viral load in plasma. J Virol 76: 2298-2305.
El Sahly, HM et al., Clinical, Virologic, and Immunologic Characteristics of Zika Virus Infection in a Cohort of US Patients: Prolonged RNA Detection in Whole Blood. Open Forum Infectious Diseases, vol. 6, Issue 1, Jan. 2019, ofy352, https://doi.org/10.1093/ofid/ofy352.
Elong Ngono A., et al., Mapping and Role of the CD8+ T Cell Response During Primary Zika Virus Infection in Mice. Cell Host Microbe. (2017) 21: 35-46.
Emini, EA et al. Priming for and induction of anti-poliovirus neutralizing antibodies by synthetic peptides. (1983) Nature 304:699-703.
Epaulard, O. et al., Anti-tumor Immunotherapy via Antigen Delivery from a Live Attenuated Genetically Engineered Pseudomonas aeruginosa Type III Secretion System-Based Vector. 2006 Mol Ther. 14:656-661.
Eschbaumer, M., "Systemic immune response and virus persistence after foot-and-mouth disease virus infection of naive cattle and cattle vaccinated with a homologous adenovirus-vectored vaccine." (2016) BMC Veterinary Research vol. 12, Art. No. 205.
Esolen, L.M., et al. Brain endothelial cell infection in children with acute fatal measles. J. Clin. Investig. 1995, 96, 2478-2481.
Fan J, , et al. Preclinical study of influenza virus A M2 peptide conjugate vaccines in mice, ferrets, and rhesus monkeys. Vaccine. 2004; 22(23-24): 2993-3003.
Fan, P and Dong, J., Replication of rep-cap Genes Is Essential for the High-Efficiency Production of Recombinant AAV. (1997) Human Gene Therapy, 8:87-98.
Farina SF,et al. Replication-Defective Vector Based on a Chimpanzee Adenovirus. (2001) Journal of Virology 75: 11603-11613.
Fermin, Gustavo, and Paula Tennant. Viruses : Molecular Biology, Host Interactions and Applications to Biotechnology, Chapter 2. Virion Structure, Genome Organization, and Taxonomy of Viruses. edited by Jerome E. Foster, Elsevier Science & Technology, 2018. ProQuest Ebook Central.
Fibriansah, G. et al., A potent anti-dengue human antibody preferentially recognizes the conformation of E protein monomers assembled on the virus surface. EMBO Mol. Med. (2014) 6: 358-71.
Fibriansah, G. et al., Cryo-EM structure of an antibody that neutralizes dengue virus type 2 by locking E protein dimers. Science (2015) 349: 88-91.
Fisher, W., et al. (2007) "Polyvalent Vaccine for Optimal Coverage of Potential T-Cell Epitopes in Global HIV-I Variants," Nat. Med. 13(1): 100-106.
Fleri, W. et al. The Immune Epitope Database and Analysis Resource in Epitope Discovery and Synthetic Vaccine Design. Frontiers in Immun. vol. 8: 278 (2017).
Flynn, M. and Mahon, B.P. Chapter 6: Immune Response to Mumps Viruses. Recent Research Developments in Virology, 5 (2003):97-115.
Fox, JM and Diamond, MS. Immune-Mediated Protection and Pathogenesis of Chikungunya Virus. The Journal of Immunology, 2016, 197: 4210-4218.
Gagnon, SJ et al. Identification of Two Epitopes on the Dengue 4 Virus Capsid Protein Recognized by a Serotype-Specific and a Panel of Serotype-Cross-Reactive Human CD41 CytotoxicT-Lymphocyte Clones. (1996) J. Virol. 70: 141-147.
Galarza, JM., et al. Virus-Like Particle (VLP) Vaccine Conferred Complete Protection against a Lethal Influenza Virus Challenge. (2005) Viral. Immunol. 18(1):244-51.
Ganem, D. and Varmus, HE. The Molecular Biology of the Hepatitis B Viruses (1987) Ann. Rev. Biochem. 56:651-693.
Gao R, et al. Human infection with a novel avian-origin influenza A (H7N9) virus. N Engl J Med. 2013; 368(20): 1888-1897.
Garcia, O. et al. Evolutionary Pattern of Human Respiratory Syncytial Virus (Subgroup A): Cocirculating Lineages and Correlation of Genetic and Antigenic Changes in the G Glycoprotein(1994) J. Virol. Sep. 1994, p. 5448-5459.

(56) References Cited

OTHER PUBLICATIONS

Garcia-Bujalance, S. et al., Persistence and infectivity of Zika virus in semen after returning from endemic areas: Report of 5 cases. J. Clin. Virol. (2017) 96: 110-115.
Garg, H. et al, Development of virus-like-particle vaccine and reporter assay for Zika Virus, J. Virol. (2017) 91(20) e00834-17.
Gellissen, G., et al., Heterologous protein production in yeast. (1992) Antonie Van Leeuwenhoek, 62(1-2):79-93.
GenBank Accession No. JN254802. Chimpanzee adenovirus Y25, complete genome, downloaded from the internet Apr. 9, 2020.
GenBank Accession No. M14923. HSV2 glycoprotein B gene, complete cds. downloaded from the internet Apr. 7, 2020.
GenBank Accession No. M19197.Dengue virus type 2 (S1 vaccine strain), complete genome. downloaded from internet Apr. 7, 2020.
GenBank Accession No. M81899. Measles virus vaccine hemagglutinin (HA) mRNA, complete cds. downloaded from the internet Apr. 7, 2020.
GenBank Accession No. Z33429. Human respiratory syncytial virus (MON-7-91) subgroup A, G gene for glycoprotein. downloaded from internet Apr. 7, 2020.
GenBank Accession No. JO2132. Influenza A virus (A/Memphis/1/1971(H3N2)) hemagglutinin precursor, gene, complete cds. downloaded from internet May 8, 2020.
German Advisory Committee Blood (Arbeitskreis Blut), Subgroup 'Assessment of Pathogens Transmissible by Blood'. (2016) "Human Immunodeficiency Virus (HIV)." Transfusion Medicine and Hemotherapy vol. 43,: 203-22. doi:10.1159/000445852.
Gerold, G. et al. Protein Interactions during the Flavivirus and Hepacivirus Life Cycle. Mol Cell Proteomics. (2017) 16:S75-S91. doi: 10.1074/mcp.R116.065649.
Ghaffar, K.A. et al, "Fast Tracks and Roadblocks for Zika Vaccines," Vaccines (2018) 6, 77; doi: 10.3390/vaccines040077.
Watson A.M., et al.. The 17D-204 vaccine strain-induced protection against virulent yellow fever virus is mediated by humoral immunity and CD4+ but not CD8+ T cells. PLoS Pathog. 2016;12(7): e1005786.
Weerasekera, D., et al., (2019) "Induction of Necrosis in Human Macrophage Cell Lines by Corynebacterium diphtheriae and Corynebacterium ulcerans Strains Isolated from Fatal Cases of Systemic Infections." Int. J. Mol. Sci. 20, 4109.
Weiskopf D. and Sette A. T-cell immunity to infection with dengue virus in humans. Front. Immunol. (2014) 5:93.
Wherry, EJ., et al. Antigen-independent memory CD8 T cells do not develop during chronic viral infection. PNAS, 2004, 101:45, 16004-16009.
Whitley RJ. Herpesviruses. In: Baron S, editor. Medical Microbiology. 4th edition. Galveston (TX): University of Texas Medical Branch at Galveston (1996). Chapter 68. Available from: https://www.ncbi.nim.nih.gov/books/NBK8157/.
Wieten R.W., et al. A single 17D yellow fever vaccination provides lifelong immunity; characterization of yellow-fever-specific neutralizing antibody and T-cell responses after vaccination PLoS ONE. 2016;11:e0149871.
Wigand R, et al. Chimpanzee Adenoviruses Are Related to Four Subgenera of Human Adenoviruses. (1989) Intervirology 30: 1-9.
Williams LD, et al. Interleukin-21-producing HIV-1-specific CD8 T cells are preferentially seen in elite controllers. (2011) J Virol 85: 2316-2324.
Williams MA, et al. (2006) lnterieukin-2 signals during priming are required for secondary expansion of CD8+ memory T cells. Nature 441: 890-893.
Wittek, R., et al. Mapping of a Gene Coding for a Major Late Structural Polypeptide on the Vaccinia Virus Genome (1984) J. Virol. 49, 371-378.
Wong. P. and Pamer. EG. CD8 T Cell Responses to Infectious Pathogens. Annu. Rev. Immunol. 2003. 21:29-70.
Wu T, et al. Lung-resident memory CD8 T cells (TRM) are indispensable for optimal cross-protection against pulmonary virus infection. J Leukoc Biol. 2014; 95(2):215-24.
Xiang, Z., et al., Chimpanzee Adenovirus Antibodies in Humans, Sub-Saharan Africa. 2006 Emerg Infect Dis 12: 1596-99.
Xiang, Z.Q., et al., Oral Vaccination of Mice with Adenoviral Vectors Is Not Impaired by Preexisting Immunity to the Vaccine Carrier. 2003 J Virol 77: 10780-89.
Xiao, X., et al., Production of High-Titer Recombinant Adeno-Associated Virus Vectors in the Absence of Helper Adenovirus. (1998) J Virol, 72:2224-2232.
Xing M, et al. Gene therapy for colorectal cancer usmg adenovirus-mediated full-length antibody, cetuximab. Oncotarget. 2016; 7(19): 28262-72.
Yanagi Y, et al. Measles virus receptors and tropism. (2006) Jpn J Infect Dis. 59:1-5.
Yang, C. et al., Development of Neutralizing Antibodies against Zika Virus Based on Its Envelope Protein Structure, Virologica Sinica (2019) 34: 168-174.
Yang, S., et al. Cross-protective immunity against influenza A/H1N1 virus challenge in mice immunized with recombinant vaccine expressing HA gene of influenza A/H5N1 virus. Virology Journal 2013, 10:291.
Yao, F. et al. Tetracycline repressor, tetR, rather than the tetR-mammalian cell transcription factor fusion derivatives, regulates inducible gene expression in mammalian cells. 1998 Human Gene Ther. 9:1939-1950.
Yauch L.E., et al., A Protective Role for Dengue Virus-Specific CD8+ T Cells. J. Immunol. (2009) 182: 4865-4873.
Yoneyama, M. and Fujita, T. Recognition of viral nucleic acids in innate immunity. Rev. Med. Virol. 2010, 20, 4-22.
Younan, P., et al. Disabling of lymphocyte immune response by Ebola virus. 2018. PLoS Pathog 14(4): e1006932.
Yu, L. et al., Delineating antibody recognition against Zika virus during natural infection. JCI Insight (2017) 2: (12): e93042.
Yu, X.L. et al. Measles virus infection in adults induces production of IL-10 and is associated with increased CD4+ CD25+ regulatory T cells. J. Immunol. (2008) 181, 7356-7366.
Zens KD, et al. Vaccine-generated lung tissue-resident memory T cells provide heterosubtypic protection to influenza infection. JCI Insight. 2016; 1(10).
Zhang S, et al. Seroprevalence of neutralizing antibodies to human adenoviruses type-5 and type-26 and chimpanzee adenovirus type-68 in healthy Chinese adults. J Med Viral. 2013; 85(6): 1077-84.
Zhang W., et al. Identification of three H-2Kd restricted CTL epitopes of NS4A and NS4B protein from Yellow fever 17D vaccine. J. Virol. Methods. 2013;187:304-313.
Zhang, Jie et al. "Immune response of T cells during herpes simplex virus type 1 (HSV-1) infection." Journal of Zhejiang University. Science. B vol. 18,4 (2017): 277-288.
Zhao, C. and Xu, J. Toward universal influenza virus vaccines: from natural infection to vaccination strategy. J., Curr. Op. Immunol. (2018) 53: 1-6.
Zhao, C. and Xu, J. Towards Universal Influenza Virus Vaccines: from Natural Infection to Vaccination Strategy. Curr. Opin Immunol. vol. 53, No. 1, 2018, pp. 1-6.
Zhao, X. et al., Pathogenicity and Immunogenicity of a Vaccine Strain of Listeria monocytogenes That Relies on a Suicide Plasmid To Supply an Essential Gene Product. 2005 Infect Immun 73:5789-5798.
Zhu Z, et al. Infection of inbred BALB/c and C57BL/6 and outbred Institute of Cancer Research mice with the emerging H7N9 avian influenza virus. Emerg Microbes Infect. 2013; 2(8): e50.
Zilliox, M.J., et al. Gene expression changes in peripheral blood mononuclear cells during measles virus infection. Clin. Vaccine Immunol. (2007) 14, 918-923.
Zimmerli, SC et al. (2005) HIV-1-specific IFN-?/IL-2-secreting CD8 T cells support CD4-independent proliferation of HIV-1-specific CD8 T cells. Proc Natl Acad Sci 102: 7239-7244.
Zimmerman, MG et al., Cross-Reactive Dengue Virus Antibodies Augment Zika Virus Infection of Human Placental. Cell Host Microbe (2018) 24: 731-742.
Ziola, B., et al., "T cell cross-reactivity among viruses of the paramyxoviridae." Viral Immunol. (1987) 1(2): 111-9.

(56) References Cited

OTHER PUBLICATIONS

Zuniga, R. et al. (2006) Relative dominance of Gag p24-specific cytotoxic T lymphocytes is associated with human immunodeficiency virus control. J Virol 80: 3122-3125.
Brown LE and Kelso A. Prospects for an influenza vaccine that induces cross-protective cytotoxic T lymphocytes. Immunol Cell Biol. 2009; 87(4):300-8.
Brown, JA et al., Dengue Virus Immunity Increases Zika Virus-Induced Damage during Pregnancy. Immunity (2019) 50(3): 751-762.e5.
Brown, M., et al. lac repressor can regulate expression from a hybrid SV40 early promoter containing a lac operator in animal cells. Cell, 49:603-612, 1987.
Busca, A. and Kumar, A. (2014) "Innate immune responses in hepatitis B virus (HBV) infection." Virology Journal, vol. 11:22.
Bzik, DJ. et al. (1986), The nucleotide sequence of the gB glycoprotein gene of HSV-2 and comparison with the corresponding gene of HSV-1. Virology 155:322-333.
Caignard, G. et al. Measles virus V protein blocks Jak1-mediated phosphorylation of STAT1 to escape IFN-alpha/beta signaling. Virology (2007) 368, 351-362.
Calisher, Ch, et al., Antigenic relationships between flaviviruses as determined by cross-neutralization tests with polyclonal antisera. J. Gen. Virol. (1989) 70: 37-43.
Campana, S. et al., Cross-dressing: an alternative mechanism for antigen presentation. Immunol. Letters (2015) 168 (2): 349-54.
Cao-Lormeau, V-M, et al, Guillain-Barré Syndrome outbreak associated with Zika virus infection in French Polynesia: a case-control study. Lancet (2016) 387: 1531-39.
Carr, B Veronica et al. (2013) "CD4+ T-cell responses to foot-and-mouth disease virus in vaccinated cattle." J. General Virology vol. 94, Pt 1: 97-107.
Casadevall, A., et al., "Exploiting the Redundancy in the Immune System" Journal of Experimental Medicine (2003) 197 (11) 1401-1404.
Cassone, A. and Rappuoli, R. (2010). Universal Vaccines: Shifting to One for Many. MBio. 1(1), e00042-10. doi:10.1128/mBio.00042-10.
Castanha, PM et al., Dengue Virus-Specific Antibodies Enhance Brazilian Zika Virus Infection. J. Infect. Dis. (2016) 215: 781-785.
Cepko, CL et al., Construction and applications of a highly transmissible murine retrovirus shuttle vector. (1984) Cell 37:1053-1062.
Chapman, B., et al., Effect of intron A from human cytomegalovirus (Towne) immediate-early gene on heterologous expression in mammalian cells. Nuc. Acids Res. (1991) 19:3979-3986.
Chattopadhyay A. et al., A recombinant virus vaccine that protects against both Chikungunya and Zika virus infections. Vaccine. (2018) 36: 3894-3900.
Chen W, et al. Immunoproteasomes shape immunodominance hierarchies of antiviral CD8(+) T cells at the levels of T cell repertoire and presentation of viral antigens. J Exp Med. 2001; 193(11): 1319-26.
Cheng, PC et al., Combined IL-12 Plasmid and Recombinant SjGST Enhance the Protective and Antipathology Effect of SjGST DNA Vaccine Against Schistosoma japonicum. PLoS Neg. Trap Dis. (2016) 10: e00044594; doi: 10.1371/journal.pntd.0004459.
Cherif, MS et al, Immunogenicity of novel nanoparticle-coated MSP-1 C-terminus malaria DNA vaccine using different routes of administration. Vaccine (2011) 29: 9038-9050.
Chevalier MF, et al. HIV-1-specific interleukin-21+ CD4+ T cell responses contribute to durable viral control through the modulation of HIV-specific CD8+ T cell function. (2011) J Virol 85: 733-741.
Childs, K. et al. Paramyxovirus V proteins interact with the RNA helicase LGP2 to inhibit RIG-I-dependent interferon induction. J. Virol. (2012), 86, 3411-3421.
Childs, K.S. et al . Mechanism of mda-5 Inhibition by paramyxovirus V proteins. J. Virol. (2009) 83, 1465-1473.
Chin J, et al. (1969) Field evaluation of a respiratory syncytial virus vaccine and a trivalent parainfluenza virus vaccine in a pediatric population. Am J Epidemiol 89:449-463.
Chun, J-H, et al. Complete Genome Sequence of Bacillus anthracis H9401, an Isolate from a Korean Patient with Anthrax. J Bacteriology vol. 194. No. 15, 4116-4117 (2012).
Clemens EB, et al. Harnessing the Power of T Cells: The Promising Hope for a Universal Influenza Vaccine. Vaccines (Basel). 2018; 6(2).
Collins, M.H., Serologic Tools and Strategies to support intervention trials to combat Zika virus infection and disease. Trop Med. Infect. Dis. (2019) 4,68; doi:10.3390/tropicalmed4010068.
Collins, PL. et al., Nucleotide sequence of the gene encoding the fusion (F) glycoprotein of human respiratory syncytial virus. (1984) Proc. Natl. Acad. Sci. USA 81:7683.
Colombo, TE et al., Clinical, laboratory and virological data from suspected ZIKV patients in an endemic arbovirus area. J. Clin. Virol. (2017) 96: 20-25.
Coombes, AGA et al., Single dose, polymeric, microparticle-based vaccines: the influence of formulation conditions on the magnitude and duration of the immune response to a protein antigen. Vaccine 14:1429-1438, 1996.
Cowan, G. (2000) "Rickettsial diseases: the typhus group of fevers—a review." Postgraduate Medical J. vol. 76: 269-72.
Cox A, and Dewhurst S. A Single Mutation at PB1 Residue 319 Dramatically Increases the Safety of PR8 Live Attenuated Influenza Vaccine in a Murine Model without Compromising Vaccine Efficacy. J Virol. 2015; 90(5): 2702-5.
Cox, R., and Plemper, R. Structure and Organization of Paramyxovirus Particles. Curr Opin Virol. Jun. 2017; 24: 105-114.
Cruz-Adalia, A. et al. Conventional CD4+ T cells present bacterial antigens to induce cytotoxic and memory CD8+ T cell responses. Nature Comm. 8:1591 (2017).
Cárdenas, L. and Clements, JD., Oral Immunization Using Live Attenuated *Salmonella* spp. as Carriers of Foreign Antigens. 1992 Clin Microbiol Rev 5:328-342.
Damaso, CRA et al., An Emergent Poxvirus from Humans and Cattle in Rio de Janeiro State: Cantagalo Virus May Derive from Brazilian Smallpox Vaccine. (2000) Virology 277:439-49.
Davis, M.E. et al. Antagonism of the phosphatase PP1 by the measles virus V protein is required for innate immune escape of MDA5. Cell Host Microbe (2014) 16, 19-30.
Davison AJ. Overview of classification. In: Arvin A, Campadelli-Fiume G, Mocarski E, et al., editors. Human Herpesviruses: Biology, Therapy, and Immunoprophylaxis. Cambridge: Cambridge University Press (2007) Chapter 1. Available from: https://www.ncbi.nlm.nih.gov/books/NBK47406/.
De Alwis, R. et al., Identification of human neutralizing antibodies that bind to complex epitopes on dengue virions. Proc. Natl. Acad. Sci. USA (2012) 109: 7439-44.
De Kruif, J., et al.(2007). A human monoclonal antibody cocktail as a novel component of rabies postexposure prophylaxis. Annu Rev Med 58, 359-68.
De Oliveira Melo, AS, et al., Congenital Zika Virus Infection Beyond Neonatal Microcephaly. Neurological Complications of Congenital Zika Virus Infection. JAMA Neurol. (2016) vol. 73, No. 12, 1407-1416.
De Vries, R.D. et al. (2010) Specific CD8+ T-lymphocytes control dissemination of measles virus. Eur. J. Immunol. 40, 388-395.
De Vries, R.D., et al. Measles immune suppression: Lessons from the macaque model. PLoS Pathog. 2012, 8, e1002885.
De Wit, J. et al. (2019) "The Human CD4+ T Cell Response against Mumps Virus Targets a Broadly Recognized Nucleoprotein Epitope." Journal of Virology, 93 (6) e01883-18.
Dejnirattisai, W. et al., Dengue virus sero-cross-reactivity drives antibody-dependent enhancement of infection with zika virus . Nature Immunol. (2016) 17: 1102-1108.
Delhon, G. et al. Genome of Bovine Herpesvirus 5. J Virology, vol. 77, No. 19, 10339-10347 (2003).
Deluca, N.A., et al. Isolation and Characterization of Deletion Mutants of Herpes Simplex Virus Type 1 in the Gene Encoding Immediate-Early Regulatory Protein ICP4. 1985 J. Virol. 56 (2): 558-70.

(56) References Cited

OTHER PUBLICATIONS

Demeure, C.E.. et al. (2019) Yersinia pestis and plague: an updated view on evolution, virulence determinants, immune subversion, vaccination, and diagnostics. Genes Immun 20, 357-370.
Diamond M.S., et al., B Cells and Antibody Play Critical Roles in the Immediate Defense of Disseminated Infection by West Nile Encephalitis Virus. J. Virol. (2003) 77:2578-2586.
Didcock, L. et al., "The V protein of simian virus 5 inhibits interferon signaling by targeting STAT1 for proteasome-mediated degradation," J. Virol. (1999) 73 (12): 9928-33.
Abbink, P., et al. Comparative Seroprevalence and Immunogenicity of Six Rare Serotype Recombinant Adenovirus Vaccine Vectors from Subgroups B and D 2007 J Virol.; 81:4654-4663.
Abdad, MY. (2018) "A Concise Review of the Epidemiology and Diagnostics of Rickettsioses: Rickettsia and Orientia spp." Journal of Clinical Microbiology 56 (8) e01728-17.
Adebanjo, T.,Update: Interim Guidance for the Diagnosis, Evaluation, and Management of Infants with Possible Congenital Zika Virus Infection—United States, Oct. 2017. Morb. Mortal. Wkly Rep. (2017) 66:(41); 1089-1099.
Adeolu, M., et al., "Genome-based phylogeny and taxonomy of the 'Enterobacteriales': proposal for Enterobacterales ord. nov. divided into the families Enterobacteriaceae, Erwiniaceae fam. nov., Pectobacteriaceae fam. nov., Yersiniaceae fam. nov., Hafniaceae fam. nov., Morganellaceae fam. nov., and Budviciaceae fam. nov". (2016) Intl J. Systemic & Evolutionary Microbiol. 66, 5575-559.
Aihara H, et al. Establishment and characterization of Japanese encephalitis virus-specific, human CD4+ T-cell clones: flavivirus cross-reactivity, protein recognition, and cytotoxic activity. 1998. J Virol 72:8032-8036.
Air, GM. Sequence relationships among the hemagglutinin genes of 12 subtypes of influenza A virus. 1981, Proc. Natl. Acad. Sci. USA 78:7639-7643.
Aitken, ML et al., A Phase I Study of Aerosolized Administration of tgAAVCF to Cystic Fibrosis Subjects with Mild Lung Disease. 2001 Hum Gene Therapy, 12:1907-1916.
Akondy R.S., et al. Origin and differentiation of human memory CD8 T cells after vaccination. Nature. (2017) 552: 362-367.
Alberts et al. The Adaptive Immune System. Molecular Biology of the Cell 4th Ed., Garland Science, New York (2002) Chapter 24 at p. 1407.
Albrecht, MT, et al., Immunogenicity and efficacy of an anthrax/plague DNA fusion vaccine in a mouse model. FEMS Immunol Med Microbiol (2012) 65: 505-509 doi: 10.1111/j.1574-695X.2012.00974.x.
Allwinn, R. et al., Cross-reactivity in flavivirus serology: new implications of an old finding?. Med. Microbiol. Immunol. (2002) 190: 199-202.
Alonso-Padilla, J. et al. Development of Novel Adenoviral Vectors to Overcome Challenges Observed With HAdV-5-based Constructs. 2016 Mol Ther.;24: 6-16.
Alter, G. and Barouch, D. Immune Correlate-Guided HIV Vaccine Design. Cell Host Microbe. 2018 24(1):25-33.
Alves, EDL, et al. Characterization of the immune response following in vitro mayaro and chikungunya viruses (Alphavirus, Togaviridae) infection of mononuclear cells. Virus Res. 256 (2018) 166-173.
Amanna, I.J.and Slifka, M.K. Mechanisms that determine plasma cell lifespan and the duration of humoral immunity. Immunol. Rev. (2010) 236, 125-138.
An G., et al., "Binary Vectors" (1988) in Plant Molecular Biology Manual A3:1-19.
Andrejeva, J, et al., "Degradation of STAT1 and STAT2 by the V proteins of simian virus 5 and human parainfluenza virus type 2, respectively: consequences for virus replication in the presence of alpha/beta and gamma interferons," J. Virol. (2002) 76(5): 2159-67.
Arauza-Ortega, L. et al., Fatal Sickle Cell Disease and Zika Virus Infection in Girl from Colombia. Emerg. Infect. Dis. (2016) 22: 925-27.
Ariotti S, et al. T cell memory. Skin-resident memory CD8+ T cells trigger a state of tissue-wide pathogen alert. Science. 2014; 346(6205): 101-5.
Arsuaga, M. et al., Probable sexual transmission of Zika virus from a vasectomised man. Lancet Infect. Dis. vol. 16, Issue 10, p. 1107 (2016).
Audibert, F.et al., Active antitoxic immunization by a diphtheria toxin synthetic oligopeptide. 1981, Nature 289:593.
Ayub, A., et al. Global Consensus Sequence Development and Analysis of Dengue NS3 Conserved Domains. Bio Res vol. 2, No. 5, 392-396, 2013.
Baker, S. and Dougan, G. (2007) The Genome of *Salmonella enterica* Serovar Typhi, Clinical Infectious Diseases, vol. 45, Issue Supplement_1, , pp. S29-S33).
Baker, TS et al., Structures of bovine and human papillomaviruses—Analysis by cryoelectron microscopy and three-dimensional image reconstruction. Biophys. J. (1991) 60:1445 1456.
Bakker, A. B., et al. (2005). Novel human monoclonal antibody combination effectively neutralizing natural rabies virus variants and individual in vitro escape mutants. J Virol 79, 9062-8.
Bakker, AB, et al, (2008) "First administration to humans of a monoclonal antibody cocktail against rabies virus: safety, tolerability, and neutralizing activity,"Vaccine 26, 5922-7.
Balmaseda, A. et al., Antibody-based assay discriminates Zika virus infection from other flaviviruses. Proc. Natl Acad. Sci. USA (2017) 114: 8384-89.
Barba-Spaeth, G. et al. Structural basis of potent Zika-dengue virus antibody cross-neutralization. Nature (2016) 536: 48-53.
Barber, DL et al. (2003) Cutting edge: Rapid in vivo killing by memory CD8 T cells. J Immunol 171: 27-31.
Bardina, SV et al., Enhancement of Zika virus pathogenesis by preexisting antiflavivirus immunity. Science (2017) 356:175-180.
Barouch DH, et al. Protective Efficacy of Adenovirus/Protein Vaccines Against SIV Challenges in Rhesus Monkeys. Science. 2015; 349(6245): 320-324.
Barrett A.D., Teuwen D.E. Yellow fever vaccine—how does it work and why do rare cases of serious adverse events take place?. Curr. Opin. Immunol. (2009) 21: 308-313. doi: 10.1016/j.coi.2009.05.018.
Barry, EM et al., Immunogenicity of multivalent Shigella-ETEC candidate vaccine strains in a guinea pig model. 2006, Vaccine 24:3727-3734.
Bassi M.R., et al., CD8+ T Cells Complement Antibodies in Protecting against Yellow Fever Virus. J. Immunol. (2015) 194: 1141-1153.
Bastos, RG et al., Recombinant Mycobacterium bovis BCG. 2009 Vaccine. 2009;27:6495-6503.
Beachey, EH. (1985) Protective Immunity Evoked by Synthetic Peptides of *Streptococcal* M Proteins. In: Atassi M.Z., Bachrach H.L. (eds) Immunobiology of Proteins and Peptides—III. Advances in Experimental Medicine and Biology, vol. 185; 193-200. Springer, Boston, MA.
Beierlein, J M, and Anderson, A C. (2011) "New developments in vaccines, inhibitors of anthrax toxins, and antibiotic therapeutics for Bacillus anthracis." Current Medicinal Chemistry vol. 18,33: 5083-94.
Belz GT, Diversity of Epitope and Cytokine Profiles for Primary and Secondary Influenza A Virus-Specific CD8+ T Cell Responses. J Immunol. 2001; 166(7): 74627-4633.
Bertholet, C. et al., One hundred base pairs of 5' flanking sequence of a vaccinia virus late gene are sufficient to temporally regulate late transcription. (1985) Proc. Natl. Acad. Sci. USA 82, 2096-2100.
Betts, MR and Harari, A (2008) Phenotype and function of protective T cell immune responses in HIV. Curr Opin HIV AIDS 3: 349-355.
Bhanuprakash, V., et al, "Animal poxvirus vaccines: a comprehensive review." Expert Review of Vaccines (2012) 11(11): 1355-1374.
Bharati, K. and Das, S. (2019) "Malaria Vaccine Development: Challenges and Prospects." Journal of Clinical and Diagnostic Research. Aug, vol. 13(8): AB01-AB03.
Blom K., et al. Temporal dynamics of the primary human T cell response to yellow fever virus 17D as it matures from an effector-to a memory-type response. J. Immunol. 2013;190: 2150-2158.

(56) References Cited

OTHER PUBLICATIONS

Bollati, M. et al., Structure and functionality in flavivirus NS-proteins: Perspectives for drug design. Antiviral Res. (2010) 87(2): 125-148.
Bonaldo, MC et al., The yellow fever 17D virus as a platform for new live attenuated vaccines. Hum. Vaccin. Immunother. (2014) 10: 1256-1265. doi: 10.4161/hv.28117.
Borucki MK, et al. (2013) Ultra-Deep Sequencing of Intra-host Rabies Virus Populations during Cross-species Transmission. PLoS Negl Trop Dis 7(11): e2555.
Bouvier, Nicole M, and Palese, P. "The biology of influenza viruses." Vaccine vol. 26 Suppl 4,Suppl 4 (2008): D49-53.
Bradfute, Steven B et al. "Filovirus vaccines." Human vaccines vol. 7,6 (2011): 701-11.
Brasil, P. et al., Zika Virus Infection in Pregnant Women in Rio de Janeiro. N. Engl. J. Med. (2016) 375: 2321-2334.
Brockstedt, DG., et al.,Listeria-based cancer vaccines that segregate immunogenicity from toxicity. 2004 Proc Natl Acad Sci U S A 101:13832-13837.
Michlmayr D., et al., Dual Function of Ccr5 during Langat Virus Encephalitis: Reduction in Neutrophil-Mediated Central Nervous System Inflammation and Increase in T Cell-Mediated Viral Clearance. J. Immunol. (2016) 196: 4622-4631.
Miki, BLA., et al. Plant DNA Infectious Agents. Chapter 10: Microinjection: An Experimental Tool for Studying and Modifying Plant Cells. pp. 249-265 (Hohn, T., et al., eds.) Springer-Verlag—Wien, Austria, 1987.
Miller, N. and Whelan, J. Progress in Transcriptionally Targeted and Regulatable Vectors for Gene Therapy. Human Gene Therapy, 8:803-815 (1997).
Mina, M.J., et al. Long-term measles-induced immunomodulation increases overall childhood infectious disease mortality. Science (2015) 348, 694-699.
Miranda-Filho, DdB; et al., Initial Description of the Presumed Congenital Zika Syndrome. Am. J. Public Health (2016) 106: 598-600.
Mocarski JR. ES. Comparative analysis of herpesvirus-common proteins. In: Arvin A, Campadelli-Fiume G, Mocarski E, et al., editors. Human Herpesviruses: Biology, Therapy, and Immunoprophylaxis. Cambridge: Cambridge University Press (2007) Chapter 4. Available from: https://www.ncbi.nlm.nih.gov/books/NBK47403/.
Moench, T.R, et al. Acute measles in patients with and without neurological involvement: Distribution of measles virus antigen and RNA. J. Infect. Dis. 1988, 158, 433-442.
Moliva, JI, et al. Immune Responses to Bacillus Calmette-Guérin Vaccination: Why Do They Fail to Protect against Mycobacterium tuberculosis?. Frontiers in Immunol. 2017, vol. 8:407.
Molla, S. Review on Human Immune Response against Hepatitis B Virus (HBV) Infection. J Emerg Dis Virol 2(3): doi http://dx.doi.org/10.16966/2473-1846.117.
Moore, R. et al., Foreign gene expression in Corynebacterium pseudotuberculosis: development of a live vaccine vector. Vaccine. 1999; 18:487-497.
Morikawa, S., et al. (2005) An Attenuated LC16m8 Smallpox Vaccine: Analysis of Full-Genome Sequence and Induction of Immune Protection. Journal Of Virology, vol. 79, No. 18. 11873-11891.
Morin, JE et al. Recombinant adenovirus induces antibody response to hepatitis B virus surface antigen in hamsters. (1987) Proc. Natl. Acad. Sci. USA 84:4626-4630.
Mosmann, TR and Coffman, RL. TH1 and TH2 Cells: Different Patterns of Lymphokine Secretion Lead to Different Functional Properties. Ann. Rev. Immunol. 7:145-173, 1989.
Moss, Bernard. "Poxvirus cell entry: how many proteins does it take?" Viruses vol. 4,5 (2012): 688-707.
Moss, Bernard. "Smallpox vaccines: targets of protective immunity." Immunological Reviews vol. 239,1 (2011): 8-26.
Moss, J. (2013) "HIV/AIDS Review" Radiologic Technology, vol. 84, No. 3, 247-267.
Moss, W.J., et al. Differential regulation of interleukin (IL)-4, IL-5, and IL-10 during measles in Zambian children. J. Infect. Dis. (2002) 186, 879-887.
Moutaftsi M, et al. A consensus epitope prediction approach identifies the breadth of murine TCD8+-cell responses to vaccinia virus. (2006) Nat Biotechnol. 24: 817-819.
Muneta, Y. et al., Development and immunogenicity of recombinant Mycoplasma gallisepticum vaccine strain ts-11 expressing chicken IFN-gamma. Vaccine. 2008;26:5449-5454.
Munoz-Jordan, JL, Diagnosis of Zika Virus Infections: Challenges and Opportunities. J. Infect. Dis. (2017) 216: S951-S956.
Murphy JR. Corynebacterium Diphtheriae. (1996) In: Baron S, editor. Medical Microbiology. 4th edition. Galveston (TX): University of Texas Medical Branch at Galveston; Chapter 32.
Murray, HW et al. (1984) "Impaired production of lymphokines and immune (?) interferon in the acquired immunodeficiency syndrome." N. Engl. J. Med. 310: 883-889.
Murray, KO, et al, Prolonged Detection of Zika Virus in Vaginal Secretions and Whole Blood. Emerg. Infect. Dis. (2017) vol. 23, No. 1, 99-101.
Muruganandah, V.et al. (2018). A Systematic Review: The Role of Resident Memory T Cells in Infectious Diseases and Their Relevance for Vaccine Development. Frontiers in Immunology, 9, 1574. doi:10.3389/fimmu.2018.01574.
Muzyczka, N. Use of Adeno-Associated Virus as a General Transduction Vector for Mammalian Cells(1992) Current Topics in Microbiology and Immunology, 158: 97-129.
Nagel, R., et al., Electroporation of binary Ti plasmid vector into Agrobacterium tumefaciens and Agrobacterium rhizogenes. (1990) FEMS Microbiol. Lett. 67:325-328.
Nair H, et al. (2010) Global burden of acute lower respiratory infections due to respiratory syncytial virus in young children: a systematic review and meta-analysis. Lancet 375:1545-1555.
Nair, N., et al. HIV-1 infection in Zambian children impairs the development and avidity maturation of measles virus-specific immunoglobulin G after vaccination and infection. J. Infect. Dis. (2009) 200, 1031-1038.
Nakanishi Y., et al., CTL mobilization to virus-infected tissue requires CD4+ T cell help Nature (2009) 462:510-513.
Nakayama, K. et al.Genome Comparison and Phylogenetic Analysis of Orientia tsutsugamushi Strains. DNA Research 17, 281-291, (2010).
Nambiar, KP., et al. Total synthesis and cloning of a gene coding for the ribonuclease S protein. (1984) Science 223:1299-1301.
Nasser Eddine, A. and Kaufmann, H.E. Improved protection by recombinant BCG. 2005, Microbes Infect 7:939-946.
Neurath, AR., et al. Antibodies to a synthetic peptide from the pre S 120-145 region of the hepatitis B virus envelope are virus-neutralizing. (1986) Vaccine 4:34.
Newton, SE et al., Sequence of the hemagglutinin gene of influenza virus a/memphis/1 /71 and previously uncharacterized monoclonal antibody-derived variants. 1983, Virology 128:495-501.
Ngumbela, KC et al. (2008) "Targeting of a CD8 T cell env epitope presented by HLA-B*5802 is associated with markers of HIV disease progression and lack of selection pressure." AIDS Res Hum Retroviruses 24: 72-82.
Nguyen, SM et al., Highly efficient maternal-fetal Zika virus transmission in pregnant rhesus macaques PLoS Pathog. (2017) 13: e1006378.
Nicastri, E. et al., Persistent detection of Zika virus RNA in semen for six months after symptom onset in a traveller returning from Haiti to Italy, Feb. 2016. Euro Surveill. 2016;21(32):pii=30314. DOI: http://dx.doi.org/10.2807/1560-7917.ES.2016.21.32.30314.
Nicolson, L. et al. The nucleotide sequence of an equine herpesvirus 4 gene homologue of the herpes simplex virus 1 glycoprotein H gene. J General Virology (1990) 71, 1793-1800.
Norder, H. et al., "Picornavirus non-structural proteins as targets for new anti-virals with broad activity." Antiviral Research 89 (2011) 204-218.
Nozawa, Y., et al. An immunohistochemical study ofWarthin-Finkeldey cells in measles. Pathol. Int. 1994, 44, 442-447.

(56) References Cited

OTHER PUBLICATIONS

Octavia S., Lan R. (2014) The Family *Enterobacteriaceae*. In: Rosenberg E., DeLong E.F., Lory S., Stackebrandt E., Thompson F. (eds) The Prokaryotes. pp. 225-286, Springer, Berlin, Heidelberg.
Oehler, E. et al., Zika virus infection complicated by Guillain-Barré syndrome-case report, French Polynesia, Dec. 2013. Euro Surveill. (2014) 19: 20720.
Ogawa, Y. et al., Oral vaccination against mycoplasmal pneumonia of swine using a live Erysipelothrix rhusiopathiae vaccine strain as a vector. 2009, Vaccine 27:4543-4550.
Oggioni, MR et al., Immunization of mice by oral colonization with live recombinant commensal streptococci. 1995, Vaccine 13:775-779.
Okada, H.et al. Comparative analysis of host responses related to immunosuppression between measles patients and vaccine recipients with live attenuated measles vaccines. Arch. Virol. (2001) 146, 859-874.
Okumura, K, et al. Construction of a virtual *Mycobacterium tuberculosis* consensus genome and its application to data from a next generation sequencer. BMC Genomics (2015) 16:218.
Oliverira, A., et al. "Insight of Genus *Corynebacterium*: Ascertaining the Role of Pathogenic and Non-pathogenic Species." (2017) Front. Microbiol., 8: 1937.
Osterloh, A. (2017) "Immune response against rickettsiae: lessons from murine infection models." Medical microbiology and immunology vol. 206, 6: 403-417.
Ota, M.O, et al. (2007) Hemagglutinin protein is a primary target of the measles virus-specific HLA-A2-restricted CD8+ T cell response during measles and after vaccination. J. Infect. Dis. 195, 1799-1807.
Panicali, D and Paoletti, E. Construction of poxviruses as cloning vectors: Insertion of the thymidine kinase gene from herpes simplex virus into the DNA of infectious vaccinia virus. (1982) Proc. Natl. Acad. Sci. USA, 79:4927 4931.
Rosel, JL.,et al., Conserved TAAATG Sequence at the Transcriptional and Translational Initiation Sites of Vaccinia Virus Late Genes Deduced by Structural and Functional Analysis of the HindIII H Genome Fragment. (1986) J. Virol. 60, 436-449.
Rosenberg, ES et al. (1997) Vigorous HIV-1-specific CD4+ T cell responses associated with control of viremia. Science 278: 1447-1450.
Rossini, G. et al., Comparison of Zika virus (ZIKV) RNA detection in plasma, whole blood and urine e Case series of travel-associated ZIKV infection imported to Italy, 2016. J. Infect. (2017) 75: 242-245.
Rota, JS et al. Genetic variability of the glycoprotein genes of current wild-type measles isolates. (1992), Virology 188:135-142.
Rothbard, JB and Schoolnik, GK (1985) The Primary Sequence and Antigenic Structure of Gonococcal Pilin: Approaches Towards a Gonococcal Vaccine. In: Atassi M.Z., Bachrach H.L. (eds) Immunobiology of Proteins and Peptides—III. Advances in Experimental Medicine and Biology, vol. 185; 247-273. Springer, Boston, MA.
Roy S, et al Isolation and Characterization of Adenoviruses Persistently Shed from the Gastrointestinal Tract of Non-Human Primates . . . (2009) PLoS pathogens 5: e1000503.
Roy S. Et al. Complete nucleotide sequences and genome organization of four chimpanzee adenoviruses. (2004) Virology 324: 361-372.
Roy S., et al. Characterization of a Family of Chimpanzee Adenoviruses and Development of Molecular Clones for Gene Transfer Vectors. (2004) Human gene therapy 15: 519-530.
Rubin, S. et al., Molecularbiology, pathogenesis and pathology of mumps virus. J. Pathol. (2015) 235 (2): 242-252.
Ruckdeschel, J.C., et al. Additional evidence that the cell-associated immune system is the primary host defense against measles (rubeola). Cell Immunol. (1975) 17, 11-18.
Rueckert C and Guzmán CA (2012) Vaccines: From Empirical Development to Rational Design. PLoS Pathog 8 (11): e1003001.
Ruffin, M. et al., Mutations in the carboxy terminus of adeno-associated virus 2 capsid proteins affect viral infectivity: lack of an RGD integrin-binding motif. (1994) J. Gen. Virol., 75: 3385-3392.

Russell RJ, et al. Structure of influenza hemagglutinin in complex with an inhibitor of membrane fusion. Proc Natl Acad Sci US A. 2008; 105(46): 17736-17741.
Russell, C., et al. Vaccines for the Paramyxoviruses and Pneumoviruses: Successes, Candidates, and Hurdles. Viral Immunology vol. 31, No. 2, 133-141. 2018.
Sabchareon A., et al. Protective efficacy of the recombinant, live-attenuated, CYD tetravalent dengue vaccine in Thai schoolchildren: a randomised, controlled phase 2b trial. Lancet (2012) 380: 1559-1567.
Sahni, SK, et al. (2013) "Recent molecular insights into rickettsial pathogenesis and immunity." Future microbiology vol. 8,10: 1265-88.
Said, ZNA, and Kouka SA (2015) "Induced immunity against hepatitis B virus." World Journal of Hepatology, vol. 7,12: 1660-70.
Sairol, CA et al (2018), A Tale of Two Viruses: Does Heterologous Flavivirus Immunity Enhance Zika Disease?. Trends in Microbiol. 26(3): 186-190.
Sakabe, S., et al. Analysis of CD8+ T cell response during the 2013-2016 Ebola epidemic in West Africa. PNAS. 115:32 E7578-E7586.
Salerno-Goncalves, R., "Cell-mediated immunity and the challenges for vaccine development." (2006) Trends Microbiol. Dec; 14(12):536-42. Epub Oct. 19, 2006.
Saletti G, et al. Influenza vaccines: 'tailor-made' or 'one fits all'. Curr Opin Immunol. 2018; 53: 102-110.
Samaniego, LA et al. Functional Interactions between Herpes Simplex Virus Immediate-Early Proteins during Infection: Gene Expression as a Consequence of ICP27 and Different Domains of ICP4. 1995 J. Virol. 69: 5705-15.
Sampathkumar, P., and Sanchez, J.L. Zika Virus in the Americas: A Review for Clinicians. Mayo Clin. Proc. (2016) 91: 514-521.
Sandgren, K., et al., "Understanding natural herpes simplex virus immunity to inform next-generation vaccine design." (2016) Clinical & Translational Immunology (2016) 5, e94; doi:10.1038/cti.2016.44.
Sarmiento-Ospina, A. et al., Zika virus associated deaths in Colombia. Lancet Infect. Dis. (2016) 16: 523-24.
Sarwar, Uzma N et al. "Filovirus emergence and vaccine development: a perspective for health care practitioners in travel medicine." Travel medicine and infectious disease vol. 9,3 (2011): 126-34.
Sato, Y. et al., Immunostimulatory DNA Sequences Necessary for Effective Intradermal Gene Immunization. Science 273:352, 1996.
Schellens, I.M. et al. (2015) Measles virus epitope presentation by HLA: Novel insights into epitope selection, dominance, and microvariation. Front. Immunol. 6, 546.
Schenkel JM, et al. Sensing and alarm function of resident memory CD8+ T cells. Nat Immunol. 2013; 14(5): 509-13.
Schmid, D. et al. Antigen-Loading Compartments for Major Histocompatibility Complex Class II Molecules Continuously Receive Input from Autophagosomes. (2007) Immunity 26(1): 79-92.
Schmitt, J and Keil, GM. Characterization of the bovine herpesvirus 1 UL8 gene and gene products. Journal of General Virology (1998), 79, 133-141.
Schuhmann, K.M, et al. The measles virus V protein binds to p65 (RelA) to suppress NF-kappaB activity. J. Virol. (2011) 85, 3162-3171.
Schweitzer, Beth K., et al. Overview of the Flaviviridae With an Emphasis on the Japanese Encephalitis Group Viruses, Laboratory Medicine, vol. 40, Issue 8, Aug. 2009, pp. 493-499, https://doi.org/10.1309/LM5YWS85NJPCWESW.
Scott, T. P., & Nel, L. H. (2016). Subversion of the Immune Response by Rabies Virus. Viruses, 8(8), 231. doi:10.3390/v8080231.
Seabright, G. E. et al., (2019) "Protein and Glycan Mimicry in HIV Vaccine Design," J. Mol. Biol. 431 (12): 2223-2247.
Seet, BT et al, Poxviruses and Immune Evasion. Annu. Rev. Immunol (2003) 21: 377-423.
Sevvana, M. et al. Refinement and Analysis of the Mature Zika Virus Cryo-EM Structure at 3.1 Å Resolution. Structure. 2018;26:1169-1177.

(56) References Cited

OTHER PUBLICATIONS

Sharma, V., et al., Comparative Genomics of Herpesviridae Family to Look for Potential Signatures of Human Infecting Strains. Int J Genomics. 2016; 2016: 9543274, 10 pages.
Shedlock, DJ and Shen, H (2003) Requirement for CD4 T cell help in generating functional CD8 T cell memory. Science 300: 337-339.
Shi T, et al. (2017) Global, regional, and national disease burden estimates of acute lower respiratory infections due to respiratory syncytial virus in young children in 2015: a systematic review and modelling study. Lancet 390:946-958.
Shivakoti, R. et al. Induction of dendritic cell production of type I and type III interferons by wild-type and vaccine strains of measles virus: Role of defective interfering RNAs. J. Virol. (2013) 87, 7816-7827.
Shivakoti, R., et al. Limited in vivo production of type I or type III interferon after infection of macaques with vaccine ar wild-type strains of measles virus. J. Interferon Cytokine Res. (2015) 35, 292-301.
Shokett, P., et al., A modified tetracycline-regulated system provides autoregulatory, inducible gene expression in cultured cells and transgenic mice. 1995 Proc. Natl. Acad. Sci. USA 92.6522-6526.
Shrivastava, S. et al., "Whole genome sequencing, variant analysis, phylogenetics, and deep sequencing of Zika virus strains." Nature: Scientific Reports (2018) 8:15843.
Siegrist, CA. Vaccine Immunology, Chapter 2, Potkin's Vaccines, Seventh Ed. 2018, pp. 16-34.e7.
Silhavy, TJ, et al. The Bacterial Cell Envelope. Cold Spring Harb Perspect Biol 2010;2:a000414.
Silva, AJ et al., Exploiting cholera vaccines as a versatile antigen delivery platform. 2008 Biotechnol Lett 30:571-579.
Singh H, and Raghava GP. ProPred1: prediction of promiscuous MHC Class-I binding sites. Bioinformatics. 2003; 19: 1009-1014.
Singh, K.R., et al., (2019) "Foot-and-Mouth Disease Virus: Immunobiology, Advances in Vaccines and Vaccination Strategies Addressing Vaccine Failures—An Indian Perspective." Vaccines 7(3), 90).
Sirohi, D. and Kuhn, R.J. Zika Virus Structure, Maturation, and Receptors, The Journal of Infectious Diseases, vol. 216, Issue suppl_10, Dec. 15, 2017, pp. S935-S944.
Drake, AC,, et al. (2011)Human CD34 CD133 Hematopoietic Stem Cells Cultured with Growth Factors Including Angptl5 Efficiently Engraft Adult NOD-SCID Il2rc 2/2 (NSG) Mice. PLoS ONE 6(4): e18382. https://doi.org/10.1371/journal.pone.0018382.
Gorantla, S., et al. Human Immunodeficiency Virus Type 1 Pathobiology Studied in Humanized BALB/c-Rag2-/-yc-/- Mice. J Virol. Mar. 2007 p. 2700-2712.
Xie, X., et al. Influenza Vaccine with Consensus Internal Antigens as Immunogens Provides Cross-Group Protection Against Influenza A Viruses. Frontiers in Microbiology, vol. 10, Article 1630, Jul. 2019.
International Search Report and Written Opinion for International Application No. PCT/US2020/066059, dated May 5, 2021, issued by the International Searching Authority dated May 5, 2021.
Pantoja, P. et al., Zika virus pathogenesis in rhesus macaques is unaffected by pre-existing immunity to dengue virus. Nat. Communic. (2017) 8: 15674.
Pappalardo, M, et al. Conserved differences in proteinsequence determine the human pathogenicity of Ebolaviruses. Scientific Reports, 6:23743 (2016).
Parche, S., et al. Corynebacterium diphtheriae: a PTS View to the Genome. J. Mol. Microbiol. Biotechnol. (2001) 3 (3): 415-122.
Parkman PD. Togaviruses: Rubella Virus. In: Baron S, editor. Medical Microbiology. 4th edition. Galveston (TX): University of Texas Medical Branch at Galveston; (1996) Chapter 55. Available from: https://www.ncbi.nlm.nih.gov/books/NBK8200/.
Pasquier, C. et al., Kinetics of anti-ZIKV antibodies after Zika infection using two commercial enzyme-linked immunoassays. Diagn. Microbiol. Infect. Dis. (2018) 90: 26-30.
Paul, W. E., "Chapter 1: The immune system: an introduction," Fundamental Immunology, 4th Edition, Ed. Paul, W. E., Lippicott-Raven Publishers, Philadelphia, (1999), at p. 102.

Peeling, RW et al., Evaluation of diagnostic tests: dengue. Nat. Rev. Microbiol. (2010) 8: S30-S38.
Penkert RR, et al. (2016) Vitamin A deficient mice exhibit increased viral antigens and enhanced cytokine/chemokine production in nasal tissues following respiratory virus infection despite the presence of FoxP3+ T cells. Int Immunol 28:139-152.
Perelygina L, et al. (2019) Infectious vaccine-derived rubella viruses emerge, persist, and evolve in cutaneous granulomas of children with primary immunodeficiencies. PLOS Pathogens 15(10): e1008080.
Perera-Lecoin, M. et al. Flavivirus entry receptors: an update . . . Viruses. (2013) 6: 69-88. doi: 10.3390/v6010069.
Pereyra F. et al. (2008) "Genetic and immunologic heterogeneity among persons who control HIV infection in the absence of therapy," J. Infect. Dis. 197: 563-571.
Permar, S.R. et al. (2003) Role of CD8(+) lymphocytes in control and clearance of measles virus infection of rhesus monkeys. J. Virol. 77, 4396-4400.
Petersen, LR., et al. Zika Virus, N Engl J Med 2016;374:1552-63.
Pham, Oh, and McSorley, SJ. (2015) "Protective host immune responses to *Salmonella* infection." Future Microbiology, vol. 10,1: 101-10.
Phillips, R.S., et al. Metabolic effects of acute measles in chronically malnourished Nigerian children. J. Nutr. Biochem. (2004) 15, 281-288.
Pica N, and Palese P. Toward a universal influenza virus vaccine: prospects and challenges. Annu Rev Med. 2013; 64: 189-202.
Pierson T.C., et al., Structural Insights into the Mechanisms of Antibody-Mediated Neutralization of Flavivirus Infection: Implications for Vaccine Development. Cell Host Microbe. (2008) 4: 229-238.
Pitcher, CJ et al. (1999) HIV-1-specific CD4+ T cells are detectable in most individuals with active HIV-1 infection, but decline with prolonged viral suppression. Nat Med 5: 518-525.
Pizzolla A, et al. Influenza—specific lung-resident memory T cells are proliferative and polyfunctional and maintain diverse TCR profiles. J Clin Invest. 2018; 128(2): 721-733.
Plata F., et al. (1975) Primary and secondary in vitro generation of cytolytic T lymphocytes in the murine sarcoma virus system. Eur J Immunol 5: 227-233.
Plemper, R. et al., Structural and Mechanistic Studies of Measles Virus Illuminate Paramyxovirus Entry. PLoS Pathog. Jun. 2011; 7(6): e1002058.
Plitnick L.M. Chapter 9-Global Regulatory Guidelines for Vaccines. In: Plitnick L.M., Herzyk D.J., editors. Nonclinical Development of Novel Biologies, Biosimilars, Vaccines and Specialty Biologies. Academic Press; San Diego, CA, USA: (2013). pp. 225-241.
Plotkin, SA. (2015) Increasing Complexity of Vaccine Development, The Journal of Infectious Diseases, vol. 212, Issue Suppl_1, pp. S12-S16.
Polack, F.P. et al. (1999) Production of atypical measles in rhesus macaques: Evidence for disease mediated by immune complex formation and eosinophils in the presence of fusion-inhibiting antibody Nat. Med. 5, 629-634.
Poland J.D., et al. Persistence of neutralizing antibody 30-35 years after immunization with 17D yellow fever vaccine. Bull. World Health Organ 1981;59:895-900.
Polen, KD et al., Update: Interim Guidance for Preconception Counseling and Prevention of Sexual Transmission of Zika Virus for Men with Possible Zika Virus Exposure—United States, Aug. 2018 . MMWR Morb. Mortal. Wkly Rep. (2018) vol. 67, No. 31, 868-871.
Porter, KR et al., Immunogenicity and protective efficacy of a vaxfectin-adjuvanted tetravalent dengue DNA vaccine. Vaccine (2012) 30:36-341 doi: 10.1016/j.vaccine.2011.10.085.
Prasad, M., et al., Rubella virus capsid protein structure and its role in virus assembly and infection. Proc Natl Acad Sci USA (2013) Dec. 10;110(50):20105-10.
Premkumar, L. et al., Development of Envelope Protein Antigens To Serologically Differentiate Zika Virus Infection from Dengue Virus Infection. J. Clin. Microbiol. (2017) 56(3); DOI: 10.1128/JCM.01504-17.
Primavada, L. et al., Human antibody responses after dengue virus infection are highly cross-reactive to Zika virus. Proc. Nat. Acad. Sci. USA (2016) 113: 7852-57.

(56) References Cited

OTHER PUBLICATIONS

Quinn, KM., et al. Comparative Analysis of the Magnitude, Quality, Phenotype, and Protective Capacity of Simian Immunodeficiency Virus Gag-Specific CD8+ T Cells following Human-, Simian-, and Chimpanzee-Derived Recombinant Adenoviral Vector Immunization. 2013 J Immunol.;190:2720-2735.
Rabe, IB et al., Interim Guidance for Interpretation of Zika Virus Antibody Test Results . Morb. Mortal. Wkly Rep (2016) vol. 65:No. 21, 543-46.
Radecke F., Billeter M.A. (1995) Appendix: Measles Virus Antigenome and Protein Consensus Sequences. In: V. ter Meulen et al (eds) Measles Virus. Current Topics in Microbiology and Immunology, vol. 191. 181-192 Springer, Berlin, Heidelberg; (HA).
Ramachandran, A., et al. STAT2 is a primary target for measles virus V protein-mediated alpha/beta interferon signaling inhibition. J. Virol. (2008) 82, 8330-8338.
Ramduth, D et al. (2005) Differential immunogenicity of HIV-1 clade C proteins in eliciting CD8+ and CD4+ cell responses. J Infect Dis 192: 1588-1596.
Rammensee, H-G., et al. SYFPEITHI: database for MHC ligands and peptide motifs. Immunogenetics (1999) 50: 213-219.
Randall, R.E. and Goodbourn, S. Interferons and viruses: An interplay between induction, signalling, antiviral responses and virus countermeasures. J. Gen. Virol. 2008, 89, 1-47.
Rastogi, N., et al., "The mycobacteria: an introduction to nomenclature and pathogenesis." (2001) Rev. Sci. Tech. Off. Int. Epiz., 20(1), 21-54.
Ratajczak, W., et al. Immunological memory cells. Centr Eur Immunol 2018; 43 (2): 194-203.
Rathore, APS et al., Maternal immunity and antibodies to dengue virus promote infection and Zika virus-induced microcephaly in fetuses Sci. Adv. (2019) 5: eaav3208.
Rey, F.A. et al, The bright and the dark side of human antibody responses to flaviviruses: lessons for vaccine design. EMBO Rep. (2018) 19: 206-224.
Reyes, Y. et al., Prolonged Shedding of Zika Virus RNA in Vaginal Secretions, Nicaragua . Emerg. Infect. Dis (2019) 25: 808-810.
Reyes-Sandoval, A., et al. Prime-Boost Immunization with Adenoviral and Modified Vaccinia Virus Ankara Vectors Enhances the Durability and Polyfunctionality of Protective Malaria CD8 T-Cell Responses. (2010) Infection and Immunity 78: 145-153.
Reynolds, MR et al, Vital Signs: Update on Zika Virus-Associated Birth Defects and Evaluation of All U.S. Infants with Congenital Zika Virus Exposure—U.S. Zika Pregnancy Registry, 2016 . Morb. Mortal. Wkly Rep. (2017) vol. 66, No. 13, 366-73.
Rice, ME et al, Rice, ME et al, Vital Signs: Zika-Associated Birth Defects and Neurodevelopmental Abnormalities Possibly Associated with Congenital Zika Virus Infection—U.S. Territories and Freely Associated States, 2018 MMWR Morb. Mortal. Wkly Rep. (2018) vol. 67, No. 31, 858-867.
Rice, SA and Knipe, DM. Genetic Evidence for Two Distinct Transactivation Functions of the Herpes Simplex Virus ot Protein ICP27. 1990 J. Virol. 64(4): 1704-15.
Richards, A. L. (2004). Rickettsial vaccines: The old and the new. Expert Review of Vaccines, 3(5), 541-55.
Robbiani, DF et al., Recurrent Potent Human Neutralizing Antibodies to Zika Virus in Brazil and Mexico. Cell. (2017) 169 (597-609).
Roehrig J.T., et al., Antibody Prophylaxis and Therapy for Flavivirus Encephalitis Infections. Ann. N. Y. Acad. Sci. (2001) 951: 286-297.
Romanos, M. A., et al., Foreign Gene Expression in Yeast: a Review. (1992)Yeast 8(6):423-488.
Beames, BB., et al., Polyhedrin initiator codon altered to AUU yields unexpected fusion protein from a baculovirus vector . . . (1991) Biotechniques 11:378-383.
Carter et al., AAV vectors for gene therapy. (2004) In "Gene and Cell Therapy: Therapeutic Mechanisms and Strategies", Second Edition (Ed. N. Templeton-Smith), pp. 53-101.

Carter, BJ.Adeno-associated virus helper functions. (1989) In "Handbook of Parvoviruses" vol. I (P. Tjissen, ed.) CRC Press, Boca Raton, pp. 255-282.
Dalrymple et al., 1981, in Replication of Negative Strand Viruses, Bishop and Compans (eds.), Elsevier, N.Y., p. 167.
Itoh Y, et al. (1986) A synthetic peptide vaccine involving the product of the pre-S(2) region of hepatitis B virus DNA: protective efficacy in chimpanzees Proc Natl Acad Sci USA 83: 9174-9178.
Ma, MM, et al., In Antimicrobial Therapy and Vaccines. Yu, VL, Merigan, Jr, TC and Barriere, SL Eds, Williams & Wilkins, Baltimore, (1999), pp. 1220-1248.
Mayr et al., The Smallpox Vaccination Strain MVA: Marker, Genetic Structure, Experience Gained with the Parental Vaccination and Behavior in Organisms with a Debilitated Defence Mechanism. [1978] Zbl. Bakt. Hyg. I, Abt. Org. B 167, 375-390.
Mayr, A. & Danner, K. Vaccination against pox diseases under immunosuppressive conditions. [1978] Dev. Biol. Stand. 41:225-34.
Stickl, H. et al., [1974] Dtsch. med. Wschr. 99, 2386-2392 (English translation of summary).
Welles, L. and Yarchoan, R., In Antimicrobial Therapy and Vaccines. Yu, VL, Merigan, Jr, TC and Barriere, SL Eds, Williams & Wilkins, Baltimore, (1999), pp. 1264-1287.
Goeddel, D. V., Systems for heterologous gene expression. (1990) Methods in Enzymology 185:3-7.
Goins, WF et al., A Novel Latency-Active Promoter Is Contained within the Herpes Simplex Virus Type 1 UL Flanking Repeats. 1994. J of Virology. 68(4): 2239-2252.
Goodman and Gilman, The Pharmacological Basis of Therapeutics, 10th Edition, McGraw-Hill (New York) Chapter 1 Pharmacokinetics (2001).
Gordon A. et al., Prior dengue virus infection and risk of Zika: A pediatric cohort in Nicaragua. PLoS med. (2019) 16 (1): e1002726.
Gorman, CM., et al. The Rous sarcoma virus long terminal repeat is a strong promoter when introduced into a variety of eukaryotic cells by DNA-mediated transfection. Proc. Natl. Acad. Sci. USA (1982) 79:6777-6781.
Gossen, M. and Bujard, H., Tight control of gene expression in mammalian cells by tetracycline-responsive promoters. 1992 Proc. Natl. Acad. Sci. USA 89: 5547-5551.
Gostin LO, et al. Virus sharing, genetic sequencing, and global health security. Science. 2014; 345(6202): 1295-1296.
Grant E, et al. Nucleoprotein of influenza A virus is a major target of immunodominant CD8+ T-cell responses. Immunol Cell Biol. 2013; 91(2): 184-94.
Graves, M., et al. Development of antibody to measles virus polypeptides during complicated and uncomplicated measles virus infections. J. Virol. (1984) 49, 409-412.
Greenspan, NS. Design challenges for HIV-1 vaccines based on humoral immunity. Frontiers in Immunol. vol. 5:335 (2014).
Greenwood B. The contribution of vaccination to global health: past, present and future. (2014). Philosophical transactions of the Royal Society of London. Series B, Biological sciences, 369(1645), 20130433. doi: 10.1098/rstb.2013.0433.
Griffin, D. The Immune Response in Measles: Virus Control, Clearance and Protective Immunity. Viruses (2016) 8: 282; doi:10.3390/v8100282.
Griffin, D.E, et al. (1990) Immune activation during measles: Interferon-gamma and neopterin in plasma and cerebrospinal fluid in complicated and uncomplicated disease. J. Infect. Dis. 161, 449-453.
Griffin, D.E. (1989) Immune activation in measles. N. Engl. J. Med. 320, 1667-1672.
Griffin, D.E. et al (1986) Peripheral blood mononuclear cells during natural measles virus infection: Cell surface phenotypes and evidence for activation. Clin. Immunol. Immunopathol. 40, 305-312.
Griffin, D.E. et al (1992) Immune activation during measles: Beta 2-microglobulin in plasma and cerebrospinal fluid in complicated and uncomplicated disease. J. Infect. Dis. 166, 1170-1173.
Griffin, D.E.; and Ward, B.J. Differential CD4 T cell activation in measles. J. Infect. Dis. (1993), 168, 275-281.
Gubser, C, et al. Poxvirus genomes: a phylogenetic analysis. J. Gen. Virol. (2004) 85, 105-117.

(56) References Cited

OTHER PUBLICATIONS

Guilland, A., Zika virus is a global public health emergency, declares WHO. BMJ 2016;352:i657.

Guzman, E., et al, Induction of a Cross-Reactive CD8+ T Cell Response following Foot-and-Mouth Disease Virus Vaccination. (2010) J. Virology, vol. 84, No. 23, p. 12375-12384.

Hagensee, ME, et al., Three-Dimensional Structure of Vaccinia Virus-Produced Human Papillomavirus Type 1 Capsids. J. Virol. (1994) 68:4503-4505.

Hahn, YS et al., Nucleotide sequence of dengue 2 RNA and comparison of the encoded proteins with those of other flaviviruses (1988), Virology 162:167-180.

Hakimi J. et al., An adjuvant-modulated vaccine response in human whole blood. 2017 Hum Vaccin Immunother. Sep. 2; 13(9):2130-2134.

Halstead ES, et al. In vivo stimulation of CD137 broadens primary antiviral CD8+ T cell responses. Nat Immunol. 2002; 3(6): 536-41.

Halstead S. B. (2015). Pathogenesis of Dengue: Dawn of a New Era. F1000Research, 4, F1000 Faculty Rev-1353. https://doi.org/10.12688/f1000research.7024.1.

Halstead S.B. Achieving safe, effective, and durable Zika virus vaccines: Lessons from dengue. Lancet Infect. Dis. (2017)17: e378-e382.

Halstead, SB. Biologic Evidence Required for Zika Disease Enhancement by Dengue Antibodies. Emerg. Infect. Dis. (2017) vol. 23: No. 4:569-573.

Hannoun C. The evolving history of influenza viruses and influenza vaccines. Expert Rev Vaccines. 2013; 12(9): 1085-1094.

Hansen, SG., et al. Effector-memory T cell responses are associated with protection of rhesus monkeys from mucosal SIV challenge. 2009 Nat. Med. 15:293-299.

Hardick, J., et al., (2016) Sequencing Ebola and Marburg Viruses Genomes Using Microarrays. J. Med. Virol. 88:1303-1308.

Hardy, WF and Sandri-Goldin, RM. Herpes Simplex Virus Inhibits Host Cell Splicing, and Regulatory Protein ICP27 Is Required for This Effect. 1994 J. Virol. 68(12): 7790-99.

Hasan, SS et al., A human antibody against Zika virus crosslinks the E protein to prevent infection. Nature Commun. (2017) 8:14722.

Haworth, KB et al., Going Back to Class I: MHC and Immunotherapies for Childhood Cancer. Pediatr Blood Cancer. Apr. 2015; 62(4): 571-576.

Haynes, J., et al., Constitutive, long-term production of human interferons by hamster cells containing multiple copies of a cloned interferon gene. (1983) Nuc. Acid. Res. 1983 11:687-706.

Heinz, FX, and Stiasny, K., Flaviviruses and their antigenic structure. J. Clin. Virol. (2012) 55: 289-95.

Herod, MR, et al. Genetic economy in picornaviruses: Foot-andmouth disease virus replication exploits alternative precursor cleavage pathways. PLoS Pathog 13 (10): e1006666. (2017).

Hillis, WD., et al. Serologic Classification of Chimpanzee Adenoviruses by Hemagglutination and Hemagglutination Inhibition. (1969) J Immunol 103: 1089-1095.

Hodgson, ALM, et al. Cloning, Nucleotide Sequence, and Expression in *Escherichia coli* of the Phospholipase D Gene from Corynebacterium pseudotuberculosis. J Bacteriology, 1990, vol. 72:3, 1256-1261.

Holloway R, et al. Updated preparedness and response framework for influenza pandemics. MMWR Recomm Rep. 2014; 63(RR-06): 1-18.

Hood, EE., et al. The Hypervirulence of Agrobacterium tumefaciens A281 Is Encoded in a Region of pTiBo542 Gutside of T-DNA. J. Bacteriol. 168:1291-1301 (1986).

Horimoto T, Kawaoka Y. Influenza: lessons from past pandemics, warnings from current incidents. Nat Rev Microbiol. 2005; 3(8): 591-601.

Houser K, Subbarao K. Influenza Vaccines: Challenges and Solutions. Cell Host Microbe. 2015; 17(3): 295-300.

Hsu, D. et al, (2017) "Progress in HIV vaccine development" Human Vaccines & Immunotherapies 13(5): 1018-1030.

Huang X, et al, et al. Mucosa! priming with PEI/DNA complex and systemic boosting with recombinant TianTan vaccinia stimulate vigorous mucosal and systemic immune responses. Vaccine. 2007; 25(14): 2620-9.

Huang X, et al. Mucosal priming with replicative Tiantan vaccinia and systemic boosting with DNA vaccine raised strong mucosa! and systemic HIV-specific immune responses. Vaccine. 2007; 25(52): 8874-84.

IARC Working Group on the Evaluation of Carcinogenic Risks to Humans. "Malaria and Some Polyomaviruses (SV40, BK, JC, and Merkel Cell Viruses" IARC Monogr Eval Carcinog Risks Hum vol. 104 pp. 41-120 (2014).

Ichinohe, T., et al. Mitochondrial protein mitofusin 2 is required for NLRP3 inflammasome activation after RNA virus infection. Proc. Natl. Acad. Sci. USA (2013) 110, 17963-17968.

Isticato, R. et al., Surface Display of Recombinant Proteins on Bacillus subtilis Spores. 2001, J Bacteriol 183:6294-6301.

Jaiswal V, et al. EpiCombFlu: exploring known influenza epitopes and their combination to design a universal influenza vaccine. Bioinformatics. 2013; 29(15):1904-7.

James, S. and Miller, L. Malaria Vaccine Development Status Report. 1999.

UniProt Accession No. Q0QDX9, UniProtKB—Q0DX9 (Q0QDX9_SARS0, Sep. 5, 2006 [online]. [Retrieved on Jun. 13, 2022]. Retrieved from the Internet: <URL: <https://www.uniprot.org/uniprot/Q0QDX9>>; Entire document.

Huang et al., A Novel Replication-Competent Vaccinia Vector MVTT Is Superior to MVA for Inducing High Levels of Neutralizing Antibody via Mucosal Vaccination. PlosOne. Jan. 13, 2009, vol. 4, No. 1, pp. 1-9; abstrac.

Zhu et al., Oral delivery of SARS-COv-2 DNA vaccines using attenuated Salmonella typhimurium as a carrier in rat. BioRxiv. Jul. 23, 2020 [online]. [Retrieved on Jun. 13, 2020]. Retreived from the Internet: <URL: <https://www.biorxiv.org/content/10.1101/2020.07.23.317174v1.abstract>>: abstract.

UniProt Accession No. QOQDX6, UniProtKB—Q0QDX6 (Q0Qdx6_SARS), Sep. 5, 2006 [online]. [Retrieved on Jun 13, 2022]. Retrieved from the Internet: <URL: <https://www.uniprot.org/uniprot/Q0QDX6>>; Entire document.

UniProt Accession No. Q315K6, UniProtKB—Q315K6 (Q315K6_SARS), Nov. 8, 2005 [online]. [Retrieved on Jun. 13, 2021]. Retrieved from the Internet: <URL: https://www.uniprot.org/uniprot/Q315K6>; Entire document.

PCT International Search Report and Written Opinion, Application No. PCT/US2022/014572, dated Jul. 1, 2022.

* cited by examiner

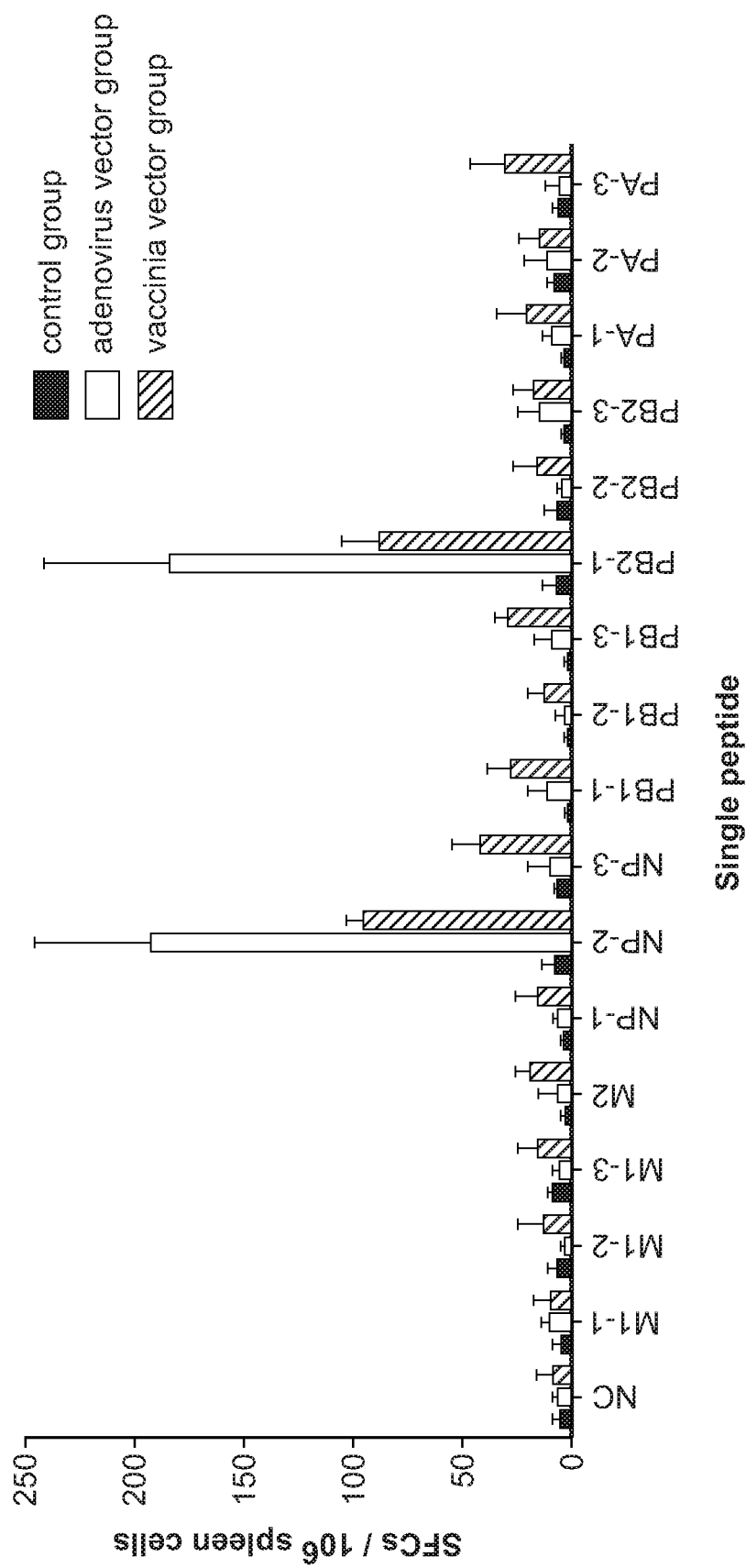

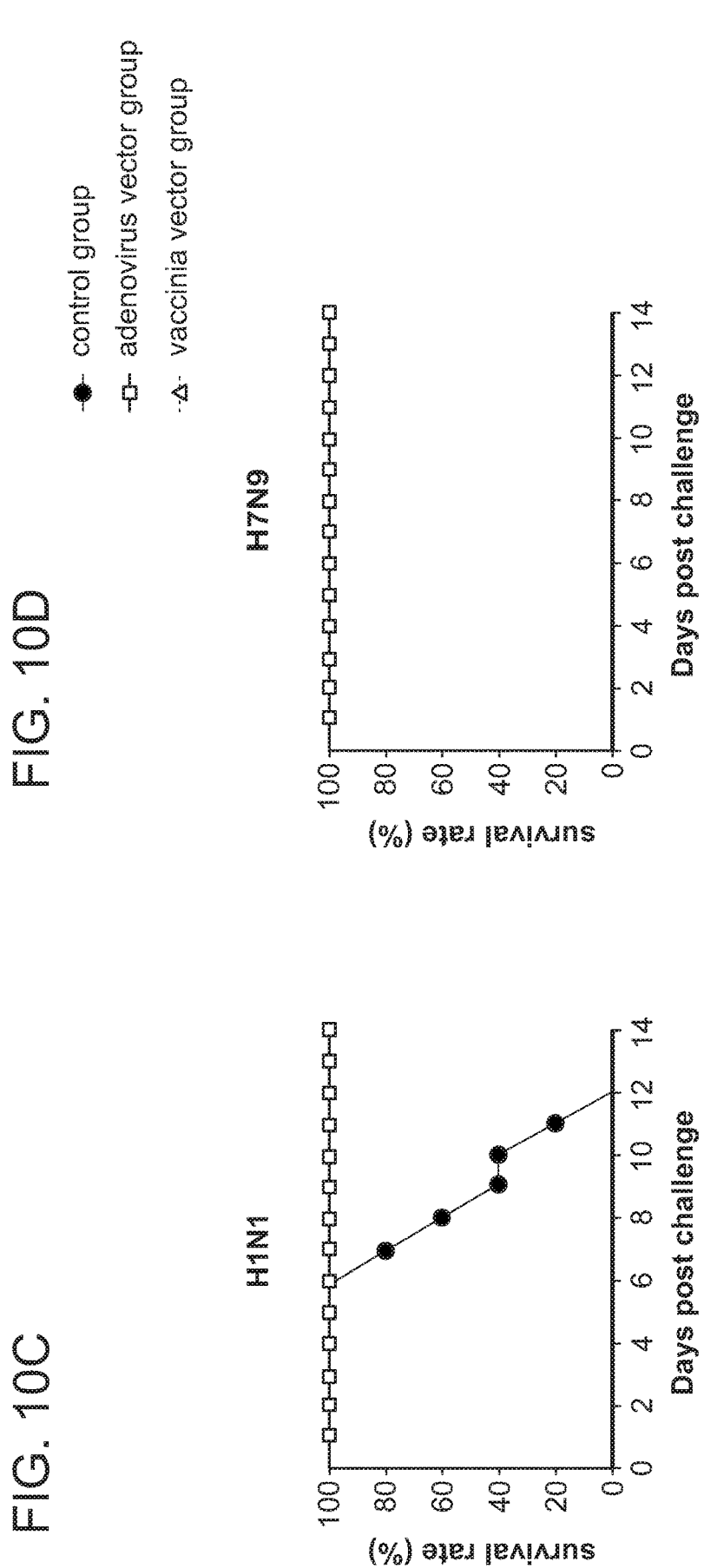

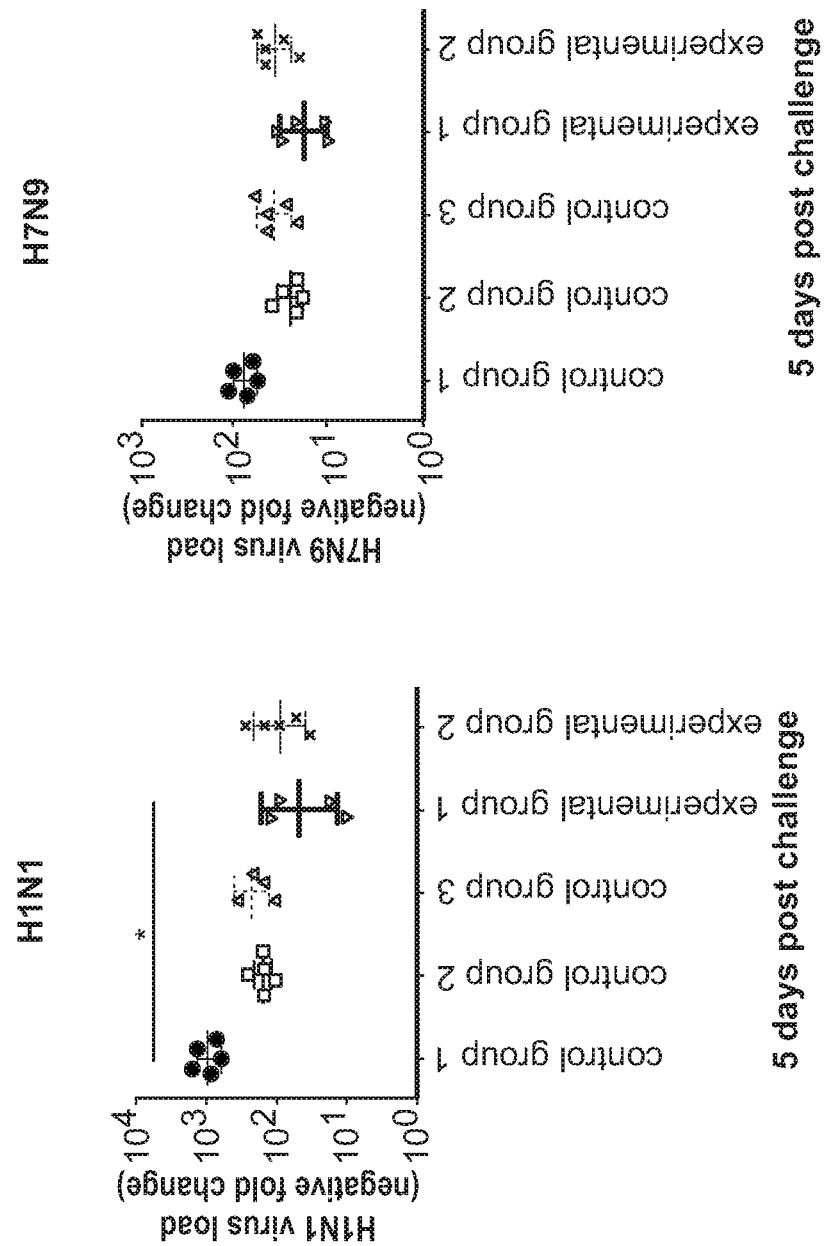

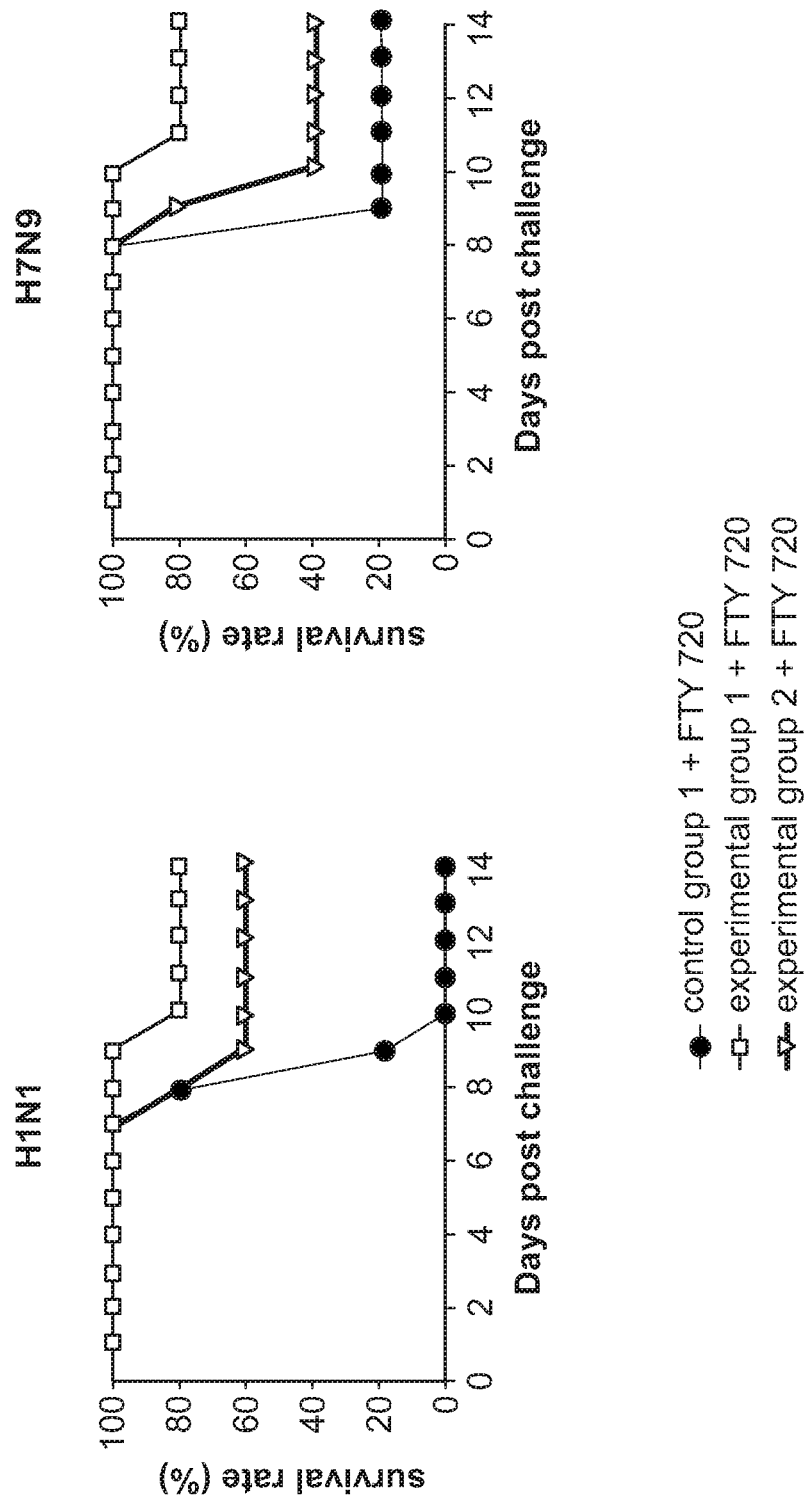

UNIVERSAL VACCINES AGAINST IMMUNOGENS OF PATHOGENIC ORGANISMS THAT PROVIDE ORGANISM-SPECIFIC AND CROSS-GROUP PROTECTION

RELATED APPLICATIONS

This application is a continuation-in-part of International Patent Application No. PCT/CN2018/105020, filed with the Chinese National Intellectual Property Administration Receiving Office on Sep. 11, 2018.

FIELD OF THE INVENTION

The described invention relates generally to universal vaccines against immunogens of pathogenic organisms that provide organism-specific and cross-group protection.

SEQUENCE LISTING

The instant application contains a Sequence Listing which has been submitted electronically in ASCII format and is hereby incorporated by reference in its entirety. Said ASCII copy, created on Feb. 3, 2020, is named 130189-00401_SL.txt and is 25,380 bytes in size.

BACKGROUND

Infectious existing and emerging pathogens continue to cause significant morbidity and mortality worldwide. In 1990 alone, an estimated 16 million people died from infections. Despite the numerous new therapeutic products that have become available since then, in 2010 the number of deaths caused by infections had fallen only to 15 million. The majority of these deaths were caused by just a few pathogens: among the 1400 or so recognized human pathogens and parasites, the majority of deaths were caused by respiratory illness, diarrhea, HIV/AIDS, TB, malaria, meningitis, pertussis, measles, hepatitis B, and sexually transmitted diseases (STDs) (Dye C. After 2015: infectious diseases in a new era of health and development. (2014) Philosophical Transactions of the Royal Society of London. Series B, Biological Sciences, 369(1645), 20130426). Certain diseases are considered particularly important, e.g., because they had a 100% lethality rate when they emerged, for example, HIV/AIDS; or because the infectious viral agent causes disease beyond the principal person of infection, for example the emergence of birth defects from infection with zika virus.

Therapeutic products used to fight pathogens include preventative immunizations, such as vaccines, and post-infection therapeutics, such as anti-bacterials and anti-virals. Vaccines are therapeutics composed of one or a few specific antigens of the causative microbial agent or the microbial or viral body with its whole set of antigens that induce an immune response in the receiving individual and/or a cellular response in the pathogen itself (Cassone, A., & Rappuoli, R. (2010). Universal vaccines: shifting to one for many. Bio. 1(1), e00042-10). Vaccines protect by inducing effector mechanisms capable of rapidly controlling replicating pathogens or inactivating their toxic components.

Generally speaking, immune responses are initiated by an encounter between an individual and a foreign substance, e.g., an infectious microorganism. The infected individual rapidly responds with both a humoral immune response with the production of antibody molecules specific for the antigenic determinants/epitopes of the immunogen, and a cell mediated immune response with the expansion and differentiation of antigen-specific regulatory and effector T-lymphocytes, including cells that produce cytokines and killer T cells, capable of lysing infected cells. Primary immunization with a given microorganism evokes antibodies and T cells that are specific for the antigenic determinants/epitopes found on that microorganism; these usually fail to recognize or recognize only poorly antigenic determinants expressed by unrelated microbes (Paul, W. E., "Chapter 1: The immune system: an introduction," Fundamental Immunology, 4th Edition, Ed. Paul, W. E., Lippicott-Raven Publishers, Philadelphia, (1999), at p. 102).

As a consequence of this initial response, the immunized individual develops a state of immunologic memory. If the same or a closely related microorganism is encountered again, a secondary response ensues. This secondary response generally consists of an antibody response that is more rapid, greater in magnitude and composed of antibodies that bind to the antigen with greater affinity and that are more effective in clearing the microbe from the body, and a similarly enhanced and often more effective T-cell response. However, immune responses against infectious agents do not always lead to elimination of the pathogen (Paul, W. E., "Chapter 1: The immune system: an introduction," Fundamental Immunology, 4th Edition, Ed. Paul, W. E., Lippicott-Raven Publishers, Philadelphia, (1999), at p. 102).

The human immune system is a complex arrangement of cells and molecules that maintain immune homeostasis to preserve the integrity of the organism by elimination of all elements judged to be dangerous. Responses in the immune system may generally be divided into two arms, referred to as "innate immunity" and "adaptive immunity." The two arms of immunity do not operate independently of each other, but rather work together to elicit effective immune responses.

The innate arm of the immune system is a nonspecific fast response to pathogens that is predominantly responsible for an initial inflammatory response via a number of soluble factors, including the complement system and the chemokine/cytokine system; and a number of specialized cell types, including mast cells, macrophages, dendritic cells (DCs), and natural killer cells (NKs).

The adaptive immune arm involves a specific, delayed and longer-lasting response by various types of cells that create long-term immunological memory against a specific antigen. It can be further subdivided into cellular and humoral branches, the former largely mediated by T cells and the latter by B cells. This arm further encompasses cell lineage members of the adaptive arm that have effector functions in the inate arm, thereby bridging the gap between the innate and adaptive immune response.

Generally speaking, vaccination educates both innate and adaptive immune systems in order to boost adaptive T and B cell memory responses and provide rapid protection against subsequent infection with related viruses. (Li, G. et al, "Memory T Cells in Flavivirus Vaccination", Vaccines (2018) 6: 73).

Vaccines and Vaccination

While vaccination provides a cost effective measure to prevent disease and to control outbreaks of infection at herd level, vaccines currently on the market have significant shortcomings and even failures.

The first vaccine developed was one in which the wild-type disease or the wild-type version of a related disease was "killed" and delivered. While such vaccines were known to work, they carried a significant risk of severe disease or even death in the recipient.

The second type of vaccine developed was attenuated vaccines. This vaccine was based on material obtained from infected rabbit brain attenuated by drying, an uncertain process; vaccines prepared in this way frequently caused serious side effects. Attenuated vaccines are mostly now based on inactivated virus grown in tissue culture. Rabies was the first virus attenuated in a laboratory to create a human vaccine. Acquisition of the ability to grow viruses in tissue culture for an extended period led to the development of attenuated vaccines against measles, poliomyelitis, rubella, influenza, rotavirus, tuberculosis and typhoid. Because the vaccine components are alive, they can spread to non-vaccinated subjects, extending the impact of vaccination to the community at large (See generally, Greenwood B. The contribution of vaccination to global health: past, present and future. (2014). Philosophical transactions of the Royal Society of London. Series B, Biological sciences, 369(1645), 20130433).

Live attenuated virus vaccines are a favored vaccination strategy, in part due to their previous success with the yellow fever virus vaccine, YF-17D, in the 1930s. (Ghaffar, K. A. et al, "Fast Tracks and Roadblocks for Zika Vaccines," Vaccines (2018) 6, 77). A single dose of YF-17D vaccine, for example, is able to induce high titers of neutralizing antibody (nAb) which confer protection on at least 95% of recipients (Id., citing Barrett A. D., Teuwen D. E. Curr. Opin. Immunol. (2009) 21: 308-313; Bonaldo, M C et al., Hum. Vaccin. Immunother. (2014) 10: 1256-1265). This strategy has been employed with many other diseases, including polio, measles and mumps (Id., citing Plitnick L. M. Chapter 9—Global Regulatory Guidelines for Vaccines. In: Plitnick L. M., Herzyk D. J., editors. Nonclinical Development of Novel Biologics, Biosimilars, Vaccines and Specialty Biologics. Academic Press; San Diego, Calif., USA: (2013). pp. 225-241). Moreover, the production of attenuated vaccines is cost effective and fairly simple in comparison to other vaccine strategies.

While a live attenuated vaccine has the advantage of being able to elicit immune responses with a single dose, drawbacks include its limited use in immunocompromised or pregnant patients due to the risk of adverse effects. Indeed, because these vaccines contain live virus, mutations may occur in the attenuated vaccine strain with a reversion to virulence, as seen with oral polio vaccine, which causes paralysis in about one in two million recipients. Further, they may cause significant illness in subjects with impaired immunity, as has been seen with the anti-tuberculosis vaccine Bacille Calmette Guérin (BCG) when given to immunodeficient patients, including those with human immunodeficiency virus (HIV) infection.

Next, researchers developed killed vaccines where the pathogens were killed and then used. These vaccines were usually poorly immunogenic and often caused significant side effects, so that whole-cell vaccines have largely given way to subunit vaccines, among other types of vaccines. (See generally, Greenwood B. The contribution of vaccination to global health: past, present and future. (2014). Philosophical transactions of the Royal Society of London. Series B, Biological sciences, 369(1645), 20130433). Subunit vaccines comprise a fragment of a pathogen, i.e. a protein, or peptides (Ghaffar, K. A. et al, "Fast Tracks and Roadblocks for Zika Vaccines," Vaccines (2018) 6, 77). While subunit vaccines are generally a safer choice, because they tend to be less immunogenic, an adjuvant and/or multiple doses are required.

The use of mRNA vaccines is a relatively new trend that has gained popularity (Ghaffar, K. A. et al, "Fast Tracks and Roadblocks for Zika Vaccines," (2018) Vaccines 6, 77; citing Plitnick L. M. Chapter 9Global Regulatory Guidelines for Vaccines. In: Plitnick L. M., Herzyk D. J., editors. Nonclinical Development of Novel Biologics, Biosimilars, Vaccines and Specialty Biologics. Academic Press; San Diego, Calif., USA: (2013). pp. 225-241). As the minimal genetic construct, mRNA contains only the elements required for expression of the specific encoded protein region. In addition, mRNA is incapable of interacting with the genome, but instead acts only as a transient carrier of information. Other advantages for its use as a vaccine platform include its safety profile (Id. citing Lundstrom, K., Futre Sci. OA (2018) 4: FS0300). However, one of the disadvantages of utilizing mRNA as an approach to vaccine design is its rapid degradation by ribonucleases.

DNA vaccines are one of the earliest vaccine platforms to be proposed for human clinical trials following the ZIKV outbreak (Id). The use of genetically engineered DNA plasmids encoding various antigens to induce both humoral and cellular responses also has been explored against various infectious diseases caused by parasites (Id.citing Cherif, M S et al, Vaccine (2011) 29: 9038-9050; Cheng, P C et al., PLoS Neg. Trop Dis. (2016) 10: e00044594); bacteria (Id., citing Li, X. et al., Clin. Vaccine Immunol. 2012; 19:723-730; Albrecht, M T, et al., Med. Microbiol. (2012) 65: 505-509); and other viruses (Id., citing Donnelly, J J et al., Nature Med. (1995) 1: 583-597; Porter, K R et al., Vaccine (2012) 30: 36-341).

Adenovirus vectors whereby the vector expresses an unknown antigenic protein have been well studied for gene and cancer therapy and vaccines (Id). Apart from its extensive safety profile, the advantages of utilizing an adenovirus vector are that it is relatively stable, easy to attain high titers and able to infect multiple cell lines which attributes to its potency. Even though recombinant adenoviral vectors are widely used today thanks to its high transduction efficiency and transgene expression, there is likelihood for pre-existing immunity against the vector, because most of the population has been exposed to adenovirus (Id). This has been proven detrimental in a human immunodeficiency virus (HIV-1) phase IIb vaccine trial in which the vector-based vaccines provided favorable conditions for HIV-1 replication (Id., citing Smaill, F. et al., Sci. Transl. Med. (2013) 5: 205ra134).

Developing the next generation of vaccines will be increasingly challenging, as many of the organisms to which they are targeted have complex structures and life cycles (e.g., the malaria parasite), or are very effective at outwitting the human immune response through antigenic diversity (e.g., HIV and influenza viruses). Development of new vaccines against other important infectious disease targets such as dengue or novel corona viruses should theoretically be easier using established technologies, but the modest efficacy of a recently tested dengue vaccine emphasizes that challenges remain even in the development of more conventional vaccines (Greenwood B. The contribution of vaccination to global health: past, present and future. (2014).Philosophical transactions of the Royal Society of London. Series B, Biological Sciences, 369(1645), 20130433).

As a result, other vaccination strategies are being developed in an attempt to overcome the above addressed failures.

Exemplary infectious agents that afflict current human populations around the globe include the following.

Viruses

I) Flaviviridae Viruses

A) Overview of the Flaviviridae Family

The Flaviviridae family contains small enveloped, positive-stranded viruses with RNA genomes of 9-13 k bases. They are typically host-specific and pathogenic. (Fermin, Gustavo, and Paula Tennant. Viruses: Molecular Biology, Host Interactions and Applications to Biotechnology, edited by Jerome E. Foster, Elsevier Science & Technology, 2018. Available from the ProQuest Ebook Central website).

The family's 11 kb genome encodes, translates, and is processed into three structural proteins-capsid (C), envelope (E), membrane (M)—and seven non-structural (NS) proteins; NS1, NS2A, NS2B, NS3, NS4A, NS4B, and NS5. (Li, G. et al, "Memory T Cells in Flavivirus Vaccination", Vaccines (2018) 6: 73) The E protein, a major virion surface protein, is involved in receptor binding and membrane fusion, and induces neutralizing antibodies in the infected hosts. Id.

Flaviviruses include Zika virus (ZIKV), dengue virus (DENV), yellow fever virus (YFV), West Nile virus (WNV), Japanese encephalitis virus (JEV), hepatitis C virus (HCV) and tick-borne encephalitis virus (TBEV). Other related viruses include, without limitation, the classical swine fever virus in the Pestivirus genus, and the viruses in the Pegivirus genus.

i) Hepatitis C Virus (HCV)

Hepatitis C Virus (HCV) is classified in genus *Hepacivirus* in the family Flaviviridae. HCV has worldwide distribution and accounts for 21% of acute viral hepatitis. (Ma, M M, et al, In Antimicrobial Therapy and Vaccines. Yu, V L, Merigan, Jr, T C and Barriere, S L Eds, Williams & Wilkins, Baltimore, (2005), pgs. 1234-1239). The virus genome exhibits significant genetic heterogeneity and at least second genotypes exist, each of which can be further subdivided into more than 80 different subtypes. The most prevalent include subtypes 1a, 1b, 2a, 2b, 2c, 3a, and 4a.

HCV has a positive sense RNA genome that codes for a single 3010-amino acid polyprotein. The polyprotein requires processing by both host and viral proteases. The capsid (C) protein is conserved, whereas the envelope proteins (E1 and E2) are more variable and result in heterogenecity of HCV (Id.).

ii) Dengue Virus (DENV)

Dengue is an acute febrile disease caused by the dengue virus (DENV), which is transmitted to humans via *Aedes* mosquitoes. It is estimated that 50-100 million people are infected annually in tropic and subtropical regions, where more than 2.5 billion people are at risk. There are four serotypes of the virus: DEN-1, DEN-2, DEN-3, or DEN-4. Within each serotype, there is significant genetic diversity (Fermin, Gustavo, and Paula Tennant. Viruses: Molecular Biology, Host Interactions and Applications to Biotechnology, edited by Jerome E. Foster, Elsevier Science & Technology, 2018. Available from the ProQuest Ebook Central website).

iii) Yellow Fever Virus (YFV)

Yellow Fever Virus (YFV) is a Flavivirus transmitted by *Aedes*, Haemagogus, and Sabethes mosquito bites. The geographic range of this disease is Africa, South America, Central America and the Caribbean. Although it's genetic diversity is under-researched, seven genotypes have been proposed: West African genotypes I and II, East African genotype, East/Central African genotype, Angolan genotype, and South American genotypes I and II (Fermin, Gustavo, and Paula Tennant. Viruses: Molecular Biology, Host Interactions and Applications to Biotechnology, edited by Jerome E. Foster, Elsevier Science & Technology, 2018. Available from the ProQuest Ebook Central website).

iv) Japanese Encephalitis Virus (JEV) and West Nile Virus (WNV)

Japanese encephalitis virus (JEV) is in the Flavivirus genus. Other related viruses include the Murray Valley encephalitis virus (MVEV), St. Louis encephalitis virus (SLEV), West Nile virus (WNV), Yaounde virus, Cacipacore virus, Koutango virus, and Usutu virus. Together they are known as the Japanese encephalitis (JE) group. JE is transmitted by mosquito vectors, typically from the Culex species, and geographically occurs in South Asia, Southeast Asia, East Asia, and the Pacific. Thirty-five thousand to 50,000 cases of JE group viruses are identified each year with up to 15,000 deaths yearly.

WNV was first isolated in the West Nile district of Uganda and spread to southern Europe, Asia, Australia, the Middle East, and North America (Beth K. Schweitzer, Nora M. Chapman, Peter C. Iwen, Overview of the Flaviviridae With an Emphasis on the Japanese Encephalitis Group Viruses, Laboratory Medicine, Volume 40, Issue 8, August 2009, Pages 493-499).

v) Zika Virus (ZIKV)

Zika virus (ZIKV) is an arbovirus, which can be transmitted to humans by Aedes mosquitoes as well as by sexual interactions. As a member of the Flaviviridae family of positive strand RNA, ZIKV is closely related to some important human pathogens, such as dengue virus (DENV), yellow fever virus (YFV), west nile virus (WNV), Japanese encephalitis virus (JEV), and tick-borne encephalitis virus (TBEV) (Yang, C. et al., Development of neutralizing antibodies against Zika virus based on its envelope protein structure," Virologica Sinica (2019) 34: 168-174, citing Wang Q, et al. J. Viorol. (2017) 91: e01049-17). Among these flaviviruses, DENV is the closest one to ZIKV. Some studies have shown that neutralizing antibodies isolated from convalescent patients infected by DENV or ZIKV showed cross-neutralizing ability (Yang, citing Barba-Spaeth, G. et al. Nature (2016) 536: 48-53; Wang, Q. et al., Sci. Trans. Med. (2016) 8: 3695a179). The emergence of ZIKV in Latin America occurred primarily in DENV-endemic regions. Id.

B) Structure-Based Functional Analysis of Flaviviruses

The overall ZIKV structure is similar to those of other flaviviruses (Yang, C. et al., Development of neutralizing antibodies against Zika virus based on its envelope protein structure," Virologica Sinica (2019) 34: 168-174, citing Kostyuchenko, V A, et al., Nature. (2016) 533: 425-428; Sirohi, D. et al., Science. 2016; 352:467-470). The virions are typically spherical in shape with a genome that is covered by a capsid, which in turn is surrounded by a lipid bilayer that has envelope glycoproteins on its surface. Virions typically have a single, small basic capsid (C) protein, two to three envelope proteins (E), and a premembrane/membrane (prM/M) protein (Fermin, Gustavo, and Paula Tennant. Viruses: Molecular Biology, Host Interactions and Applications to Biotechnology, edited by Jerome E. Foster, Elsevier Science & Technology, 2018. Available from the ProQuest Ebook Central website). Flaviviruses comprise a 10.8 kb RNA genome; the RNA is translated into a single polyprotein (3423 amino acids in length) encoding 3 structural proteins—capsid (C); membrane (M), which is generated from its precursor premembrane (prM); and envelope (E)—as well as 7 nonstructural proteins (NS1, NS2A, NS2B, NS3, NS4A, NS4B, and NS5) (FIG. 1). The structural proteins, as the name suggests, form the virus particle. The nonstructural proteins assist in replication and packaging of the genome as well as in subverting the host pathways in favor of the virus. (Devika Sirohi, Richard J Kuhn, Zika Virus Structure, Maturation, and Receptors, The Journal of Infectious Diseases, Volume 216, Issue suppl_10, 15 Dec. 2017, Pages S935-S944).

ZIKV is composed of 180 copies of E protein and forms a compact particle with icosahedral symmetry. Each copy of E protein contains three distinct domains in its ectodomain, named DI, DII and DIII. Domain I (DI) contains the N-terminus of E protein, domain II (DII) is an extended finger-like structure that includes the dimerization domain and also a pH-sensitive fusion loop that mediates viral fusion. The domain III (DIII) is an immunoglobulin-like domain that mediates attachment to target cells (Id., citing Robbiani, D F et al., Cell. (2017) 169(597-609):e511). These three domains are connected to the viral membrane by two helices called stem anchor. The DI, DII and DIII are arranged so as to place DI in the center with DII and DIII flanking the two sides to form a monomer. The E monomer interacts with an adjacent monomer in an antiparallel way to form a dimer. Three E-dimers lay parallel to each other and form a structural unit known as a "raft" (Id., citing Kostyuchenko, V A, et al., Nature. (2016) 533:425-428; Sirohi, D. et al., Science. (2016) 352: 467-470; Sevvana, M. et al. Structure. 2018; 26:1169-1177).

To enter the host cell, the E protein needs to interact with its receptor on the target cell (Id. Citing Hasan, S S et al., Nature Commun. (2017) 8:14722). To date, although no specific receptor appears to be involved in the interaction of ZIKV with the host cell, studies from DENV and other flaviviruses show that E protein can bind many cellular factors, such as C-type lectin receptors, laminin receptor, T cell immunoglobulin and mucin domain (TIM) and TYRO3, AXL and MER (TAM) receptors, and integrin αvβ3 (Id. Citing Perera-Lecoin, M. et al. Viruses. (2013) 6: 69-88; and Kuhn, R J, Science. (2016) 352: 467-470). After binding to a receptor(s), the virions undergo low pH-dependent endocytosis and conformational rearrangement of E proteins, which happens in the endosomes. The viral membrane then fuses with the host membrane, and the RNA genome of the virus is released into the cytoplasm (Id. citing Stiasny, K. and Heinz, F X, J Gen Virol. (2006) 87:2755-2766; Harrison, S C, Nat Commun. 2017; 8:14722; Gerold, G. et al. Mol Cell Proteomics. (2017) 16:S75-S91). However, the detailed process of the entry of the flavivirus into the host cell is not fully understood.

C) Immune Response to Infection with Flaviviruses

Human flavivirus infection elicits a complex antibody (Ab) response, which also has a central role in immunity and pathogenesis (Collins, M. H., Serologic Tools and Strategies to support intervention trials to combat Zika virus infection and disease," Trop Med. Infect. Dis. (2019) 4,68; citing Wahala, WMPB and De Silva, A M, Viruses (2011) 3: 2374-95; Mansfield, K L, et al., J. Gen. Virol. (2011) 92: 2821-29; Allwinn, R. et al., Med. Microbiol. Immunol. (2002) 190: 199-202; Rey, F. A. et al, EMBO Rep. (2018) 19: 206-224).

ZIKV infection is frequently inapparent, with approximately 20% of those infected developing a self-limiting illness most often characterized by rash, fever, conjunctivitis, and/or arthralgia/myalgia (Collins, M. H., Serologic Tools and Strategies to support intervention trials to combat Zika virus infection and disease," Trop Med. Infect. Dis. (2019) 4,68; citing Duffy, M R et al., N. Engl. J. Med. (2009) 360: 2536-2543, Sampathkumar, P., Mayo Clin. Proc. (2016) 91: 514-521, Brasil, P. et al., N. Engl. J. Med. (2016)_375: 2321-2334; Petersen, L R et al, N. Engl. J. Med. (2016) 374: 1552-1563). The incubation period is presumed to be less than one week, and symptom duration is less than one week in most cases (Id., citing Petersen, L R et al., N. Engl. J. Med. (2016) 374: 1552-1563). Viremia is typically cleared quickly after symptom onset, but the infectious virus has been isolated from semen for several weeks after infection (Id., citing Polen, K D et al., MMWR Morb. Mortal. Wkly Rep. (2018) 67, 868; Arsuaga, M. et al., Lancet Infect. Dis. 92016) 16: 1107; Garcia-Bujalance, S. et al., J. Clin. Virol. (2017) 96: 110-115), and ZIKV RNA can be detected in blood or vaginal secretions for prolonged times following infection, particularly in pregnancy (Id., citing Driggers, R W et al., N. Engl. J. Med. (2016) 374: 2142-2151, Nguyen, S M et al., PLoS Pathog. (2017) 13: e1006378; Reyes, Y. et al., Emerg. Infect. Dis. (2019) 25: 808-810), and for at least 6 months in semen, (Id., citing Polen, K D et al., MMWR. Morb. Mortal. Wkly. Rep. (2018) 67: 868; Nicastri, E. et al., Euro Surveill. Bull. Eur. Mal. Transm. Eur. Commun. Dis. Bull. (2016) 21, El Sahly, H M et al., Open Forum Infect. Dis. (2019) 6, ofy352, Lustig, Y. et al., Eurosurveillance (2016) 21: 30269; Rossini, G. et al., J. Infect. (2017) 75: 242-245; Murray, K O, et al, Emerg. Infect. Dis. (2017) 23, Fibriansah, G. et al., Science (2015) 349: 88-91; Fibriansah, G. et al., EMBO Mol. Med. (2014) 6: 358-71; Kiermayr, S. et al., J. Virol. (2009) 83: 8482-91). Microcephaly and other birth defects and neurodevelopmental problems are the most concerning manifestations of ZIKV infection when it occurs during pregnancy and the virus is vertically transmitted to the fetus (Id., citing Miranda-Filho, DdB; et al., Am. J. Public Health (2016) 106: 5998-600; Reynolds, M R et al, Morb. Mortal. Wkly Rep. (2017) 66: 366-73; Guilland, A., BMJ (2016) 352: i657; De Melo, A S O, et al., JAMA Neurol. (2016) 73: 1407; Rice, M E et al, MMWR Morb. Mortal. Wkly. Rep. (2018) 67: 858). Additionally, an increased incidence of Guillain-Barré syndrome consistently has been noted after Zika outbreaks in multiple countries (Id., citing Dos Santos, T. et al., N. Engl. J. Med. (2016) 375: 1598-1601; Oehler, E. et al., Euro Surveill. (2014) 19: 20720; Cao-Lormeau, V-M, et al, Lancet (2016) 387: 1531-39). Other complications and severe outcomes have been very rarely reported, ranging from low platelets to death, usually in patients with additional comorbid factors that may have contributed to the pathogenicity of their illness (Id., citing Sarmiento-Ospina, A. et al., Lancet Infect. Dis. (2016) 16: 523-24; Krow-Lucal, E R et al., Emerg. Infect. Dis. (2017) 23: 1260-67; Colombo, T E et al., J. Clin. Virol. (2017) 96: 20-25; Arauza-Ortega, L. et al., Emerg. Infect. Dis. (2016) 22: 925-27).

During infection by the virus, the humoral immune response plays an important role in its clearance. Antibodies execute their protective effects by virus neutralization or Fc-mediated effector functions (e.g., ADCC and CDC) (Yang, C. et al., Development of neutralizing antibodies against Zika virus based on its envelope protein structure," Virologica Sinica (2019) 34: 168-174, citing Lu, L L et al. Nat Rev Immunol. (2018) 18:46-61).

Key features of the human antibody response to ZIKV have been defined or extrapolated from extensive experience with closely related viruses. ZIKV-reactive IgM is detectable within 4-7 days of symptom onset. ZIKV IgM testing is useful for diagnosing symptomatic infections and recent asymptomatic infections (Collins, M. H., Serologic Tools and Strategies to support intervention trials to combat Zika virus infection and disease," Trop Med. Infect. Dis. (2019) 4,68; citing Wahala, WMPB and De Silva, A M, Viruses (2011) 3: 2374-95; Mansfield, K L, et al., J. Gen. Virol. (2011) 92: 2821-29; Allwinn, R. et al., Med. Microbiol. Immunol. (2002) 190: 199-202; Rey, F. A. et al, EMBO Rep. (2018) 19: 206-224, citing Munoz-Jordan, J L, J. Infect. Dis. (2017) 216: S951-S956). IgM testing remains useful for diagnosing congenital zika syndrome (CZS) but is no longer recommended in evaluating asymptomatic pregnant women in non-endemic areas with potential exposure to ZIKV (Id., citing Adebanjo, T., Morb. Mortal. Wkly Rep. (2017) 66: 1089-99). A positive test is supportive but not definitive for ZIKV infection, and confirmatory neutralization may be required (Id., citing Munoz-Jordan, J L, J. Infect. Dis. (2017) 216: S951-S956, Adebanjo, T., Morb. Mortal. Wkly Rep. (2017) 66: 1089-99). The duration of the anti-ZIKV IgM response is unclear, but it can persist beyond 12 weeks in some cases (Id., citing Munoz-Jordan, J L, J. Infect. Dis. (2017) 216: S951-S956; Rabe, I B et al., Morb. Mortal. Wkly Rep (2016) 65: 543-46; Pasquier, C. et al., Diagn. Microbiol. Infect. Dis. (2018) 90: 26-30), which limits the reliability of this assay to narrowly define a recent ZIKV infection.

IgG against ZIKV becomes detectable by 10-14 days and presumably lasts for years, as with other flaviviruses (Id., citing Peeling, R W et al., Nat. Rev. Microbiol. (2010) 8: S30-S38, Munoz-Jordan, J L, J. Infect. Dis. (2017) 216: S951-S956, Wahala, WMPB and De Silva, A M, Viruses (2011) 3: 2374-95, Pasquier, C. et al., Diagn. Microbiol. Infect. Dis. (2018) 90: 26-30). The kinetics of the IgG response have a direct bearing on performance of serologic testing. Assays that detect IgG may not reach peak sensitivity until after the first 10 to 15 days post onset (DPO) (Id., citing Balmaseda, A. et al., Proc. Natl Acad. Sci. USA (2017) 114: 8384-89). Additionally, the magnitude of cross-reactive antibodies (Abs) and their relative abundance may be highest early after infection (Id., citing Lanciotti, R. S, et al., Emerg. Infect. Dis. (2008) 14: 1232-1239, Wahala, WMPB; de Silva, A M, Viruses (2011) 3: 2374-95, Premkumar, L. et al., J. Clin. Microbiol. (2017) 56(3)), compromising assay specificity until the late convalescent period. The targets of these Abs include structural proteins as well as nonstructural proteins (ns), most notably NS1 (Id., citing Stettler, K. et al., Science (2016) 353 (6301): 823; Slon Campos, J L, et al, Nat. Immunol. (2018) 19: 1189-98). One hundred eighty envelope protein (E) monomers decorate the surface of the ZIKV virion, organizing into head-to-tail homodimers, which further arrange into higher order structures that give a herringbone appearance and icosahedral symmetry (Id., citing Kostyuchenko, V A, et al., Nature (2016) 533: 425-28; Sirohi, D. et al., Science (2016) 352: 467-70). ZIKV and DENV E are approximately 50% conserved (Id., citing Primavada, L. et al., Proc. Nat. Acad. Sci. USA (2016) 113: 7852-57; Stettler, K. et al., Science (2016) 353 (6301): 823, Kostyuchenko, V A, et al., Nature (2016) 533: 425-28), but the homology is not homogenous; the fusion loop of E domain II is highly conserved, whereas E domain III is the most divergent and may be more likely to be targeted by ZIKV-specific Ab responses (Id., citing Stettler, K. et al., Science (2016) 353 (6301): 823; Robbiani, D F et al., Cell (2017): 597-609; Premkumar, L. et al., J. Clin. Microbiol. (2017); Slon Campos, J L, et al, Nat. Immunol. (2018) 19: 1189-98; Yu, L. et al., JCI Insight (2017) 2: 93042). In addition to epitope, flavivirus-elicited Abs also vary in terms of their specificity, kinetics, and function. Abs may be very specific for one virus or cross-react to two or more viruses (Id., citing Allwinn, R. Et al., Med. Microbiol. Immunol. (2002) 190: 199-202; Heinz, F X, Stiasny, K., J. Clin. Virol. (2012) 55: 289-95; Calisher, Ch, et al., J. Gen. Virol. (1989) 70: 37-43).

A subset of binding Abs also exhibit neutralization properties, and it has been shown that neutralizing Abs (nAbs) tend to bind serotype-specific epitopes that often require the three-dimensional structural integrity of the virus particle (Id., citing Wahala, WMPB and de Silva, A M, Viruses (2011) 3: 2374-95; Fibransah, G. et al., Science (2015) 349: 8-91; Fibriansah, G. et al., EMBO Mol. Med. (2014) 6: 358-71; Kiermayr, S. et al., J. Virol. (2009) 83: 8482-91; Teoh, E P et al., Sci. Trans. Med. (2012) 4: 139ra83, Kaufman, B. et al., Proc. Natl Acad. Sci. USA (2010) 107: 18950-18955; De Alwis, R. et al., Proc. Natl. Acad. Sci. USA (2012) 109: 7439-44). In DENV infection, poorly neutralizing, cross-reactive Abs, frequently binding to epitopes in precursor membrane protein (PrM) or the fusion loop (Id., citing Wahala, WMPB and de Silva, A M, Viruses (2011) 3: 2374-2395, Slon Campos, J L, et al, Nat. Immunol. (2018) 19: 1189-98), are implicated in the pathophysiology of severe diseases via Ab-dependent enhancement (ADE) (Id., citing Halstead, SB, FY1000Research (2015) 4: F1000; Katzelnick, L C, et al, Science (2017) 358: 929-932). There remains concern that non-neutralizing cross-reactive Ab elicited by prior DENV infection may exacerbate ZIKV infection or potentiate vertical transmission (Id., citing Bardina, S V et al., Science (2017) 356: 175-180; Brown, J A et al., Immunity (2019) 50 (3): 751-762.e5; Rathore, A P S et al., Sci. Adv. (2019)5: eaav3208; Zimmerman, M G et al., Cell Host Microbe (2018) 24: 731-742 e6; Dejnirattisai, W. et al., Nature Immunol. (2016) 17: 1102-1108; Castanha, P M et al., J. Infect. Dis. (2016) 215: jiw638); however, there is nonhuman primate data to the contrary (Id., citing Pantoja, P. et al., Nat. Communic. (2017) 8: 15674; McCracken, M K et al, PLoS Pathog. (2017) 13: e1006487), and no epidemiologic data in humans support the hypothesis (Id., citing Halstead, SB Emerg. Infect. Dis. (2017) 23: 569; Gordon A. et al., PLoS med. (2019) 16: e1002726; Martin-Acebes, M A, et al., Front. Cell Infect. Microbiol. (2018) 8: 44). The possibility of ZIKV infection enhancing subsequent DENV infection is even less well studied.

In JE group viruses, it has been reported that the initial illness caused by the bite of an infected mosquito is localized to the subcutaneous regions of the skin where viral replication begins. The virus then subsequently extends from the lymphatic system to the circulatory system and to the internal organs, which may involve the brain and spinal cord. At the site of initial infection, a subset of CD3+ T cells, the γδ T cells, have been shown to be stimulated and to produce the cytokine interferon-γ (IFN-γ), which controls infection during the initial stages of disease. As the disease progresses, these T cells stimulate αβ T cells (a subset of CD4/CD8 positive cells) to produce more IFN-γ. Once virus-specific double-stranded RNA is detected within the infected human cell, the cell is stimulated to produce more IFN-α/β in an attempt to suppress viral replication within infected cells, thus preventing the further spread of the virus to normal tissues.

Immunological cells such as macrophages, B cells, and dendritic cells were shown to be important antigen presenting cells involved in the human immune response to JE group viruses, specifically, dendritic cells, as they are located in the skin which is the site of initial exposure. Upon vector release of the virus into the skin, these cells are stimulated to migrate to the lymph nodes and subsequently to activate T cells. Research has shown that CD4+ T cells in the peripheral blood and CD8+ T cells in the cerebrospinal fluid helps to clear the virus from the tissues.

The complement system also plays a role by preventing the spread of virus via cytolytic activities of membrane-attack complex on the infected cells, and by priming the B cells to respond to the infection. The humoral immune system further produces antibodies as an attempt for protection from early infection and for long-term immunity to reinfection. IgM antibody is produced during acute disease.

However, some individuals develop a severe disease course and some develop only mild disease. While antibody production is a key component of the immune response, the antibodies are not sufficient by themselves to eliminate the JE group infection without the help of the cellular immune system. (Beth K. Schweitzer, Nora M. Chapman, Peter C. Iwen, Overview of the Flaviviridae With an Emphasis on the Japanese Encephalitis Group Viruses, Laboratory Medicine, Volume 40, Issue 8, August 2009, Pages 493-499).

B cells and specific antibodies are believed critical in the control of disseminated flavivirus infection (Id., citing Diamond M. S., et al., J. Virol. (2003) 77:2578-2586; Roehrig J. T., et al., Ann. N. Y. Acad. Sci. (2001) 951: 286-297). Although neutralizing antibody titer is the FDA-accepted primary endpoint of vaccine immunogenicity for flavivirus vaccines, increasing evidence suggests that while neutralizing antibody correlates only mildly with protection, T cell mediated immunity may play a protective role in the absence of neutralizing antibody (Li, G. et al, "Memory T Cells in Flavivirus Vaccination", Vaccines (2018) 6: 73, citing Akondy R. S., Fitch M., Edupuganti S., Yang S., Kissick H. T., Li K. W., Youngblood B. A., Abdelsamed H. A., McGuire D. J., Cohen K. W., et al. Origin and differentiation of human memory CD8 T cells after vaccination. Nature. (2017) 552: 362-367; Halstead S. B. Achieving safe, effective, and durable Zika virus vaccines: Lessons from dengue. Lancet Infect. Dis. (2017)17: e378-e382; Sabchareon A., et al. Lancet. (2012) 380: 1559-1567).

Neutralizing antibodies have been primarily associated with epitopes on the E protein, while most T cell epitopes have been mapped to flavivirus NS proteins (Id., citing Pierson T. C., et al., Cell Host Microbe. (2008) 4: 229-238; Weiskopf D., Sette A. Front. Immunol. (2014) 5:93). NS proteins are thought to co-translationally assemble on the membranes of the endoplasmic reticulum (ER) forming the replication competent complex, which consists of morphologically distinct, membrane-bound compartments that also differ with respect to both function and NS proteins composition (Bollati, M. et al., Antiviral Res. (2010) 87(2): 125-148, citing Mackenzie, J., Traffic (2005) 6: 967-977). Both CD4+ and CD8+ effector and memory T cells have been shown to directly contribute to host protective immune responses, including viral clearance, and providing help for B cells and antibody maturation Li, G. et al, "Memory T Cells in Flavivirus Vaccination", Vaccines (2018) 6: 73, citing Bassi M. R., et al., J. Immunol. (2015) 194: 1141-1153; Michlmayr D., et al., J. Immunol. (2016) 196: 4622-4631; Elong Ngono A., et al., Cell Host Microbe. (2017) 21: 35-46; Larena M., et al., J. Virol. (2011); 85: 5446-5455; Mathews J. H., et al., J. Virol. (1992) 66: 6555-6562; Sitati E. M., Diamond M. S., J. Virol. (2006) 80: 12060-12069; Yauch L. E., et al., J. Immunol. (2009) 182: 4865-4873).

YFV-17D vaccine elicits a strong humoral immune response against yellow fever, with neutralizing antibodies detectable in serum for over 30 years after vaccination; however, memory CD8+ T cells specific for the YFV-tetrameric antigen can also expand into effector pools at least 10 years after vaccination (Id., citing Poland J. D., Calisher C. H., Monath T. P., Downs W. G., Murphy K. Persistence of neutralizing antibody 30-35 years after immunization with 17D yellow fever vaccine. Bull. World Health Organ. 1981; 59:895-900; Wieten R. W., Jonker E. F. F., Leeuwen E. M. M. V., Remmerswaal E. B. M., Berge I. J. M. T., Visser A. W. D., Genderen P. J. J. V., Goorhuis A., Visser L. G., Grobusch M. P., et al. A single 17D yellow fever vaccination provides lifelong immunity; characterization of yellow-fever-specific neutralizing antibody and T-cell responses after vaccination. PLoS ONE. 2016; 11:e0149871). Recent evidence from animal models suggests that both humoral and cell-mediated immunity work in tandem to produce the lasting immunity seen following YFV 17D vaccination. (Id., citing Watson A. M., Lam L. K., Klimstra W. B., Ryman K. D. The 17D-204 vaccine strain-induced protection against virulent yellow fever virus is mediated by humoral immunity and CD4+ but not CD8+ T cells. PLoS Pathog. 2016; 12:e1005786).

D) Flavivirus Vaccine Development and Challenges or Failures

Over the last seven decades, various strategies have been utilized to develop flavivirus vaccines. Currently, effective vaccines have been licensed for human use to combat YFV, JEV, DENV and TBEV infection. Neutralizing antibodies generated by these vaccines provide host protection; however, the role of T cell-mediated immunity is not yet fully understood. (Id).

Different strategies pursued for Zika virus vaccine development include recombinant live attenuated vaccines, purified inactivated vaccines (PIVs), DNA vaccines, and viral vectored vaccines. Most of the vaccines against ZIKV today focus on the induction of long-lived neutralizing antibody (nAb) responses.

While the development of a single ZIKV vaccine is ongoing, a multiple antigenic approach following the measles, mumps, rubella and varicella (MMRV) vaccine model was explored by Chattopadhyay and colleagues (Id., citing Chattopadhyay A. et al., Vaccine. (2018) 36: 3894-3900). In their combinatorial vaccine against Chikungunya virus (CHIKV) and ZIKV, they utilized recombinant vesicular stomatitis virus (VSV) expressing CHIKV envelope polyprotein and ZIKV E protein. Sera from BALB/C mice immunized with a single dose of 107 PFU of recombinant VSV vaccine were able to neutralize 70% of ZIKV (Brazilian strain PE243), whereas those given two doses of the vaccine were able to neutralize 80% of ZIKV. In addition, sera from the single immunization of BALB/C mice were also able to neutralize 100% of the VSVΔG-eGFP/CHIKV pseudotype. In order to determine the protective efficacy of the vaccine, 7 week old A129 mice were immunized intramuscularly prior to challenge with either MR 766 Zika virus or CHIKV. None of the vaccinated mice showed signs of viremia following infection with either virus. Although the authors proved that the mice were free from infection, the mice were past 15 weeks old when challenged. In this particular murine model, it is known that ZIKV infection would not have resulted in death of mice, but the mice would only show transient signs of illness following infection. Nonetheless, the negative control mice given CHIKV succumbed to infection by day 3 whereas all immunized mice survived. Overall, the study managed to prove that the vaccine was able to prevent viremia in immunocompromised mice, though the authors did not mention any physical signs of infection. However, there was no proof that the vaccine would be useful in inducing production of maternal nAb in pregnant dams which is able to confer protection to newborns.

Utilizing predictive algorithm software, Zhang et al. (Id., citing Zhang W., Li X., Lin Y., Tian D. Identification of three H-2Kd restricted CTL epitopes of NS4A and NS4B protein from Yellow fever 17D vaccine. J. Virol. Methods. 2013; 187:304-313) identified three nonameric epitopes from YFV NS4A and NS4B proteins capable of eliciting a robust IFN-γ+ CD3+CD8+ T cell response in YFV 17D-immunized mice. These epitopes were also found to be highly conserved across several strains of YFV, in addition to the YFV 17D vaccine strain. The effector functions of human CD8+ T cells during the course of YFV 17D infection have been characterized. (Id., citing Blom K., Braun M., Ivarsson M. A., Gonzalez V. D., Falconer K., Moll M., Ljunggren H. G., Michaelsson J., Sandberg J. K. Temporal dynamics of the primary human T cell response to yellow fever virus 17D as it matures from an effector-to a memory-type response. J. Immunol. 2013; 190:2150-2158). Blom et al. found a decline in polyfunctional effector CD8+ T cells between days 10, 14, and 90 post-infection, corresponding to peak CD4+, effector CD8+, and effector memory CD8+ T cell response respectively. Additionally, monofunctional CD8+ T cells expressed CD107a during peak CD4+ T cell response, but later switched to produce TNF-α as their effector molecule. While YFV-specific memory CD8+ T cells express similar surface molecules as naïve CD8+ T cells, such as CD45RA, CCR7, CD127, and CD28 (all of which are distinct from effector CD8+ T cells), memory T cells have significantly faster proliferative kinetics than the naïve cells (Id., citing Akondy R. S., Fitch M., Edupuganti S., Yang S., Kissick H. T., Li K. W., Youngblood B. A., Abdelsamed H. A., McGuire D. J., Cohen K. W., et al. Origin and differentiation of human memory CD8 T cells after vaccination. Nature. 2017; 552:362-367).

Both immune status prior to vaccination and virus replication contribute to memory T cell development upon vaccination. Further characterization of CD8+ memory T cells also revealed that the memory pool divided extensively during the first two weeks after infection, and is maintained by quiescent cells that divide less than once every year. Unlike effector CD8+ T cells, memory CD8+ T cells do not produce the cytotoxic effector proteins granzyme B or perforin. However, patterns of CpG methylation at the granzyme B and perforin promoters did not significantly differ between the two cell populations, suggesting an epigenetic role in maintaining lasting memory CD8+ T cells (Id., citing Akondy R. S., Fitch M., Edupuganti S., Yang S., Kissick H. T., Li K. W., Youngblood B. A., Abdelsamed H. A., McGuire D. J., Cohen K. W., et al. Origin and differentiation of human memory CD8 T cells after vaccination. Nature. 2017; 552:362-367).

Studies have also suggested that T cells play an important role in generating a functional immune response in the presence of the viral capsid for hepatitis B and C viruses (Garg, H. et al, Development of virus-like-particle vaccine and reporter assay for Zika Virus, J. Virol. (2017) 91(20); citing Duenas-Carrera S, Alvarez-Lajonchere L, Alvarez-Obregon J C, Herrera A, Lorenzo L J, Pichardo D, Morales J. 2000.

Similarly, for dengue virus 4 (DENV-4), epitopes in the capsid were shown to be recognized by cytotoxic T lymphocytes (CTLs) that were cross-reactive with other dengue virus serotypes (Id., citing Gagnon, S J et al. (1996) J. Virol. 70: 141-147). In fact, immunization with capsid alone was shown to generate a protective immune response that was independent of neutralizing antibodies and largely dependent on cell-mediated immunity (Id. Citing Lazo L, Hermida L, Zulueta A, Sanchez J, Lopez C, Silva R, Guillen G, Guzman M G. 2007. A recombinant capsid protein from dengue-2 induces protection in mice against homologous virus. Vaccine 25:1064-1070).

Moreover, CD4 T cells may also be involved in protection as specialized subsets have been implicated in lysing flavivirus-infected cells (Id., citing Gagnon S J, Zeng W, Kurane I, Ennis F A. 1996. Identification of two epitopes on the dengue 4 virus capsid protein recognized by a serotype-specific and a panel of serotype-cross-reactive human CD4+ cytotoxic T-lymphocyte clones. J Virol 70:141-147; Aihara H, Takasaki T, Matsutani T, Suzuki R, Kurane I. 1998. Establishment and characterization of Japanese encephalitis virus-specific, human CD4(+) T-cell clones: flavivirus cross-reactivity, protein recognition, and cytotoxic activity. J Virol 72:8032-8036). Inclusion of capsid in virus-like particles (VLPs) requires a functional flaviviral protease, here the WNV NS2B-3 fusion protein. The NS2B-3 fusion protein coding sequence itself is about 2 kb long and can be included in VLP platforms, DNA vaccines, and modified mRNA vaccines.

II) Paramyxoviridae and Pneumonvirinae Viruses

A) Overview of the Paramyxoviridae and Pneumonvirinae Families

The Paramyxoviridae are enveloped, non-segmented, negative-strand RNA viruses that include major human pathogens belonging to two subfamilies. The Pneumonvirinae subfamily includes respiratory syncytial virus (RSV) and the metapneumoviruses, while the Paramyxovirinae subfamily includes, amongst others, measles virus (MeV), Morbillivirus genus, mumps virus (MuV) of the Rubulavirus genus, human parainfluenza viruses (hPIV1-4), and the recently emerged, highly pathogenic henipaviruses Hendra (HeV) and Nipah (NiV). Members of both subfamilies are responsible for significant human morbidity and mortality. MeV, in particular, remains a major cause of childhood mortality worldwide despite the availability of a live-attenuated vaccine. (Plemper, R. et al., Structural and Mechanistic Studies of Measles Virus Illuminate Paramyxovirus Entry. PLoS Pathog. 2011 June; 7(6): e1002058).

Paramyxovirus particles are pleomorphic, with a lipid envelope, nonsegmented RNA genomes of negative polarity, and densely packed glycoproteins on the virion surface. Like the rhabdo-, filo-, borna- and pneumoviruses, the paramyxoviruses form the order Mononegavirales that features enveloped virions with single-stranded, non-segmented RNA genomes of negative polarity. (Cox, R., and Plemper, R. Structure and Organization of Paramyxovirus Particles. Curr Opin Virol. 2017 June; 24: 105-114).

i) Measles Virus (MeV)

Measles virus (MeV), the causative agent of measles, is a human virus without an animal reservoir that is efficiently transmitted by aerosol or respiratory droplets. (Griffin, D. The Immune Response in Measles: Virus Control, Clearance and Protective Immunity. Viruses (2016) 8: 282).

ii) Mumps Virus (MuV)

Mumps is caused by the mumps virus (MuV), a member of the Paramyxoviridae family of enveloped, non-segmented, negative-sense RNA viruses. It is an enveloped particle containing a non-segmented negative strand RNA molecule of 15,384 nucleotides. MuV is transmitted via the respiratory route by inhalation or oral contact with infected respiratory droplets or secretions, Mumps is characterized by painful inflammatory symptoms, such as parotitis and orchitis. The virus is highly neurotropic, with laboratory evidence of central nervous system (CNS) infection in approximately half of cases. Symptomatic CNS infection occurs less frequently; nonetheless, prior to the introduction of routine vaccination, MuV was a leading cause of aseptic meningitis and viral encephalitis in many developed countries. (Rubin, S. et al., Molecularbiology, pathogenesis and pathology of mumps virus," J. Pathol. (2015) 235 (2): 242-252).

B) Structure-Based Functional Analysis of Paramyxoviruses

Two membrane glycoprotein complexes, the attachment (H, HN, or G) and the fusion (F) proteins that are responsible for receptor binding and cell entry through fusion of the viral envelope with target cell membranes, respectively, are common to all members of the paramyxovirus family. (Yanagi Y, Takeda M, Ohno S, Seki F. Measles virus receptors and tropism. (2006) Jpn J Infect Dis. 59:1-5). The RNA genome is encapsidated by the viral nucleocapsid (N) protein, resulting in the formation of a helical ribonucleoprotein (RNP) complex that serves as the template for the viral RNA-dependent RNA-polymerase complex composed of the viral phospho-(P) and large (L) proteins. The matrix (M) protein organizes particle assembly through interaction with both N proteins in the RNP complex and the membrane-embedded glycoprotein complexes. Some members of the family, such as pathogens of the rubulavirus genus, contain a small hydrophobic (SH) transmembrane protein in addition to these six structural proteins. Only J paramyxovirus encode a fourth integral membrane protein, transmembrane (TM), that stimulates cell-to-cell fusion but not viral entry. (Li Z, Hung C, Paterson R G, Michel F, Fuentes S, et al. Type II integral membrane protein, TM of J paramyxovirus promotes cell-to-cell fusion. (2015) Proc Natl Acad Sci USA. 112:12504-12509).

The ectodomains of all Paramyxovirinae attachment proteins are composed of a membrane-proximal stalk, which supports a terminal globular head that mediates receptor binding. (Plemper, R. et al., Structural and Mechanistic Studies of Measles Virus Illuminate Paramyxovirus Entry. PLoS Pathog. 2011 June; 7(6): e1002058).

In MeV, target cell entry is mediated by two viral envelope glycoproteins, the attachment (H) and fusion (F) proteins, which form a complex that achieves merger of the envelope with target cell membranes. (Plemper, R. et al., Structural and Mechanistic Studies of Measles Virus Illuminate Paramyxovirus Entry. PLoS Pathog. 2011 June; 7(6): e1002058).

The enveloped particles of mumps virus are pleomorphic, in the size range 100-600 nm. Within this structure lies the long, coiled electron-dense ribonucleoprotein (RNP), containing the MuV genome. The encapsidated genome contains seven tandemly linked transcription units, in the order: nucleo-(N), V/P/I (V/phospho-/I proteins), matrix (M), fusion (F), small hydrophobic (SH), haemagglutinin-neuraminidase (HN) and large (L) proteins. Small spikes can be observed on the surface of the particle, corresponding to the viral HN and F glycoproteins. The M protein interacts with the envelope, glycoproteins and the ribonucleoprotein (RNP). The V, I and SH proteins are expressed in infected cells, but are not thought to be incorporated within the virion.

The template for viral replication and transcription is the RNP complex, which is composed of the negative-strand viral RNA encapsidated by N protein. The RNA-dependent RNA polymerase, a complex of the L and P proteins, acts as a replicase to copy the negative sense (−) RNA to a positive sense (+) RNA and as a transcriptase to generate mRNAs from the (−) RNP by entering at a single promoter at the 3' end of the genome. In infected cells, the HN and F glycoproteins are transported through the endoplasmic reticulum and Golgi complex to the cell surface. The M protein is involved in localizing the viral RNP to regions of the host cell membrane expressing the F and HN glycoproteins, facilitating budding of the infectious virions from the infected cells. The HN glycoprotein is responsible for attachment of the newly budded virus to neighbouring cells via its receptor, sialic acid, which is abundantly present on the surface of most animal cells. The HN glycoprotein, in concert with the F glycoprotein, mediates virus-to-cell fusion and cell-to-cell membrane fusion, facilitating virus spread. The SH protein is thought to play a role in evasion of the host antiviral response by blocking the TNFα-mediated apoptosis pathway and is not essential for virus replication. The V and I proteins are encoded by the same transcriptional unit that encodes the P protein. Like the SH protein, the V protein is also involved in evasion of the host antiviral response, where it inhibits IFN production and signalling. The role of theI protein is unknown. (Rubin, S. et al., "Molecular biology, pathogenesis and pathology of mumps virus." J Pathol. 2015 January; 235(2): 242-252).

C) Immune Response to Paramyxovirus Infection

After introduction of MeV into the respiratory tract, immature pulmonary dendritic cells (DCs) or alveolar macrophages capture and transport MeV to regional lymph nodes (LNs) where the immune response is initiated, virus is amplifie, and spread of infection facilitated. (Ludlow, M.; Lemon, K.; de Vries, R. D.; McQuaid, S.; Millar, E. L.; van Amerongen, G.; Yiiksel, S.; Verburgh, R. J.; Osterhaus, A. D.; de Swart, R. L. Measles virus infection of epithelial cells in the macaque upper respiratory tract is mediated by subepithelial immune cells. J. Virol. 2013, 87, 4033-4042); Mesman, A. W.; de Vries, R. D.; McQuaid, S.; Duprex, W. P.; de Swart, R. L.; Geijtenbeek, T. B. A prominent role for DC-SIGN+ dendritic cells in initiation and dissemination of measles virus infection in non-human primates. PLoS ONE 2012, 7, e49573). Infected immune cells (B cells, CD4+ and CD8+ memory T cells, monocytes) then enter the circulation and spread the virus to multiple lymphoid (e.g., spleen, thymus, LNs) and non-lymphoid (e.g., skin, conjunctivae, kidney, lung, liver) organs where it replicates in endothelial cells, epithelial cells, lymphocytes and macrophages. (De Vries, R. D.; McQuaid, S.; van Amerongen, G.; Yüksel, S.; Verburgh, R. J.; Osterhaus, A. D.; Duprex, W. P.; de Swart, R. L. Measles immune suppression: Lessons from the macaque model. PLoS Pathog. 2012, 8, e1002885); (Moench, T. R.; Griffin, D. E.; Obriecht, C. R.; Vaisberg, A. J.; Johnson, R. T. Acute measles in patients with and without neurological involvement: Distribution of measles virus antigen and RNA. J. Infect. Dis. 1988, 158, 433-442); (Nozawa, Y.; Ono, N.; Abe, M.; Sakuma, H.; Wakasa, H. An immunohistochemical study of Warthin-Finkeldey cells in measles. Pathol. Int. 1994, 44, 442-447; McChesney, M. B.; Miller, C. J.; Rota, P. A.; Zhu, Y. D.; Antipa, L.; Lerche, N. W.; Ahmed, R.; Bellini, W. J. Experimental measles. I. Pathogenesis in the normal and the immunized host. Virology 1997, 233, 74-84; Lightwood, R.; Nolan, R. Epithelial giant cells in measles as an acid in diagnosis. J. Pediatr. 1970, 77, 59-64; Esolen, L. M.; Takahashi, K.; Johnson, R. T.; Vaisberg, A.; Moench, T. R.; Wesselingh, S. L.; Griffin, D. E. Brain endothelial cell infection in children with acute fatal measles. J. Clin. Investig. 1995, 96, 2478-2481; Takahashi, H.; Umino, Y.; Sato, T. A.; Kohama, T.; Ikeda, Y.; Iijima, M.; Fujisawa, R. Detection and comparison of viral antigens in measles and rubella rashes. Clin. Infect. Dis. 1996, 22, 36-39).

Typically, the innate response to an RNA virus infection is dominated by infected cell production of types I and III IFNs. Induction of IFN occurs through recognition of viral RNA or protein by toll-like receptors or by cytoplasmic RNA helicases that lead to activation of the cytoplasmic transcription factors IFN regulatory factor (IRF)-3 and nuclear factor kappa-light-chain-enhancer of activated B cells (NFκB). Translocation of IRF-3 and NFκB to the nucleus induces transcription of the mRNAs for early response proteins such as Regulated on Activation, Normal T Cell Expressed and Secreted/Chemokine (C-C motif) ligand 5 (RANTES/CCL5), IRF-7 and IFN-β with subsequent induction of IFN-stimulated genes (ISGs) with antiviral activity including myxovirus resistance (Mx), adenosine deaminase acting on RNA 1 (ADAR1), ISG15, ISG56 and IFN-α that can act to suppress virus replication (Randall, R. E.; Goodbourn, S. Interferons and viruses: An interplay between induction, signalling, antiviral responses and virus countermeasures. J. Gen. Virol. 2008, 89, 1-47); (Yoneyama, M.; Fujita, T. Recognition of viral nucleic acids in innate immunity. Rev. Med. Virol. 2010, 20, 4-22).

However, the initial innate immune response is restricted due to inhibition of the interferon (IFN) response through the combined activities of the MeV P, C and V proteins, which allows extensive virus replication and spread during a clinically silent latent period of 10-14 days. (Davis, M. E.; Wang, M. K.; Rennick, L. J.; Full, F.; Gableske, S.; Mesman, A. W.; Gringhuis, S. I.; Geijtenbeek, T. B.; Duprex, W. P.; Gack, M. U. Antagonism of the phosphatase PP1 by the measles virus V protein is required for innate immune escape of MDA5. Cell Host Microbe (2014) 16, 19-30; Kessler, J. R.; Kremer, J. R.; Muller, C. P. Interplay of measles virus with early induced cytokines reveals different wild type phenotypes. Virus Res. (2011) 155, 195-202; Li, Z.; Okonski, K. M.; Samuel, C. E. Adenosine deaminase acting on RNA 1 (ADAR1) suppresses the induction of interferon by measles virus. J. Virol. (2012), 86, 3787-3794; Schuhmann, K. M.; Pfaller, C. K.; Conzelmann, K. K. The measles virus V protein binds to p65 (RelA) to suppress NF-kappaB activity. J. Virol. (2011) 85, 3162-3171; Childs, K.; Randall, R.; Goodbourn, S. Paramyxovirus V proteins interact with the RNA helicase LGP2 to inhibit RIG-I-dependent interferon induction. J. Virol. (2012), 86, 3411-3421; Childs, K. S.; Andrejeva, J.; Randall, R. E.; Goodbourn, S. Mechanism of mda-5 Inhibition by paramyxovirus V proteins. J. Virol. (2009) 83, 1465-1473; Caignard, G.; Guerbois, M.; Labernardiere, J. L.; Jacob, Y.; Jones, L. M.; Infectious Mapping Project I-MAP; Wild, F.; Tangy, F.; Vidalain, P. O. Measles virus V protein blocks Jak1-mediated phosphorylation of STAT1 to escape IFN-alpha/beta signaling. Virology (2007) 368, 351-362; Ramachandran, A.; Parisien, J. P.; Horvath, C. M. STAT2 is a primary target formeasles virus V protein-mediated alpha/beta interferon signaling inhibition. J. Virol. (2008) 82, 8330-8338; Shivakoti, R.; Siwek, M.; Hauer, D.; Schultz, K. L.; Griffin, D. E. Induction of dendritic cell production of type I and type III interferons by wild-type and vaccine strains of measles virus: Role of defective interfering RNAs. J. Virol. (2013) 87, 7816-7827 with little to no evidence of IFN induction during measles (Shivakoti, R.; Hauer, D.; Adams, R. J.; Lin, W. H.; Duprex, W. P.; de Swart, R. L.; Griffin, D. E. Limited in vivo production of type I or type III interferon after infection of macaques with vaccine or wild-type strains of measles virus. J. Interferon Cytokine Res. (2015) 35, 292-301; Yu, X. L.; Cheng, Y. M.; Shi, B. S.; Qian, F. X.; Wang, F. B.; Liu, X. N.; Yang, H. Y.; Xu, Q. N.; Qi, T. K.; Zha, L. J.; et al. Measles virus infection in adults induces production of IL-10 and is associated with increased CD4+CD25+ regulatory T cells. J. Immunol. (2008) 181, 7356-7366).

The first appearance of measles is a 2-3 day prodrome of fever, runny nose, cough, and conjunctivitis that is followed by the appearance of a characteristic maculopapular rash that spreads from the face and trunk to the extremities. The rash is a manifestation of the MeV-specific adaptive cellular immune response and coincides with clearance of infectious virus. However, clearance of viral RNA from blood and tissues is much slower than clearance of infectious virus and proceeds over weeks to months after resolution of the rash. The period of RNA persistence coincides with decreased host resistance to infection that can be prolonged. Recovery is associated with life-long protection from MeV re-infection. (Mina, M. J.; Metcalf, C. J.; de Swart, R. L.; Osterhaus, A. D.; Grenfell, B. T. Long-term measles-induced immunomodulation increases overall childhood infectious disease mortality. Science (2015) 348, 694-699).

There is evidence for engagement of stress-response proteins and inflammasome activation by MeV infection. In antigen presenting cells (APCs), MeV interaction with DC-specific intercellular adhesion molecule-3 grabbing non-integrin (DC-SIGN) suppresses RNA helicase activation so that infection increases expression of stress-induced genes without inducing IFN (Shivakoti, R.; Siwek, M.; Hauer, D.; Schultz, K. L.; Griffin, D. E. Induction of dendritic cell production of type I and type III interferons by wild-type and vaccine strains of measles virus: Role of defective interfering RNAs. J. Virol. (2013) 87, 7816-7827; Mesman, A. W.; Zijlstra-Willems, E. M.; Kaptein, T. M.; de Swart, R. L.; Davis, M. E.; Ludlow, M.; Duprex, W. P.; Gack, M. U.; Gringhuis, S. I.; Geijtenbeek, T. B. Measles virus suppresses RIG-I-like receptor activation in dendritic cells via DC-SIGN-mediated inhibition of PP1 phosphatases. Cell Host Microbe (2014) 16, 31-42). In vitro studies show that MeV infection of myeloid cells stimulates assembly of the NACHT, LRR and PYD domains-containing protein (NLRP3) inflammasome in a mitofusin 2-dependent process with activation of caspase-1 followed by cleavage and secretion of mature interleukin (IL)-1β and IL-18 (Ichinohe, T.; Yamazaki, T.; Koshiba, T.; Yanagi, Y. Mitochondrial protein mitofusin 2 is required for NLRP3 inflammasome activation after RNA virus infection. Proc. Natl. Acad. Sci. USA (2013) 110, 17963-17968; Komune, N.; Ichinohe, T.; Ito, M.; Yanagi, Y. Measles virus V protein inhibits NLRP3 inflammasome-mediated interleukin-1beta secretion. J. Virol. (2011) 85, 13019-13026). Transcriptional analysis of peripheral blood mononuclear cells (PBMCs) during MeV infection shows up-regulated expression of NLRP3 and IL-1β mRNAs necessary for inflammasome activation. Further in vivo evidence of the innate response during measles includes increased plasma levels of NFκB-induced proteins IL-6 and IL-8/CXCL8 (Zilliox, M. J.; Moss, W. J.; Griffin, D. E. Gene expression changes in peripheral blood mononuclear cells during measles virus infection. Clin. Vaccine Immunol. (2007) 14, 918-923; Phillips, R. S.; Enwonwu, C. O.; Okolo, S.; Hassan, A. Metabolic effects of acute measles in chronically malnourished Nigerian children. J. Nutr. Biochem. (2004) 15, 281-288) and inflammasome products IL-1β and IL-18 (Zilliox, M. J.; Moss, W. J.; Griffin, D. E. Gene expression changes in peripheral blood mononuclear cells during measles virus infection. Clin. Vaccine Immunol. (2007) 14, 918-923); Okada, H.; Sato, T. A.; Katayama, A.; Higuchi, K.; Shichijo, K.; Tsuchiya, T.; Takayama, N.; Takeuchi, Y.; Abe, T.; Okabe, N.; et al. Comparative analysis of host responses related to immunosuppression between measles patients and vaccine recipients with live attenuated measles vaccines. Arch. Virol. (2001) 146, 859-874). Therefore, the innate response does not include IRF-3-mediated induction of type I or III IFNs, but does include induction of a subset of NFκB- and inflammasome-associated cytokines and chemokines that are important for initiating the adaptive immune response.

Not only have paramyxoviruses been shown to disrupt the interferon signalling pathway; Sendai virus (SeV) infection also renders both human and murine cells unresponsive to IFN-α/β.

Most paramyxoviruses encode the P, V, and C proteins from the same gene by using alternative initiation codons and mRNA editing mechanisms. The P protein is a structural component of the viral RNA polymerase, whereas V and C proteins are virus-encoded accessory factors whose function in some paramyxoviruses is inhibition of the IFNα/β signalling pathway. Studies on the V protein of SV5 (simian virus 5) by Didcock et al. showed that the STAT1 levels decline from around 4 hours after infection and eventually become undetectable. Didcock, L. et al., "The V protein of simian virus 5 inhibits interferon signaling by targeting STAT1 for proteasome-mediated degradation," J. Virol. (1999) 73 (12): 9928-33). The ability of the SV5 V protein to degrade STAT1 and block IFN signalling was confirmed by Andrejeva et al., using 2fTGH cells constitutively expressing SV5 V protein. Andrejeva, J, et al, "Degradation of STAT1 and STAT2 by the V proteins of simian virus 5 and human parainfluenza virus type 2, respectively: consequences for virus replication in the presence of alpha/beta and gamma interferons," J. Virol. (2002) 76(5): 2159-67). These results demonstrated that the SV5 V protein blocks IFN signalling by targeting STAT1 for proteasome mediated degradation. The cysteine-rich V protein of mumps virus inhibits the JAK/STAT pathway by inducing the degradation of STAT1. (Rubin, S. et al., "Molecular biology, pathogenesis and pathology of mumps virus." J Pathol. 2015 January; 235(2): 242-252)

STAT1 also serves as a molecule involved in the constitutive expression of certain genes including caspases, and low molecular polypeptide 2 (LMP2). LMP2 is a subunit of the proteasome involved in the processing of T-cell antigens. MHC class-I antigen is necessary for the presentation of endogenous virus antigens on cell surface membranes. It is well known that the IFN-γ signaling pathway through induction or activation of the ISGF-3 complex regulates MHC class-I expression. Thus, it has been hypothesized that inactivation of STAT-1α could be correlated with a decrease in MHC class-I expression. This decrease allows cells persistently infected with mumps virus to escape host immune surveillance.

Mumps virus elicits the production of specific IgM and IgG antibodies, whose high serum levels are evidence of the exposure of the immune system to viral antigens.

ii) T-Cell Responses to Paramyoxvirus Infection

Detailed quantitative studies of RNA clearance and the immune responses in individual macaques combined with mathematical modeling indicate that T cell responses (as indicated by IFN-γ-producing cells) correlate with clearance of infectious measles virus from blood, but that both antibody and T cells are required to explain the decline in viral RNA (Lin, W. H.; Kouyos, R. D.; Adams, R. J.; Grenfell, B. T.; Griffin, D. E. Prolonged persistence of measles virus RNA is characteristic of primary infection dynamics. Proc. Natl. Acad. Sci. USA (2012) 109, 14989-14994). Antibody is induced to most viral proteins (Graves, M.; Griffin, D. E.; Johnson, R. T.; Hirsch, R. L.; de Soriano, I. L.; Roedenbeck, S.; Vaisberg, A. Development of antibody to measles virus polypeptides during complicated and uncomplicated measles virus infections. J. Virol. (1984) 49, 409-412), but the relative contributions of functionally distinct antibodies and T cells for clearance from different sites are not known.

Immune activation and lymphocyte proliferation, particularly for CD4+ T cells, is evident acutely and then for months after resolution of the rash. During this period, there is a shift in cytokine production from type 1 T cell cytokines (e.g., IFN-γ) to type 2 cytokines (e.g., IL-4, IL-10, IL-13) and appearance of IL-17-producing cells (Lin, W. H.; Vilalta, A.; Adams, R. J.; Rolland, A.; Sullivan, S. M.; Griffin, D. E. Vaxfectin adjuvant improves antibody responses of juvenile rhesus macaques to a DNA vaccine encoding the measles virus hemagglutinin and fusion proteins. J. Virol. (2013) 87, 6560-6568); Ward, B. J.; Johnson, R. T.; Vaisberg, A.; Jauregui, E.; Griffin, D. E. Cytokine production in vitro and the lymphoproliferative defect of natural measles virus infection. Clin. Immunol. Immunopathol. (1991) 61, 236-248; Moss, W. J.; Ryon, J. J.; Monze, M.; Griffin, D. E. Differential regulation of interleukin (IL)-4, IL-5, and IL-10 during measles in Zambian children. J. Infect. Dis. (2002) 186, 879-887; Griffin, D. E.; Ward, B. J. Differential CD4 T cell activation in measles. J. Infect. Dis. (1993), 168, 275-281. This shift is likely to promote B cell maturation and contribute to the continued production of antibody-secreting cells (Nair, N.; Moss, W. J.; Scott, S.; Mugala, N.; Ndhlovu, Z. M.; Lilo, K.; Ryon, J. J.; Monze, M.; Quinn, T. C.; Cousens, S.; et al. HIV-1 infection in Zambian children impairs the development and avidity maturation of measles virus-specific immunoglobulin G after vaccination and infection. J. Infect. Dis. (2009) 200, 1031-1038). Ongoing improvement in antibody quality, as evidenced by increasing avidity, suggests continued activity of T follicular helper (THF) cells and B cell selection in the germinal centers of lymphoid tissue. Development of long-lived plasma cells is necessary to sustain plasma antibody levels for life (Amanna, I. J.; Slifka, M. K. Mechanisms that determine plasma cell lifespan and the duration of humoral immunity. Immunol. Rev. (2010) 236, 125-138).

T cell immunity has also been implicated as directly protective in individuals with low levels of antibody (Ruckdeschel, J. C.; Graziano, K. D.; Mardiney, M. R., Jr. Additional evidence that the cell-associated immune system is the primary host defense against measles (rubeola). Cell Immunol. (1975) 17, 11-18). The antiviral effects of T cells can be mediated both by secretion of cytokines that suppress virus replication (e.g., IFN-γ) and by cytotoxic elimination of infected cells. Because T cells do not directly block infection but rather react to control or eliminate virus-infected cells once infection has occurred, the contribution of T cells to protection is generally considered minor in comparison to neutralizing antibodies. Studies in macaques have shown that T cell immunity alone cannot protect from MeV infection or disease, but does facilitate RNA clearance and generation of a robust T cell and antibody response after challenge infection (Lin, W. H.; Pan, C. H.; Adams, R. J.; Laube, B. L.; Griffin, D. E. Vaccine-induced measles virus-specific T cells do not prevent infection or disease but facilitate subsequent clearance of viral RNA. mBio (2014) 5, e01047). Therefore, generation of both immune-mediated clearance and long-lived protection requires development of effective and durable MeV-specific antibody and CD4+ and CD8+ T cell responses.

Researchers have demonstrated that the Paramyxoviridae cross-react at the T-cell level, but not at the antibody level (Ziola, B., et al., "T cell cross-reactivity among viruses of the paramyxoviridae." Viral Immunol. (1987) 1(2): 111-9). T-cell reactivity between mumps virus and parainfluenza virus is expected as these viruses are serologically related.

These researchers uncovered a strong bi-directional T-cell cross-reactivity between respiratory syncytial virus (RSV), measles virus and mumps virus. RSV typically infects children before one year of age, and thus many children will have acquired T-cell immunity before they reach the recommended age for MMR vaccination (12-15 mths). This means that RSV-induced T-cells, through cross reactivity with mumps and measles virus antigens, could influence subsequent development of immunity to either or both of these vaccine viruses. (Ziola, B., et al., "T cell cross-reactivity among viruses of the paramyxoviridae." Viral Immunol. (1987) 1(2): 111-9)

It is known that rubulaviruses target STAT1 for degradation, which may be correlated to a decrease in MHC class-I expression. This decrease results in reduced CTL activation, thus favouring mumps virus replication and dissemination. The role of cellular immunity in infection with mumps virus is supported by data derived from experimental animals, as well as from humans. Mumps meningitis is a common complication of mumps virus infections, and MuV-specific CTL accumulated in the CNS can be detected in cerebrospinal fluid (CSF). Researchers have demonstrated that at the acute phase of mumps meningitis, CD8+ and HLA-DR+ cells increased in the CSF, and that cytotoxic-suppressor T cells activated by MuV antigens may accumulate. Others focused on the T-cell receptor (TCR) gene repertoire in patients with infectious CNS diseases. They evaluated TCR Vα gene expression in T lymphocytes from patients with mumps meningitis, and showed that the use in the CSF was widespread but biased toward three or less families in each patient. The biased use of the Vα gene suggests that T cells with dominant Vα genes may be mumps-specific T lymphocytes, which were selectively recruited to the CNS. (Flynn, M., Chapter 6: Immune Response to Mumps Viruses. Recent Research Developments in Virology, 5 (2003):97-115).

D) Paramyxovirus Vaccine Development, Challenges or Failures

Licensed vaccines exist for paramyxoviruses and are usually formulated as elements of the mumps, measles, and rubella (MMR) pediatric vaccine product, which is widely distributed throughout the world.

The MMR vaccine is usually recommended only for older infants or children over the age of 1 year. These children no longer harbor protective maternal antibodies at high titer, and are therefore particularly vulnerable to measles virus infections. (Kowalzik F, Faber J, and Knuf M. MMR and MMRV vaccines. Vaccine 36:5402-07 (2018)). Maternal antibodies therefore may weaken vaccines in young infants. (Jones B G, Sealy R E, Surman S L, et al. Sendai virus-based RSV vaccine protects against RSV challenge in an in vivo maternal antibody model. Vaccine (2014) 32:3264-3273).

III) Togaviridae and Matonaviridae Viruses

A) Overview of the Togaviridae and Matonviridae Families

The family Togaviridae comprises four genera: *Alphavirus* comprising 26 species, Rubivirus comprising one species, Pestivirus comprising three species, and *Arterivirus* comprising one species. Viruses in this family important to human diseases include: *Chikungunya* virus, Eastern equine encephalitis virus, Venezuelan equine encephalitis virus, and Western equine encephalitis virus in the Alphavirus genus; and Rubella virus in the Rubivirus genus.

Togaviruses have the following characteristics: spherical virus particles, a diameter of 50-70 nm in diameter, an envelope with surface projections that incorporate two or three polypeptides, usually glycosylated, a nucleocapsid comprising a core protein and a single strand of positive-sense RNA, the molecular weight of which is about $4\times10^6$. Typically, maturation occurs by budding of spherical nucleocapsids 30-35 nm in diameter, likely with icosahedral symmetry, through cytoplasmic membranes. The translation of structural proteins occurs on subgenomic messenger RNA(s). Nearly all alphavirus species are transmitted by mosquitoes. Transmission also occurs transovarially (Alphavirus) or transplacentally (Rubivirus and Pestivirus). Members of a genus are serologically related, but are not related to members of other genera.

i) Chikungunya Virus (CHIKV)

Chikungunya virus (CHIKV) is a zoonotic virus that has been identified in Africa and Asia, and more recently in North and South America, as well as Europe. It is transmitted through an infected mosquito bite of the Aedes genus; an urban cycle of transmission is possible as sufficiently high levels of viremia develop in infected individuals.

The pathology of a CHIKV infection starts with an incubation period of 2-10 days, which then develops into the acute phase, and then chronic phase. In the acute phase, polyathralgia is reported, which develops into chronic arthritis in the chronic phase. In the acute phase, clinical symptoms also include, high fever, severe joint and muscle pain, skin rash, weakness and headache as well as lymphopenia, or low lymphocyte count, and moderate thrombocytopenia, or low blood platelet count.

ii) Rubella Virus (RV)

Rubella virus (RV), a single-stranded, positive-sense RNA virus in the Rubivirus genus, has been recently moved from the Togaviridae to a new family, Matonaviridae. A total of 13 RV genotypes, which represent 2 clades, have been recognized, but 2 genotypes, 1E and 2B, are currently the most common worldwide. (Perelygina L, Chen Mh, Suppiah S, Adebayo A, Abernathy E, et al. (2019) Infectious vaccine-derived rubella viruses emerge, persist, and evolve in cutaneous granulomas of children with primary immunodeficiencies. PLOS Pathogens 15(10): e1008080). Rubella occurs worldwide with a seasonal distribution. The peak incidence of infection is in late winter or early spring. Rubella was a leading cause of birth defects in the United States before immunization programs were implemented in the 1970s. There have been no major epidemics in the United States since vaccine licensure in 1969, and the incidence has decreased by 99 percent. Continued cases of congenital rubella are due to infection in unvaccinated, susceptible young women. (Parkman P D. Togaviruses: Rubella Virus. In: Baron S, editor. Medical Microbiology. 4th edition. Galveston (Tex.): University of Texas Medical Branch at Galveston; (1996) Chapter 55. Available from the National Center for Biotechnology Information website.

The disease is transmitted via direct or droplet contact with respiratory secretions. Rubella virus multiplies in cells of the respiratory system; this is followed by viremic spread to target organs. Congenital infection is transmitted transplacentally. (Parkman P D. Togaviruses: Rubella Virus. In: Baron S, editor. Medical Microbiology. 4th edition. Galveston (Tex.): University of Texas Medical Branch at Galveston (1996) Chapter 55. Available from the National Center for Biotechnology Information website.

Rubella remains a public health concern. A rubella epidemic in Japan, with more than 11,000 rubella cases occurring in the first 6 months of 2013 and at least 13 congenital rubella syndrome (CRS) cases occurring, highlights the fact that a partial vaccination strategy leads to major outbreaks. Seventy percent of the rubella cases in the Japanese outbreak occurred among males ages 20 to 39 years, indicating the weakness of an initial strategy that provided rubella vaccine only to adolescent girls. In 2012, Poland and Romania also experienced rubella outbreaks that predominantly affected males as a result of a vaccination strategy that initially focused on vaccination of females. (Lambert, N., "Rubella" Lancet. (2015) Jun. 6; 385(9984): 2297-2307).

Just as for measles virus and the mumps virus, there has been a noted decreasing rate of immunization for rubella virus globally.

One of the major factors limiting universal use of the existing rubella vaccine has been concern about a "paradoxical effect"—that sustained low rubella immunization coverage in infants and young children might decrease exposure to rubella during childhood, which may lead to increased susceptibility among women of childbearing age compared to the pre-vaccine era because such women are neither vaccinated nor exposed to virus. (Lambert, N., "Rubella" Lancet. (2015) Jun. 6; 385(9984): 2297-2307).

Further, there are limited occurrences of vaccine failure, and this is thought to arise when preexisting antibodies neutralize the live viral vaccine strain. Low level immunity, for example, could result from a previous infection, such as from a parvovirus or Epstein-Barr virus infection, or the presence of Rh factor. (Lambert, N., "Rubella" Lancet. (2015) Jun. 6; 385(9984): 2297-2307).

B) Structure-Based Functional Analysis of Togaviruses and Matonvirus

RV is an enveloped virus with a 9.6-kb single-stranded, positive-sense RNA genome. The virions have particle diameters ranging from 600 to 800 Å, with most of the spherical virions having a diameter of about 700 Å. RV contains three structural proteins, namely, the capsid protein (~31 kDa) and the glycoproteins E1 (58 kDa) and E2 (42-47 kDa). The capsid protein interacts with the RNA genome and forms the nucleocapsid, which is surrounded by a lipid membrane upon which E1 and E2 are arranged. Two non-structural proteins, p90 and p150, involved with virus replication, are also encoded by the virus.

Alphaviruses and RV share a similar gene order and expression strategy, but differ in that alphaviruses are icosahedral, their nucleocapsids assemble in the cytoplasm, and virions bud from the plasma membrane, while RV virions are pleomorphic, and the nucleocapsid assembles on Golgi membranes followed by budding of the virus into this organelle. The pleomorphic nature of RV virions has been a limiting factor in determining the structure of the virus particles. As with all Togaviruses, the structural proteins of RV are synthesized as a polyprotein precursor in association with the endoplasmic reticulum in the host cell. The polyprotein is cotranslationally cleaved by the host-cell signal peptidase but, unlike alphavirus capsid proteins, the RV capsid protein remains attached to the cytoplasmic side of the membrane by virtue of the hydrophobic E2 signal peptide. (Prasad, M., et al., Rubella virus capsid protein structure and its role in virus assembly and infection. Proc Natl Acad Sci USA (2013) Dec. 10; 110(50):20105-10).

Rubella virus is a spherical, 40- to 80-nm, positive-sense, single-stranded RNA virus with spike-like, hemagglutinin-containing surface projections. An electron-dense 30 to 35 nm core is surrounded by a lipoprotein envelope. Rubella virus contains a pleomorphic nucleocapsid enveloped in a host-derived lipid membrane. Two proteinaceous spikes, E1 and E2, are anchored to the external layer of the membrane. The E1 protein is responsible for receptor-mediated endocytosis and is the immunodominant antigen. The measurement of antibodies against the neutralizing domain of E1 can be used as a correlate of protection against rubella virus. The E2 protein is membrane bound and forms connections between rows of E1 proteins. (Lambert, N., "Rubella" Lancet. (2015) Jun. 6; 385(9984): 2297-2307).

Humans are the only known reservoir of rubella virus, with postnatal person-to-person transmission occurring via direct or droplet contact with the respiratory secretions of infected persons. Although the early events surrounding infection are incompletely characterized, the virus almost certainly multiplies in cells of the respiratory tract, extends to local lymph nodes, and then undergoes viremic spread to target organs. Subsequent additional replication in selected target organs, such as the spleen and lymph nodes, leads to a secondary viremia with wide distribution of rubella virus. At this time (approximately 7 days after infection and 7 to 10 days before the onset of rash) the virus can be detected in the blood and respiratory secretions. Viremia disappears shortly after the onset of rash; it is also associated with the appearance of circulating neutralizing antibodies. However, virus shedding from the respiratory tract may continue for up to 28 days following the onset of rash. (Parkman P D. Togaviruses: Rubella Virus. In: Baron S, editor. Medical Microbiology. 4th edition. Galveston (Tex.): University of Texas Medical Branch at Galveston (1996). Chapter 55. Available from the National Center for Biotechnology Information website.

C) Immune Response to Togaviridae and Matonviridae Virus Infection

The role of cellular immunity in rubella is as yet poorly defined, although symptomatically, Togaviridae infections are defined by lymphopenia and moderate thrombocytopenia.

D) Togaviridae and Matonviridae Vaccine Development, Challenges or Failures

The current live rubella virus vaccine strain licensed for use in the United States is the RA27/3 strain employed as part of the MMR vaccine. The vaccine has been known to persist in immunologically competent individuals for a limited time causing mild complications, such as transient arthralgia or arthritis in adult women. The vaccine virus' involvement in the pathology of Fuchs uveitis is also suspected. The vaccine virus has not been associated with congenital defects, but asymptomatic persistent infections of the fetus have been reported after inadvertent vaccination of unknowingly pregnant women (Perelygina L, Chen M h, Suppiah S, Adebayo A, Abernathy E, et al. (2019) Infectious vaccine-derived rubella viruses emerge, persist, and evolve in cutaneous granulomas of children with primary immunodeficiencies. PLOS Pathogens 15(10): e1008080). Further discussion of the MMR vaccine can be seen in the discussion of Paramyxoviruses.

IV) Filoviridae Viruses

A) Overview of the Filoviridae Family

The family of Filoviridae is a family of enveloped, single-stranded RNA(−) viruses comprising three different genera: monospecific Cuevavirus, Ebolavirus (EBOV), and monospecific Marburgvirus (MARV). Filoviruses get their name from their filamentous or thread-like virions which exhibit extreme pleomorphism: virions may appear U-shaped, 6-shaped, or circular. Their lengths may vary but they generally have a uniform diameter of ~80 nm.

The typical filoviral particle has a lipid envelope covered with glycoprotein spikes of about 10 nm in length. Under this lipid envelope is the helical nucleocapsid. The genome is about 19 kb in length and consists of seven structural proteins where viral proteins NP, VP35, VP30 and L form the viral nucleocapside structure, L is also the RNA dependent RNA polymerase that performs virus transcription and replication, GP is the surface viral glycoprotein that mediates entry into host cells via receptor-binding and fusion; VP24 and VP40 are membrane associated matrix proteins. (Fermin, Gustavo, and Paula Tennant. Viruses: Molecular Biology, Host Interactions and Applications to Biotechnology, edited by Jerome E. Foster, Elsevier Science & Technology, 2018. Available from the ProQuest Ebook Central website).

i) Marburg Marburgvirus (MARV)

The Marburg marburgvirus genus contains a single species, Lake Victoria marburg virus, which contains two strains: Marburg virus (MARV) and Ravn virus (RAVV). This virus has only had a few geographic instances of outbreak: Marburg, Germany, Zimbabwe, South Africa, Democratic Republic of Congo, and Angola.

ii) Ebolavirus (EBOV)

EBOVs comprises of the following species that have pathogenicity in humans: Bundibugyo ebolavirus (BDBV), Zaire ebolavirus (ZEV), Sudan evolavirus (SUDV), and Tai Forest ebolavirus (TAFV).

B) Structure Based Functional Analysis of Filoviruses

Filoviruses share a common genome organization with seven open reading frames that encode all viral proteins: a nucleoprotein (NP), the viral proteins VP35 and VP40, the surface glycoprotein (GP), the viral proteins VP30 and VP24, and the "large" polymerase (L). (Martin, B., Filovirus proteins for antiviral drug discovery: Structure/function bases of the replication cycle. Antiviral Res. (2017) May; 141:48-61).

Filoviruses enter cells through the interaction of GP, the sole viral glycoprotein in the envelope, which has two distinct regions—GP1 and GP2. GP1 acts in the manner of a Class I membrane fusion protein and has a receptor binding region (RBR). This RBR has a high amino acid identity between MARV and EBOV (~47%) and attaches to a cellular receptor thought to be shared by the two filovirus genera. Virus enters the cell by endocytosis where cysteine proteases cleave the GP1 region of the viral glycoprotein. This allows GP1 to bind to an internal endosomal protein receptor called Niemann-Pick C1 (NPC1). Once this occurs, fusion of the viral membrane with that of the endosome is facilitated by the GP2 region and the viral genome is released into the cytoplasm. Transcription of the viral genome into mRNA is initiated by the binding of viral nucleocapsid protein VP30 and starts at the 3' end. The viral protein L acts as the RNA-dependent RNA polymerase (RdRp) and, in tandem with its cofactor VP35 and the DNA topoisomerase of the host cell, orchestrates replication of the genome. Translation of the viral genome leads to the accumulation of viral proteins, and VP35 and NP initiate the production of antigenomes. These antigenomes are in turn used as templates for producing additional viral genomes. Viral proteins then accumulate at the cell membrane, where the viral glycoprotein G spikes become inserted into the host cell membrane. Expression of the NP protein leads to inclusion bodies in the host cell, which, in addition to NP, also encapsulate proteins VP24, VP30, VP35, and L, and associate with the G proteins embedded in the cell membrane. This then leads to budding of the characteristic filamentous virions from the cell, mainly under the influence of VP40. (Fermin, Gustavo, and Paula Tennant. Viruses: Molecular Biology, Host Interactions and Applications to Biotechnology, edited by Jerome E. Foster, Elsevier Science & Technology (2018) Available from the ProQuest Ebook Central website).

The viral glycoprotein GP allows for entry into monocytes and macrophages and subsequent damage to these cells results in the production of cytokines associated with fever and inflammation. It also allows entry of the virus into endothelial cells, and damage to these directly results in a loss of vascular integrity resulting in hemorrhaging. Other viral proteins act as virulence factors at different points of infection. VP35 sequesters viral RNA, helping the foreign genome evade detection by innate immunity. The protein also competitively inhibits the activation of host IFN regulation factors preventing IFN-β production. VP24, VP 30, and VP40 have also been shown to be suppressors of protective host RNAi pathways, further decreasing the innate immune response. EBOV also evades the cell's immune system, one that discriminates between self-RNA (capped) and nonself-RNA (uncapped), by capping and polyadenylating its mRNAs—another process orchestrated by VP35. (Fermin, Gustavo, and Paula Tennant. Viruses: Molecular Biology, Host Interactions and Applications to Biotechnology, edited by Jerome E. Foster, Elsevier Science & Technology (2018) ProQuest Ebook Central).

Immune Response to Filoviridae Virus Infection. Aerosol administration of a human parainfluenza virus type 3-vectored vaccine expressing an Ebola envelope glycoprotein was capable of not only eliciting neutralizing antibodies, but also a CD103+ T cell response in the lungs of macaques. A large proportion of these tissue-resident memory ($T_{RM}$) T cells were polyfunctional, demonstrating positivity for two or more activation markers. Furthermore, a single dose of this vaccine conferred 100% protection against infection challenge. Since a large proportion of transmission in recent Ebola epidemics was through skin contact, vaccination via scarification has been considered worth exploring. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

C) Filoviridae Vaccine Development, Challenges or Failures

There is no approved vaccine for EBOV or MARV infection and no effective therapy available against filoviruses. Initial attempts to generate filovirus vaccines focused on the use of inactivated whole virions had mixed success in non-human primate (NHP) models. Later studies began to test virus-like particles, viral vectors or plasmid DNA expressing filovirus genes as vaccine platforms. Most platforms were based on generating immune responses against GP, with the hope of generating neutralizing antibody that would protect against filovirus infection. However, it is still unclear what types of immune responses need to be induced for successful vaccination against filovirus infection (Bradfute, Steven B et al. "Filovirus vaccines." *Human vaccines* vol. 7,6 (2011): 701-11).

Due to theoretical safety concerns, conventional vaccine platforms such as live attenuated and killed virus vaccines are unlikely to be used in humans. Several animal models have been developed to study the pathogenesis of filovirus infection and to assess the efficacy of vaccination strategies, but experts believe that the animal models and inconsistency with vaccination efforts still do not justify widespread vaccinations in humans. Further research is necessary to evaluate the most ideal strategy for immunization, including platforms that will be safe and immunogenic in a broad population (Sarwar, Uzma N et al. "Filovirus emergence and vaccine development: a perspective for health care practitioners in travel medicine." *Travel medicine and infectious disease* vol. 9,3 (2011): 126-34).

V) Orthomyxoviridae Viruses

A) Overview of the Orthomyxoviridae Family

The Orthomyxoviridae family is comprised of segmented single-stranded RNA viruses with five genera: Influenzavirus A, Influenzavirus B, Influenzavirus C, Isavirus, and Thogotovirus. The family is named as such because it is characterized by the ability of the viruses to attach to mucous proteins on cell surfaces ("myxo" is Greek for mucous) but more "orthodox" in comparison to the Paramyxoviridae—another group of RNA viruses (discussed infra), also characterized by the ability to attach to mucus-producing cells. The influenza A, B, and C viruses, representing three of the five genera of the family Orthomyxoviridae, are characterized by segmented, negative-strand RNA genomes. Sequencing has confirmed that these viruses share a common genetic ancestry; however, they have genetically diverged, such that reassortment (meaning the exchange of viral RNA segments between viruses) has been reported to occur within each genus, or type, but not across types (Bouvier, Nicole M, and Peter Palese. "The biology of influenza viruses." Vaccine vol. 26 Suppl 4, Suppl 4 (2008): D49-53).

i) Influenza A, B, and C Viruses

Influenza virus genomes can gradually change over time, accumulating new mutations due to the error-prone nature of the RNA-dependent RNA polymerase (RdRp) that catalyzes the replication cycle. This process of gradual change in genes is termed antigenic drift. Because of the segmented nature of Orthomyxovirus genomes, they also can undergo genome reassortment. In a cell co-infected with two related viruses, for example, an exchange of segments may occur, with the production of viable and stable reassortants/new genetic strains. Such reassortment occurs in nature and is an important source of genetic variability. Influenza A viruses also can undergo an abrupt major change, for example when an influenza virus from an animal population gains the ability to infect humans, resulting in new HA and/or new HA and NA proteins in influenza viruses that infect humans, producing a new influenza A subtype. Such an "antigenic shift" occurred in the spring of 2009, when an H1N1 virus with genes from North American Swine, Eurasian Swine, humans and birds emerged to infect people and quickly spread, causing a pandemic.

Influenza strains are typically defined by the antigenic properties of the HA and NA proteins embedded in the viral particle membrane. Type A viruses are divided into serological subtypes according to the nature of hemagglutinin (H1 to H16) and neuraminidase (N1 to N9). Strain differentiation further includes the host organism of origin, the geographical location of the first viral isolation, strain number, and year of isolation, as well as being defined by the numbers corresponding to the antigenic description of HA and NA proteins, for example, Virus A/California/04/09 (H1N1), or Virus A/Swine/Iowa/15/30 (H1N1). (Fermin, Gustavo, and Paula Tennant. Viruses: Molecular Biology, Host Interactions and Applications to Biotechnology, edited by Jerome E. Foster, Elsevier Science & Technology (2018). Available from the ProQuest Ebook Central website).

B) Structure-Based Functional Analysis of Orthomyxoviruses

Orthomyxovirus particles are spherical or pleomorphic in shape, and range from 80 to 120 nm in diameter. The capsids have a tubular helical symmetry with segmented negative polarity RNA. The typical orthomyxovirus genome is segmented and consists of ribonucleoproteins of varying lengths (50-150 nm) surrounded by a membrane embedded with viral glycoproteins and nonglycosylated proteins. The following membrane-associated viral proteins exist on the surface of the viral particle: hemagglutinin (HA, responsible for host cell binding and virus entry), neuraminidase (NA, responsible for virus budding and release), and matrix protein (M2; an ion channel involved in viral genome replication). Within the virion, the RNA genome segments are bound to nucleoprotein (NP), along with several viral proteins that form the viral RNA polymerase complex (RNA polymerase acidic, RNA polymerase basic 1, and RNA polymerase basic 2) (RNP). Surrounding the RNP is a layer of matrix protein 1 (M1), which is involved in nuclear transport of the RNP. Nonstructural proteins 1 and 2 (NS1 and NS2) are involved in regulating viral protein expression and replication, respectively, where NS2 is also present in low amounts. (Fermin, Gustavo, and Paula Tennant. Viruses: Molecular Biology, Host Interactions and Applications to Biotechnology, edited by Jerome E. Foster, Elsevier Science & Technology (2018) Available from the ProQuest Ebook Central website).

Influenza A and B viruses have eight genome segments of single-stranded RNA(−), and Influenza C virus has seven. RNA segments 1, 2, and 3 code for PB2, PB1, and PB-A respectively (which comprise the viral polymerase complex, P), while segments 4, 5, and 6 encode the HA, NP, and NA proteins, respectively. Segments 7 and 8 encode two proteins each with overlapping reading frames: M1/M2 and NS1/NS2. Influenza C viruses differs from Influenza A and B viruses by lacking the NA gene. Each segment has 50- and 30-untranslated regions (UTRs) vital for transcription, translation, replication, and efficient packaging of segments into new virus particles.

Influenzavirus A, Influenzavirus B, Influenzavirus C share similarities in their stages of viral replication. The first stage consists of viral adsorption to the cell by the interaction between the receptor N-acetylneuraminic acid (NeuAc) or sialic acid and viral HA. Human viruses typically present in a NeuAc interaction in which the glycoside bounded to galactose in an α2, 6 type bond (avian viruses typically present with an α2, 3 bond). In a process referred to as viropexis, the virus enters the host cell via receptor-mediated endocytosis, facilitated by the HA' domain of HA. The virus is then transported to the cell's endoplasmic reticulum (ER); the decreased pH inside the endosome leads to a conformational change in the HA2 domain of HA. The conformation change mediates the fusion between viral envelope and the endosomal membrane and consequently RNP is released into the cytoplasm. The RNP migrates to the nucleus of the infected cell, a phenomenon driven by several nuclear localization signals in the viral NP protein. Once inside the nucleus, replication events begin whereby complementary RNA (+) (cRNA) is synthesized and serves as a template for the synthesis of new viral RNA (vRNA) and simultaneously for the messenger RNAs (mRNA(s)) for the synthesis of viral proteins. Synthesis of mRNA is done through a process known as cap-snatching whereby the virus appropriates caps via its PA subunit from cellular RNAs for use as primers for viral mRNA synthesis. This requires the ongoing production of pre-mRNA by the cellular DNA-dependent RNA polymerase (Pol II). The virus further utilizes the transcript-splicing ability of the Pol II for some viral products as the virus lacks this activity.

The viral proteins responsible for replication and transcription include the three subunits of the transcription complex (PB1, PB2, and PA) and NP. This three subunit complex interacts with cellular proteins in a sequential fashion to synthetize vRNA and cRNA. Another key viral protein is NS1, which is expressed very early and plays an important role in regulating the expression of viral genes; it is the main mediator in inhibiting the synthesis of cellular mRNA and hence host protein synthesis in the infected cell. Eventually vRNA associates with newly synthesized RNPs, and these in turn bind to the matrix protein (M1). The vRNA-RNP complexes are exported to the cytoplasm by the viral NS2 protein. RNP-M1-NS2 complexes are directed to the cell membrane while viral surface proteins (H, N, and M2) when synthesized are located in the endoplasmic reticulum and Golgi, respectively. Assembly of new viral particles is carried out at the apical pole of infected epithelial cells just eight hours from the onset of infection. M1 protein, which interacts both with the internal queue of the surface proteins and RNP, plays a key role in the budding of viral particles. The mechanism by which eight RNA segments are included in each viral particle is still unknown. The sialidase activity of the NA contributes to the release of the viral particles from the cell surface. It actually breaks the bond between the H and NeuAc, thus avoiding the formation of aggregates. Typically apoptosis is induced by NA, NS1, and PB1 proteins. (Fermin, Gustavo, and Paula Tennant. Viruses: Molecular Biology, Host Interactions and Applications to Biotechnology, edited by Jerome E. Foster, Elsevier Science & Technology (2018) Available from the ProQuest Ebook Central website).

C) Immune Response to Orthomyxoviridae Infections

Analysis of human samples has revealed that influenza-specific $T_{RM}$ can be found in substantial numbers in lung tissue, highlighting their role in natural infection. Despite expressing low levels of granzyme B and CD107a, these CD8+$T_{RM}$ had a diverse T cell receptor (TCR) repertoire, high proliferative capacities, and were polyfunctional (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574). Influenza infection history suggests a greater level of protection against re-infections is likely due to the accumulation of CD8+ $T_{RM}$ in the lungs. Furthermore, the natural immune response to influenza A virus infection in a rhesus monkey model demonstrated that a large portion of influenza-specific CD8+ T cells generated in the lungs were phenotypically confirmed as CD69+CD103+ $T_{RM}$. Unlike lung parenchymal $T_{RM}$, airway CD8+ TRM are poorly cytolytic and participate in early viral replication control by producing a rapid and robust IFN-γ response. Bystander CD8+ $T_{RM}$ may also take part in the early immune response to infection through antigen non-specific, NKG2D-mediated immunity. The generation of functional $T_{RM}$ that protect against heterosubtypic influenza infection appear to be dependent on signals from CD4+ T cells. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

A role for CD4+ $T_{RM}$ has also been reported. Much like their CD8+ counterparts, CD4+ $T_{RM}$ also produce a significant IFN-γ response during early infection. Aside from the CD8+ and CD4+ subsets of $T_{RM}$, a subset of NK1.1+ double negative T memory cells which reside in the lungs also play a role in influenza infection. Taken together, these studies and others demonstrate that $T_{RM}$ are required for optimal protection. However, unlike $T_{RM}$ in other locations, such as the skin, lung $T_{RM}$ are not maintained for extended periods of time. The gradual loss of lung $T_{RM}$ appears to be the reason for the loss in heterotypic immunity against influenza infection. Lung $T_{RM}$ exhibit a transcriptional profile that renders them susceptible to apoptosis. Despite conflicting evidence, it appears that maintenance of the lung CD8+ $T_{RM}$ populations relies on the continual seeding from circulating CD8+ T cells. However, with time, circulating CD8+ T cells adopt a transcriptional profile that reduces their capacity to differentiate into $T_{RM}$. There is also conflicting evidence regarding the requirement of local antigen for the generation of $T_{RM}$ within the lung. Intranasal administration of Live Attenuated Influenza Vaccine (FluMist®) in a mouse model induced both CD4+ and CD8+ TRM that provided a degree of cross-strain protection independent of TCM and antibodies. The intranasal administration of a PamCys2 or Adjuplex™ has demonstrated capacity for producing protective influenza-specific lung CD8+ $T_{RM}$ in similar numbers and IFN-γ secreting potential when compared to the natural response to influenza infection. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

D) Orthomyxoviridae Vaccine Development, Challenges or Failures

The influenza viruses are relatively simple, RNA-containing viruses with strongly immunogenic surface proteins, especially the HA. However, their segmented genomes and their error-prone RNA-dependent RNA polymerases enable these viruses to undergo antigenic shift and antigenic drift, which in turn results in evasion of the adaptive immune responses in a range of mammalian and avian species, including humans. Because of their adaptive ability, influenza viruses continue to confound efforts to produce long-lasting vaccines against the disease (Bouvier, Nicole M, and Peter Palese. "The biology of influenza viruses." Vaccine vol. 26 Suppl 4, Suppl 4 (2008): D49-53).

The protection provided by current influenza vaccines is largely dependent on the induction of neutralizing antibody against the globular head domain of the viral surface protein HA to block viral entry. Since the HA head domain is highly variable among different influenza virus styrains, current seasonal vaccines are only effective against well-matching circulating virus strains. (See Zhao, C. and Xu, J., Curr. Op. Immunol. (2018) 53: 1-6).

Other vaccine efforts have been made. For example, a vaccine containing virus-like particles with tandem repeat M2e epitopes generated heterotypic immunity through the induction of antibodies, and protection correlated with IFN-γ-secreting CD8+ $T_{RM}$. A Modified Vaccinia Ankara-vectored virus expressing conserved influenza nucleoprotein and matrix protein 1 elicited an IFN-γ secreting CD4+ T cell and CD8+ $T_{RM}$ response. Co-administration of 4-1BBL (CD137 signal) along with an influenza nucleoprotein expressing replication defective adenovirus vector via the intranasal route stimulated and boosted a lung CD8+ $T_{RM}$ response through the recruitment of circulating T cells. A Intranasal administration of Fc-fused IL-7 was used as a pre-treatment before influenza A infection, and demonstrated protective capacities in mice against lethal challenge. It appears that Fc-fused IL-7 recruits polyclonal circulating T cells into the lungs, which subsequently reside in the lung tissue as "$T_{RM}$-like cells". An antibody targeted vaccination strategy in which antigens are coupled to monoclonal antibodies against CD103+ or DNGR-1+ dendritic cells has also been shown to elicit a protective CD8+ $T_{RM}$ response. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

VI) Poxviridae Viruses

A) Overview of the Poxviridae Family

Poxviruses comprise a family of genetically related, large, enveloped, DNA viruses that replicate exclusively within the cytoplasm of vertebrate or invertebrate cells. The most intensively studied poxviruses belong to the Orthopoxvirus genus, including variola virus (causative agent of smallpox, eradicated from nature), vaccinia virus (VACV; the modern smallpox vaccine, now endemic in Brazil), cowpox virus (the original smallpox vaccine, indigenous in Europe, occasionally infects humans) and monkeypox virus (indigenous in Africa, causes a smallpox-like disease of humans). (Moss, Bernard. "Poxvirus cell entry: how many proteins does it take?" Viruses vol. 4,5 (2012): 688-707.

i) Variola Virus (Small Pox)

Vaccinia virus is a poxvirus of the genus Orthopoxvirus of the same family as the variola virus that usually causes a very mild or asymptomatic infection in immunocompetent individuals. Immunity to vaccinia virus also provides sufficient protection against smallpox, which allowed for its eradication following administration of the live vaccinia virus. Despite elimination, smallpox remains a priority on the global agenda given the potential for the virus to be used as a biological weapon. For this reason and for its ability to serve as a vector, vaccinia virus continues to be used in research. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

B) Structure-Based Functional Analysis of Poxviruses

Poxviruses, specifically, orthopoxyviruses, are double-stranded DNA genomes are about 200,000 bp in length and encode about 200 proteins, most of which have 90% or more sequence identity between species. The complete genome sequences of a large number of VARV isolates and other OPXVs are available. While all OPXVs encode homologous proteins for vital functions such as entry, gene expression, genome replication, and virion assembly, there are differences with regard to proteins involved in immune evasion and other host interactions. The basic infectious poxvirus particle is the mature virion (MV), which consists of a nucleoprotein core containing the genome and a complete early transcription system, flanked by lateral bodies, and surrounded by a lipoprotein envelope. A subset of MVs becomes surrounded by modified Golgi or endosomal membranes, transported to the cell periphery on microtubules, and released by exocytosis as enveloped virions (EVs). The EV consists of an MV with an additional lipoprotein membrane containing eight EV-specific viral proteins, although there are other small differences in protein composition. Most of the EVs remain adherent to the plasma membrane and mediate cell-to-cell spread at the tips of long actin-containing microvilli, which are important for virulence in animals. (Moss, Bernard. "Smallpox vaccines: targets of protective immunity." Immunological Reviews vol. 239, 1 (2011): 8-26).

Four proteins enable attachment of MVs to the cell. The A27 protein exists as trimers and hexamers on the surface of MVs and binds heparan and cell surface proteoglycans. H3, another MV surface protein, also binds heparan and cell surface proteoglycans. D8 is an MV surface protein that binds chondroitin sulfate. The fourth attachment protein, A26, is physically associated with A27 and binds cell surface laminin. Fusion with the cell membrane and entry of the core into the cytoplasm requires at least 12 additional MV transmembrane proteins that form a complex known as the entry fusion complex or EFC. There are a number of known entry proteins. The transmembrane proteins exposed on the outer surface of the EVs include A33, A34, A36, A56 hemagglutinin, and B5. (Moss, Bernard. "Smallpox vaccines: targets of protective immunity." Immunological Reviews vol. 239, 1 (2011): 8-26).

C) Immune Response to Poxviridae Viruses

The poxvirus infection generally follows one of two courses: a localized infection resulting in benign skin lesions, or a systemic infection, resulting in viral dissemination and usually death. Local pathogenesis of molluscum contagiosum virus (MCV) and Shope fibroma virus (SFV) infection has been well documented. Although the pathogenesis and host response to infection is quite different, both poxvirus diseases are self-limiting and remain localized to the skin. The generalized infections, however, are characterized by several stages, ending in an explosion of viral lesions. Ectromelia virus infection of mice starts with an infection of the skin, usually through the footpad. After some replication, the virus spreads through the local lymphatics to the bloodstream, resulting in primary viremia. The virus then replicates to high titers in the spleen and liver before reentering the blood, resulting in a secondary viremia. Finally, the virus spreads to the skin, and a severe rash of ulcerating lesions very rapidly overcomes the mouse. The disease progression of variola virus infection in humans occurs similarly, with high mortality rate (Smith, S., and Kotwa, G., "Immune Response to Poxvirus Infections in Various Animals." Critical Reviews in Microbiology vol. 28, 3 (2002)).

Although both the humoral and cell-mediated immunity (CMI) components of the vertebrate acquired immune system jointly participate in the host response to infection, CMI is particularly critical for the clearance of poxvirus-infected cells. An effective CMI response requires both innate effector cells, such as natural killer (NK) cells, and educated effector cells, such as cytotoxic T lymphocytes (CTLs), to rapidly identify and eliminate infected cells before the virus can replicate and spread. Some viruses have evolved mechanisms to reduce the efficiency of the CMI response, including the masking of outward signs of infection, a strategy that has been named virostealth. (See, B T et al, Annu. Rev. Immunol (2003) 21: 377-423). Poxviruses target many of the primary mediators of innate immunity including interferons, tumor necrosis factors, interleukins, complement, and chemokines. Poxviruses also manipulate a variety of intracellular signal transduction pathways such as the apoptotic response (Id.).

Murine models demonstrate that $T_{RM}$ are generated in response to vaccinia and play a significant role in mediating protection against infection. Dermal-resident γδ T cells have also been implicated in the immune response against cutaneous vaccinia infection. Following skin infection, CD8+ T cells are recruited independently of CD4 T+ cells and IFN-γ, many of which subsequently assume the $T_{RM}$ phenotype and are capable of initiating potent inflammatory responses upon re-stimulation. Local vaccinia skin inoculations can globally seed skin tissue even at remote sites with long lasting $T_{RM}$ and can generate $T_{RM}$ responses in non-related non-lymphoid organs such as the lungs and liver. Multiple exposures to cognate viral antigens have also been shown to selectively expand $T_{RM}$. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

In a lung infection model of vaccinia, higher numbers of lung $T_{RM}$ correlated with better protection against subsequent infection as indicated by a rapid reduction in viral loads. TRM seem to expand more rapidly and localize to the infection site as indicated by a 5-ethynyl-2'-deoxyuridine proliferation assay when compared to their circulating counter parts. Depletion of lung CD8+ T cells by intranasal administration of αCD8 antibody resulted in previously protected mice becoming susceptible to infection, indicating that CD8+ $T_{RM}$ play a vital role in mediating immunity. In another study, parabiosis experiments demonstrated that $T_{RM}$ were better at clearing vaccinia virus skin infection than TCM within a shorter timeframe. In fact, it appears that skin TRM can clear vaccinia skin infection even in the absence of neutralizing antibodies and central memory T cells ($T_{CM}$). (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

However, vaccinia-specific CD8+ skin $T_{RM}$ appear to have an impaired ability to recruit circulating effector cells during polymicrobial sepsis infection. Studies of vaccinia lung infections revealed that not all $T_{RM}$ are equally capable of conferring protection. For example, $T_{RM}$ that resided in the lung interstitium were better positioned to rapidly kill infected lung cells in a contact-dependent manner when compared to TRM situated in association with the tissue vasculature. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574). Furthermore, $T_{RM}$ found within the interstitium, unlike vascular-associated $T_{RM}$, were able to up-regulate CD69 expression, potentially indicating an enhanced ability to respond during early infection. Epithelial immunization routes, such as skin scarification and intranasal exposure, demonstrate significant efficacy for generating protective TRM responses. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

D) Poxviridae Vaccine Development, Challenges or Failures

Vaccines for poxviruses, and specifically, the vaccinia virus, have been developed eventually leading to the global eradication of smallpox in 1980. However, this resulted in the cessation of vaccination against smallpox thereby rendering the population potentially susceptible to smallpox disease. It has also made the population susceptible to spill-over VACV during the production of VACC as a vaccine against smallpox in animals. Emerging and re-emerging poxvirus infections, particularly VACV-like-viruses, namely, buffalopox virus (BPXV), Aracatuba virus, Cantagalo virus, Guarani virus, Passatempo virus, Belo Horizonte virus, SPAn232 virus and BeAn 58058 virus (BAV) have been reported in animals and humans. Similarly, monkeypox virus and orfvirus in animals and humans have been frequently described. However, vaccines developed for these viruses have cross-protection failure and therefore have been found to have no substantial impact on the control of subsequent infections (See Veerkyathappa, B., et a., "Animal poxvirus vaccines: a comprehensive review." Expert Review of Vaccines (2012) 11(11): 1355-1374).

Moreover, while vaccination via skin scarification is capable of protecting against clinical disease (pock lesions of the skin), not all mice vaccinated via systemic routes (e.g., intramuscular and intraperitoneal) were protected from pock lesions. Further, mice immunized via skin scarification demonstrated greater resistance to disease when challenged via a heterologous route (intranasal), compared to mice immunized subcutaneously or intraperitoneally, in spite of generating reduced antibody titers. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

VII) Rhabdoviridae Viruses

A) Overview of the Rhabdoviridae Family

Rhabdoviridae includes the Vesiculovirus, Ephemerovirus and Lyssavirus genera which infect a wide range of mammals, including man; transmission is commonly vector-borne, typically hematophagous insects or animals (meaning those that feed on blood). There are seven recognized genotypes or species of the Lyssavirus genus, the most important of which to humans is the rabies virus (RABV).

ii) Rabies Virus (RABV)

Rabies virus, a member of the Lyssavirus genus, is transmitted to humans by infected animals, typically through a bite, scratch or lick on damaged skin or by projection of infectious material (i.e. saliva or lacrymal liquid) on mucosae. It is seen in high prevalence in Africa and Asia but treatment is largely neglected. Each year, at least 15 million people receive treatment after being exposed to suspected rabid animals; however, 55,000 people still die in Asia and Africa, based on the WHO estimation. The main reservoir of the disease is the dog, but several other species of the Carnivora and Chiroptera orders act also as reservoir of different species (or genotypes) of lyssaviruses.

B) Structure-Based Functional Analysis of Rhabdoviruses

All mononegaviruses, like rhabdoviruses, employ a monopartite genome whose size varies two-fold, from ~9 k to 19 kb. The antigenome replica of mononegavirales encodes several positionally conserved genes located in separate open reading frames (ORFs) that may be interspersed by genes unique to distinct lineages. The order of the backbone genes from the 3'- to 5'-ends of the genome is N-P-M-G-L, where N is nucleoprotein, P—phosphoprotein, M—matrix protein, G—glycoprotein and L—large protein, also known as polymerase. The products of the first four genes produce major proteins forming enveloped virions, and they may be known under other names in some viruses The L gene encodes a multidomain protein, including a putative RNA-dependent RNA polymerase that is virion associated and mediates replication and expression of the virus genome.

C) Immune Response to Rhabdovirus Infection

Rabies virus, like all members of the Lyssavirus genus, is neurotropic and following a bite infects peripheral nerves close to the bite site. The virus then moves by retrograde axonal transport to the dorsal root ganglia where virus replication becomes detectable. This movement can be extremely rapid: axoplasmic transport of rabies virus within cultured rat sensory neurons reached 12-24 mm/day. It is retrogradely transported by peripheral neurons before being passed on to second and higher-order neurons without being taken up by glia (Research Advances in Rabies, Elsevier Science & Technology (2011). Available from the ProQuest Ebook Central website, at pages 33-53).

Seemingly, the body doesn't detect RABV until it reaches the nervous system (NS). The NS innate system is made up of cells, such as microglia, astrocytes, and neurons, that express receptors such as toll like receptor (TLR) or retinoic acid inducible gene-1 (RIG-1-like receptor; RLR) that allow them to recognize and respond to danger signals and PAMPS encoded by RABV, thereby triggering the production of type I IFN (predominantly IFN-beta in the brain, no IFN-alpha, and no type III IFN-lambda). (Research Advances in Rabies, Elsevier Science & Technology (2011) Available from the ProQuest Ebook Central website, at pages 33-53).

The infection is responsible for high neurological disorders and is invariably fatal in the absence of timely administration of a post-exposure prophylaxis (PEP) consisting of several doses of vaccines and of a passive immunoprophylaxis. However, when the symptoms appear, post-exposure prophylaxis is no longer active and no specific therapy is available. Further, PEP administration becomes less effective when there is a delay between the start of the PEP and the exposure, and is no longer effective after the onset of the symptoms.

i) T-Cell Response to Rhabdoviridae Viruses Infection

Typically, infections of the nervous system are controlled by infiltrating T cells, for example, the infected NS produces chemokines which attract CD8+ cells that respond to the pathogen. In contract, studies have shown that despite heavy loading with viral antigens, in neurons infected with the rabies virus, the migrating T cells were apoptotic. (Research Advances in Rabies, Elsevier Science & Technology, (2011) Available from the ProQuest Ebook Central website, at page 34).

Mononuclear leukocytes, monocytes and macrophages are recruited to the nervous system upon infection. Once activated, the T and B cells from the periphery expressing surface adhesion molecules have the capacity to enter the nervous system. This entry is independent of blood brain barrier integrity. After their entry into the nervous system, migratory immune cells face unfavorable conditions for survival, limiting T-cell activity. T cell activity can be limited, for example, by the secretion of several neuropeptides and neurotransmitters by neurons such as vasointestinal peptide, calcitonin-gene-related peptide, norepinephrine, and alpha-melanocyte-stimulating hormone, which downregulate the activity of T cells. Further, a RABV-infected brain has been seen to upregulate the expression of calcitonin-related gene peptide, somatostatin, and vasointestinal peptides, three molecules known to contribute to limit T-cell activity in the NS.

Further, RABV evade T cell immunity through upregulating the expression of HLA-G, Fas-L, and B7-H1, death ligands on the surface of host cells that trigger death signaling in activated T cells when interacting with corresponding death receptors, CD8, Fas, and PD-1, respectively, on the surface of T cells. RABV also drives T cells into an apoptosis pathway by upregulating the expression of the death.

D) Rhabdovirus Vaccine Development

Vaccination is highly effective at preventing disease when administered before or shortly after exposure to virus. Early RABV vaccines were derived from neural tissue from a variety of animal sources and were effective and affordable throughout the world. However, the high content of myelin basic protein in this type of vaccine leads to a small number of cases of fatal encephalitis; because of this, these types of vaccines are not recommended for use.

Current vaccines consist of inactivated virus grown in continuous cell-lines. Two vaccines are licensed in the UK for human use, human-diploid-cell-vaccine (HDCV) manufactured by Aventis Pasteur and purified chick-embryo-cell-vaccine (PCECV) manufactured by Chiron. (Scott, T. P., & Nel, L. H. (2016). Subversion of the Immune Response by Rabies Virus. Viruses, 8(8), 231).

Pre-exposure vaccination, such as that given to healthcare and laboratory workers, and travelers to rabies-endemic areas, is administered in three doses intramuscularly at 0, 7 and 28 days. Immunoglobulin M (IgM) is detectable within 4 days post-inoculation with HDCV with IgG appearing at day 7. Follow-up studies have shown that responses persist for up to 2 years after vaccination; passive transfer studies suggest that IgG provides the most effective protection against disease, probably because of the inability of IgM to penetrate tissue. Prompt post-exposure treatment or prophylaxis (PEP) is the only effective treatment for the prevention of rabies. (Scott, T. P., & Nel, L. H. (2016). Subversion of the Immune Response by Rabies Virus. Viruses, 8(8), 231).

Unlike pre-exposure vaccination, the regimens recommended by the World Health Organisation (WHO) for post exposure prophylaxis (PEP) consist of intensive re-exposure to vaccine over a short period of time. A standard course, for example, is repeated intramuscular inoculation at 0, 2, 7, 14 and 28 days. Alternative regimens use intradermal inoculation that can use a lower volume of vaccine and is thus more cost-effective where resources are limited. This approach is gaining wide acceptance, especially in Asia. Improved responses to intradermal vaccination over the intramuscular route are believed to result from improved antigen presentation from the skin, although this explanation has not been demonstrated experimentally for RABV. (Scott, T. P., & Nel, L. H. (2016). Subversion of the Immune Response by Rabies Virus. Viruses, 8(8), 231).

A cocktail of human monoclonal antibodies has been developed (Bakker, A. B., et al. (2005). Novel human monoclonal antibody combination effectively neutralizing natural rabies virus variants and individual in vitro escape mutants. J Virol 79, 9062-8), but data confirming safety, tolerability, and neutralizing activity is lacking. (Bakker, A B, et al, (2008) "First administration to humans of a monoclonal antibody cocktail against rabies virus: safety, tolerability, and neutralizing activity," Vaccine 26, 5922-7; de Kruif, J., et al. (2007). A human monoclonal antibody cocktail as a novel component of rabies postexposure prophylaxis. Annu Rev Med 58, 359-68).

A lot of effort has been expended to develop a curative treatment active in rabid patients, but so far no effective therapy has been found. Very few molecules have been so far reported to exert activity against the rabies virus.

II) Herpesviridae Viruses

A) Overview of the Herpesviridae Family

The Herpesviridae family is a significant viral family comprising major pathogens of a wide range of hosts. Known as a DNA virus, this family includes at least eight species of viruses known to infect humans. The family further includes a number of species that infect other mammals important to economies worldwide, including the livestock industry and the competition industry, potentially causing severe economic losses. (Sharma, V., et al., Comparative Genomics of Herpesviridae Family to Look for Potential Signatures of Human Infecting Strains. Int J Genomics. 2016; 2016: 9543274).

The Herpesviridae family includes viruses from the Alphaherpesvirinae subfamily, such as Varicella-zoster virus (VZV), which causes diseases known colloquially as chicken pox and shingles, Human herpesvirus-1 (HHV-1), Herpes simplex virus-1 (HSV-1), Human herpesvirus-2

(HHV-2), Herpes simplex virus-2 (HSV-2), Human herpesvirus-3 (HHV-3), Herpes simplex virus-3 (HSV-3), Bovine herpesvirus-1 (BHV-1), Bovine herpesvirus-5 (BHV-5), Equid herpes virus 1 (EHV-1), Equid herpes virus 3 (EHV-3), Equid herpes virus 4 (EHV-4), Equid herpes virus 8 (EHV-8), and Equid herpes virus 9 (EHV-9). (Davison A J. Overview of classification. In: Arvin A, Campadelli-Fiume G, Mocarski E, et al., editors. Human Herpesviruses: Biology, Therapy, and Immunoprophylaxis. Cambridge: Cambridge University Press (2007) Chapter 1. Available from the National Center for Biotechnology Information website.

Further, the Herpesviridae family also includes viruses from the Gammaherpesvirinae subfamily, such as Human herpesvirus-4 (HHV-4) otherwise known as Epstein-Barr virus, Equid herpes virus 2 (EHV-2), Equid herpes virus 5 (EHV-5), and Equid herpes virus 7 (EHV-7). (Davison A J. Overview of classification. In: Arvin A, Campadelli-Fiume G, Mocarski E, et al., editors. Human Herpesviruses: Biology, Therapy, and Immunoprophylaxis. Cambridge: Cambridge University Press (2007) Chapter 1. Available from the National Center for Biotechnology Information website.

i) Varicella-Zoster Virus (VZV)

Varicella zoster virus (VZV), the causative agent of chicken pox, is an alpha-herpes virus that can establish latency within the dorsal root ganglia. Reactivation of the virus results in a painful disease called shingles. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

ii) Herpes Simplex Virus (HSV)

HSV-1 and HSV-2 are closely related, sharing >80% identity on the amino acid level. HSV is a neurotropic virus that invades the skin and mucosal lining of the anogenital and oral tracts. HSV can penetrate into the epidermis, especially where the outermost, cornified layer is thin (e.g., labia, inner foreskin, facial lips), absent (e.g., rectum, endocervix, vagina) or traumatically destroyed. (Sandgren, K., et al., "Understanding natural herpes simplex virus immunity to inform next-generation vaccine design." (2016) Clinical & Translational Immunology 5(7)). HSV-1 transmission is primarily oral, and HSV-2 is primarily genital. Transmission requires intimate contact. (Whitley R J. Herpesviruses. In: Baron S, editor. Medical Microbiology. 4th edition. Galveston (Tex.): University of Texas Medical Branch at Galveston (1996). Chapter 68. Available from the National Center for Biotechnology Information website.

HSV-1 infection is widespread, and its seropositivity may cover more than 70% of the world population. In developing countries, HSV-1 infection is universal, and acquired from intimate contact in early childhood. HSV-1 can cause serious diseases at every stage of life including fatal disseminated disease in newborns, cold sores, eye disease, and fatal encephalitis in adults. (Zhang, Jie et al. "Immune response of T cells during herpes simplex virus type 1 (HSV-1) infection." Journal of Zhejiang University. Science. B vol. 18,4 (2017): 277-288). Genital herpes caused by HSV1/2 is now the most common sexually transmitted infection, and causes severe disease in neonates. Additionally, HSV1 is the leading cause of infectious blindness in western countries. Prior HSV2 infection leads to a two- to threefold increased risk of HIV infection globally. (Sandgren, K., et al., "Understanding natural herpes simplex virus immunity to inform next-generation vaccine design." (2016) Clinical & Translational Immunology 5(7)).

iii) Bovine Herpesvirus (BHV)

Bovine herpesvirus 1 (BHV-1), also known as infectious bovine rhinotracheitis virus, belongs to the Alphaherpesvirinae subfamily, and shares a number of biological properties with HSV-1 and HSV-2. BHV-1 infection can cause conjunctivitis, pneumonia, genital disorders, abortions, and an upper respiratory infection referred to as shipping fever. BHV-1 is not the sole infectious agent associated with shipping fever, but it initiates the disorder by immunosuppressing infected cattle. BHV-1-induced immunosuppression frequently leads to secondary bacterial infections (for example, *Pasteurella haemolytica*, *Pasteurella multocida*, and *Haemophilus somnus*) that can cause pneumonia. (Clinton Jones, "Herpes Simplex Virus Type 1 and Bovine Herpesvirus 1 Latency" Clinical Microbiology Reviews. (2003) 16 (1) 79-95).

BHV-1 infection costs the cattle industry at least $500 million per year in the United States. Although vaccines are available, the virus is still known to cause disease in young calves and abortions in cows. (Id.).

iv) Equid Herpesvirus (EHV)

Nine species of EHV have been reported. The species EHV1, EHV3, EHV4, EHV8 and EHV9 have been classified under the genus Varicellovirus, subfamily Alphaherpesvirinae, family Herpesviridae of the order Herpesvirales. The species EHV2 and EHV5 have been put under a new genus Percavirus, subfamily Gamaherpesvirinae, family Herpesviridae of the order Herpesvirales. The species EHV6 and EHV7 have been tentatively placed as species in the subfamily Alphaherpesvirinae and Gammaherpesvirinae, respectively. Only five of the nine herpes viruses (viz. EHV1, 2, 3, 4 and 5) have the ability to produce disease in horses. EHV3 is responsible for coital exanthema while EHV2 and EHV5 are not associated with a specific disease, but may remain associated with upper respiratory tract diseases, inappetance, lymphadenopathy, immunosuppression, keratoconjunctivitis, general malaise and poor performance. Both EHV1 and EHV4 are economically important viruses affecting the respiratory tracts of horses globally. However, only EHV1 causes abortion and neurological disorders (Kapoor et al., Equine Herpesviruses: A Brief Review. (2014) Advances in Animal and Veterinary Sciences 2(2S): 46-54).

B) Structure-Based Functional Analysis of Herpesviridae Viruses

The Herpesviridae virion is spherical, and comprises four major components: the core, the capsid, the tegument and the envelope. The diameter of the virion depends on the viral species, and is approximately 200 nm. The core consists of a single copy of a linear, double-stranded DNA molecule packaged at high density into the capsid. (Davison A J. Overview of classification. In: Arvin A, Campadelli-Fiume G, Mocarski E, et al., editors. Human Herpesviruses: Biology, Therapy, and Immunoprophylaxis. Cambridge: Cambridge University Press (2007) Chapter 1. Available from the National Center for Biotechnology Information website. Icosohedral herpesvirus capsids are composed of five herpesvirus-conserved proteins, the major capsid protein (MCP, HSV-1UL19 gene product), triplex monomer and dimer proteins (TRI1 and TRI2, HSV-1 UL38 and UL18 gene products, respectively), the smallest capsid protein (SCP, HSV-1 35 gene product) and the portal protein (PORT, HSV-1 UL6 gene product). (Mocarski Jr. E S. Comparative analysis of herpesvirus-common proteins. In: Arvin A, Campadelli-Fiume G, Mocarski E, et al., editors. Human Herpesviruses: Biology, Therapy, and Immunoprophylaxis.

Cambridge: Cambridge University Press (2007) Chapter 4. Available from the National Center for Biotechnology Information website.

HSV-1 is an enveloped, nuclear-replicating, and large double-stranded DNA virus. The genome of HSV-1 is an about 152 kb linear double-stranded GC-rich DNA sequence, and contains two unique regions called the long unique region (UL) and the short unique region (US), which encode at least 84 proteins. The genome of HSV-1 is located within the nucleocapsid, which is surrounded by a group of tegument proteins. The nucleocapsid and tegument proteins are surrounded by a lipid envelope studded with glycoproteins which are important for binding to and entry into new susceptible cells. The major steps of the life cycle of HSV-1 are: entry into the host cell, viral gene expression, genome replication, virion assembly, and release of new infectious virus. Three classes of genes of HSV-1 are expressed in a consecutive manner, including immediate early (IE) genes, early genes, and late genes. The products of IE genes regulate the expressions of early genes and late genes. (Zhang, Jie et al. "Immune response of T cells during herpes simplex virus type 1 (HSV-1) infection." Journal of Zhejiang University. Science. B vol. 18,4 (2017): 277-288).

Binding to and entry of HSV-1 into cells are mediated by viral glycoproteins and cellular factors. A cellular mediator of viral entry (HveA or HVEM) is expressed primarily in activated T cells and belongs to the tumor necrosis factor (TNF) receptor family. Entry of HSV-1 into epithelial and other nonlymphoid cells is mediated by an unrelated membrane glycoprotein that resembles the poliovirus receptor (HveB and HveC). HveC is active as an entry mediator for all herpesviruses tested so far (e.g., HSV-1, BHV-1, and pseudorabies virus, PRV). HveC is abundantly expressed in neurons and can block viral entry in several neuronlike cell lines. After uncoating, the viral genome is present in the nucleus and viral gene expression ensues. HSV-1 gene expression is temporally regulated in three distinct phases: immediate-early (IE), early (E), and late (L). IE RNA expression does not require protein synthesis and is stimulated by the tegument protein VP16 and by active cyclin-dependent kinases. E RNA expression is dependent on at least one IE protein, and generally E genes encode nonstructural proteins that play a role in viral DNA synthesis. L RNA expression is maximal after viral DNA replication and requires IE protein expression Most L proteins are structural proteins that comprise the virion particle. (Clinton Jones, "Herpes Simplex Virus Type 1 and Bovine Herpesvirus 1 Latency" (2003) Clinical Microbiology Reviews, 16 (1) 79-95).

C) Immune Responses to Herpesviridae Virus Infection

HSV productively infects the epidermal keratinocytes and Langerhans cells (LCs; a type of dendritic cell (DC)). It then enters cutaneous nerve endings and is transported along axons to a collection of nerve cells close to the spine, the dorsal root ganglion, to establish lifetime latent infection. After periodic reactivation, the virus is transported back along neurons to the mucosa where it causes recurrent lesions, or is shed asymptomatically. (Sandgren, K., et al., "Understanding natural herpes simplex virus immunity to inform next-generation vaccine design." (2016) Clinical & Translational Immunology 5(7)).

Although vaccines are available against both chicken pox and shingles, recent evidence suggests that $T_{RM}$ cells may be key players in controlling latent infection, a phenomenon that could be exploited to improve current vaccines. One study analyzed skin samples from human donors of varying ages who were serologically confirmed varicella zoster virus (VZV) positive. 80-90% of T cells from the sampled tissue expressed CD69, suggesting that the majority of T cells in skin were $T_{RM}$ cells. IL-2 responses from stimulated VZV-specific T cells demonstrated that host age did not influence the numbers of responsive cells. However, it was found that skin from older donors demonstrated a lesser capacity to mount a clinical response and decreased CD4+ T cell infiltration when challenged with VZV antigen. This correlated with higher proportions of Foxp3+ cells. Furthermore, $T_{RM}$ of older skin expressed PD-1 in higher amounts. Together, this data suggest that VZV-specific $T_{RM}$ may be suppressed with age, which may explain the high incidence of reactivation of VZV in older individuals. Results from a different study that utilized samples of human trigeminal ganglia suggests that $T_{RM}$ do not play a role in controlling latent infection in the trigeminal ganglia. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

During HSV-1 infection, virus-specific CD8+ $T_{RM}$ cells are created in both ganglia and mucosa. CD8+ $T_{RM}$ cells exist in non-lymphoid tissue compartments for long periods, and in brain, kidney, joints, and other non-barrier tissues, which can trigger protective innate and adaptive immunity. Without being limited by theory, CD8+ $T_{RM}$ cells could express the effector molecules IFN-γ and granzyme B (GrB); these cells are not replenished from the circulating CD8+ T cell pool. (Zhang, Jie et al. "Immune response of T cells during herpes simplex virus type 1 (HSV-1) infection." Journal of Zhejiang University. Science. B vol. 18, 4 (2017): 277-288).

Upon ocular HSV-1 infection of mice, memory CD8 T cells selectively accumulate in latently infected sensory ganglia. In C57BL/6 mice, the majority of the CD8 T cells found in the sensory ganglia are specific for a glycoprotein B-derived HSV-1 epitope (gB-498-505), which has been shown to block HSV-1 reactivation from latently infected sensory ganglia cultured ex-vivo; a major mechanism of CD8 T cell-mediated protection is through IFN-γ secretion and release of non-cytotoxic lytic granules. It has been reported that a population of non-migrating virus-specific CD8 T cells persisted in the skin upon resolution of the primary infection in the absence of viral antigen. These cells were classified as $T_{RM}$, up-regulate the expression of CD103 once they enter the epidermis, are phenotypically distinct from their recirculating counterpart (high expression of CD69, low expression of CD62L) and they visibly change their morphology, becoming dendritic-shaped. In contrast to memory CD4 T cells which are mainly localized the dermal layer of the skin and are highly motile and in equilibrium with the blood, $T_{RM}$ CD8 T cells do not recirculate and can be found in the epidermis long after the control of infection. Both migration and persistence of memory T cells in the skin as well as their conversion to $T_{RM}$ were shown to be independent of cognate antigen, but could be induced by local inflammation alone. (Torti N, Oxenius A. T cell memory in the context of persistent herpes viral infections. Viruses. (2012) 4(7):1116-1143; Mackay L. K., Stock A. T., Ma J. Z., Jones C. M., Kent S. J., Mueller S. N., Heath W. R., Carbone F. R., Gebhardt T. Long-lived epithelial immunity by tissue-resident memory T (TRM) cells in the absence of persisting local antigen presentation. Proc. Natl. Acad. Sci. USA. (2012) 109:7037-7042).

Using a model of vaginal HSV-2 infection in mice, Nakanishi et al. showed that CD8 T lymphocyte mobilization to virus-infected tissue requires the help of CD4 T cells, not only by promoting their expansion, but also by inducing local chemokine secretion via IFNγ production, which in turn attracted effector CD8 T cells to the infected site. (Nakanishi Y., Lu B., Gerard C., Iwasaki A. CD8(+) T lymphocyte mobilization to virus-infected tissue requires CD4(+) T-cell help. Nature (2009) 462:510-513).

In HSV-1 infections, while specific CD8 T cells accumulate and persist at the infected sites upon local infections (shown in model of skin, vaginal and ocular infections), they don't do so systemically, where they are present in low numbers with a resting $T_{CM}$ phenotype. However, in response to systemic HSV-1 infection, gB-498-505-CD8 T cells show accumulation and maintenance of an elevated number of $T_{EM}$ CD8 T cells during latency. These cells are maintained at a constant high number throughout the life of the infected mouse and never lose their ability to secrete IFNγ and to proliferate in response to secondary infections. While the KLRG1− population was superior to its KLRG1+ counterpart, KLRG1− and KLRG1+ cells increased in number to the very same extent when transferred into lymphopenic hosts, and both divided extensively. It has been reported that reinfection with HSV is not antigen dependent for the maintenance of inflationary cells. Specifically, HSV-specific cells declined in naïve recipients but not in systemically infected HSV-1 mice where they were maintained at stable number (and even slightly increased) over a period of 60 days. In addition, blocking viral replication with the antiviral compound famcyclovir had a major impact on memory inflation in HSV, although a complete inhibition of memory inflation was seen if the treatment was started before infection. (Torti N, Oxenius A. T cell memory in the context of persistent herpes viral infections. Viruses. (2012) 4(7):1116-1143).

Increased susceptibility to secondary infection correlates with depressed cell-mediated immunity after BHV-1 infection. CD4+ T-cell function is impaired during acute infection of calves because BHV-1 infects CD4+ T cells and induces apoptosis. (Clinton Jones, "Herpes Simplex Virus Type 1 and Bovine Herpesvirus 1 Latency" (2003) Clinical Microbiology Reviews 16 (1) 79-95).

i) Challenges in Herpesviridae Vaccine Design

Developments in herpesviridae vaccine design has resulted in vaccines that only have partial efficacy. (Sandgren, K., et al., "Understanding natural herpes simplex virus immunity to inform next-generation vaccine design." (2016) Clinical & Translational Immunology 5(7)).

III) Picornaviridae Viruses

A) Overview of the Picornaviridae Family

The Picornavirus family consists of a large number of small RNA viruses, many of which are significant pathogens of humans and livestock. Picornaviridae, one of the largest viral families, is composed of 14 genera, six of which include human pathogens. The best known picornaviruses are enteroviruses (including polio, PV, and rhinoviruses), foot-and-mouth disease virus (FMDV), and hepatitis A virus (HAV). Although infections often are mild, certain strains may cause pandemic outbreaks accompanied with meningitis and/or paralysis. (Norder, H. et al., "Picornavirus non-structural proteins as targets for new anti-virals with broad activity." Antiviral Research 89 (2011) 204-218). The family encompasses a variety of human and animal diseases, such as poliomyelitisk, the common cold, hepatitis A, foot and mouth disease and the like.

Picornaviruses comprise a single stranded positive sense RNA genome of approximately 7,000-8,500 nucleotides with similar but not identical organizations across the family within a T=1 (quasi T=3) icosahedral protein capsid of approximately 30 nm diameter. The 5' end of the genome is linked to a small peptide (VPg), and the 3' end terminates with a poly(A) tract. There is a single open reading frame flanked by untranslated regions (UTRs) at both ends. The 5' UTR is especially long (~600-1,200 nts) and contains a number of important replication and translation control elements, including an internal ribosome entry site that is directly involved in the initiation of protein translation. The genome is translated into a single polyprotein, which is subsequently cleaved into mature protein products by virally encoded proteases. The structural proteins are located within the N terminal one third of the polyprotein, while the remainder includes proteins involved in modifying the cellular environment to optimize virus replication and the proteins directly responsible for replication. In some picornaviruses (e.g., the enteroviruses), the structural precursor protein is situated directly at the N terminus of the polyprotein, while in others (e.g., aphthoviruses and cardioviruses), the structural precursor is preceded by nonstructural protein sequence. In the majority of picornaviruses, the N terminus of the structural precursor protein (P1) is modified by the covalent addition of a myristic acid residue, which is thought to play important roles both in particle assembly and in the cell entry process. P1 is typically about 90 kD and is further proteolytically processed into the mature viral proteins (VP1-4 or P1 A-D) found in the viral capsid. The VP designation system was first used to distinguish the structural proteins according to their apparent molecular weights, while the P1 system describes their order on the viral genome. Accordingly, P1A is equivalent to VP4, P1B to VP2, P1C to VP3, and P1D to VP. VP1-3 together form the icosohedral shell of the virion, while VP4 is distributed on the inner surface of the particle. (Tuthill, Tobias J et al. "Picornaviruses." (2010) Current Topics In Microbiology and Immunology Vol. 343: 43-89).

i) Picornavirus (FMDV)

Foot-and-mouth disease virus (FMDV; family Picomaviridae; genus Aphthovirus) causes a highly contagious, acute disease of cloven-hoofed animals. FMD is a difficult and expensive disease to control and eradicate due to its wide host range, low minimum infectious dose, rapid rate of replication, high level of viral shedding, and multiple modes of transmission. The situation is further complicated by an important subclinical divergence that occurs after acute infection of ruminants: some animals remain subclinically infected for up to 3 years ("FMDV carriers"), while others completely clear the virus within 1 to 2 weeks ("non-carriers"). The definition of an FMDV carrier established by the World Organisation for Animal Health (OIE) is an animal from which infectious FMDV can be recovered at greater than 28 days after infection. (Eschbaumer, M., "Systemic immune response and virus persistence after foot-and-mouth disease virus infection of naïve cattle and cattle vaccinated with a homologous adenovirus-vectored vaccine." (2016) BMC Veterinary Research Vol. 12, Art. No.: 205).

The virus occurs as seven genetically and antigenically distinct serotypes-, A, C, Asia 1, and Southern African Territories (SAT) 1-3. Each serotype has multiple subtypes within each serotype.

B) Structure-Based Functional Analysis of Picornaviruses

The Picornavirus family has several conserved proteins across its family members. These proteins are known as leader proteins (L genomic region), capsid proteins (P1 genomic region), membrane proteins (2B), helicase (2C), protease (3C), and polymerase (3D).

The FMDV particle consists of a positive-strand RNA molecule of approximately 8,500 nucleotides, enclosed within an icosahedral capsid. The genome encodes a unique polyprotein from which four structural proteins (P1A, P1B, P1C, and P1D; also referred to as VP4, VP2, VP3, and VP1, respectively) and nine nonstructural proteins are cleaved by viral proteases. (Guzman, E., et al, Induction of a Cross-Reactive CD8+ T Cell Response following Foot-and-Mouth Disease Virus Vaccination. (2010) J. Virology, Vol. 84, No. 23, p. 12375-12384).

Specifically, the viral genome is approximately 8.3 kb in length and is enclosed within a protein capsid. The RNA genome contains a large open reading frame that encodes four viral structural proteins (VP1, VP2, VP3, and VP4) from the P1 polypeptide and seven non-structural proteins (Lpro, 2A, 2B, 2C, 3A, 3b, 3Cpro, and 3Dpol) from the P2 and the P3 polypeptides. The 5' and the 3' untranslated regions (UTRs) are important for viral replication and translation. The capsid contains 60 copies each of four different structural proteins (VP1-4). VP1-3 are surface exposed, while VP4 is internalized. The crystallographic structure of the FMDV capsid revealed that immunological epitopes are mostly found on surface-oriented interconnecting loops between structural elements. The highly conserved Arg-Gly-Asp (RGD) amino acid motif within the G-H loop plays a major role in viral entry into host cells and contributes to protective immunity in the host. The αV family of integrin receptors binds with the G-H loop for receptor-mediated viral entry. Absence of this receptor on host cells diminishes the ability of viral entry. The low fidelity RNA polymerase leads to error prone viral replication and genome mutations. The involvement of immunologically critical sites can lead to the emergence of immunological variants of FMDV. (Singh, K. R., et al., (2019) "Foot-and-Mouth Disease Virus: Immunobiology, Advances in Vaccines and Vaccination Strategies Addressing Vaccine Failures—An Indian Perspective." Vaccines 7(3), 90).

C) Immune Responses to Picornaviridae Virus Infection

High body temperature and appearance of vesicular lesions on oro-nasal mucosa, interdigital cleft, coronary band, udder, and teats epithelium are primary characteristics of the disease. FMD results in loss of appetite and body weight, milk yield, draft power, and abortions in advanced pregnant animals. (Singh, K. R., et al., (2019) "Foot-and-Mouth Disease Virus: Immunobiology, Advances in Vaccines and Vaccination Strategies Addressing Vaccine Failures—An Indian Perspective." Vaccines 7(3), 90). Specifically, FMDV infection in susceptible animals results in viremia 1-3 days post-infection, followed by a rapid onset of clinical disease, with an incubation period of 2-10 days. (Diaz-San Segundo F, Rodriguez-Calvo T, de Avila A, Sevilla N (2009) Immunosuppression during Acute Infection with Foot-and-Mouth Disease Virus in Swine Is Mediated by IL-10. PLoS One 4(5): e5659).

Protection against FMDV is often associated with the induction of high levels of circulating neutralizing antibodies in serum; these neutralizing antibodies can be found as early as 4 days post-infection, although this response does not ensure clinical protection, and animals with low levels of neutralizing antibodies may nevertheless be protected. This indicates that cell-mediated immunity may play a role in the elimination of the virus. Thus, given that exposure to the virus results in the production of T-cell dependent neutralizing IgG class antibodies, and subsequent T-cell dependent memory, it appears that CD4+ cells must be stimulated. (Diaz-San Segundo F, Rodriguez-Calvo T, de Avila A, Sevilla N (2009) Immunosuppression during Acute Infection with Foot-and-Mouth Disease Virus in Swine Is Mediated by IL-10. PLoS One 4(5): e5659).

D) Picornaviridae Vaccine Development

Control measures include slaughter, restrictions on the movement of livestock and vaccination of susceptible animals. Current inactivated FMD vaccines that have been developed empirically generate short-term, serotype-specific protection, mainly through neutralizing antibodies and protection is generally correlated with high levels of neutralizing antibodies. (Carr, B Veronica et al. (2013) "CD4+ T-cell responses to foot-and-mouth disease virus in vaccinated cattle." J. General Virology vol. 94, Pt 1: 97-107).

Ongoing efforts worldwide are trying to refine the existing vaccine or to develop an alternate vaccine formulation for effective vaccination. Some of the recent approaches, including virus-like particles, gene-deleted modified virus vaccine, and vector-mediated vaccines, have been explored with variable success. Other options that have been advocated include the use of vaccines without handling live virus, such as DNA vaccine, peptide vaccines, and sub-unit vaccines. Presently, all these vaccines are in the experimental stage and have not been tested in the field. (Singh, K. R., et al., (2019) "Foot-and-Mouth Disease Virus: Immunobiology, Advances in Vaccines and Vaccination Strategies Addressing Vaccine Failures—An Indian Perspective." Vaccines 7(3), 90).

Vaccines are available for PV, HAV and FMDV. When the oral vaccines are given to immunocompromised individuals, they may be chronically infected, and remain secretors of vaccine-derived variants of virus for years. There is no effective prophylaxis available for these or other picornaviruses.

The available vaccines do not prevent primary infection and offer protection only from generalized clinical disease. Disadvantages of current vaccines include the insufficient block of virus shedding, failure to prevent virus carriers, short duration of immunity and difficulty in distinguishing vaccinated from infected animals. (Carr, B Veronica et al. (2013) "CD4+ T-cell responses to foot-and-mouth disease virus in vaccinated cattle." J. General Virology Vol. 94, Pt 1:97-107). The current, chemically inactivated trivalent vaccine against serotype O, A, and Asia 1 suffers limitations, including the requirement of a biosafety level III facility for mass production of virus antigen, thermolability, and only short-lived immunity. (Singh, K. R., et al., (2019) "Foot-and-Mouth Disease Virus: Immunobiology, Advances in Vaccines and Vaccination Strategies Addressing Vaccine Failures—An Indian Perspective." Vaccines 7(3), 90).

Moreover, immunity against one serotype does not provide protection against other serotypes or sometimes to the variants within the same serotype. (Id.).

One of the major difficulties in implementing vaccination is the inability to distinguish vaccinated animals from infected/recovered animals, which may still be shedding virus. (Guzman, E., et al. (2010) "Induction of a Cross-Reactive CD8+ T Cell Response following Foot-and-Mouth Disease Virus Vaccination." J. Virology, Vol. 84, No. 23, p. 12375-12384).

IV) Hepadnaviridae Viruses

A) Overview of the Hepadnaviridae Family

The Hepadnaviridae family, whose member genuses include Orthohepadnavirus and Avihepadnavirus, are spherical, occasionally pleomorphic, 42-50 nm in diameter, with no evident surface projections after negative staining. Projections are visible in cryo-EM pictures. The outer, detergent-sensitive, envelope contains the surface proteins and surrounds an icosahedral nucleocapsid core that is composed of one major protein species, the core protein. The nucleocapsid encloses the viral genome (DNA), the viral DNA polymerase, and associated cellular protein(s), including protein kinase and chaperones that appear to play a role in the initiation of viral DNA synthesis. (King, Andrew. Virus Taxonomy: Ninth Report of the International Committee on Taxonomy of Viruses. Elsevier, 2011).

Hepadnavirus infection induces overproduction of surface proteins that are secreted into the blood as pleomorphic lipoprotein particles together with virus. The genome consists of a partially double-stranded DNA that is held in a circular conformation by base pairing in a cohesive overlap between the 5' ends of the two DNA strands. The length of the cohesive overlap is about 240 bp for the orthohepadnaviruses and 50 bp for the avihepadnaviruses, and the size of the genome ranges from 3.0 to 3.3 kb in different family members. Virions and empty subviral particles may contain two or three surface proteins, with a common C-terminus but distinct N-termini due to different sites of translation initiation. The core protein has a large N-terminal domain and a small RNA-binding domain at the C-terminus. Core protein above a threshold concentration can self-assemble via dimers to complete nucleocapsids in the absence of other viral components. (King, Andrew. Virus Taxonomy: Ninth Report of the International Committee on Taxonomy of Viruses. Elsevier, 2011).

i) Hepatitis B Virus (HBV)

Hepatitis B virus (HBV) is part of the Orthohepadnavirus genus. Chronic viral hepatitis infections are a major public health concern, with an estimated 290 million individuals infected with HBV globally. This virus has been a passenger in human populations for >30,000 years, and remains highly prevalent in some settings. (Lumley, Sheila F et al. (2018) "Hepatitis B Virus Adaptation to the CD8+ T Cell Response: Consequences for Host and Pathogen." Frontiers in Immunology vol. 9 1561).

B) Structure-Based Functional Analysis of Hepadnaviridae Viruses

HBV are small, enveloped, primarily hepatotropic viruses. The majority of nucleocapsid cores are about 36 nm in diameter and contain 240 core protein subunits, while a minority are approximately 32 nm in diameter and consist of only 180 subunits. (King, Andrew. Virus Taxonomy: Ninth Report of the International Committee on Taxonomy of Viruses. Elsevier, 2011).

At only 3,200 bp, HBV has one of the smallest genomes of all known pathogenic viruses. The partially double-stranded DNA (dsDNA) circular genome consists of four genes, X, Polymerase (P), Core (C), and Surface (S), and a high proportion of the genome is encoded on overlapping open reading frames. During transcription, the partially dsDNA genome is "completed" to form a fully dsDNA molecule, which is subsequently supercoiled to form covalently closed circular DNA (cccDNA). This cccDNA is reverse transcribed by HBV reverse transcriptase (RT), an enzyme lacking 3'-5' exonuclease proof-reading capacity, thereby introducing mutations into the HBV genome during each round of replication (in duck hepadnavirus, the mutation rate is estimated at between $0.8 \times 10^{-5}$ and $4.5 \times 10^{-5}$ substitutions per nucleotide per replication). The mutations generated result in a viral quasispecies, comprised of dominant genotype(s) surrounded by clouds of closely related HBV variants. (Lumley, Sheila F et al. (2018) "Hepatitis B Virus Adaptation to the CD8+ T Cell Response: Consequences for Host and Pathogen." Frontiers in Immunology vol. 9, 1561).

C) Immune Response to Hepadnaviridae Infection

HBV causes variable degrees of liver disease in humans. Infection with HBV can be either acute or chronic; while adult infections have a relatively low rate of chronicity (around 5%), neonatal infections usually have a high persistence rate. Chronic infection is mostly asymptomatic, but HBV carriers are at risk of developing life threatening cirrhosis and later on hepatic carcinoma. (Busca, Aurelia, and Ashok Kumar. (2014) "Innate immune responses in hepatitis B virus (HBV) infection." Virology Journal vol. 11 22).

Two studies, both of which utilized human donor liver tissue and paired blood samples, analyzed the role of $T_RM$ in the context of viral hepatitis. One study focused on patients with hepatitis B viral infections (HBV), while the other study included patients with HBV or hepatitis C viral infections. A higher proportion of liver T cells from patients who demonstrated partial control of HBV infection had a $T_{RM}$ phenotype, when compared to healthy controls. Given that the overall numbers of T cells in the liver of healthy and HBV-infected individuals were similar, this threefold increase in $T_{RM}$ numbers appears to be due to an increased predisposition of T cells to adopt the $T_{RM}$ phenotype in virally infected liver tissue, rather than expansion of pre-existing $T_{RM}$. The numbers of T cells co-expressing CD69 and CD103 increased by fourfold in chronic hepatitis C patients. (Muruganandah, V., Sathkumara, H. D., Navarro, S., & Kupz, A. (2018). "A Systematic Review: The Role of Resident Memory T Cells in Infectious Diseases and Their Relevance for Vaccine Development." Frontiers in Immunology, 9, 1574).

The reciprocal relationship between viral loads and liver $T_{RM}$ numbers suggests that $T_{RM}$ play a vital role in infection control. Ex vivo stimulation of $T_{RM}$ showed heterogeneous antigen specificity, with a number of HBV antigens being able to initiate effector responses. However, viral envelope peptides seemed to generate the greatest capacity to induce production of IFNγ, TNFα, and IL-2. Analysis of $T_{RM}$ from healthy liver tissue revealed a noticeably reduced expression of granzyme B, when compared to non-resident counter parts. This suggests that hepatic $T_{RM}$ have less cytolytic capacity than circulating T cells. (Id.).

However, liver $T_{RM}$ of patients with chronic hepatitis B (CHB) expressed markedly higher amounts of granzyme B when compared to healthy controls. Liver $T_{RM}$ also showed increased expression of the inhibitory molecule PD-1 compared to non-resident T memory cells. Without being limited by theory, the downregulation of granzyme B and upregulation of PD-1 in healthy liver tissue may be a precautionary measure intended to prevent immunopathology, given the liver's role in filtering high amounts of antigen draining from the mesenteric circulation. This is of great importance in viral hepatitis infections as immunopathology is largely involved in the progression of viral hepatitis that leads to cirrhosis and hepatocellular cancer. The increased production of granzyme by $T_{RM}$ in CHB patients may be part of the pathogenesis of fulminant hepatitis. (Id.).

D) Hepadnaviridae Vaccine Development

The first HBV vaccine was prepared from the plasma of asymptomatic carriers of HBV in the form of purified inactivated HBsAg particles. Later on, the r-HBsAg vaccines that contain the major (s) small protein spanning the hydrophilic amino acids 124-149 as the dominant immunogenic epitope were developed. HBV vaccinations induce neutralizing antibodies (anti-HBs) that are directed mainly towards the "a" determinant of HBsAg in all HBV genotypes from A to H. The r-HBsAg vaccine elicits active synthesis of anti-HBs and prolonged immunological memory which provides continuous protection. Persistent memory for 5 years or more is recognized from large, fast increases in anti-HBs level after booster vaccination, even in those who showed undetectable anti-HBs as measured by the available commercial kits. Using an in vitro enzyme linked immunosorbent assay (spot-ELISA), it was shown that the number of memory B lymphocytes able to induce anti-HBs does not decrease with decline of the anti-HBs level. Both dose and structure of vaccine antigen influence the primary antibody response as well as the development of immune memory. (Said, Zeinab Nabil Ahmed, and Kouka Saadeldin Abdelwahab. (2015) "Induced immunity against hepatitis B virus." World Journal of Hepatology, Vol. 7,12: 1660-70).

Current vaccination and treatment approaches are hindered by poor diagnosis and access to treatment, drug and vaccine escape mutants, viral rebound on treatment cessation or immunosuppression, and lack of curative therapy.

V) Retroviridae Viruses

A) Overview of the Retroviridae Family

The family Retroviridae is a large diverse group of enveloped RNA viruses which include the following genera: Alpharetrovirus, Betaretrovirus, Deltaretrovirus, Epsilonretrovirus, Gammaretrovirus, Lentivirus, and Spumavirus. Retroviridae viruses include members of the Lentivirus genus, which are complex retroviruses that include human pathogens such as Human Immunodeficiency Virus (HIV) and Equine Infectious Anemia (EIAV), and feline immunodeficiency virus. Other Retrovirdae virus families include Human T-Lymphotrophic viruses (HTLV), and Hepadnaviridae which encompasses Hepatitis B (HVB). Members of Retroviridae are characterized by the ability to transcribe their RNA genome into linear double-stranded DNA during their replication cycle with a reverse transcriptase enzyme. During the replication cycle, viral dsDNA is usually integrated into the host genome as a DNA provirus which can remain silent (i.e., latent) or become transcriptionally active to produce virions (Fermin, Gustavo, and Paula Tennant. Viruses: Molecular Biology, Host Interactions and Applications to Biotechnology, edited by Jerome E. Foster, Elsevier Science & Technology (2018). Available from the ProQuest Ebook Central website).

Many lentiviral viruses may be characterized by a long latency period and progressive infection in which the virus evades the immune response of the host. Lentiviruses insert genetic information into the deoxyribonucleic acid (DNA) of the host cell and have the unique ability to replicate in dividing and non-dividing cells.

All replication-competent retroviruses, including HIV, contain the following three genes: gag (group antigen, encoding the core and matrix proteins, p24 and p17), pol (polymerase, encoding the enzymatic proteins, reverse transcriptase, RNAase, protease and integrase), and env (encoding the envelope and transmembrane glycoproteins, gp 120 and gp 41) (Welles, L. and Yarchoan, R., In Antimicrobial Therapy and Vaccines. Yu, V L, Merigan, Jr, T C and Barriere, S L Eds, Williams & Wilkins, Baltimore, (2005), pgs. 1264-1287). They share the presence of antigens, the ability to replicate, and a viral envelope.

i) Human Immunodeficiency Virus (HIV)

Human Immunodeficiency Virus (HIV) is a complex retrovirus which may be transmitted to humans from primates and between humans through the exchange of fluid, such as semen, vaginal and anal mucus, blood, and breast milk, through cuts, openings or mucous membranes of the human body. HIV is a rapidly mutating and recombining RNA virus that exhibits considerable genetic diversity with nine subtypes within just the major group of HIV Type I (HIV-1), rapid turnover rates, and persistency. HIV-1 can further be classified into 4 viral groups, or isolates: M, N, O, and P. The other major group of HIV is HIV Type 2 (HIV-2) (Moss, J. (2013) "HIV/AIDS Review" Radiologic Technology, Vol. 84, No. 3, 247-267). The majority of HIV/AIDS related deaths are concentrated in South Africa, however, the HIV infection is seen globally, including in sub-Saharan Africa, the United States, Europe, and Asia (Id.).

B) Structure-Based Functional Analyses of Retroviradae Viruses

The mature HIV particle is round, measuring approximately 100 nm in diameter, with an outer lipid membrane as its envelope. The envelope contains 72 knobs, composed of trimers of the Env proteins. The trimers of gp120 surface protein (SU) are anchored to the membrane by the trimers of the transmembrane protein gp41 (TM). Conformation-dependent neutralizing epitopes are found on the gp120 protein. These are present on the native protein but are only partially expressed on the unfolded denatured protein. The viral envelope is composed of a lipid bi-layer and, in mature virus particles, the envelope proteins SU and TM. It covers the symmetrical outer capsid membrane, which is formed by the matrix protein (MA, p17). The conical capsid is assembled from the inner capsid protein p24 (CA). Depending on the section plane, the capsid appears as a cone, a ring or an ellipse. The tapered pole of the capsid is attached to the outer capsid membrane. Two identical molecules of viral genomic RNA are located inside the capsid and several molecules of the viral enzymes RT/RNase H and IN bound to the nucleic acid. Also present in virus particles are oligopeptides that are generated after release from the cell during the maturation of virions by proteolytic processing of the precursor proteins (p55, p160). (German Advisory Committee Blood (Arbeitskreis Blut), Subgroup 'Assessment of Pathogens Transmissible by Blood'. (2016) "Human Immunodeficiency Virus (HIV)." Transfusion medicine and hemotherapy: offizielles Organ der Deutschen Gesellschaft fur Transfusionsmedizin and Immunhamatologie, Vol. 43,3: 203-22).

C) Immune Response to Infection with Retroviruses

During the first stage of infection, known as the primary infection stage, the immune system of the infected person begins responding to the virus by generating HIV antibodies (in response to HIV antigens, a process known as seroconversion) and cytotoxic lymphocytes. Following seroconversion, a clinically asymptomatic period normally follows initial HIV infection, where levels of HIV in the peripheral blood decrease but function highly in the lymph nodes to destroy CD4 lymphocytes. The immune system becomes progressively damaged as the patient's immune system deteriorates from excessive damage to tissues and lymph nodes, viral mutation and increased destruction and reduced replacement of T cells (see Moss, J. (2013) "HIV/AIDS Review" Radiologic Technology, Vol. 84, No. 3, 247-267). In the second stage, laboratory results indicate 14% to 29% CD4+ T cells per L of blood and mild symptoms are perceived. In the third stage, CD4+ T cell count is below 14% and advanced symptoms are seen. By the fourth stage, acquired immunodeficiency syndrome has developed and severe symptoms are seen. (Id.).

A substantial reduction in the number of T cells seriously weakens the immune system. As CD4 lymphocyte counts decrease to fewer than 200 cells/µL of blood, symptomatic HIV infection can be triggered by the emergence of certain opportunistic infections that the immune system would normally prevent. Examples include pneumonia, diarrhea, eye infections, and meningitis. HIV patients are also susceptible to cancers and illnesses for example Kaposi sarcoma, non-Hodgkin lymphoma, central nervous system lymphoma, HIV encephalopathy, progressive multifocal leukoencephalophathy, lymphoid interstitial pneumonia, and HIV wasting syndrome. (Id.).

HIV initially infects CD4+CCR5+ T cells. The virus then spreads via the blood from the mucosal-associated lymphoid tissue to other lymphoid tissue, especially in the gut associated lymphoid tissue where it can replicate liberally. See Id. In acute HIV-1 infection, memory CD4+ T cells are massively depleted from the lymphoid system, particularly in the gut involving both direct targeting by the virus and bystander activation-induced cell death (See Mattapallil J J, Douek D C, Hill B, Nishimura Y, Martin M, Roederer M (2005) Massive infection and loss of memory CD4+ T cells in multiple tissues during acute SIV infection. Nature 434: 1093-1097; see also Douek D C, Brenchley J M, Betts M R, Ambrozak D R, Hill B J, Okamoto Y, Casazza J P, Kuruppu J, Kunstman K, Wolinsky S, et al. (2002) HIV preferentially infects HIV-specific CD4+ T cells. Nature 417: 95-98). This applies to all memory CD4+ T-cell populations but those specific for HIV may be preferentially infected and destroyed (See Douek D C, Roederer M, Koup R A (2009) Emerging concepts in the immunopathogenesis of AIDS. Annu Rev Med 60: 471-484). However, the percentage of HIV-specific CD4+ T cells that are infected, even in the presence of high level viremia, is typically only a few percent or less, suggesting that the majority of these cells somehow escape infection despite being activated at a time of very high viremia.

Despite initial and persistent damage to CD4+ T cells, and a lack of detectable HIV-specific CD4+ T helper cells, the magnitude and breadth of CD8+ T-cell responses to HIV in infected humans were found to be robust, with direct effector function of such a magnitude that it could be readily detected in freshly isolated lymphocytes from peripheral blood and brochoalveolar lavage in persons with AIDS. (Walker, B and McMichael, A. "The T-Cell Response to HIV. (2012 November)" Cold Spring Harb Perspect Med. 2(11): a007054; citing Murray, H W et al. (1984) "Impaired production of lymphokines and immune (γ) interferon in the acquired immunodeficiency syndrome." N. Engl. J. Med. 310: 883-889; Lane, H C et al. (1985) "Qualitative analysis of immune function in patients with the acquired immunodeficiency syndrome; Evidence for a selective defect in soluble antigen recognition," N. Engl. J. Med. 313: 79-84). Acute phase CD8+ T-cell responses occur in the setting of acute phase proteins and proinflammatory cytokines. The initial response is narrowly directed, predominantly at epitopes in Env and Nef, regions that are among the most variable in the virus. The breadth of responses increases over time, as do the number of HLA alleles that are involved in recognition of infected cells. Immunization studies in animal models indicate that the CD8+ T-cell compartment has enormous expansion capacity, without affecting the size of the naïve CD4+, CD8+, or B-cell populations, and while preserving memory CD8+ T-cell populations to other pathogens. HIV-specific CD8+ T-cell responses remain detectable throughout the course of disease, and are actually broader and higher in persons with progressive infection than in those with controlled infection. (Id., citing (Vezys, V. et al. (2009) "Memory CD8 T cell compartment grows in size with immunological experience," Nature 457: 196-199; Pereyra F. et al. (2008) "Genetic and immunologic heterogeneity among persons who control HIV infection in the absence of therapy," J. Infect. Dis. 197: 563-571).

Specificity of responses during the chronic phase of infection repeatedly suggests that Gag targeting is associated with lower viral load. (Id., citing Edwards, B H et al. (2002) "Magnitude of functional CD8+ T-cell responses to the gag protein of human immunodeficiency virus type 1 correlates inversely with viral load in plasma. J Virol 76: 2298-2305; Zuniga, R. et al. (2006) Relative dominance of Gag p24-specific cytotoxic T lymphocytes is associated with human immunodeficiency virus control. J Virol 80: 3122-3125; Kiepiela et al. (2007) "CD8+ T-cell responses to different HIV proteins have discordant associations with viral load." Nat Med 13: 46-53). In a large study of persons with clade C virus infection, the broader the Gag-specific response, the lower the viral load, and somewhat paradoxically, the broader the Env-specific response, the higher the viral load. (Id.; citing Kiepiela et al. (2007) "CD8+ T-cell responses to different HIV proteins have discordant associations with viral load." Nat Med 13: 46-53; Ngumbela, K C et al. (2008) "Targeting of a CD8 T cell env epitope presented by HLA-B*5802 is associated with markers of HIV disease progression and lack of selection pressure." AIDS Res Hum Retroviruses 24: 72-82).

Generally, in those infected with HIV-1, the T-cell responses are dominated by CD8+ T cells. These are much stronger than CD4+ T-cell responses which are damaged by the virus. (Id., citing (Ramduth, D et al. (2005) Differential immunogenicity of HIV-1 clade C proteins in eliciting CD8+ and CD4+ cell responses. J Infect Dis 192: 1588-1596). In murine models in which CD4+ T cells are depleted either with antibody infusion or genetically, CD8+ T-cell responses are greatly impaired. (Id., citing (Janssen, E M et al. (2003) CD4+ T cells are required for secondary expansion and memory in CD8+ T lymphocytes. Nature 421: 852-856; Shedlock, D J and Shen, H (2003) Requirement for CD4 T cell help in generating functional CD8 T cell memory. Science 300: 337-339; Sun, J C and Bevan, M J (2003) Defective CD8 T cell memory following acute infection without CD4 T cell help. Science 300: 339-342). On antigen stimulation, they expand rapidly to exhaustion and their IL-2-dependent progression to long term memory populations is abrogated. (Id., citing (Kamimura, D and Bevan, M J (2007) Naive CD8+ T cells differentiate into protective memory-like cells after IL-2 anti IL-2 complex treatment in vivo. J Exp Med 204: 1803-1812). In HIV-1 infection CD4+ T cells, though greatly depleted, are not entirely absent, but abnormalities in the development of CD8+ T-cell responses could be consistent with partial loss of CD4+ T-cell help, or impaired function of what cells remain (Id., citing (Pitcher, C J et al. (1999) HIV-1-specific CD4+ T cells are detectable in most individuals with active HIV-1 infection, but decline with prolonged viral suppression. Nat Med 5: 518-525).

Cross-sectional data in chronically infected persons indicate a link between strong CD4+ T-cell responses and effective CD8+ T-cell responses. (Id., citing (Kalams, S A et al. (1999) Association between virus-specific cytotoxic T-lymphocyte and helper responses in human immunodeficiency virus type 1 infection. J Virol 73: 6715-6720). Recent data implicate CD4+ T cells that make IL-21 as particularly important in maintaining CD8+ responses. (Id., citing (Chevalier M F, Jülg B, Pyo A, Flanders M, Ranasinghe S, Soghoian D Z, Kwon D S, Rychert J, Lian J, Muller M I, et al. HIV-1-specific interleukin-21+CD4+ T cell responses contribute to durable viral control through the modulation of HIV-specific CD8+ T cell function. (2011) J Virol 85: 733-741; Williams L D, Bansal A, Sabbaj S, Heath S L, Song W, Tang J, Zajac A J, Goepfert P A Interleukin-21-producing HIV-1-specific CD8 T cells are preferentially seen in elite controllers. (2011) J Virol 85: 2316-2324)). While early studies showed a lack of CD4+ T-cell responses, it has been reported that, when patients were treated very early with antiretroviral drugs, strong CD4+ T-cell responses to HIV antigens could be rescued.

Antiviral CD8+ T cells were first identified as T cells that mediate lysis of virus-infected cells and are often referred to as cytotoxic T lymphocytes (Id., citing Plata F., et al. (1975) Primary and secondary in vitro generation of cytolytic T lymphocytes in the murine sarcoma virus system. Eur J Immunol 5: 227-233). Although most antigen-specific CD8+ T cells have this activity, they can use other effector mechanisms in addition. These include production of interferon-γ, IL-2, TNF-α, MIP-1α (renamed CCL3), MIP-1β (CCL4), and RANTES (CCL5). However, this effector function may not always be present and may take several days to appear. In contrast memory CD8+ T cells respond rapidly producing interferon-γ within a few hours. (Id., citing Lalvani, A. et al. (1997) Rapid effector function in CD8+ memory T cells. J Exp Med 186: 859-865). Production of lytic granules requires a bit longer but once activated, effector memory CD8+ T cells can release perforin and granzymes within minutes. (Id., citing Barber, D L et al. (2003) Cutting edge: Rapid in vivo killing by memory CD8 T cells. J Immunol 171: 27-31). The delay in activating lytic functions in memory T cells probably protects the body from autoimmune attack when the TCR encounters weakly binding self antigens.

Although lytic potential may still be essential, during chronic infection, once viral set point is established, the other functions of CD8+ T cells may become more important, although lytic potential may still be essential. (Id., citing (Betts, M R and Harari, A (2008) Phenotype and function of protective T cell immune responses in HIV. Curr Opin HIV AIDS 3: 349-355). In patients who control virus well, the T cells are more quiescent than in acute infection. Many studies have shown that T cells in those who control HIV-1 well are polyfunctional, showing not only cytolytic potential but also have the capacity to produce cytokines and chemokines, although it is not clear whether this is cause or effect. (Id., citing (Betts, M R and Harari, A (2008) Phenotype and function of protective T cell immune responses in HIV. Curr Opin HIV AIDS 3: 349-355). Prolonged antigen stimulation in the absence of excessive activation and exhaustion, as occurs in slow progressors, could favor expression of multiple functions. Production of IL-2 may be important in the long term persistence of CD8+ T cells and can be provided by the CD8+ T cell itself or by CD4+ T cells, which survive much better in those whose disease progresses slowly. (Id.; citing (Rosenberg, E S et al. (1997) Vigorous HIV-1-specific CD4+ T cell responses associated with control of viremia. Science 278: 1447-1450; Zimmerli, S C et al. (2005) HIV-1-specific IFN-γ/IL-2-secreting CD8 T cells support CD4-independent proliferation of HIV-1-specific CD8 T cells. Proc Natl Acad Sci 102: 7239-7244). Similar observations have been made in HIV-2 infection in which elite controllers are relatively common. (Id.; citing (Duvall, M G et al. (2008) Polyfunctional T cell responses are a hallmark of HIV-2 infection. Eur J Immunol 38: 350-363). These findings are entirely consistent with data in CD4+ T-cell-depleted mice that show the importance of IL-2 in the maintenance of long-term CD8+ T-cell memory. (Id.; citing Williams M A, Tyznik A J, Bevan M J (2006) Interleukin-2 signals during priming are required for secondary expansion of CD8+ memory T cells. Nature 441: 890-893)).

Evidence shows that CD8+ T cells are vital in controlling early HIV infection. Studies of human tissue samples have revealed that $T_{RM}$ are generated in response to HIV infection in multiple locations, including the gastrointestinal tract and the female reproductive tract. Furthermore, individuals who appeared to naturally control infection had $T_{RM}$ that were capable of producing the highest polyfunctional immune responses when compared to individuals who did not. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574). However, the $T_{RM}$ population within the HIV-specific CD8+ T cell compartment in individuals who controlled infection was under-represented when compared to individuals who were viremic. (Id.)

Similar to other infections in various sites, CD8+ $T_{RM}$ in the context of HIV can be sub-divided into two subsets based on the expression of CD103 (also called human mucosal lymphocyte antigen 1, alpha E beta 7 integrin). Analysis of the ectocervical epithelium and menstrual blood revealed that HIV-infected women were more likely to have CD103− $T_{RM}$ when compared to healthy individuals. This reduced expression of CD103 may be explained by the HIV-induced depletion of CD4+ T cells which appear to be vital in providing help to CD8+ T cells for up-regulating CD103. The CD103− populations of the ectocervix resided closer to the basement membrane of the epithelium when compared to their CD103+ counterparts. The CD103+ population from infected individuals appears to express higher levels of PD-1. In a separate study, adipose PD-1+ CD4+ $T_{RM}$, appeared to remain relatively inactive during HIV infection and may serve as a reservoir for HIV. As such chronically activated $T_{RM}$ and $T_{RM}$ exposed to immunomodulated environments (such as the adipose tissue) may be unable to elicit a full effector response, favoring the progression of HIV infection. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

It also appears that HIV has the ability to disrupt CCR5-mediated CD8+ T cell migration into the cervical mucosa, thereby impairing the development of $T_{RM}$ populations. Human studies suggest that $T_{RM}$, especially CD8+ $T_{RM}$, play an important role in combating HIV infection In a Simian Immunodeficiency Virus model of rhesus macaques, intravenous administration of SIVmac239Δnef generated a population of CD8+ $T_{RM}$ in vaginal tissue and the gut that participated in protection. In a murine model, a mucosal vaccination strategy in which intranasal administration of an influenza-vector expressing the HIV-1 Gag protein p24 followed by an intravaginal booster induced CD8+ $T_{RM}$ in the vagina. Antigen stimulation of these CD8+ $T_{RM}$ resulted in the recruitment of B cells, natural killer cells, and CD4+ T cells. While the recruitment of innate and adaptive immune cells may be beneficial in early viral clearance, the recruitment of CD4+ T cells may be detrimental in the context of HIV as they are the target for HIV. Hence, incidental recruitment of CD4+ T cells to sites of HIV entry (female reproductive tract and rectum) by prime and pull vaccination strategies may unintentionally increase susceptibility to infection. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

D) Retroviridae Viruses Vaccine Development

Vaccine development for retroviruses, lentiviruses, and specifically HIV have been largely unsuccessful. Both antibodies and cytotoxic T lymphocytes are produced upon infection with HIV (Seabright, G. E. et al., (2019) "Protein and Glycan Mimicry in HIV Vaccine Design," J. MOl/Biol. 431 (12): 2223-2247). However, there have been some protective immune responses to vaccines that invoke T cell-mediated immunity, polyfunctional antibody responses, antibody-dependent cellular cytotoxicity, and broadly neutralizing antibodies (bNab) (MacGregor, R. et al. (2002) "T-cell responses induced in normal volunteers immunized with a DNA-based cavvine containing HIV-1 env and rev." AIDS 16, 2137-2143).

Despite the growing understanding of human immunodeficiency virus (HIV) disease pathogenesis and the structure of its key antigenic targets, efforts to develop effective vaccines against HIV continue to fail.

DNA vaccines that invoke T cell mediated immunity developed for HIV still lack the ability to induce long-term immune responses. For example, a DNA vaccine that encoded env and rev was shown to induce CD4+ T cell responses and poorly induce CD8+ T cell responses (MacGregor, R. et al. (2002) "T-cell responses induced in normal volunteers immunized with a DNA-based cavvine containing HIV-1 env and rev." AIDS 16, 2137-2143). Similar results were seen in DNA vaccines that encode gag and pol genes (Tavel, J. A., et al., (2007) "Safety and Immunogenecity of a Gag-Pol candidate HIV-1 DNA vaccine administered by a need-free device in HIV-1-seronegative subjects." J. AIDS 44, 601-605).

Bacteria

VI) Cornebacteriaceae

A) Overview of the Corynebactericeae Family

The family Corynebacteriaceae is composed of the type genus *Corynebacterium* with almost 90 species and the monospecific genus *Turicella*. The status of *Turicella* as a genus is supported by phenotypic characteristics. Both taxa form a distinct clade in the order Corynebacteriales which is clearly separated from the related families Dietziaceae and Tsukamurellaceae. Most *Corynebacterium* species contain mycolic acids with 22-36 carbons. Members of the family Corynebacteriaceae are found in diverse environments. The closely related organisms *Corynebacterium diphtheria (C. diphtheria)*, *Corynebacterium ulcerans*, and *Corynebacterium pseudotuberculosis* are the only species which may produce potent exotoxins, i.e., diphtheria toxin and phospholipase D, both of which play a significant role in pathogenicity. (Tauch A., Sandbote J. (2014) The Family Corynebacteriaceae. In: Rosenberg E., DeLong E. F., Lory S., Stackebrandt E., Thompson F. (eds) The Prokaryotes. Springer, Berlin, Heidelberg).

*C. diphtheria* causes diphtheria, a disease that primarily infects children. In the United States, Europe, and Eastern Europe recent outbreaks of diphtheria have occurred largely among alcohol and/or drug abusers. (Murphy J R. *Corynebacterium Diphtheriae*. (1996) In: Baron S, editor. Medical Microbiology. 4th edition. Galveston (Tex.): University of Texas Medical Branch at Galveston; Chapter 32). Cases of diphtheria further occur in India, Indonesia, Nepal, Angola, and Brazil.

i) *Corynebacterium diphtheria (C. diphtheria)*

*C. diphtheria* is a nonmotile, noncapsulated, club-shaped, Gram-positive *bacillus* known to produce the diphtheria toxin. Toxigenic strains are lysogenic for one of a family of corynebacteriophages that carry the structural gene for diphtheria toxin, tox. *C. diphtheriae* is classified into biotypes (mitis, intermedius, and gravis) according to colony morphology, as well as into lysotypes based upon corynebacteriophage sensitivity. (Murphy J R. *Corynebacterium Diphtheriae*. (1996) In: Baron S, editor. Medical Microbiology. 4th edition. Galveston (Tex.): University of Texas Medical Branch at Galveston; Chapter 32). The most severe diseases are associated with the gravis biotype.

*C. diphtheriae* is spread by droplets, secretions, or direct contact. In situ lysogenic conversion of nontoxigenic strains to a toxigenic phenotype has been documented. Infection is spread solely among humans, although toxigenic strains have been isolated from horses. In regions where immunization programs are maintained, isolated outbreaks of disease are often associated with a carrier who has recently visited a subtropical region where diphtheria is endemic. Large-scale outbreaks of disease may occur in populations where active immunization programs are not maintained. (Murphy J R. *Corynebacterium Diphtheriae*. (1996) In: Baron S, editor. Medical Microbiology. 4th edition. Galveston (Tex.): University of Texas Medical Branch at Galveston. Chapter 32).

B) Structure Based Functional Analysis of Cornebacteriaceae Bacteria

Diphtheria toxin can be proteolytically cleaved into two fragments: an N-terminal fragment A (catalytic domain), and fragment B (transmembrane and receptor binding domains). Fragment A catalyzes the NAD+-dependent ADP-ribosylation of elongation factor 2, thereby inhibiting protein synthesis in eukaryotic cells. Fragment B binds to the cell surface receptor and facilitates the delivery of fragment A to the cytosol. (Murphy J R. *Corynebacterium Diphtheriae*. (1996) In: Baron S, editor. Medical Microbiology. 4th edition. Galveston (Tex.): University of Texas Medical Branch at Galveston. Chapter 32).

C) Immune Response to Infection with Cornebacteriaceae Bacteria

There are two types of clinical diphtheria: nasopharyngeal and cutaneous. Symptoms of pharyngeal diphtheria vary from mild pharyngitis to hypoxia due to airway obstruction by the pseudomembrane. The involvement of cervical lymph nodes may cause profound swelling of the neck (bull neck diphtheria), and the patient may have a fever (≥103° F.). The skin lesions in cutaneous diphtheria are usually covered by a gray-brown pseudomembrane. Life-threatening systemic complications, principally loss of motor function (e.g., difficulty in swallowing) and congestive heart failure, may develop as a result of the action of diphtheria toxin on peripheral motor neurons and the myocardium. (Murphy J R. *Corynebacterium Diphtheriae*. (1996) In: Baron S, editor. Medical Microbiology. 4th edition. Galveston (Tex.): University of Texas Medical Branch at Galveston. Chapter 32).

Asymptomatic nasopharyngeal carriage is common in regions where diphtheria is endemic. In susceptible individuals, toxigenic strains cause disease by multiplying and secreting diphtheria toxin in either nasopharyngeal or skin lesions. The diphtheritic lesion is often covered by a pseudomembrane composed of fibrin, bacteria, and inflammatory cells.

i) T-Cell Responses to Infection with Cornebacteriaceae Bacteria

Limited information is available regarding T-cell responses to infection with Cornebacteriaceae bacteria, mainly because the bacteria have a number of mechanisms that disable the innate immune response. While escape mechanisms of pathogenic corynebacteria with respect to host defense systems are generally not well understood, it is understood that toxins derived from Cornebacteriaceae bacteria, such as cornebacterium diphtheria interact with the human innate immune system and can cause system failure (Weerasekera, D., et al., (2019) "Induction of Necrosis in Human Macrophage Cell Lines by *Corynebacterium diphtheriae* and *Corynebacterium ulcerans* Strains Isolated from Fatal Cases of Systemic Infections." Int. J. Mol. Sci. 20, 4109).

On the chance that the innate system is not disabled by infection, the T cell response can be seen as essential to fighting against Cornebacteriaceae bacteria. For example, *C. pseudotuberculosis* is an intracellular pathogen that can replicate in host cells and attain a selective advantage over the host; the protective immune response to the bacterium is based on a $T_{H1}$ cellular response, and infection with virulent strains of the bacteria induces the production of $T_{H1}$ response-related cytokines such as IFN-gamma. The production of IFN-gamma and TNF following stimulation of murine splenocytes with the bacterium is driven by the activation of MAPK p38 and ERK 1/2 signaling pathways. Mice inoculated with anti-IFN-gamma antibodies showed an increased bacterial proliferation in the organs, and inoculation with anti-TNF antibodies also led to a higher bacteremia (Oliverira et al., "Insight of Genus *Corynebacterium*: Ascertaining the Role of Pathogenic and Non-pathogenic Species." (2017) Front. Microbiol., 8: 1937).

D) Cornebacteriace Bacteria Vaccine Development

Diphtheria toxoid, tetanus toxoid and pertussis antigens were combined in the diphtheria-tetanus-pertussis vaccine (DTP) used widely for childhood immunization throughout the world. DTP may also be combined with additional vaccine antigens, such as hepatitis B surface antigen (HBsAg) and *Haemophilus influenzae* type b (Hib) conjugates as pentavalent vaccines, and with inactivated polio vaccine (IPV) as hexavalent vaccines. Tetanus-diphtheria (Td, low-dose diphtheria toxoid) formulations and tetanus-diphtheria-acellular pertussis (Tdap) formulations are licensed for use from 5 years of age and 3 years of age, respectively. After the 3-dose primary series of DTP-containing vaccine, 94-100% of children have protective anti-diphtheria antibody levels >0.01 IU/mL, but booster doses are needed to ensure continuing protection. The effectiveness of the vaccine can be seen in outbreak settings: most recent data on vaccine effectiveness stem from the epidemic in the 1990s in countries of the former Soviet Union. Case-control studies showed that 3 or more doses of diphtheria toxoid induced 95.5% (95% CI: 92.1-97.4%) protective effectiveness among children aged <15 years. Protection increased to 98.4% (95% CI: 96.5-99.3%) after 5 or more doses of this vaccine. (World Health Organization, (2017) "Summary of WHO Position Paper on Diphtheria Vaccines, August 2017". Retrieved from the World Health Organization website.

i) Challenges with Cornebacteriaceae Bacteria Vaccine Design

The diphtheria vaccine involves microbes that cause acute rather than chronic infections. They rely on levels of specific antibodies above a defined threshold as surrogate markers for protection. The importance of stimulating both main effector arms, cell-mediated immunity (CMI) and antibodies, to develop effective vaccines against intracellular organisms has been increasingly brought into the limelight. (Salerno-Goncalves, R., "Cell-mediated immunity and the challenges for vaccine development." (2006) Trends Microbiol. December; 14(12):536-42. Epub 2006 Oct. 19).

Additionally, diphtheria and tetanus (caused by *Clostridium tetani*) are toxoids are heat- or chemically-inactivated toxins that retain immunogenicity, but lack the capacity of the native toxin to induce host damage. While the use of toxoid vaccines has practically eliminated diphtheria and tetanus in vaccinated populations, their success in preventing disease stands in stark contrast to the fact that recovery from diphtheria or tetanus does not reliably confer immunity to recurrance of disease. The absence of lasting immunity after recovery from disease may reflect the rapidity with which toxins are able to induce damage, that damage can be mediated by a small amount of toxin and/or that the native toxin is not highly immunogenic, each of which could preclude the development of a protective antibody response to the toxin. Hence, recovery from diphtheria or tetanus may involve different immune mechanisms and/or an immune response to different determinants than those elicited by toxoid vaccination. Therefore, infections by dipetheria may be unpredictable. (Casadevall, A., et al., "Exploiting the Redundancy in the Immune System" Journal of Experimental Medicine (2003) 197 (11) 1401-1404).

VII) Mycobacteriaceae

A) Overview of the Mycobacteriaceae Family

There is only one genus, *Mycobacterium*, in the family Mycobacteriaceae. Organisms belonging to this genus include *Mycobacterium bovis* and *Mycobacterium tuberculosis*, both of which cause tuberculosis (TB) in humans and other animals. TB is one of the oldest recorded human afflictions, and is still one of the biggest killers among the infectious diseases, killing approximately 2 million people each year despite the worldwide use of a live attenuated vaccine and several antibiotics. The geographical incidence of TB spreads from North America, Asia, Western Russia, and Southern and Central Africa. (Smith, Issar. "*Mycobacterium tuberculosis* pathogenesis and molecular determinants of virulence." Clinical microbiology reviews vol. 16, 3 (2003): 463-96).

i) *Mycobacterium bovis* (Mbc)

*Mycobacterium bovis*, (Mbv) is the causative agent of bovine tuberculosis in cattle. *M. bovis* can be transmitted to humans through consumption of contaminated, unpasteurized diary products, contact with an exposed wound, or inhaling the bacteria in the air exhaled by animals infected with *M. bovis*.

ii) *Mycobacterium tuberculosis* (Mtb)

*Mycobacterium tuberculosis* (Mtb), an acid-fast staining intracellular bacterium, is the causative agent of TB. The deadly infection can present as a pulmonary, as well as extra pulmonary disease. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574). TB is an important disease in immunocompromised individuals, for example, one-third of exposed HIV-negative individuals become infected, and of this number 3 to 5% develop TB in the first year. An additional 3 to 5% of those infected develop TB later in their lives. It is thought that most adult TB in non-HIV-infected patients is caused by reactivation of preexisting infection. HIV-positive persons infected with *M. tuberculosis* have a 50% chance of developing reactivation (postprimary) TB at some time in their lives. These individuals and others who are immunosuppressed can also be newly infected with *M. tuberculosis* and in many cases show rapid progression to active disease. (Smith, Issar. "*Mycobacterium tuberculosis* pathogenesis and molecular determinants of virulence." Clinical microbiology reviews vol. 16, 3 (2003): 463-96).

B) Structure Based Functional Analyis of Mycobacterieaceae Bacteria

Mycobacteria are slender, curved rods that are cid-fast and resistant to acids, alkalis and dehydration. The cell wall contains complex waxes and glycolipids. Multiplication on enriched media in vitro is very slow, with doubling times of 18 to 24 hours; clinical isolates may require 4 to 6 weeks to grow. The cell envelope (E) is crucial in the adaptation of mycobacteria to intracellular growth. They are also known to possess a capsule-like structure which is important to its permeability barrier of the cell envelope and protection from host cell phagocytic activity. The capsule comprises surface antigens including the outerlayer protein (OL), along with capsular structure (CAP) proteins. Other important structural components include a matrix of phospholipids (PL and PIM), wall proteins (P), cell wall skeleton (CWS), long-sized amphils (LAM) which is anchored through E from the cell membrane (CM) (Rastogi, N., et al., "The mycobacteria: an introduction to nomenclature and pathogenesis." (2001) Rev. Sci. Tech. Off. Int. Epiz., 20(1), 21-54).

C) Immune Response to Mycobacteriaceae Bacteria Infection

The bacteria enter the alveoli by airborne transmission. They resist destruction by alveolar macrophages and multiply, forming the primary lesion or tubercle. They then spread to regional lymph nodes, enter the circulation, and reseed the lungs. (Smith, Issar. "*Mycobacterium tuberculosis* pathogenesis and molecular determinants of virulence." (2003) Clinical Microbiology Reviews, Vol. 16,3 463-96). Tissue destruction results from cell-mediated hypersensitivity.

Susceptibility is influenced by genetic, ethnic and extrinsic factors, e.g., insults to the immune system and the nutritional and physiological state of the host. Acquired resistance is mediated by T lymphocytes, which lyse infected macrophages directly or activate them via soluble mediators (e.g., gamma IFN) to destroy intracellular bacilli; antibodies play no protective role.

i) T-Cell Response to Infection by Mycobacteriaceae Bacteria

Studies in humans infected with *M. tuberculosis* have shown that many of the results obtained using experimental infection of mice also apply to humans. It is well established that cell-mediated responses are important in protection, and several subpopulations of T cells appear to be involved. Protective immunity to mycobacteria is considered to be mediated predominantly by T helper ($T_{H1}$ CD4+ and CD8+ T-cell secretion of interferon-γ (IFN-γ) but other T-cell populations, such as γδ T cells and natural killer (NK) T cells, are probably also involved. Specifically, IFN-γ and other Th1 cytokines upregulate the antimicrobial function of macrophages (Mφ) to kill the bacilli which they harbor. Bactericidal and bacteriostatic functions of activated Mφs can be demonstrated in vitro but it is clear that virulent mycobacteria are hard to kill. There may be mechanisms, other than those involving Mφs that are engaged in the killing of virulent mycobacteria. Cytotoxic T lymphocytes (CTL) have the ability to kill human and mouse Mφs infected with *M. tuberculosis*. (Skinner, Margot A et al. (2003) "Cytotoxic T-cell responses to *Mycobacterium bovis* during experimental infection of cattle with bovine tuberculosis." Immunology, Vol. 110,2: 234-41).

Bovine CTL have been shown to kill cells infected with other intracellular pathogens. At least in vitro, the direct killing of mycobacteria by CTL has been demonstrated and the involvement of molecules, such as granulysin, in the cytotoxic granules of CTL, have been implicated in this killing. CTL may also have a role in more efficient antigen presentation, so that intracellular mycobacteria released from infected cells can be taken up by more proficient antigen-presenting cells. (Skinner, Margot A et al. "Cytotoxic T-cell responses to *Mycobacterium bovis* during experimental infection of cattle with bovine tuberculosis." (2003) Immunology, Vol. 110,2: 234-41). As early as 6 weeks after *M. bovis* infection, CD4+ $T_{CM}$ cells (CD45RO+, CCR7+) were detected in long-term, antigen-stimulated PBMC cultures upon recall stimulation with specific (i.e., rESAT-6:CFP-10) or complex (i.e., PPDb) antigens of *M. bovis*. Antigen-specific CD4 cells, as detected by IFN-γ production via either ELISPOT or intracellular cytokine staining, within long-term PBMC cultures were predominately (~76%) TCM cells (CD45RO+/CCR7+), with the remainder being $T_{EM}$ cells (CD45RO+/CCR7−, ~23%). Bovine $T_{CM}$ were highly proliferative, as antigen restimulation of cells within long-term cultures induced robust proliferation of CD4+ cells that significantly exceeded that of short-term culture cells. Further phenotypic analyses of repeat stimulated cultures indicated that a sub-population of bovine $T_{CM}$ reverted to effector (both $T_{EM}$ and $T_{effector}$) phenotypes upon repeat exposure to *M. bovis* antigens. (Maggioli M F, Palmer M V, Thacker T C, Vordermeier H M, Waters W R (2015) Characterization of Effector and Memory T Cell Subsets in the Immune Response to Bovine Tuberculosis in Cattle. PLOS ONE 10(4): e0122571).

$T_{CM}$ and ex vivo responses were detected in M. tb-infected patients and loss of $T_{CM}$ responses (as measured by cultured IFN-γ ELISPOT) is associated with clinical disease progression. Likewise, $T_{CM}$ responses in the absence of ex vivo IFN-γ production indicate disease remission, either by self-healing or anti-mycobacterial therapy, reinforcing the role that pathogen clearance has on Tcm function and/or maintenance. In spite of the presence of $T_{CM}$ cells, patients receiving curative treatment are still susceptible to M tb re-infection. For example, in one experiment on calves, each had mild progressive disease and were responsive to TB antigens in both cultured and ex vivo IFN-γ ELISPOT assays—similar to what occurs in humans with the mild active form of *M. tb* infection. Flow cytometric analysis demonstrated that both $T_{EM}$ and $T_{CM}$ cells are elicited relatively early after infection (3 weeks post-infection). It is uncertain if $T_{CM}$ responses by the animals would decrease as the disease progresses, but it is frequently reported that animals in late stages of infection become anergic to measures of cell-mediated immunity, yielding false negative results upon skin test or ex vivo IFN-γ assays. (Maggioli M F, Palmer M V, Thacker T C, Vordermeier H M, Waters W R (2015) Characterization of Effector and Memory T Cell Subsets in the Immune Response to Bovine Tuberculosis in Cattle. PLOS ONE 10(4): e0122571).

Lymphocyte homing and trafficking to sites of inflammation and lymphoid organs are mediated by the expression of numerous surface adhesion molecules, such as CCR7, CD62L and CD44. CD62L mediates cell adhesion to peripheral lymph node vascular addressins (e.g., GlyCAM-1 and MAdCAM-1). The expression of CD62L on naïve and memory T cells facilitates cell rolling on endothelium in secondary lymphatic organs, contributing to the compartmentalization of the immune response. CD44 expression on T cells is up regulated upon activation, thereby promoting movement through the extracellular matrix via interactions with hyaluronic acid and fibronectin. In vitro stimulation of antigen specific T cells is known to up-regulate CD44 while concurrently down regulating CD62L expression in humans, mice and cattle. As in humans, bovine T cells expressing CD44 upon ex vivo stimulation frequently co-express CD45RO, while down regulating CD62L. Research has shown that CD44 expression on CD4 cells did not differ between $T_{EM}$ and effector cells under ex vivo or long-term culture conditions. Research has also shown that the expression of CD62L was down regulated in effector cells, intermediate on $T_{EM}$ cells, and high on $T_{CM}$ cells. Although TCM cells highly expressed CD62L, these cells maintained high CD44 expression. The relevance of the level of CD44 expression by memory T cells is controversial for both mice and humans. Data from mice suggest that although the expression of CD44 is dispensable for early expansion, trafficking and cytokine production of T cells; expression of CD44 is required for long-term cell survival and anamnestic responses to re-infection. In humans and mice it is known that, together with CD62L, CCR7 plays a major role for cell homing to secondary lymphoid organs (SLO). For cattle, CCR7 expression is required for CD4 T cell migration to SLO, while homing of γδ T cells to SLO is not mediated by CCR7 expression. Similarly, in a *Mycoplasma mycoides* infection, a subset of CD4 cells with Tcm characteristics was reported after infection and pathogen clearance. Upon restimulation, cells expressing CD62L were highly proliferative, while being less prone to down regulate CCR7 transcription. Conversely, cells lacking CD62L showed greater IFN-γ production, lower proliferation and down regulation of CCR7 transcription. Studies indicate that in response to antigenic stimulation, Tcm cells strongly proliferated and were capable of switching to Tcm and effector cells (CCR7 down regulation). (Maggioli M F, Palmer M V, Thacker T C, Vordermeier H M, Waters W R (2015) Characterization of Effector and Memory T Cell Subsets in the Immune Response to Bovine Tuberculosis in Cattle. PLoS One 10(4): e0122571).

Immune control of Mtb infection largely relies on the production of IFNγ by CD4+ T cells, which enhances macrophage killing of persisting intracellular Mtb and leads to the formation of granulomas around sites of bacterial replication. A clinical study revealed that individuals previously exposed to tuberculosis were likely to have a population of lung-resident $T_{H1}$ effector memory cells that released IFNγ in response to Mtb antigen re-exposure. However, the delay in activation and recruitment of TB-specific T cells to the lungs during primary infection allowed for Mtb to proliferate, resulting in a high bacterial burden. The importance of airway-residing memory T cells (then called airway luminal cells) in mediating protection against TB was described well before the dawn of $T_{RM}$. However, these cells most likely represent the same cell type. Lung $T_{RM}$ induced by mucosal vaccination have shown to be effective in limiting the early control of bacterial replication. Despite the defined role of CD4+ T cells in controlling TB, recent evidence from vaccine studies suggest that CD8+ lung $T_{RM}$ also play an important role in protection against Mtb. Only mucosal administration of BCG led to the generation of airway $T_{RM}$ that produce higher levels of pro-inflammatory cytokines, including IFN-γ than CD8+ $T_{EM}$.

Adoptive transfer of sorted airway CD8+ $T_{RM}$ from BCG-vaccinated mice demonstrated enhanced protection against Mtb challenge in recipient mice. Transfer of CD8+ $T_{RM}$ decreased the numbers of alveolar macrophages, while increasing the number of CD4+ T cells and B cells in the infected lung tissues. It was hypothesized that CD8+ $T_{RM}$ kill Mtb-infected alveolar macrophages, thereby depleting intracellular reservoirs of the bacteria and limiting the entry into the lung parenchyma. Likewise, the viral-vectored vaccines SeV85AB and AdAg85A, administered via the intranasal route have also shown to elicit an immune response that favors the production of CD8+ rather than CD4+ $T_{RM}$. In a rhesus monkey model, a cytomegalovirus vector delivering a range of Mtb antigens (RhCMV/TB) provided significant protection against tuberculosis, presumably through it its ability to generate and maintain pathogen-specific CD4+ and CD8+ circulating and more importantly resident memory T cells that selectively express VLA-1.

Finally, aerosol vaccination with an attenuated Mtb strain lacking sigH not only led to an enormous influx of T cells expressing CD69 into the lung airways (likely to include TRM), but also to a significant long-term protection against virulent Mtb challenge. Collectively, these studies indicate that it is possible to prevent the establishment of infection and/or provide sterilizing immunity against Mtb by inducing both lung CD4+ TRM and CD8+ TRM in the lungs. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

D) Mycobacteriaceae Bacteria Vaccine Development

Currently, *Mycobacterium bovis bacillus* Calmette-Guérin (BCG) is the only licensed vaccine against TB, and prevents dissemination in children. However, BCG does not provide strong enough immunity against pulmonary TB in adults, therefore, allowing transmission. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574). While there are vaccines that can prevent TB and drugs (e.g., isoniazid; rifampin; ethambutol, pyrazinamide) that can treat it, TB bacteria are becoming increasingly resistant to current medications.

VIII) Bacillaceae

A) Overview of the Bacillaceae Family

The family Bacillaceae, consisting of rod-shaped bacteria that form endospores, has two principal subdivisions: the anaerobic spore-forming bacteria of the genus *Clostridium*, and the aerobic or facultatively anaerobic spore-forming bacteria of the genus *Bacillus*, frequently known as ASB (aerobic spore-bearers). (Turnbull PCB. *Bacillus*. (1996) In: Baron S, editor. Medical Microbiology. 4th edition. Galveston (Tex.): University of Texas Medical Branch at Galveston; Chapter 15).

i) *Bacillus anthracis* (*B. anthracis*)

Species in the *Bacillus* genus are rod-shaped, endospore-forming aerobic or facultatively anaerobic, Gram-positive bacteria; in some species cultures may turn Gram-negative with age. The many species of the genus exhibit a wide range of physiologic abilities that allow them to live in every natural environment. Only one endospore is formed per cell. The spores are resistant to heat, cold, radiation, desiccation, and disinfectants. (Turnbull PCB. *Bacillus*. (1996) In: Baron S, editor. Medical Microbiology. 4th edition. Galveston (Tex.): University of Texas Medical Branch at Galveston. Chapter 15).

*Bacillus anthracis* is the causative agent of anthrax, which has afflicted humans throughout history. Humans acquire it as a result of contact with infected animals or animal products. It also is a potential bioterror agent. In humans the disease takes one of three forms, depending on the route of infection. Cutaneous anthrax, which accounts for more than 95 percent of cases worldwide, results from infection through skin lesions; intestinal anthrax results from ingestion of spores, usually in infected meat; and pulmonary anthrax results from inhalation of spores. (Turnbull PCB. *Bacillus*. (1996) In: Baron S, editor. Medical Microbiology. 4th edition. Galveston (Tex.): University of Texas Medical Branch at Galveston; Chapter 15).

B) Structure-Based Functional Analysis of Bacillaceae Bacteria

The pathogenicity of *B anthracis* depends on two virulence factors: a poly-y-D-glutamic acid polypeptide capsule, which protects it from phagocytosis by the defensive phagocytes of the host, and a toxin produced in the log phase of growth. This toxin consists of three proteins: protective antigen (PA) (82.7 kDa), lethal factor (LF) (90.2 kDa), and edema factor (EF) (88.9 kDa). Host proteases in the blood and on the eukaryotic cell surface activate protective antigen by cutting off a 20-kDa segment, exposing a binding site for LF and EF. The activated 63 kDa PA polypeptide binds to specific receptors on the host cell surface, thereby creating a secondary binding site for which LF and EF compete. The complex (PA+LF or PA+EF) is internalized by endocytosis and, following acidification of the endosome, the LF or EF cross the membrane into the cytosol via PA-mediated ion-conductive channels. This is analogous to the A-B structure-function model of cholera toxin with PA behaving as the B (binding) moiety. EF, responsible for the characteristic edema of anthrax, is a calmodulin-dependent adenylate cyclase. (Calmodulin is the major intracellular calcium receptor in eukaryotic cells). The only other known bacterial adenylate cyclase is produced by *Bordetella pertussis*, but the two toxins share only minor homologies. LF appears to be a zinc-dependent metalloprotease though its substrate and mode of action have yet to be elucidated. The toxin and capsule of *B anthracis* are encoded on two large plasmids called pXO 1 (110 MDa) and pX02 (60 MDa), respectively.

The 110-MDa pXO1 plasmid contains genes pagA, lef and cya that encode the protective antigen (PA), the lethal factor (LF), and the edema factor (EF) virulence factors. LF is a zinc-mediated metalloprotease that inactivates the MAPK pathway of the host. EF is an adenylyl cyclase that, upon activation by calmodulin, increases the intracellular concentration of cyclic AMP in the host. PA can bind a toxin receptor on the host cell, forming a heptameric structure that can bind either LF or EF. The PA/LF/EF complex can then be incorporated into the cell as the lethal toxin (LT) or edema toxin (ET), collectively called the anthrax toxins. (Beierlein, J M, and A C Anderson. (2011) "New developments in vaccines, inhibitors of anthrax toxins, and antibiotic therapeutics for *Bacillus anthracis.*" *Current Medicinal Chemistry vol.* 18, 33: 5083-94).

C) Immune Response to Bacillaceae Bacteria Infection

Although anthrax remains the best-known *Bacillus* disease, in recent years other *Bacillus* species have been increasingly implicated in a wide range of infections including abscesses, bacteremia/septicemia, wound and burn infections, ear infections, endocarditis, meningitis, ophthalmitis, osteomyelitis, peritonitis, and respiratory and urinary tract infections. Most of these occur as secondary or mixed infections fr inimmunodeficient or otherwise immunocompromised hosts (such as alcoholics and diabetics), but a significant proportion are primary infections in otherwise healthy individuals. Species that induce these types of infections include *B cereus*, followed by *B licheniformis* and *B subtilis*. *Bacillus alvei, B brevis, B circulans, B coagulans, B macerans, B pumilus, B sphaericus*, and *B thuringiensis* cause occasional infections. As secondary invaders, *Bacillus* species may exacerbate preexisting infections by producing either tissue-damaging toxins or metabolites such as penicillinase that interfere with treatment. (Turnbull PCB. *Bacillus*. (1996) In: Baron S, editor. Medical Microbiology. 4th edition. Galveston (Tex.): University of Texas Medical Branch at Galveston. Chapter 15).

Cutaneous anthrax usually occurs through contamination of a cut or abrasion, although in some countries, biting flies may also transmit the disease. After a 2- to 3-day incubation period, a small pimple or papule appears at the inoculation site. A surrounding ring of vesicles develops. Over the next few days, the central papule ulcerates, dries, and blackens to form the characteristic eschar. The lesion is painless and is surrounded by marked edema that may extend for some distance. Pus and pain appear only if the lesion becomes infected by a pyogenic organism. Similarly, marked lymphangitis and fever usually point to a secondary infection. In most cases the disease remains limited to the initial lesion and resolves spontaneously. The main dangers are that a lesion on the face or neck may swell to occlude the airway or may give rise to secondary meningitis. If host defenses fail to contain the infection, however, fulminating septicemia develops. Approximately 20 percent of untreated cases of cutaneous anthrax progress to fatal septicemia. However, *B anthracis* is susceptible to penicillin and other common antibiotics, so effective treatment is almost always available. (Turnbull PCB. *Bacillus*. (1996) In: Baron S, editor. Medical Microbiology. 4th edition. Galveston (Tex.): University of Texas Medical Branch at Galveston. Chapter 15).

Intestinal anthrax is analogous to cutaneous anthrax but occurs on the intestinal mucosa. In pulmonary anthrax, inhaled spores are transported by alveolar macrophages to the mediastinal lymph nodes, where they germinate and multiply to initiate systemic disease. Gastrointestinal and pulmonary anthrax are both more dangerous than the cutaneous form because they are usually identified too late for treatment to be effective.

D) Bacillaceae Vaccine Development, Challenges or Failure

Currently, a vaccine is not available to the general public and few antibiotics have been approved by the FDA for the treatment of inhalation anthrax. There is a threat of natural or engineered bacterial resistance to antibiotics.

Vaccines that have been developed include a live avirulent vaccine against anthrax in livestock. Live spore vaccines are used in some countries, such as the former U.S.S.R., for the vaccination of humans, however, because of concerns regarding residual virulence, Western countries like the U.S. and U.K. have not approved the use of a spore-based vaccine in humans. Instead, an acellular vaccine using the Protective Antigen to induce immunity has been developed. Prepared by aluminum hydroxide precipitation of non-encapsulated Sterne strain *B. anthracis*, the vaccine, Anthrax Vaccine Adsorbed (AVA, now known as Biothrax®) is the only FDA-approved anthrax vaccine in the US. However, the intensive dosing regimen and issues with ease and homogeneity of preparation have combined to keep the reserves of the vaccine low and deter administration to the general population. In its current form, the vaccine must be stored at 4° C., which increases storage cost and limits locations. In addition, inherent in the method of preparation, vaccines can vary from lot to lot in their content of PA and other cellular components, including LF and EF. This may be responsible for some of the reactogenicity associated with the vaccine (Beierlein, J M, and A C Anderson. "New developments in vaccines, inhibitors of anthrax toxins, and antibiotic therapeutics for *Bacillus anthracis*." Current Medicinal Chemistry Vol. 18,33 (2011): 5083-94).

IX) Yersiniaceae

A) Overview of the Yersiniaceae Family

The order 'Enterobacteriales' is a large and diverse group of Gram-negative, facultatively anaerobic, non-spore-forming, rod-shaped bacteria within the class Gammaproteobacteria. Members of this group inhabit a number of different ecological niches and have been found in soil, water and in association with living organisms including plants, insects, animals and humans. Many members of Enterobacteriales have been implicated as pathogens in humans and animals, such as the species *Escherichia coli*, *Salmonella enterica*, and *Yersinia pestis*. (Adeolu, M., et al., "Genome-based phylogeny and taxonomy of the 'Enterobacteriales': proposal for Enterobacterales ord. nov. divided into the families Enterobacteriaceae, Erwiniaceae fam. nov., Pectobacteriaceae fam. nov., Yersiniaceae fam. nov., Hafniaceae fam. nov., Morganellaceae fam. nov., and Budviciaceae fam. (2016) Intl J. Systemic & Evolutionary Microbiol. 66(12).

i) *Yersinia pestis* (*Y. pestis*)

*Yersinia pestis*, a gram-negative bacterium and plague pathogen, is classified as a category A agent of bioterrorism. It gains its notoriety from causing three massive pandemics in history that killed hundreds of millions of people. One of its forms, pneumonic plague, is difficult to treat because of the speed of the disease's progress (a typical incubation period is 1 to 3 days), and by the time individuals are symptomatic, they are often close to death. (Adeolu, M., et al., "Genome-based phylogeny and taxonomy of the 'Enterobacteriales': proposal for Enterobacterales ord. nov. divided into the families Enterobacteriaceae, Erwiniaceae fam. nov., Pectobacteriaceae fam. nov., Yersiniaceae fam. nov., Hafniaceae fam. nov., Morganellaceae fam. nov., and Budviciaceae fam. (2016) Intl J. Systemic & Evolutionary Microbiol. 66(12)).

B) Structure Based Functional Analysis of Yersiniaceae Bacteria

*Y. pestis* requires the three well-characterized virulence plasmids pYV/pCD1, pPla/pPCP1, and pFra/pMT1, as well as chromosomally encoded virulence factors to cause disease.

C) Immune Response to Yersiniaceae Bacteria Infection

*Y. pestis* infection, either through a flea bite or through contamination via respiratory droplets, has a brutal transition from an absence of immune response and clinical symptoms, to a bursting inflammation and fatal sepsis with abundant bacteria in the body. This lag period has been termed "pre-inflammatory phase" and benefits *Y. pestis*, which migrates toward lymph nodes (bubonic plague) or lungs (pneumonic plague) to multiply silently. If not treated with proper antimicrobial drugs, the bacteria rapidly escape from containment in the lymph node, spread systemically through the blood, and cause fatal sepsis. (Demeure, C. E., Dussurget, O., Mas Fiol, G. et al. (2019)*Yersinia pestis* and plague: an updated view on evolution, virulence determinants, immune subversion, vaccination, and diagnostics. Genes Immun 20, 357-370).

i) T-Cell Response to Infection by Yersiniaceae Bacteria

Cell-mediated protection against bacteria often relies upon the development of type 1 immune responses, characterized by the expansion of pathogen-specific T cells that secrete IFN-γ and TNF-α and by the CD8+ cytotoxic T-lymphocyte response. Studies from the Trudeau Institute showed that IFN-γ, TNF-α, and nitric oxide synthase 2, key elements of cellular immunity, provided critical protective functions during humoral defense against lethal pulmonary *Y. pestis* infection. Vaccination with live *Y. pestis* (KIM5 pCD1+, pMT+, pPCP+, pgm−) primes CD4 and CD8 T cells that synergistically protect against lethal pulmonary *Y. pestis* infection. Moreover, the transfer of *Y. pestis*-primed T cells to naive μ-MT mice protects against lethal intranasal *Y. pestis* challenge. These studies confirm that cellular immunity, in the absence of antibody, can protect the animal against pulmonary *Y. pestis* infection. (Li, B., et al. (2008) "Interaction between *Yersinia pestis* and the Host Immune System." Infection and Immunity April, 76 (5) 1804-1811).

However, *Yersinia* has the ability to influence adaptive immunity by directly suppressing T-lymphocyte activation. YopH is the first documented effector protein to inhibit the adaptive immune responses in a cell culture model. It paralyzes T cells rapidly by inducing cells to undergo mitochondrially regulated programmed cell death but also ensures that the cells will not be recovered to induce a protective immune responses. The functional analysis of *Y. pseudotuberculosis* YopP shows that it can suppress the development of a CD8 T-cell response in a mouse infection model.

D) Yersiniaceae Bacteria Vaccine Development

Three types of vaccines, namely, killed whole-cell (KWC) vaccines, live attenuated vaccines (EV76), and recombinant subunit vaccines, have been developed against plague. Although KWC and EV76 vaccines provide protection against plague in animal models, both have side effects and need repeated immunizations for developing immunity in humans. They are no longer used in humans in the Western world. EV76 is still the vaccine of choice for humans in China. Subunit vaccines based on the capsular protein F1 and one of the type III secretion system proteins, LcrV, have been the focus of recent efforts. This subunit vaccine has been shown to protect mice against respiratory infection by *Y. pestis* and has been reported for entry into a phase II study. However, it failed to adequately protect African green monkeys from pneumonic plague. (Li, Bei et al. (2012) "Humoral and cellular immune responses to *Yersinia pestis* infection in long-term recovered plague patients." Clinical and vaccine immunology: CVI vol. 19,2: 228-34).

X) Enterobacteriaceae

A) Overview of the Enterobacteriaceae Family

Enterobacteriaceae is a family of Gram-negative, facultatively anaerobic, non-spore-forming rods. Characteristics of this family include being motile, catalase positive, and oxidase negative; reduction of nitrate to nitrite; and acid production from glucose fermentation. However, there are also many exceptions. Currently, the family comprises 51 genera and 238 species. The number of species per genus ranges from 1 to 22. The genome size ranges from 422,434 bp, coding for just 362 ORFs, to 6,450,897 bp, coding for 5, 909 ORFs. The Enterobacteriaceae are ubiquitous in nature. Many species can exist as free living in diverse ecological niches, both terrestrial and aquatic environments, and some are associated with animals, plants, or insects only. Many are significant human, other animal, and/or plant pathogens causing a range of infections. (Octavia S., Lan R. (2014) The Family Enterobacteriaceae. In: Rosenberg E., DeLong E. F., Lory S., Stackebrandt E., Thompson F. (eds) The Prokaryotes. Springer, Berlin, Heidelberg).

i) *Salmonella enterica* (*S. enterica, S. Typhii*)

*Salmonella* is a bacterial genus within the Family Enterobacteriaceae that consists of a large group of genetically similar organisms with the ability to infect a large number of animal hosts. The majority of clinical disease in animals and humans is caused by serovars within the *Salmonella enterica* subspecies and this can range from local gastroenteritis to a fatal disseminated disease. (Pham, Oanh H, and Stephen J McSorley. (2015) "Protective host immune responses to *Salmonella* infection." Future Microbiology, Vol. 10,1: 101-10).

*Salmonella enterica* serovar *Typhi* (S. *Typhi*), the causative agent of typhoid fever, is an invasive bacterium that rapidly and efficiently passes through the intestinal mucosa of humans, its only natural host, to reach the reticuloendothelial system. It is estimated that ~21,650,000 episodes of typhoid fever and 216,500 deaths due to the disease occurred in areas of endemicity in 2000. The risk of acquiring typhoid fever is increased among clinical microbiologists and travelers to regions where the disease is endemic. (Pham, Oanh H, and Stephen J McSorley. (2015) "Protective host immune responses to *Salmonella* infection." Future Microbiology, Vol. 10,1: 101-10). Transmission of the disease occurs through faecal-oral route, upon ingestion of contaminated water and food and inadequate sanitation, consuming raw milk products, flavored drinks and ice-creams. This disease can also spread through consumption of raw fruits and vegetables grown in fields irrigated with sewage water and fertilizer. (Marathe, S., et al. (2012) "Typhoid fever & vaccine development: a partially answered question." Indian J Med Res. February; 135(2): 161-169).

B) Structure-Based Functional Analysis of Enterobacteriaceae Bacteria

All sequenced enteric bacteria have a single chromosome, normally 4.3-5.0 Mb in size. Different strains may also harbor extrachromosomal DNA in the form of plasmids. Plasmids often carry genes associated with virulence or antibiotic resistance and can be considered to be a rapidly evolving gene pool. Comparison of the chromosomes of different enteric bacteria identifies a common set of so called "core genes" that are, in general, shared among enteric species. These core genes can be regarded as genes that perform "household" functions associated with the common shared lifestyle of intestinal colonization and transmission (environmental survival). The core genome is mainly organized with these genes aligned in the same conserved order along the single chromosome, a characteristic referred to as "synteny." (Stephen Baker, Gordon Dougan, (2007) The Genome of *Salmonella enterica* Serovar *Typhi*, Clinical Infectious Diseases, Volume 45, Issue Supplement_1, Pages S29-S33).

Most *S. Typhi* isolates express the Vi polysaccharide capsule. Vi capsule production is associated with a set of genes that are situated within a novel gene island that has been designated as SPI-7. This island is 134 kb in length and encodes a variety of putative virulence-associated gene clusters, including the Vi locus, a phage encoding the sopE effector protein of SPI-1, a type IV pilus, and a putative type IV secretion system. SPI-7 has many typical features that are associated with horizontally acquired DNA, and the structure is indicative of several independent integration events. There is also some evidence that SPI-7 may be able to act in a fashion similar to that of a conjugative transposon. (Stephen Baker, Gordon Dougan, (2007) The Genome of *Salmonella enterica* Serovar *Typhi*, Clinical Infectious Diseases, Volume 45, Issue Supplement_1, Pages S29-S33).

Additionally YfdX is a prokaryotic protein encoded by several pathogenic bacteria including *Salmonella enterica* serovar *Typhi*. (Lee, H. S., et al., (2019) "Structural and Physiological Exploration of *Salmonella Typhi* YfdX Uncovers Its Dual Function in Bacterial Antibiotic Stress and Virulence." Front. Microbiol., 9: 3329).

C) Immune Response to Enterobacteriaceae Bacteria Infection

The exact clinical outcome of *Salmonella* infection depends largely on the individual serotype involved, the infected host species and the immunological status of the individual. (Marcelo B. Sztein, (2007) Cell-Mediated Immunity and Antibody Responses Elicited by Attenuated *Salmonella enterica* Serovar *Typhi* Strains Used as Live Oral Vaccines in Humans, Clinical Infectious Diseases, Volume 45, Issue Supplement_1, Pages S15-S19). Typhoid fever is a systemic disease caused by the human specific Gram-negative pathogen *Salmonella enterica* serovar *Typhi* (S. *Typhi*). The extra-intestinal infections caused by *Salmonella* are fatal. The incidence of typhoid fever remains very high in impoverished areas and the emergence of multidrug resistance has made the situation worse. (Marathe, S., et al. (2012) "Typhoid fever & vaccine development: a partially answered question." Indian J Med Res. February; 135(2): 161-169).

The incubation period of the disease is usually 10-14 days and varies considerably from 8-15 days, but may be as short as 5 days and as long as 30 or 35 days depending upon the inoculum size and the state of host defenses. Occurrence of the disease has to be confirmed by the presence of the pathogen either *S. Typhi* or *S. Paratyphi* in the patient, which requires isolation of the bacteria from blood, stool or bone marrow. The sensitivity of the test decreases with increased duration of fever. Another method is the Widal test, which identifies the presence of antibodies against *Salmonella* specific O (somatic) and H (flagellar) antigens in the serum which appear only in the 2nd week after the disease onset. (Marathe, S., et al., (2012) "Typhoid fever & vaccine development: a partially answered question." Indian J Med Res. February; 135(2): 161-169).

*S. Typhi* initially penetrates the small intestinal epithelial cells and then spreads through the bloodstream to other organs such as the spleen, liver, and bone marrow, where this bacterium multiplies and reenters the bloodstream causing symptoms including a high fever. (Lee, H. S., et al., (2019) "Structural and Physiological Exploration of *Salmonella Typhi* YfdX Uncovers Its Dual Function in Bacterial Antibiotic Stress and Virulence." Front. Microbiol., 9: 3329).

CD4 T-cell activation was initially detected in specialized microfold cell (M cell) population overlying lymphoid structures called Peyer's patches (PPs) and then in the draining mesenteric lymph nodes (MLNs) following oral infection with *S. Typhi*. These S. *Typhi*-specific CD4 T cells were activated to express surface CD69 and produced maximal levels of interleukin-2 (IL-2) a few hours later. Studies show that there is such a large degree of CD4 clonal expansion after initial infection with *S. Typhi* that over 50% of peripheral T cells show some evidence of activation and the acquisition of effector function. These expanded T-cell populations also gain the capacity to relocate to infected tissues and secrete effector cytokines. Recent studies suggest that the elicitation of this effector response can occur in response to noncognate stimuli in addition to direct cognate TCR stimulation. Noncognate activation of T cells has been studied extensively for virus-specific CD8 T cells and has been shown to involve inflammatory cytokines such as IL-12 and IL-18. In addition, a recent study has shown that OVA-specific memory CD8 T cells can be stimulated via noncognate signals during *S. Typhi* infection. This mechanism was observed to require NLRC4 inflammasome activation and IL-18 release by CD8$\alpha^+$ DCs (Pham, Oanh H, and Stephen J McSorley. "(2015) Protective host immune responses to *Salmonella* infection." *Future Microbiology* vol. 10,1: 101-10).

D) Enterobacteriaceae Bacteria Vaccine Development

At present, only two licensed vaccines for typhoid fever—a subunit (Vi PS) and a live attenuated *S. Typhi* strain (Ty21a)—are commercially available. (Marathe, S., et al. (2012) "Typhoid fever & vaccine development: a partially answered question." Indian J Med Res. February; 135(2): 161-169).

In 1896, heat killed phenol preserved and acetone killed lyophilized injectable whole cell *S. Typhi* vaccine was generated and used in England and Germany. The efficacy of this vaccine was assessed in a trial in 1960 in Yugoslavia, USSR, Poland, and Guyana. This vaccine is still in use in a few countries but most countries have withdrawn the usage of this vaccine due to side effects. Inactivated whole-cell vaccine causes local inflammation, pain, systemic fever, malaise and disease like symptoms in 9-34 percent of the recipients. (Marathe, S., et al. (2012) "Typhoid fever & vaccine development: a partially answered question." Indian J Med Res. 135(2): 161-169).

An injectable subunit vaccine Vi-polysaccharide vaccine was then developed (sold as Typhim Vi by Sanofi Pasteur and Typherix by GlaxoSmithKline).This vaccine has certain drawbacks: it is non-immunogenic in children below 2 yr of age and unable to induce a booster effect. Many *S. Typhi* strains are negative for Vi polysaccharide or lose their Vi-antigen, and in such cases, the Vi-PS vaccine will not be able to protect the patient. (Marathe, S., et al. (2012) "Typhoid fever & vaccine development: a partially answered question." Indian J Med Res. 135(2): 161-169).

Ty21a was the first live oral attenuated *Salmonella* vaccine (sold as Vivotif by Berna Biotech, now Crucell and was developed in Switzerland by chemical mutagenesis of wild-type *S. Typhi* strain Ty2. This strain lacks both functional galactose-epimerase (galE) gene and the Vi antigen and is highly attenuated. However, Ty21a has certain drawbacks. To obtain sufficient immunity, high numbers (109) of bacteria are required for an oral dose; its use is recommended for children only above 5-6 yr of age. This vaccine is highly acid-labile and hence stomach acidity has to be either neutralized or bypassed when Ty21a is to be fed orally. (Marathe, S., et al. (2012) "Typhoid fever & vaccine development: a partially answered question." Indian J Med Res. 135(2): 161-169).

None of the currently available typhoid vaccines are ideal. Ty21a (the only licensed attenuated live oral vaccine) and purified Vi capsular polysaccharide vaccines are well tolerated but only moderately protective.

The emergence of multidrug-resistant strains of *S. Typhi* has further complicated the situation of the disease and its treatment with existing antibiotics. (Pham, Oanh H, and Stephen J McSorley. (2015) "Protective host immune responses to *Salmonella* infection." Future Microbiology vol. 10,1: 101-10).

There is no licensed vaccine effective for paratyphoid fever. Increasing emergence of multidrug resistance strains of *Salmonella* has further complicated treatment with existing antibiotics.

XI) Rickettsieae

A) Overview of the Rickettsieae Family

The rickettsiae are a diverse collection of obligately intracellular Gram-negative bacteria found in ticks, lice, fleas, mites, chiggers, and mammals. They include the genera Rickettsiae, *Ehrlichia*, *Orientia*, and *Coxiella*. These zoonotic pathogens cause infections that disseminate in the blood to many organs. (Walker D H. Rickettsiae. (1996) In: Baron S, editor. Medical Microbiology. 4th edition. Galveston (Tex.): University of Texas Medical Branch at Galveston. Chapter 38. Available from the National Center for Biotechnology Information website. The members of the genus *Rickettsia* are traditionally characterized into two main groups, the spotted fever group (SFG) and the typhus group (TG), with most of known species belonging to the SFG. Two species, *Rickettsia typhi* and *Rickettsia prowazekii*, make up the TG. Rickettsial organisms have been found on all continents except *Antarctica*. Most rickettsial species are region-locked due to climatic conditions and vector and natural host constraints. However, there are rickettsiae that are globally distributed, such as *Rickettsia felis* and *Rickettsia typhi*. These two species of *Rickettsia* are transmitted by fleas, deviating significantly from most rickettsiae that require a tick vector, which tend to be limited to the geographical distribution of the ticks. Other vectors that are known to harbor and transmit rickettsiae are mites (*Rickettsia akari*) and lice (*Rickettsia prowazekii*). (Mohammad Yazid Abdad, Rita Abou Abdallah, Pierre-Edouard Fournier, John Stenos, Shawn Vasoo, (2018) "A Concise Review of the Epidemiology and Diagnostics of Rickettsioses: *Rickettsia* and Orientia spp." Journal of Clinical Microbiology 56 (8) e01728-17).

i) *Rickettsia prowazekii* (*R. prowazekii*)

*R prowazekii*, the agent of classical epidemic typhus, is transmitted by the human body (clothing) louse, *Pediculus humanus* (but not by head lice) from active human cases or from healthy carriers or subclinical cases, so-called Brill-Zinsser disease. Typical circumstances were evident in the Burundi outbreak, which started in a prison at N'Gozi in 1995 and spread to the malnourished inhabitants of refugee camps in the central highlands (over 1500 m), causing over 50,000 cases with a mortality of 2.6%. The infectious agent in the faeces of the body louse is usually inoculated by scratching of the site of the louse bite, but in epidemics in closed communities, an aerosol of dried louse faeces may be inhaled. The genome of the organism has recently been sequenced, providing new evidence of an evolutionary relationship between rickettsiae and intracellular mitochondria in general. (Cowan, G. (2000) "Rickettsial diseases: the typhus group of fevers—a review." Postgraduate Medical J. vol. 76,895: 269-72).

i) *Rickettsia typhi* (*R. typhi*)

*R. typhi* infection causes a disease similar to, but milder than, epidemic typhus. The case fatality rate is below 5% in untreated cases. *R mooseri* (*R typhi*), the causal agent of endemic typhus, is carried by the rat flea *Xenopsylla cheopis*, and typically infects man in markets, grain stores, breweries, and garbage depots. It is often a mild illness, but can become more aggressive in refugee camps, and can even be fatal. (Cowan, G. (2000) "Rickettsial diseases: the typhus group of fevers—a review." Postgraduate Medical Journal vol. 76, 895: 269-72. doi:10.1136/pmj.76.895.269).

B) Structure-Based Functional Analysis of Rickettsieae Bacterium

*R. typhi* is an obligate intracellular pathogen. In order to survive, multiply and successfully establish an infection, Rickettsiae need to adhere to, and invade, target host cells. Spotted fever group *Rickettsia* bacteria (*Rickettsia aeschlimanii, Rickettsia africae, R. conorii, Rickettsia heilongjiangensis, Rickettsia helvetica, Rickettsia honei, Rickettsia japonica, Rickettsia massiliae, Rickettsia montanensis, Rickettsia parkeri, Rickettsia peacockii, Rickettsia rhipicephali, R. rickettsii, Rickettsia sibirica* and *Rickettsia slovaca*) possess two well-characterized, surface-exposed proteins, known as OmpA and OmpB; OmpA is not found on typhus group organisms. Other putative rickettsial adhesins, encoded by gene Adr1 (RC1281) in *R. conorii* and Adr2 (RP828) in *R. prowazekii* were subsequently identified by proteomics-based analysis and proposed to be involved in rickettsial host invasion. There are at least 17 surface cell antigen (Sca) encoding proteins similar to autotransporter proteins, involved in rickettsial adhesion to host cell receptors. Four (Sca0 (OmpA), Sca1, Sca2 and Sca5 (OmpB)), have been shown to play important roles in rickettsial adhesion, invasion, or both. Sca4 of rickettsiae colocalizes with vinculin in cells at the site of focal adhesions, and binds and activates vinculin through two vinculin-binding sites that are conserved in all rickettsial species. Ku70, a subunit of nuclear DNA-dependent protein kinase localized in the cytoplasm as well the plasma membrane, serves as a receptor for rickettsial OmpB and, thus, plays an important role in rickettsiae internalization. Rickettsiae likely utilize membranolytic proteins, hemolysin C and phospholipase D, encoded by tlyC and pldA genes, respectively, to disrupt the phagosomal membranes and gain access to host cytosol. A phospholipase A2 (PLA2)-like activity is also involved in rickettsial entry into host cells—the gene RT0522 (pat2) in *R. typhi* encodes PLA2 activity. Further, RT0590 (pat1) encoded by *R. typhi* has also been shown to have PLA2 activity, which is required for adherence and entry into host cells during infection. Unlike RT0522 (pat2), which appears to be pseudogenized in 76% of *Rickettsia* genomes, *R. typhi* pat1 is ubiquitously present in all rickettsial genomes and is expressed, secreted into host cytosol, and functionally activated by unidentified host activator(s) for its PLA2 activity.

Prototypical membrane-associated transporter systems known as type IV secretion systems (T4SSs), which accomplish delivery of effectors into target host cells, are composed of 11 VirB proteins (VirB1-VirB11) and VirD4. These secretion systems are known to play a role in the transfer of DNA to other bacteria and host cells, in both acquisition of genetic material from, as well as release into, the extracellular environment, and in the injection of toxin(s), virulence factors or other effector mediators into the host cytoplasm. *R. typhi* encodes orthologs for VirD4, VirB3, VirB10, VirB11, two copies each of VirB4, VirB8 and VirB9, and five different genes with homology to VirB6. The three major structural features of the type 1 secretion system are an outer membrane protein belonging to the TolC family, a periplasmic membrane fusion protein and an ATP-binding transporter associated with the inner protein. Further, Rickettsi ankyrin repeat protein-1 (RARP-1) is conserved among all rickettsial genomes, and is cotranscribed with adjacent genes RT0217 encoding a hypothetical protein and RT0216 (TolC) and secreted by *R. typhi* in a TolC-dependent manner and hypothesized to be part of the mechanism for rickettsial virulence (Sahni, Sanjeev K et al. (2013) "Recent molecular insights into rickettsial pathogenesis and immunity." *Future microbiology* vol. 8, 10: 1265-88).

Immune Response to Infection by Rickettsieae Bacteria-Viable rickettsiae may remain latent in host tissues for months or years after the original infection. The immune response to rickettsiae initially involves the innate immune response followed by both the humoral and cell-mediated adaptive immune responses. While the adaptive immune response takes time to develop, the innate response is actively involved with the rickettsiae at the initial site of infection. Although the role of dendritic cells (DCs) and professional phagocytes in the early stages of infection are not understood, rickettsiae appear to grow in inactivated macrophages. Antigen-presenting cells (dendritic and monocytic cells) along with infected endothelial cells may be the means of systemic spread of rickettsiae early in the infection and not a sufficient means of control. With time, however, endothelial cells, phagocytes, DCs and natural killer (NK) cells become activated by the invading *rickettsia*, producing an environment rich in cytokines and chemokines necessary for enhancing the innate immune response to better deal with the infection.

Antibodies alone are not effective in controlling rickettsial infections, as demonstrated in passive transfer studies. However, antibody coating of rickettsiae enhances phagocytosis and digestion of rickettsiae in vitro. The cellular immune response is capable of protecting the host from infection with various rickettsiae, as shown in passive transfer studies. In particular, it is the T-lymphocytes that are necessary; more specifically CD8+ T-lymphocytes are essential for an effective immune response against rickettsiae (Richards, A. L. (2004). Rickettsial vaccines: The old and the new. Expert Review of Vaccines, 3(5), 541-55).

C) Rickettsieae Bacteria Vaccine Development

Initial typhus vaccines utilized killed, ground-up infected lice intestines. Next, a killed infected mouse lung vaccine was developed on a large scale, from formalin-killed lung tissue preparations of *R. prowazekii*, extracted by differential centrifugation. However, due to the significant hazard of laboratory acquired typhus from vaccines prepared from infected lungs (laboratory animals sneezing produce infectious aerosols), alternative vaccines were sought. (Richards, A. L. (2004). Rickettsial vaccines: The old and the new. Expert Review of Vaccines, 3(5), 541-55).

The Cox vaccine (*R. prowazekii* Breinl) cultivated in the yolk sac of chicken embryos (ether extracted and formalin killed) was the main vaccine licensed for manufacture in the USA. However, it did not provide full protection from infection, but the vaccine did appear to make the illness shorter, milder and prevented death from epidemic typhus. Further, the lack of standardization, adequate information on the efficacy of the vaccine and the adverse side effects (pain and tenderness at the site of injection, fever due to its high endotoxin content and hypersensitive response to yolk-sac contents) would prevent it from meeting modern standards for bacterial vaccines. (Richards, A. L. (2004). Rickettsial vaccines: The old and the new. Expert Review of Vaccines, 3(5), 541-55). Living vaccines were then studied, but also were not found to be standardized nor ideal at acquiring sufficient immune responses.

Rickettsial killed vaccines required large amounts of antigen, multiple doses and time to produce homologous immunity that was short-lived and incomplete. (Richards, A. L. (2004). Rickettsial vaccines: The old and the new. Expert Review of Vaccines, 3(5), 541-55). No single vaccine has been able to provide long-term protection against any of the rickettsial agents.

Protozoan Parasites

XII) Plasmodiidae

A) Overview of the Plasmodiidae Family

Plasmodidae, a family in the order Haemosporidida, includes *Plasmodium*, the genus that is important for human health *Plasmodium* encompasses malarial parasites. *Plasmodium* has two obligate hosts in its life cycle a mosquito host, which also serves as a vector to a vertebrate host. All *Plasmodium* species examined to date have 14 chromosomes, one mitochondrion and one plastid. Like other parasites in the phylum Apicomplexa, Plasmodia have specialized complexes of apical organelles, known as micronemes, rhoptries and dense granules. They also have a vestigial plastid organelle, the apicoplast, which has its own genome and gene expression machinery. (World Health Organization (2014) "Malaria and Some Polyomaviruses (SV40, BK, JC, and Merkel Cell Viruses)" IARC Monographs on the Evaluation of Carcinogenic Risks to Humans Volume 104 pps. 41-120).

i) *Plasmodium falciparum* (*P. falciparum*), *P. vivax, P. malariae, P. ovale*, and *P. knowlesi*

There are 5 types of *plasmodium* (P). species that cause malaria in humans: *P. falciparum, P. vivax, P. malariae, P. ovale*, and *P. knowlesi. P. falciparum* is by far the most deadly. There are 500 million annual cases of malaria, and of that, approximately 1-2 million perish from the disease a year. The disease is mainly presented by children under 5 years, as seen by the about 1 million children deaths per year. (Todryk, Stephen M, and Michael Walther. (2005) "Building better T-cell-inducing malaria vaccines." Immunology, Vol. 115,2: 163-9).

B) Structure Based Functional Analysis of Plasmodidae Parasites

During the blood meal of an infected female anopheline mosquito, 5-20 sporozoites are injected from the fly's salivary glands; they enter the bloodstream and rapidly invade hepatocytes within 30 min to 1 hr. Sporozoites express several surface proteins, two of which are the highly expressed antigens; circumsporozoite (CS) protein and thrombospondin-related adhesion protein (TRAP). Once within the hepatocytes, additional antigens are expressed, including liver stage antigen-1 (LSA-1) and LSA-3, and exported (Exp)-1. It takes about 1 week for the development of merozoites, typically 20,000-40,000 per original sporozoite, which are released into the bloodstream following the rupture of hepatocytes. Merozoites, which express a range of blood-stage antigens that are largely different from those of sporozoites, e.g. merozoite surface proteins (MSP)-1, -2 and -3, apical membrane antigen (AMA)-1 and glutamate-rich protein (GLURP), invade red blood cells, replicate, and cause the red blood cells to rupture, thus releasing more merozoites. After several blood-stage cycles a proportion of merozoites differentiate into male and female gametocytes which, if ingested by mosquitoes during a blood meal, form oocysts within the mosquito gut that give rise to sporozoites capable of infecting a new host. Although the blood stage of infection may lead to a serious illness, and in some cases death, of the host, clinical immunity develops after repeated exposure and not only protects against severe forms of the disease but eventually reduces the level of parasitaemia. However, sterile immunity indicating protection against re-infection is hardly ever seen. The objective of vaccination against the liver stage is to induce, especially in young children who are most at risk, either sterile immunity or a sufficient reduction in parasite numbers reaching the blood-stage to attenuate disease. The latter effect would also provide the opportunity for beneficial natural immunity to develop. (Todryk, Stephen M, and Michael Walther. (2005) "Building better T-cell-inducing malaria vaccines." Immunology, Vol. 115,2: 163-9).

Immune Response to Plasmodiidae Parasite Infection-Natural immunity to *Plasmodium* infection involves a mixture of humoral, CD4+, and CD8+ T cell responses. However, liver $T_{RM}$ have emerged as a promising target for protecting against malaria. Unlike $T_{RM}$ of the epithelium, such as the lungs, intestines, and skin, liver-$T_{RM}$ appear to reside in sinusoids (the blood vessels of the liver), rather than the parenchymal tissue. The heavily fenestrated architecture of these blood vessels and the distinct slow flow rate of blood allows for $T_{RM}$ to traverse through the organ without being dispatched into circulation. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574).

Liver sinusoids provide a prime niche for close interaction of $T_{RM}$ and antigen presenting cells, such as Kupffer cells and dendritic cells. This allows for the rapid detection of antigen. Each hepatocyte is also in close association with a sinusoid, thereby providing easy access to liver $T_{RM}$ for assessment of surface antigen presentation. Intravital imaging revealed that these $T_{RM}$ traversed around 10 μm per minute and, as reported in HSV-1 infection of skin, $T_{RM}$ assume an amoeboid form, extending dendrites to survey the liver for antigens. Rather than relying on CD103-αE integrin interactions for maintaining tissue residence, liver $T_{RM}$ appear to utilize the adhesion molecule LFA-1. A rhesus monkey *P. knowlesi* infection model that assessed sporozoite immunization demonstrated capacity for generating liver $T_{RM}$. These $T_{RM}$ appear to be protective, as their depletion resulted in the loss of immunity. (Muruganandah, V., Sathkumara, H. D., Navarro, S., & Kupz, A. (2018). A Systematic Review: The Role of Resident Memory T Cells in Infectious Diseases and Their Relevance for Vaccine Development. Frontiers in Immunology, 9, 1574). The immunity generated by this strategy was attributed to the increased numbers of CD8+ liver TRM.

C) Plasmodiidae Vaccine Development and Challenges or Failures

Despite extensive research and several candidates utilizing several vaccine designs, there is only a single publicly available vaccine against plasmodiidae parasites. Most vaccines, such as recombinant based, DNA-based, and transgenic-based, were shown to ultimately have limited efficacy and could not produce long-term immunity. (James, S., "Malaria Vaccine Development Status Report" Foundation for the National Institute of Health (1999) available at the Research Gate website). Despite its shortcomings the RTS, S/AS01 vaccine, also known as Mosquirix™ is the world's first approved malaria vaccine (Bharati, K. (2019) "Malaria Vaccine Development: Challenges and Prospects." Journal of Clinical and Diagnostic Research. August, Vol 13(8): AB01-AB03).

Researchers hypothesize that the development of a malaria vaccine is challenging because the genome of a parasite is more complex than bacterial and viral genomes. Furthermore, parasites will undergo several stages in their life cycle, and reproduction phases which will alter targeted antigens (Bharati, K. (2019) "Malaria Vaccine Development: Challenges and Prospects." Journal of Clinical and Diagnostic Research. August, Vol 13(8): AB01-AB03)

Vaccination Mediated Protection and its Shortcomings

Vaccine-induced immune effectors are essentially antibodies, produced by B lymphocytes, which are capable of binding specifically to a toxin or a pathogen. Other potential effectors are cytotoxic CD8+ T lymphocytes that may limit the spread of infectious agents by recognizing and killing infected cells or secreting specific antiviral cytokines and CD4+ T-helper ($T_H$) lymphocytes. These $T_H$ cells may contribute to protection through cytokine production and provide support to the generation and maintenance of B and CD8+ T-cell responses. Effector CD4+ $T_H$ cells were initially subdivided into T-helper 1 ($T_H1$) or T-helper 2 ($T_H2$) subsets depending on their main cytokine production (interferon-γ or interleukin [IL]-4), respectively. $T_H$ cells are increasingly shown to include a large number of subsets with distinct cytokine-producing and homing capacities. For example, follicular T-helper (f$T_H$) cells are specially equipped and positioned in the lymph nodes to support potent B-cell activation and differentiation into antibody secreting cells; they were identified as directly controlling antibody responses and mediating adjuvanticity. T-helper 17 ($T_H17$) essentially defend against extracellular bacteria that colonize the skin and mucosa, recruiting neutrophils and promoting local inflammation. These effectors are controlled by regulatory T cells ($T_{regs}$) involved in maintaining immune tolerance.

Although the nature of a vaccine exerts a direct influence on the type of immune effectors that are elicited, the induction of antigen-specific immune effectors (and/or immune memory cells) by an immunization process does not imply that the resulting antibodies, cells, or cytokines represent surrogates, or even correlates, of vaccine efficacy (Rueckert C, Guzmán CA (2012) Vaccines: From Empirical Development to Rational Design. PLoS Pathog 8(11): e1003001).

The protection provided by current vaccination efforts is largely dependent on the induction of neutralizing antibodies. Antibody-mediated neutralization of viruses is the direct inhibition of viral infectivity resulting from antibody docking to virus particles. Neutralization occurs when the process of virion binding to the cell surface receptors is inhibited, or when the fusion process of virion with cellular endosomal or plasma membranes is disrupted. Neutralizing antibodies precisely target specific antigens. In addition to directly interfering with virus entry into cells, antibodies can further counteract viral infection through their Fc fragments, triggering immune regulatory mechanisms, including ADCC, antibody-dependent cellular pathogenicity (ADCP), and CDCC.

However, neutralizing antibody protection has its limitations. First, there are a number of issues with the process of vaccine development itself, such as animal model unavailability. Second, pathogens present themselves in numerous variants and may undergo mutations to enable immune escape. Third, vaccine induced immunity may not be effective enough to confer long-term immunity. Fourth, despite experimental models, some vaccines may not invoke the desired functional response. Fifth, there are a number of population specific challenges that may alter the immune response to the vaccine. Sixth, there is insufficient information about the mechanisms of protection, as well as the antigens/epitopes required for sufficient activation of the targeted mechanism.

First, vaccine development is a complicated and length process which is hampered by the lack of a sufficient animal model. For example, in targeting Flaviviridae viruses, there is currently no perfect small animal model for pre-clinical testing; so far, non-human primates (NHP), one of the natural reservoirs of the virus, are the best pre-clinical models as discussed in depth by Lee & Ng (Id., citing Lee, CYP, Ng, LFP, (2018) Microbes Infect.). However, the cost of testing vaccines on NHP and their maintenance is extremely high, which poses a high hurdle in vaccine development.

Second, pathogens frequently have multiple strains and variants that cause antigenic shift or antigeneic drift. Influenza viruses utilize RNA-dependent RNA polymerase (RdRp) to catalyze the replication cycle; RdRp is prone to error thus accumulating new mutations and changing the genome over time in a process termed "antigenic drift." (Fermin, Gustavo, and Paula Tennant. (2018) Viruses: Molecular Biology, Host Interactions and Applications to Biotechnology, edited by Jerome E. Foster, Elsevier Science & Technology. Available from the ProQuest Ebook Central website). Antigenic shift also allows some influenza strains to adapt to new species, such as has been observed in recent times with avian influenza. Further, segmented genomes, such as those of Orthomyxovirus they can undergo genome reassortment. Moreover, when the protein antigens are highly variable among the different strains, the antibody produced is non-neutralizing. (Stanley A. Plotkin, (2015) Increasing Complexity of Vaccine Development, *The Journal of Infectious Diseases*, Volume 212, Issue Suppl_1, Pages S12-S16).

In the development of virus vaccines against the Rhabdoviridae, the rapid evolution and consequently high diversity and fitness of these viruses are the major driving forces of virus virulence, tropism, host range, transmission, and thus their perpetuation. An important determinant of this genetic variability is the error-prone nature of RNA dependent RNA polymerases which, during virus replication, may result in high rates of mutation, sequence deletion, insertion, and recombination between RNA genomes. Due to the absence of efficient proofreading and post-replicative repair activities associated with RNA replicases, mutation rates of RNA viruses have been estimated to vary between approximately $10^3$ to $10^5$ substitutions per nucleotide copy. As a result, viral populations are constantly shaped by evolutionary driven forces and genetic diversification is a common process in virus evolution. In the long term this leads to the segregation of new variants, species or genus, providing challenges to achieving a rhavdovirus vaccine. (Scott, T. P., & Nel, L. H. (2016). Subversion of the Immune Response by Rabies Virus. Viruses, 8(8), 231).

When considering Picornaviridae vaccine development, the current, chemically inactivated trivalent vaccine against serotype O, A, and Asia 1 of the foot and mouth disease virus suffers limitations, including thermolability, and only short-lived immunity. (Singh, K. R., et al., (2019) "Foot-and-Mouth Disease Virus: Immunobiology, Advances in Vaccines and Vaccination Strategies Addressing Vaccine Failures—An Indian Perspective." Vaccines, 7(3), 90). Moreover, immunity against one serotype does not provide protection against other serotypes or sometimes even to the variants within the same serotype. (Id.).

The extreme diversity of human immunodeficiency virus (HIV), a member of the family Retroviridae is a major obstacle to vaccine development, since strains belonging to different subtypes can differ by to 35% in some of their proteins, such as the env proteins. Therefore, while some vaccines may be effective against some virus clades, they may not be effective against other clades (see Hsu, D. et al, (2017) "Progress in HIV vaccine development" Human Vaccines & Immunotherapeutics 13(5): 1018-1030).

Third, current vaccines display signs of partial efficacy and short effector memory. For example, developments in Herpesviridae vaccine design have resulted in vaccines that only have partial efficacy. (Sandgren, K., et al., (2016) "Understanding natural herpes simplex virus immunity to inform next-generation vaccine design." Clinical & Translational Immunology 5(7)).

While Pertussis acellular vaccines replaced whole inactivated bacteria vaccines, which solved issues with reactogencity (being capable of causing an immunological reaction), pertussis (whooping cough) became resurgent after those vaccines went into standard use in developed countries. Although strain change may play a role, the principal problem is the rapid waning of antibodies, particularly to the pertussis toxin (Stanley A. Plotkin, (2015) Increasing Complexity of Vaccine Development, *The Journal of Infectious Diseases*, Volume 212, Issue suppl_1, July Pages S12-S16).

Subjects immunized with a Yersiniaceae bacteria vaccine (EV76) only acquired approximately 6 to 12 months of protection (Li, Bei et al. (2012) "Humoral and cellular immune responses to *Yersinia pestis* infection in long-term recovered plague patients." Clinical and Vaccine Immunology: CVI vol. 19,2: 228-34).

It is also known that no single vaccine has been able to provide long-term protection against any of the rickettsial agents. (Osterloh, Anke. (2017) "Immune response against rickettsiae: lessons from murine infection models." Medical microbiology and immunology vol. 206, 6: 403-417).

Fifth, whether vaccination will produce the desired immune response can be unpredictable. For example, when designing a therapeutic monoclonal antibody vaccine against the arbovirus ZIKV, there is a risk of antibody-dependent enhancement (ADE) of heterologous flavivirus infection, due to the sequence and antigenic similarity between them. ADE of ZIKV by dengue and West Nile immune sera has been shown in vitro and induced in immunosuppressed mice by dengue and West Nile immune sera. Sairol, C A et al (2018), Trends in Microbiol. 26(3): 186-190. During this phenomenon, cells bearing FcR can uptake and internalize antibody-coated viruses and be further infected (Yang, C. et al., (2019) Development of neutralizing antibodies against Zika virus based on its envelope protein structure," Virologica Sinica 34: 168-174, citing Dowd, K A and Pierson, T C, (2011) Virology. 411: 306-315). Several factors have been proposed to explain why the mAbs do not neutralize the viruses but instead enhance infection: (1) The neutralizing activity of these mAbs is too weak to neutralize the viruses. (2) The blocking sites of E proteins do not affect the viral infection ability. (3) The concentration of these neutralizing mAbs is too low to neutralize the viruses.

Fifth, population specific factors may also impact vaccine efficacy. For example, neutralization of viral vaccines in vivo prior to achieving its replication and/or effector function in the body may account for decreased vaccine efficacy (Stanley A. Plotkin (2015) Increasing Complexity of Vaccine Development, *The Journal of Infectious Diseases*, Volume 212, Issue Suppl_1, Pages S12-S16).

It has been reported that rotavirus vaccines have been highly effective against infantile gastroenteritis in developed countries, but in poor tropical countries, their effectiveness is greatly reduced (See id).

Similarly, in Togaviridae viruses, for example, the occurrences of vaccine failure are thought to arise when preexisting antibodies neutralize the live viral vaccine strain. It has been suggested that low level immunity could result from a previous infection, such as from a parvovirus or Epstein-Barr virus infection, or the presence of Rh factor. (Lambert, N., (2015) "Rubella" Lancet. June 6; 385(9984): 2297-2307).

Other population factors include immunocompromised or vulnerable populations. For example, in Paramyxoviruses, some vaccines exist, but the MMR vaccine is usually recommended only for older infants or children over the age of 1 year, who no longer harbor protective maternal antibodies at high titer, and are therefore particularly vulnerable to measles virus infections. (Kowalzik F, Faber J, and Knuf M. MMR and MMRV vaccines. Vaccine 36:5402-07 (2018)). Therefore, maternal antibodies may weaken vaccines in young infants. (Jones B G, Sealy R E, Surman S L, et al. (2014) Sendai virus-based RSV vaccine protects against RSV challenge in an in vivo maternal antibody model. Vaccine 32:3264-3273). Immune deficiencies affecting CD4 T cells (e.g., HIV infection) and IL-12/IFN-γ/STAT1 signaling pathways result in more severe disease upon infection with *Mycobacterium tuberculosis* in humans. (Maggioli M F, Palmer M V, Thacker T C, Vordermeier H M, Waters W R (2015) Characterization of Effector and Memory T Cell Subsets in the Immune Response to Bovine Tuberculosis in Cattle. PLOS ONE 10(4): e0122571).

The paramyxoviruses and pneumoviruses often strike the respiratory tracts of the youngest infants. A fear of inflammation in the pediatric respiratory tract is warranted, because excessive cell influx into the airways can block respiration which is what happened in the 1960's with an FI-RSV vaccine. (Chin J, Magoffin R L, Shearer L A, et al. (1969) Field evaluation of a respiratory syncytial virus vaccine and a trivalent parainfluenza virus vaccine in a pediatric population. Am J Epidemiol 89:449-463). To avoid consequences similar to those observed with the FI-vaccines, new respiratory virus vaccines must induce a balanced inflammatory response, with aa robust, acute, local immune response in respiratory tissues to support rapid virus clearance and to avoid tissue damage and consequent, enhanced inflammatory responses, but the initial cell recruitment into respiratory tissues must not be so great as to constrict the airways. (Penkert R R, Surman S L, Jones B G, et al. (2016) Vitamin A deficient mice exhibit increased viral antigens and enhanced cytokine/chemokine production in nasal tissues following respiratory virus infection despite the presence of FoxP3+ T cells. Int Immunol 28:139-152).

Another challenge is a lack of community awareness. Because morbidity and mortality caused by infections with paramyxoviruses and pneumoviruses are underappreciated, the value of potential protective vaccines is not understood. Acute lower respiratory viral infections in the youngest children are most often caused by paramyxoviruses or pneumoviruses. (Nair H, Nokes D J, Gessner B D, et al. (2010) Global burden of acute lower respiratory infections due to respiratory syncytial virus in young children: a systematic review and meta-analysis. Lancet 375:1545-1555); (Shi T, McAllister D A, O'Brien K L, et al. (2017) Global, regional, and national disease burden estimates of acute lower respiratory infections due to respiratory syncytial virus in young children in 2015: a systematic review and modelling study. Lancet 390:946-958). Indeed, complacency and concerns about safety, along with philosophical and religious objections to vaccination, have resulted in measles being re-established as an endemic disease in many industrialized nations. (Griffin, D., (2016) The Immune Response in Measles: Virus Control, Clearance and Protective Immunity. Viruses 2016, 8, 282).

Further, recent trends suggest the waning of vaccine-induced immunity of paramyxoviruses. (de Wit, J. et al. (2019) "The Human CD4+ T Cell Response against Mumps Virus Targets a Broadly Recognized Nucleoprotein Epitope." Journal of Virology, 93 (6) e01883-18). For example, despite high vaccination coverage with live attenuated MuV vaccine, over the last decade several mumps outbreaks have been reported worldwide, in particular among vaccinated young adults (3, 4).Moreover, logistical and financial difficulties in sustaining the current mass campaign strategy in developing countries have resulted in a resurgence in deaths related to diseases previously prevented by the MMR vaccine.

Lastly, the lack of knowledge about the mechanisms of protection, viral replication and structure, as well as the antigens/epitopes required for sufficient activation of the targeted protection mechanism may complicate vaccine development. For example, recent data showed that the structure of dengue virus differs according to the temperature at which virus replication takes place. In cell culture or in the human at 37° C. the structure of the virus is expanded, whereas at lower temperatures in the mosquito the particle is more compact. It has been suggested that epitopes exposed on the vaccine virus may not be exposed on the mosquito challenge virus, which is therefore able to enter cells without being neutralized. (Stanley A. Plotkin, (2015) Increasing Complexity of Vaccine Development, *The Journal of Infectious Diseases*, Volume 212, Issue Suppl_1, Pages S12-S16).

It has been reported that only viral replication induces homotypic antibodies (meaning an immune response that is type-specific), but in dengue vaccines targeting dengue types 1, 2, 3, and 4, the vaccine induces homotypic antibodies to itself and heterotypic antibodies (meaning cross-reactive with a different type) to dengue type 2. Yet, the type 2 virus does not replicate and therefore does not induce homotypic antibodies. Therefore, an attempt to create universal neutralizing antibodies may need to account for the difference between homotypic and heterotypic antibodies as it may involve differences in epitopic specificity crucial to protection. (Stanley A. Plotkin (2015) Increasing Complexity of Vaccine Development, *The Journal of Infectious Diseases*, Volume 212, Issue Suppl_1, July 2015, Pages S12-S16).

Furthermore, many vaccines are highly specific and only focus on a single pathogen or disease. When numerous vaccines are used separately, their acceptability by the population decreases, as they require an increase in the number of visits, administrations, side effects, and costs. When a new vaccine is approved, its insertion into the established vaccination schedule without affecting compliance with vaccination may become problematic. (Dye C. (2014) After 2015: infectious diseases in a new era of health and development. Philosophical transactions of the Royal Society of London. Series B, Biological sciences, 369 (1645), 20130426).

Even within current immunization/vaccination schedules, most vaccination programmes, whose focus is on minimizing the number of cases and deaths through routine immunization, are not eradication campaigns. Yet there are large portions of the populations that become vulnerable to the schedules set by available vaccines, such as, for example, infants and adolescents, whose immune systems are not yet developed enough to receive available vaccines (e.g., hepatitis B and human papilloma virus, which are the causes of, respectively, liver and cervical cancers). Other parts of the population, such as older children, adolescents, and adults only acquired a limited duration of protection from infant vaccination (e.g. pertussis), or have no vaccination protection from having missed vaccination in infancy. Additionally, there are a growing number of elderly people with weakening immune systems against life threatening infections, such as influenza (Dye C (2014). After 2015: infectious diseases in a new era of health and development. Philosophical transactions of the Royal Society of London. Series B, Biological sciences, 369(1645), 20130426).

In summary then, despite the development of vaccines, morbidity and mortality from pathogens worldwide has not truly decreased. There are no universally accepted strategies and tools to rationally design vaccines, and vaccine development generally is still a tedious and costly empiric process. In many cases, rationally designed vaccines have not been successful, due to insufficient knowledge about the mechanisms of protection. Although the repertoire of immune clearance mechanisms to fight pathogens is known, the specific contributions of different effector mechanisms are well-characterized for only a few pathogens. It is also largely unclear what determines the immunogenicity and selection of particular epitopes among all possible antigenic options offered by a pathogen. For example, it is not known which factors determine dominant or balanced immune responses, and what are the mechanisms leading to long-term protection for each individual pathogen (Dye C. (2014). After 2015: infectious diseases in a new era of health and development. Philosophical transactions of the Royal Society of London. Series B, Biological sciences, 369 (1645), 20130426).

Cell mediated reactions depend on direct interactions between specific T cells and target or antigen presenting cells which display the specific antigen in the context of either class I or II MHC molecules.

CD4+ and CD8+ T cell epitopes are present in many viral proteins (Jaye, A.; Herberts, C. A.; Jallow, S.; Atabani, S.; Klein, M. R.; Hoogerhout, P.; Kidd, M.; van Els, C. A.; Whittle, H. C. (2003) Vigorous but short-term gamma interferon T-cell responses against a dominant HLA-A*02-restricted measles virus epitope in patients with measles. J. Virol., 77, 5014-5016); (Ota, M. O.; Ndhlovu, Z.; Oh, S.; Piyasirisilp, S.; Berzofsky, J. A.; Moss, W. J.; Griffin, D. E. (2007) Hemagglutinin protein is a primary target of the measles virus-specific HLA-A2-restricted CD8+ T cell response during measles and after vaccination. J. Infect. Dis. 195, 1799-1807); (Schellens, I. M.; Meiring, H. D.; Hoof, I.; Spijkers, S. N.; Poelen, M. C.; van Gaans-van den Brink, J. A.; Costa, A. I.; Vennema, H.; Ke, smir, C.; van Baarle, D.; et al. (2015) Measles virus epitope presentation by HLA: Novel insights into epitope selection, dominance, and microvariation. Front. Immunol. 6, 546) and MeV-specific cytotoxic CD8+ T lymphocytes, IFN-γ-producing type 1 CD4+ and CD8+ T cells, along with soluble indicators of T cell activation (e.g., β2 microglobulin, cytokines and soluble CD4, CD8 and Fas), are in circulation during the rash phase of disease when infectious virus is being cleared (Lin, W. H.; Kouyos, R. D.; Adams, R. J.; Grenfell, B. T.; Griffin, D. E. (2012) Prolonged persistence of measles virus RNA is characteristic of primary infection dynamics. Proc. Natl. Acad. Sci. USA 109, 14989-14994); (Griffin, D. E.; Moench, T. R.; Johnson, R. T.; Lindo de Soriano, I.; Vaisberg, A. (1986) Peripheral blood mononuclear cells during natural measles virus infection: Cell surface phenotypes and evidence for activation. Clin. Immunol. Immunopathol. 40, 305-312); Griffin, D. E.; Ward, B. J.; Juaregui, E.; Johnson, R. T.; Vaisberg, A. (1992) Immune activation during measles: Beta 2-microglobulin in plasma and cerebrospinal fluid in complicated and uncomplicated disease. J. Infect. Dis. 166, 1170-1173); Griffin, D. E.; Ward, B. J.; Jauregui, E.; Johnson, R. T.; Vaisberg, A. (1990) Immune activation during measles: Interferon-gamma and neopterin in plasma and cerebrospinal fluid in complicated and uncomplicated disease. J. Infect. Dis. 161, 449-453; Griffin, D. E.; Ward, B. J.; Jauregui, E.; Johnson, R. T.; Vaisberg, A. (1989) Immune activation in measles. N. Engl. J. Med. 320, 1667-1672; Ward, B. J.; Johnson, R. T.; Vaisberg, A.; Jauregui, E.; Griffin, D. E. (1990) Spontaneous proliferation of peripheral mononuclear cells in natural measles virus infection: Identification of dividing cells and correlation with mitogen responsiveness. Clin. Immunol. Immunopathol. 55, 315-326; Jaye, A.; Magnusen, A. F.; Sadiq, A. D.; Corrah, T.; Whittle, H. C. (1998) Ex vivo analysis of cytotoxic T lymphocytes to measles antigens during infection and after vaccination in Gambian children. J. Clin. Investig., 102, 1969-1977). Depletion of CD8+ T cells from experimentally infected macaques results in higher and more prolonged viremias (Permar, S. R.; Klumpp, S. A.; Mansfield, K. G.; Kim, W. K.; Gorgone, D. A.; Lifton, M. A.; Williams, K. C.; Schmitz, J. E.; Reimann, K. A.; Axthelm, M. K.; et al. (2003) Role of CD8(+) lymphocytes in control and clearance of measles virus infection of rhesus monkeys. J. Virol. 77, 4396-4400) and CD8+ T cells can control virus spread in vitro (De Vries, R. D.; Yuksel, S.; Osterhaus, A. D.; de Swart, R. L. (2010) Specific CD8(+) T-lymphocytes control dissemination of measles virus. Eur. J. Immunol. 40, 388-395). As CD4+ and CD8+ T cells infiltrate sites of virus replication (Polack, F. P.; Auwaerter, P. G.; Lee, S. H.; Nousari, H. C.; Valsamakis, A.; Leiferman, K. M.; Diwan, A.; Adams, R. J.; Griffin, D. E. (1999) Production of atypical measles in rhesus macaques: Evidence for disease mediated by immune complex formation and eosinophils in the presence of fusion-inhibiting antibody. Nat. Med. 5, 629-634), infectious virus decreases rapidly to undetectable levels, the rash fades and the fever resolves.

The described invention provides priming and boosting vector-based platforms to develop vaccines against pathogens, which are tailored to elicit a broad T cell response targeting conserved viral epitopes by expressing conserved sequences of pathogen proteins.

SUMMARY OF THE INVENTION

According to one aspect, the described invention provides a universal vaccine against an immunogen of an infectious pathogenic organism selected from a virus, a bacteria, a fungus or a protozoan comprising at least one ribonucleic acid (RNA) polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens. (a) wherein a cytotoxic T lymphocyte (CTL) epitope consists of peptides of from 8-11 residues in length; and (b) wherein an immune response elicited in response to the vaccine comprises one or more of: (i) activation of one or more T cell populations directed to at least one antigen present in the vaccine; or (ii) neutralization of infectivity of the pathogen; or (iii) an antigen-specific response comprising destruction of the pathogen; lysis of cells infected with the pathogen, or both; compared to an control.

According to one embodiment of the universal vaccine, the activated cell populations comprise activated cytotoxic T lymphocytes (CTLs). According to some embodiments, the activated CTLs comprise one or more of an NK cell population, an NKT cell population, an LAK cell population, a CIK cell population, an MAIT cell population, a CD8+ CTL population, or a CD4+ CTL population.

According to some embodiments, the conserved immunogenic polypeptide or immunogenic fragment is a viral internal matrix protein, a viral capsid protein, a viral nuclear protein, a viral nucleoprotein, a viral glycoprotein, a viral phosphoprotein, a viral envelope protein, a viral protease, a reverse transcriptase, or a viral polymerase.

According to some embodiments, the universal vaccine is prepared by a process comprising a. identifying and selecting from a consensus amino acid sequence a highly conserved internal protein of an infectious pathogen or an immunogenic fragment thereof enriched in CD8+ T cell recognition antigens; b. constructing immunogen sequences of the highly conserved internal proteins in (a); c. constructing: i. a Streptomyces phage SV1.0 DNA vector comprising the immunogen sequences of (b); ii. an adenovirus-based (AdV) vector comprising the immunogen sequences of (b); iii. an attenuated, replication-competent recombinant vaccinia virus based (VV) vector comprising the immunogen sequences of (b); d. propagating separately each of the recombinant vectors comprising encoded immunogens in (c) for immunizing a subject in vivo in an amount effective to elicit or stimulate a therapeutic or prophylactic cell mediated immune response against an infection with the infectious pathogen by: i. priming the fully human immune system by immunizing with the phage DNA vector of (c)(i); ii. boosting the fully human immune system by immunizing with the AdV vector of (c)(ii) followed by the VV vector of (c)(iii), or the VV vector of (c)(iii) followed by the AdV vector of (c)(ii). According to some embodiments, the conserved immunogenic protein or immunogenic fragment is a viral internal matrix protein, a viral capsid protein, a viral nuclear protein, a viral nucleoprotein, a viral glycoprotein, a viral phosphoprotein, a viral envelope protein, a viral protease, a reverse transcriptase, or a viral polymerase.

According to another aspect, the described invention provides an engineered nucleic acid encoding at least one RNA polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens of a universal vaccine.

According to another aspect, the described invention provides an expression vector comprising engineered nucleic acid encoding at least one RNA polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens of a universal vaccine.

According to another aspect, the described invention provides a host cell comprising an engineered nucleic acid encoding at least one RNA polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens of a universal vaccine.

According to another aspect, the described invention provides a method of inducing an immune response in a subject, the method comprising administering to the subject a universal vaccine against an immunogen of an infectious pathogenic organism selected from a virus, a bacteria, a fungus or a protozoan comprising at least one ribonucleic acid (RNA) polynucleotide comprising an open reading frame encoding at least one antigenic polypeptide or an immunogenic fragment thereof, wherein the antigenic peptide, or the immunogenic fragment thereof, comprises a conserved internal protein that is enriched in CD8+ T cell recognition antigens, wherein a CD8+ T cell recognition antigen consists of peptides of from 8-11 residues in length; and wherein an immune response produced in response to the vaccine may comprise one or more of (i) activation of one or more T cell populations directed to an antigen(s) present in the vaccine; (ii) neutralization of infectivity of the pathogen; (iii) an antigen-specific response comprising destruction of the infectious pathogenic organism; lysis of cells infected with the infectious pathogenic organism, or both; compared to an control. According to one embodiment, the method comprises priming the subject with a Streptomyces phage SV1.0 DNA vector comprising a first immunogen sequence encoding a conserved internal protein that is enriched in CD8+ T cell recognition antigens and then boosting the subject with an adenovirus-based (AdV) vector or an attenuated, replication-competent recombinant vaccinia virus based (VV) vector comprising a second immunogen sequence encoding a conserved internal protein that is enriched in CD8+ T cell recognition antigens. According to some embodiments, the method comprises administering the vaccine to the subject by intradermal injection, intranasally, or by intramuscular injection. According to some embodiments, the mode of administration of the priming dose and the mode of administration of the booster dose are different. According to some embodiments, the subject is a mouse of phenotype NOD-scid γc–/– or BALB/c Rag2–/– γc–/–. According to some embodiments, the method comprise reconstituting the mouse of phenotype NOD-scid γc–/– with human C34+CD133+ cord blood cells injected intracardially as newborns into the NOD-scid γc–/– mouse.

According to another aspect, the described invention provides a method for inducing a pan-influenza specific cellular immune response in vivo in an animal model comprising a fully human functional immune system comprising: (1) identifying and selecting from a consensus amino acid sequence a plurality of highly conserved internal influenza viral proteins enriched in CD8+ T cell recognition antigens; (2) constructing concatenated immunogen sequences of the highly conserved internal influenza viral proteins in (a); (3) constructing: a. a Streptomyces phage SV1.0 DNA vector comprising the concatenated immunogen sequences of (b); b. an adenovirus-based (AdV) vector comprising the concatenated immunogen sequences of (b); c. an attenuated, replication-competent recombinant vaccinia virus based (VV) vector comprising the concatenated immunogen sequences of (b); (4) propagating separately each of the recombinant vectors comprising encoded immunogens in (3); (5) immunizing the animal model comprising the fully human functional immune system in vivo by: a. priming the fully human immune system by immunizing with the phage DNA vector of 3(a); b. boosting the fully human immune system by immunizing with the AdV vector of 3(b) followed by the VV vector of 3(c), or the VV vector of 3(c) followed by the AdV vector of 3(b); and (6) after the immunizing in (5), challenging the animal model comprising the immunized fully human functional immune system with either influenza A/PR8 (H1N1) or Influenza A/Shanghai (H7N9) virus.

According to one embodiment, the method comprises administering the vaccine to the subject by intradermal injection, intranasally or by intramuscular injection. According to some embodiments, the mode of administration of the single dose and the booster dose are different. According to some embodiments the animal model is a mouse of phenotype NOD-scid γc–/– or BALB/c Rag2–/– γc–/–. According to some embodiments the method comprises reconstituting the mouse of phenotype NOD-scid γc–/– with human C34+CD133+ cord blood cells injected intracardially as newborns into the NOD-scid γc–/– mouse. According to some embodiments, the method comprises reconstituting the mouse of phenotype BALB/c Rag2–/– γc–/– comprises CD34+ hematopoietic progenitor cells (HPCs) isolated from human fetal liver transferred intrahepatically into newborn BALB/c Rag2–/– γc–/–. According to some embodiments, the pan-influenza specific cellular immune response in the animal model is effective to reduce spread of infection in a population of unimmunized reconstituted mice.

BRIEF DESCRIPTION OF DRAWINGS

FIG. 1A is a schematic diagram of two synthetic immunogens PB1PAM1 (SEQ ID NO:1) and PB2NPM2 (SEQ ID NO:2), which were designed on the basis of amino acid conservation and CD8+ T cell epitope prediction of influenza MI, M2, NP, PA, PB1, PB2 sequences. FIG. 1A discloses "(GGGGS)3" as SEQ ID NO: 28. FIG. 1B and FIG. 1C show the expression of immunogens with western blotting. FIG. 1B shows the results of a western blot which confirmed that the DNA vector pSV1.0, the adenovirus vector AdC68 and the vaccinia vector TTV effectively expressed the immunogen SEQ ID NO:1. After incubation with the influenza matrix protein 1 antibody, no specific bands were found in the empty vectors pSV1.0, AdC68, and TTV which did not contain the sequence of the immunogen SEQ ID NO:1, while a significant ~130 kD band was found in the vectors containing the sequence of immunogen SEQ ID NO:1, demonstrating the DNA vector pSV1.0, the adenovirus vector AdC68 and the vaccinia vector TTV effectively expressed the immunogen SEQ ID NO:1. After incubation with β-actin antibody, the detection of ~42 kD protein band further established that the experimental steps are accurate, and the results are reliable. FIG. 1C shows the results of a western blot which confirmed that the DNA vector pSV1.0, the adenovirus vector AdC68 and the vaccinia vector TTV can effectively express the immunogen SEQ ID NO:2. After incubation with the influenza matrix protein 2 antibody, no specific bands were found in the empty vectors pSV1.0, AdC68, and TTV which did not contain the sequence of the immunogen SEQ ID NO:2, while a significant ~130 kD band was found in the vectors containing the sequence of immunogen SEQ ID NO:2, demonstrating the DNA vector pSV1.0, the adenovirus vector AdC68 and the vaccinia vector TTV effectively expressed the immunogen SEQ ID NO:2. After incubation with β-actin antibody, the detection of 42 kD protein band further established that the experimental steps are accurate, and the results are reliable.

FIG. 2A is a schematic representation of the immunization regimens. FIG. 2B, FIG. 2C and FIG. 2D show cellular responses elicited in vaccinated mice. Splenocytes of vaccinated C57 mice were isolated four weeks after vaccination and subjected to both IFN-γ ELISpot assay (FIG. 2B) and intracellular cytokine staining assay (FIG. 2C, FIG. 2D). The IFN-γ ELISpot assays were performed in response to stimulation with a single influenza A virus-specific peptide and described as numbers of spot forming cells (SFCs) per $10^6$ splenocytes. A total of sixteen peptides were tested (Table 4). The intracellular cytokine staining assays were performed upon stimulation with a peptide pool composed of all the sixteen peptides, and represented as the percentage of CD8+ T cells that were single positive or double positive for IFN-γ, TNF-α, and CD107a expression. All experiments were carried out in triplicate; the error bars are represented as standard deviations (SDs); where * indicates p<0.001; where indicates p<0.01; and where * indicates p<0.05.

FIG. 4A is a schematic illustration of immunization regimens. Control group were immunized with one dose of control pSV1.0 vector (100 g) via intramuscular (i.m.) route and two doses of control AdC68 empty vector ($1 \times 10^{11}$ vp) separately via intramuscular (i.m.) and intranasal (i.n.) route. Experimental groups were sequentially immunized with DNA, AdC68 and TTV in the indicated order, the intramuscular route was treated as default to be omitted whereas the intranasal administration was labeled as "i.n." Splenocytes and bronchoalveolar lavage (BAL) were isolated four weeks after vaccination for measurement of influenza-specific immune responses. FIG. 4B shows the results to IFN-γ ELISpot assay of splenocytes in response to stimulation with a single indicated influenza-specific epitope peptide. FIG. 4C shows the results of IFN-γ ELISpot assay of BAL in response to stimulation with NP-1 and PB2-1 peptides. FIG. 4D and FIG. 4E shows the results of an intracellular cytokine staining assay to measure the induction of CD8+ cells secreting IFN-γ, TNF-α or both, and CD107a-expressing cells after stimulation with the peptide pool. All determinations were carried out in triplicate and the error bars represent the SDs; where * indicates p <0.001; where  indicates p<0.01; and where * indicates p<0.05.

(FIG. 5A, FIG. 5D) Body weight curves of virus-challenged mice (n=5). (FIG. 5B, FIG. 5E) Survival curve of virus-infected mice (n=5). (FIG. 5C, FIG. 5F) Relative lung viral loads at day 5 after virus challenge as measured by RT-PCR quantifications of influenza-specific RNA (n=5). The error bars represent the SDs where * indicates p<0.001; where  indicates p<0.01; and where * indicates p<0.05.

(FIG. 6A, FIG. 6D) Body weight curve of PR8-infected mice during virus challenge (n=5). (FIG. 6B, FIG. 6E) Survival curve of H7N9-infected mice (n=5). (FIG. 6C, FIG. 6F) Relative lung viral loads in infected mice (n=5) at day 5 after virus challenge as measured by RT-PCR quantifications of influenza-specific RNA. The error bars represent the SDs; where * indicates p<0.001; where  indicates p<0.01; and where * indicates p<0.05.

FIG. 9A-FIG. 9C show an immunogen-based assay for influenza-specific T cell immune responses. FIG. 9A shows the level of influenza-specific T cell immune response in mouse spleen cells determined by ELISpot assay. The results demonstrate that the control mice showed no spot-forming cells and showed no influenza-specific T cell immune response; the adenovirus group exhibited higher level cellular response for both NP-2 and PB2-1 epitopes; vaccinia group mice have a higher T cell immune response for NP-2, NP-3, PB1-1, PB1-3, PA-3 and other epitopes. FIG. 9B shows the detection of the level of influenza-specific immune response in mouse spleen cells with intracellular cytokines interferon γ (IFNγ) and tumor necrosis factor alpha (TNFα) staining. The results shown in FIG. 9B demonstrate that T cells expressing IFNγ and TNFα were not observed in the control group, while they were observed in the adenovirus group and the vaccinia group, thus showing T cell immune response with influenza characteristics. FIG. 9C shows the detection of the level of influenza-specific immune response in mouse spleen cells by intracellular factor CD107a staining. The results shown in FIG. 9C demonstrate that T cells expressing CD107a were not observed in the control group, while they were observed in the adenovirus group, and thus had a T cell immune response with influenza characteristics.

FIG. 10A and FIG. 10B show the mouse body weight curve. After infection with the H1N1 and H7N9 influenza viruses, the weight of the control group continued to decrease, while the weight of the adenovirus group and the vaccinia group decreased first and then increased. FIG. 10C and FIG. 10D show the survival curve of mice. After infection with the H1N1 influenza virus, all the mice in the control group died, while the mice in the adenovirus group and the vaccinia group survived to 14 days.

FIG. 11A shows the level of influenza-specific T cell immune response in mouse spleen cells determined by ELISpot assay. No influenza-specific T cell immune response was observed in the control group 1 mice; while there was a high level of T cell immune response in the control group 2, 3 and the experimental groups 1, 2 (control groups and experimental groups are described in Table 5). FIG. 11B shows the level of influenza-specific immune response in mouse lung lavage cells by ELISpot assay. Under the stimulation of peptide NP-2 and PB2-1, no spotted cells were found in the control group 1, 2 and 3, and the influenza-specific immune response could not be established in the lungs of these groups. More spotted cells were observed in the experimental groups 1 and 2, showing a high level of influenza-specific T cell immune response. FIG. 11C shows the detection of the level of influenza-specific immune response in mouse spleen cells with intracellular cytokines IFNγ and TNFα staining. The results showed that T cells expressing IFNγ and TNFα were not observed in control group 1, while were observed in control group 2, 3 and experimental groups 1 and 2, thus showing T cell immune response induced by influenza A. FIG. 11D shows the detection of the level of influenza-specific immune response in mouse spleen cells with CD107a staining. The results show that T cells in control group 3 and experimental group 2 can express CD107a, and thus having a T cell immune response with influenza characteristics.

FIG. 12A-FIG. 12F show the protective effect of immunization with different methods on mice infected with H1N1 and H7N9 influenza viruses. FIG. 12A and FIG. 12B show mouse body weight curve. When subjected to the combinatorial immunizations, the experimental group 1 and 2 mice recovered after the H1N1 and H7N9 influenza virus infection, and then rebounded, which was a better result than the control group 1, 2 and 3. FIG. 12C and FIG. 12D show the mouse survival curve. When subjected to the combinatorial immunizations, the experimental group 1 and 2 mice survived to 14 days after the H1N1 and H7N9 influenza virus infection. In contrast, mice in the control group 1, 2, and 3 died before the 14th day. FIG. 12E and FIG. 12F show the detection of viral load in the lungs of mice on the 5th day after H1N1 and H7N9 influenza challenge. As shown, after the virus challenge, the viral load of the experimental group 1 and 2 mice was slightly lower than that of the control groups 1, 2, and 3.

FIG. 13A-FIG. 13F show the evaluation of the protective effect of mice in the nasal immunization boosting after influenza virus challenge. FIG. 13A and FIG. 13B show mouse body weight curve. After the H1N1 and H7N9 influenza virus challenge, the mice in experimental group 1+FTY720 (fingolimod) and the mice in experimental group 2+FTY720 first showed a decreased body weight, which then rose, a result which was better compared to the control group 1+FTY720. FIG. 13C and FIG. 13D show the survival curve of mice. After the H1N1 and H7N9 influenza viruses challenge, some mice in experimental group 1+FTY720 and experimental group 2+FTY720 survived to 14 days, a result which was better than the control group+FTY720 mice. FIG. 13E and FIG. 13F show the detection of lung viral load on the 5th day after virus challenge. After the H1N1 and H7N9 influenza virus challenge, the viral load of the mice in experimental group 1+FTY720 and the mice in experimental group 2+FTY720 was lower than the mice in the control group+FTY720.

DETAILED DESCRIPTION

While improving humoral immunity to viral infection is the target of many current conventional vaccines, for example influenza vaccines, such vaccines are generally not cross-protective. Moreover, most conserved viral proteins lie within the virus, and thus out of reach of antibodies. Determining the peptide epitopes that are naturally generated by antigen presenting cells during virus infection would allow for the development of other vaccine formulations (i.e. peptide based) that can induce robust and cross reactive T cell responses. The present disclosure describes universal vaccines targeting conserved virus T cell epitopes. The present disclosure is based, in part, on the identification of virus-specific CD8+ T cells which have a broad-spectrum anti-viral effect and importantly, can kill cells infected with different viral subtypes.

The described immunogens, and vaccines comprising the same, offer a number of advantages over current vaccine strategies. One such advantage is that the immunogen comprises a highly conserved viral CD8+ T cell epitope that binds to human MHC class I molecules with high affinity, and is capable of inducing a broad spectrum of high levels of virus-specific T cell immunity. Notably, the broad immune response can effectively respond to virus escape from the host immune response due to antigenic drift and antigenic shift, and further may confer cross-protection effects across different viral subtypes. The immunization methods described herein employ, in some embodiments, a plurality of different vectors for sequential immunization, and use different inoculation methods to effectively activate a broad-spectrum T cell immune response both locally and systemically to enhance immune response across different viral subtypes. Accordingly, the present disclosure provides compositions and methods to stimulate the immune system more comprehensively, effectively, and permanently through a variety of different vaccine vectors, which are strategically combined to provide broader and more effective virus protection.

Definitions

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure by virtue of prior disclosure.

As used in the specification and the appended claims, the singular forms "a," "an" and "the" include plural referents unless the context clearly dictates otherwise.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer. According to some embodiments, to A without B (optionally including elements other than B). According to some embodiments, to B without A (optionally including elements other than A); in yet another embodiment, to both A and B (optionally including other elements); etc.

Figure 1A:
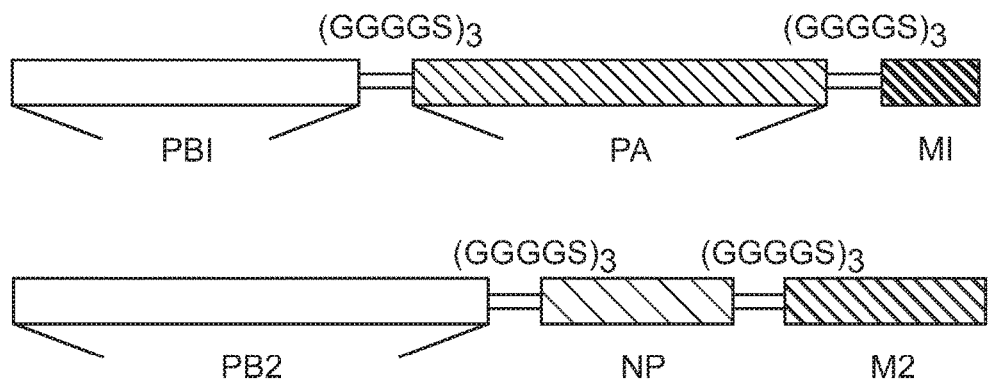
FIG. 1A-FIG. 1C show immunogen design and expression through three different vaccine platforms.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues (e.g. tag and targeting peptides as mentioned herein). "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

As used herein, "substantially equal" means within a range known to be correlated to an abnormal or normal range at a given measured metric. For example, if a control sample is from a diseased patient, substantially equal is within an abnormal range. If a control sample is from a patient known not to have the condition being tested, substantially equal is within a normal range for that given metric.

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, preferred materials and methods are described herein.

The terms "activate," "stimulate," "enhance" "increase" and/or "induce" (and like terms) are used interchangeably to generally refer to the act of improving or increasing, either directly or indirectly, a concentration, level, function, activity, or behavior relative to the natural, expected, or average, or relative to a control condition. "Activate" refers to a primary response induced by ligation of a cell surface moiety. For example, in the context of receptors, such stimulation entails the ligation of a receptor and a subsequent signal transduction event. Further, the stimulation event may activate a cell and upregulate or downregulate expression or secretion of a molecule. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cellular responses.

The terms "activating CD8+ T cells" or "CD8+ T cell activation" as used herein are meant to refer to a process (e.g., a signaling event) causing or resulting in one or more cellular responses of a CD8+ T cell (CTL), selected from: proliferation, differentiation, cytokine secretion, cytotoxic effector molecule release, cytotoxic activity, and expression of activation markers. As used herein, an "activated CD8+ T cell" refers to a CD8+ T cell that has received an activating signal, and thus demonstrates one or more cellular responses, selected from proliferation, differentiation, cytokine secretion, cytotoxic effector molecule release, cytotoxic activity, and expression of activation markers. Suitable assays to measure CD8+ T cell activation are known in the art and are described herein.

The terms "activating an NK cell" or "NK cell activation" as used herein is meant to refer to a process (e.g., a signaling event) causing or resulting in an NK cell being capable of killing cells with deficiencies in MHC class I expression. As used herein, an "activated NK cell" refers to an NK cell that has received an activating signal, and is thus capable of killing cells with deficiencies in MHC class I expression. Suitable assays to measure NK cell activation are known in the art and are described herein.

The term "active immunization" as used herein refers to The term "active immunization" as used herein refers to the production of active immunity, meaning immunity resulting from a naturally acquired infection or intentional vaccination (artificial active immunity).

The terms "adoptive immunity" and "acquired immunity" are used interchangeably to refer to passive cell mediated immunity produced by the transfer of living lymphoid cells from an immune cell source.

The term "adjuvant" as used herein, is meant to refer to a compound that, when used in combination with a specific immunogen (e.g. a VLP) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

The term "administration" and its various grammatical forms as it applies to a mammal, cell, tissue, organ, or biological fluid, as used herein is meant to refer without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. "Administration" also encompasses in vitro and ex vivo treatments, e.g., of a cell, by a reagent, diagnostic, binding composition, or by another cell.

The terms "amino acid residue" or "amino acid" or "residue" are used interchangeably herein to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide. The single letter designation for amino acids is used predominately herein. Such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine. The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The term "antigen" as used herein, is meant to refer to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, as long as the protein maintains the ability to elicit an immunological response, as defined herein. These modifications may be deliberate, as through site-directed mutagenesis, or may be accidental, such as through mutations of hosts which produce the antigens.

The term "antigen presentation" as used herein, refers to the display of antigen on the surface of a cell in the form of peptide fragments bound to MHC molecules.

The term "antigen-presenting cell (APC)" as used herein is meant to refer to a cell that can process and display foreign antigens in association with major histocompatibility complex (MHC) molecules on its surface.

The terms "B lymphocyte" or "B cell" are used interchangeably to refer to a broad class of lymphocytes, which are precursors of antibody-secreting cells. Immunoglobulin, the B cell's receptor, binds to individual epitopes on soluble molecules or on particulate surfaces. B-cell receptors see epitopes expressed on the surface of native molecules. Antibody and B-cell receptors evolved to bind to and to protect against microorganisms in extracellular fluids.

The term "binding" and its various grammatical forms means a lasting attraction between chemical substances. Binding specificity involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

The term "clade" as used herein refers to related organisms descended from a common ancestor.

The term "cell line" as used herein, is meant to refer to a permanently established cell culture developed from a single cell and therefore consisting of cells with a uniform genetic makeup that will proliferate indefinitely.

The term "coding region" as used herein, is meant to refer to that portion of a gene that either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis. A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

The term "component" as used herein, is meant to refer to a constituent part, element or ingredient.

The term "composition" as used herein, is meant to refer to a material formed by a mixture of two or more substances.

As used herein, the term "condition" as used herein, is meant to refer to a variety of health states and is meant to include disorders or diseases caused by any underlying mechanism or disorder.

As used herein, the term "consensus sequence" is used to describe a theoretical representative nucleotide or amino acid sequence in which each nucleotide or amino acid is the one which occurs most frequently at that site in the different sequences which occur in nature. The phrase also refers to an actual sequence which approximates the theoretical consensus. For example, a consensus sequence can be used to represent a known conserved sequence set which is a sequence of amino acids in a polypeptide or of nucleotides in DNA or RNA that is similar across multiple species.

The term "contact" and its various grammatical forms as used herein, are meant to refer to a state or condition of touching or of immediate or local proximity. Contacting a composition to a target destination may occur by any means of administration known to the skilled artisan.

The term "control elements" as used herein is a generic term for a region of DNA, such as a promoter or enhancer adjacent to (or within) a gene that allows the regulation of gene expression by the binding of transcription factors.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences; and/or sequence elements controlling an open chromatin structure see e.g., McCaughan et al. (1995) PNAS USA 92:5431-5435; Kochetov et al (1998) FEBS Letts. 440:351-355.

As used herein, the term "cross-protection" is used to describe immunity against at least two subgroups, subtypes, strains and/or variants of a virus, bacteria, parasite or other pathogen with a single inoculation with one subgroup, subtype, strain and/or variant thereof.

The term "culture" and its other grammatical forms as used herein, is meant to refer to a process whereby a population of cells is grown and proliferated on a substrate in an artificial medium.

The term "cytotoxic T lymphocytes" (CTLs) as used herein, is meant to refer to effector CD8+ T cells. Cytotoxic T cells kill by inducing their targets to undergo apoptosis. They induce target cells to undergo programmed cell death via extrinsic and intrinsic pathways.

The term "dendritic cell" or "DC" as used herein, is meant to refer to a diverse population of morphologically similar cell types found in a variety of lymphoid and non-lymphoid tissues that present foreign antigens to T cells, see Steinman, Ann. Rev. Immunol. 9:271-296 (1991).

The term "derived from" as used herein, is meant to encompasses any method for receiving, obtaining, or modifying something from a source of origin The term "detectable marker" encompasses both selectable markers and assay markers.

The term "detectable response" as used herein, is meant to refer to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "differentiate" and its various grammatical forms as used herein, are meant to refer to the process of development with an increase in the level of organization or complexity of a cell or tissue, accompanied with a more specialized function.

The term "dose" as used herein, is meant to refer to the quantity of a therapeutic substance prescribed to be taken at one time.

The term "effective dose" as used herein, generally refers to that amount an immunogen comprising an internal conserved protein, or an immunogenic fragment thereof, of an infectious agent or pathogen described herein, or a vaccine comprising the immunogen, sufficient to induce immunity, to prevent and/or ameliorate an infection or to reduce at least one symptom of an infection and/or to enhance the efficacy of another dose of a immunogen or vaccine comprising the immunogen. An effective dose may refer to the amount of immunogen or vaccine comprising the immunogen sufficient to delay or minimize the onset of an infection. An effective dose may also refer to the amount of immunogen or vaccine comprising the immunogen that provides a therapeutic benefit in the treatment or management of an infection. Further, an effective dose is the amount with respect to an immunogen or vaccine comprising the immunogen of the disclosure alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

The term "effective amount" as used herein, is meant to refer to an amount of immunogen or vaccine comprising the immunogen necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to immunogens or vaccines comprising the immunogen of the disclosure. The term is also synonymous with "sufficient amount."

The term "effector cell" as used herein refers to a cell that carries out a final response or function. The main effector cells of the immune system, for example, are activated lymphocytes and phagocytes.

The term "enrich" as used herein refers to increasing the proportion of a desired substance, for example, to increase the relative frequency of a subtype of cell compared to its natural frequency in a cell population. Positive selection, negative selection, or both are generally considered necessary to any enrichment scheme. Selection methods include, without limitation, magnetic separation and FACS. Regardless of the specific technology used for enrichment, the specific markers used in the selection process are critical, since developmental stages and activation-specific responses can change a cell's antigenic profile.

The terms "expanding a CD8+ T cell" or "CD8+ T cell expansion" as used herein, are meant to refer to a process wherein a population of CD8+ T cells undergoes a series of cell divisions and thereby increases in cell number. The term "expanded CD8+ T cells" relates to CD8+ T cells obtained through CD8+ T cell expansion. Suitable assays to measure T cell expansion are known in the art and are described herein.

The terms "expanding an NK cell" or "NK cell expansion" as used herein, are meant to refer to a process wherein a population of NK cells undergoes a series of cell divisions and thereby increases in cell number. The term "expanded NK cells" relates to NK cells obtained through NK cell expansion. Suitable assays to measure NK cell expansion are known in the art and are described herein.

The terms "expanding a population of type-I NKT cells" or "type-I NKT cell expansion" are meant to refer to a process wherein a population of type-INKT cells undergoes a series of cell divisions and thereby expands in cell number (for example, by in vitro culture).

The term "express" or "expression" as used herein, is meant to encompasses the biosynthesis of mRNA, polypeptide biosynthesis, polypeptide activation, e.g., by post-translational modification, or an activation of expression by changing the subcellular location or by recruitment to chromatin. Expression may be, e.g., increased by a number of approaches, including: increasing the number of genes encoding the polypeptide, increasing the transcription of the gene (such as by placing the gene under the control of a constitutive promoter), increasing the translation of the gene, knock out of a competitive gene, or a combination of these and/or other approaches.

The term "expression vector" as used herein, is meant to refer to a DNA molecule comprising a gene that is expressed in a host cell. Typically, gene expression is placed under the control of certain regulatory elements including, but not limited to, promoters, tissue specific regulatory elements, and enhancers. Such a gene is said to be "operably linked to" the regulatory elements.

The term "flow cytometry" as used herein, is meant to refer to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Flow Analysis and differentiation of the cells is based on size, granularity, and whether the cell is carrying fluorescent molecules in the form of either antibodies or dyes. As the cell passes through the laser beam, light is scattered in all directions, and the light scattered in the forward direction at low angles (0.5-10°) from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007). Fluorescence-activated cell sorting (FACS), which allows isolation of distinct cell populations too similar in physical characteristics to be separated by size or density, uses fluorescent tags to detect surface proteins that are differentially expressed, allowing fine distinctions to be made among physically homogeneous populations of cells.

The term "functional equivalent" or "functionally equivalent" are used interchangeably herein to refer to substances, molecules, polynucleotides, proteins, peptides, or polypeptides having similar or identical effects or use.

As used herein, the term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

The term "herd immunity" as used herein refers to protection conferred to unvaccinated individuals in a population produced by vaccination of others and reduction in the natural reservoir for infection.

The term "heterosubtypic immunity" ("HIS") as used herein refers to immunity based on immune recognition of antigens conserved across all viral strains.

The term "heterotypic" as used herein is used to refer to being of a different or unusual type or form (e.g., different subgroup, subtype, strain and/or variant of a virus, bacteria, parasite or other pathogen).

The term "homotypic" as used herein is used to refer to being of the same type or form, e.g., same subgroup, subtype, strain and/or variant of a virus, bacteria, parasite or other pathogen.

The terms "immune response" and "immune-mediated" as used herein, are meant to be are used interchangeably herein to refer to any functional expression of a subject's immune system, against either foreign or self-antigens, whether the consequences of these reactions are beneficial or harmful to the subject. The term "immunological response" to an antigen or composition as used herein, is meant to refer to the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The term "integrate into the genome" as used herein refers to a recombinant DNA sequence being concomitantly joined to the genomic DNA comprising a host cell's genome.

The term "isolated" as used herein, is meant to refer to that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. According to some embodiments, and isolated population of a particular cell type refers to greater than 10% pure, greater than 20% pure, greater than 30% pure, greater than 40% pure, greater than 50% pure, greater than 60% pure, greater than 70% pure, greater than 80% pure, greater than 90% pure, or greater than 95% pure.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "lymphocyte" as used herein refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens. This commitment, which exists before the first contact of the immune system with a given antigen, is expressed by the presence on the lymphocyte's surface membrane of receptors specific for determinants (epitopes) on the antigen. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "mediate" and its various grammatical forms as used herein, are meant to refer to bringing about a result.

The term "MHC (major histocompatibility complex) molecule" as used herein, is meant to refer to one of a large family of ubiquitous cell-surface glycoproteins encoded by genes of the major histocompatibility complex (MHC). They bind peptide fragments of foreign antigens and present them to T cells to induce an immune response." Class I MHC molecules, which are encoded by a series of highly polymorphic genes, are present on almost all cell types and present viral peptides on the surface of virus-infected cells, where they are recognized by cytotoxic T cells. In the MHC class I mechanism, foreign peptides are endocytosed for transport within an antigen presenting cell. Then, at least some of the foreign protein is proteolyzed by the cytosolic proteasome to form short peptides, which are transported into the lumen of the endoplasmic reticulum of the antigen presenting cell. There, the foreign peptides are loaded onto MHC class I molecules and transported by vesicles to the cell surface of the antigen presenting cell for recognition by CD8+ cytotoxic T cells. For example, MHC I expression on cancer cells is required for detection and destruction by T-cells, and cytotoxic T lymphocytes (CTLs, CD8+) require tumor antigen presentation on the target cell by MHC Class I molecules to delineate self from non-self. One of the most common means by which tumors evade the host immune response is by down-regulation of MHC Class I molecule expression by tumor cells, such that the tumor has low MHCI expression, thereby rendering any endogenous or therapeutic anti-tumor T cell responses ineffective (Haworth et al., Pediatr Blood Cancer. 2015 April; 62(4): 571-576). Most often, the loss of MHC expression on tumor cells is mediated by epigenetic events and transcriptional down-regulation of the MHC locus and/or the antigen processing machinery. Lack of a processed peptide antigen leads to decreased MHC expression since empty MHC molecules are not stable on the cell surface.

A class II MHC molecule, which is present on professional antigen presenting cells, presents foreign peptides to helper T cells. Foreign peptides are endocytosed and degraded in the acidic environment of the endosome, which means that the peptides are never presented in the cytosol and remain in a subcellular compartment topologically equivalent to the extracellular space. The peptides bind to preassembled MHC class II proteins in a specialized endosomal compartment, and the loaded MHC class II molecule is then transported to the plasma membrane of the antigen presenting cell for presentation to CD4+ helper T cells. (Alberts et al. Molecular Biology of the Cell 4th Ed., Garland Science, New York (2002) p. 1407). Antigens also can be loaded onto antigen presenting cells by acquisition of MHC class II molecules from the surface of donor cells. Peptide-MHC transfer (cross-dressing"), involves generation of peptide-MHC class II complexes within the donor cell, and their subsequent transfer to recipient antigen presenting cells, which are then able to present the intact, largely unprocessed peptide-MHC class II complexes to helper T cells. (Campana, S. et al., Immunol. Letters (2015) 168(2): 349-54). Endogenous antigens can also be presented by MHC class II when they are degraded through autophagy. (Schmid, D. et al. (2007) Immunity 26(1): 79-92).

The term "modify" and its various grammatical forms as used herein, are meant to refer to a change of the form or qualities of.

The term "modulate" and its various grammatical forms as used herein, are meant to refer to regulating, altering, adapting or adjusting to a certain measure or proportion. Such modulation may be any change, including an undetectable change.

The term "modified" or "modulated" as used herein with respect to an immune response to tumor cells is meant to refer to changing the form or character of the immune response to the tumor cells via one or more recombinant DNA techniques such that the immune cells are able to recognize and kill tumor cells.

The term "natural killer (NK) cells" as used herein is meant to refer to lymphocytes in the same family as T and B cells, classified as group I innate lymphocytes. They have an ability to kill tumor cells without any priming or prior activation, in contrast to cytotoxic T cells, which need priming by antigen presenting cells. NK cells secrete cytokines such as IFNγ and TNFα, which act on other immune cells, like macrophages and dendritic cells, to enhance the immune response. Activating receptors on the NK cell surface recognize molecules expressed on the surface of cancer cells and infected cells and switch on the NK cell. Inhibitory receptors act as a check on NK cell killing. Most normal healthy cells express MHCI receptors, which mark them as "self." Inhibitory receptors on the surface of the NK cell recognize cognate MHCI, which switches off the NK cell, preventing it from killing. Once the decision is made to kill, the NK cell releases cytotoxic granules containing perforin and granzymes, which leads to lysis of the target cell. Natural killer reactivity, including cytokine secretion and cytotoxicity, is controlled by a balance of several germ-line encoded inhibitory and activating receptors such as killer immunoglobulin-like receptors (KIRs) and natural cytotoxicity receptors (NCRs). The presence of the MHC Class I molecule on target cells serves as one such inhibitory ligand for MHC Class I-specific receptors, the Killer cell Immunoglobulin-like Receptor (KIR), on NK cells. Engagement of KIR receptors blocks NK activation and, paradoxically, preserves their ability to respond to successive encounters by triggering inactivating signals. Therefore, if a KIR is able to sufficiently bind to MHC Class I, this engagement may override the signal for killing and allows the target cell to live. In contrast, if the NK cell is unable to sufficiently bind to MHC Class I on the target cell, killing of the target cell may proceed. Consequently, those tumors which express low MHC Class I and which are thought to be capable of evading a T-cell-mediated attack may be susceptible to an NK cell-mediated immune response instead.

The term "natural killer T cell" or "NKT" as used herein, is meant to refer to invariant natural killer T (iNKT) cells, also known as type-I NKT cells, as well as all subsets of non-invariant (Vα24− and Vα24+) natural killer T cells, which express CD3 and an αβ T cell receptor (TCR) (herein termed "natural killer αβ T cells") or γΔ TCR (herein termed "natural killer γΔ T cells"), all of which have demonstrated capacity to respond to non-protein antigens presented by CD1 antigens. The non-invariant NKT cells encompassed by the methods of the described disclosure share in common with type-I NKT cells the expression of surface receptors commonly attributed to natural killer (NK) cells, as well as a TCR of either a α or γΔ TCR gene locus rearrangement/recombination.

The term "invariant natural killer T cell" as used herein, is meant to be used interchangeably with the term "iNKT," and is meant to refer to a subset of T-cell receptor (TCR) α-expressing cells that express a restricted TCR repertoire that, in humans, is composed of a Vα24-Jα18 TCRα chain, which is, for example, coupled with a Vβ11 TCRβ chain. iNKT is meant to encompass all subsets of CD3+Vα24+ type-I NKT cells (CD3+CD4+CD8−Vα24+, CD3+CD4−CD8−+Vα24−.+, and CD3+CD4−CD8−Vα24+) as well as those cells, which can be confirmed to be type-I NKT cells by gene expression or other immune profiling, but have down-regulated surface expression of Vα24 (CD3+Vα24−). This includes cells which either do or do not express the regulatory transcription factor FOXP3. Unlike conventional T cells, which mostly recognize peptide antigens presented by MHC molecules, iNKT cells recognize glycolipid antigens presented by the non-polymorphic MHC class 1-like CD1d.

The term "non-expanded" as used herein, is meant to refer to a cell population that has not been grown in culture (in vitro) to increase the number of cells in the cell population.

The term "non-replicating" or "replication-impaired" virus refers to a virus that is not capable of replication to any significant extent in the majority of normal mammalian cells or normal primary human cells.

The term "nucleic acid" as used herein, is meant to refer to a deoxyribonucleotide or ribonucleotide polymer in either single- or double-stranded form, and, unless otherwise limited, encompasses known analogues having the essential nature of natural nucleotides in that they hybridize to single-stranded nucleic acids in a manner similar to naturally occurring nucleotides (e.g., peptide nucleic acids). Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).Measuring the effects of base incompatibility by quantifying the rate at which two strands anneal can provide information as to the similarity in base sequence between the two strands being annealed. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids.

The term "nucleotide sequence" as used herein, is meant to refer to a heteropolymer of deoxyribonucleotides. The nucleotide sequence encoding for a particular peptide, oligopeptide, or polypeptide may be naturally occurring or they may be synthetically constructed.

The term "open reading frame" as used herein, is meant to refer to a sequence of nucleotides in a DNA molecule that has the potential to encode a peptide or protein: it starts with a start triplet (ATG), is followed by a string of triplets each of which encodes an amino acid, and ends with a stop triplet (TAA, TAG or TGA).

The phrase "operably linked" as used herein, is meant to refer (1) to a first sequence(s) or domain being positioned sufficiently proximal to a second sequence(s) or domain so that the first sequence(s) or domain can exert influence over the second sequence(s) or domain or a region under control of that second sequence or domain; and (2) to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, are in the same reading frame. According to some embodiments, the phrase "operatively linked" refers to a linkage in which two or more protein domains or polypeptides are ligated or combined via recombinant DNA technology or chemical reaction such that each protein domain or polypeptide of the resulting fusion protein retains its original function.

The term "optimized viral polypeptide" as used herein, is meant to refer to an immunogenic polypeptide that is not a naturally-occurring viral peptide, polypeptide, or protein. Optimized viral polypeptide sequences are initially generated by modifying the amino acid sequence of one or more naturally-occurring viral gene products (e.g., peptides, polypeptides, and proteins) to increase the breadth, intensity, depth, or longevity of the antiviral immune response (e.g., cellular or humoral immune responses) generated upon immunization (e.g., when incorporated into a vaccine of the disclosure) of a mammal (e.g., a human). Thus, the optimized viral polypeptide may correspond to a "parent" viral gene sequence; alternatively, the optimized viral polypeptide may not correspond to a specific "parent" viral gene sequence but may correspond to analogous sequences from various strains or quasispecies of a virus. Modifications to the viral gene sequence that can be included in an optimized viral polypeptide include amino acid additions, substitutions, and deletions. According to some embodiments of the disclosure, the optimized viral polypeptide is the composite or merged amino acid sequence of two or more naturally-occurring viral gene products (e.g., natural or clinical viral isolates) in which each potential epitope (e.g., each contiguous or overlapping amino acid sequence of 5, 6, 7, 8, 9, 10, 11, 12, 13, 14, 15, 16, 17, 18, 19, 20, 21, 22, 23, 24, 25, 26, 27, 28, 29, 30 or more amino acids in length) is analyzed and modified to improve the immunogenicity of the resulting optimized viral polypeptide. Optimized viral polypeptides that correspond to different viral gene products can also be fused to facilitate incorporation in a vaccine of the disclosure. Methods of generating an optimized viral polypeptides are described in, e.g., Fisher et al. (2007) "Polyvalent Vaccine for Optimal Coverage of Potential T-Cell Epitopes in Global HIV-I Variants," Nat. Med. 13(1): 100-106 and International Patent Application Publication WO 2007/024941, herein incorporated by reference. Once the optimized viral polypeptide sequence is generated, the corresponding polypeptide can be produced or administered by standard techniques as described herein.

The term "overall survival" (OS) as used herein, is meant to refer to the length of time from either the date of diagnosis or the start of treatment for a disease, such as cancer, that patients diagnosed with the disease are still alive.

The term "parenteral" and its other grammatical forms as used herein, is meant to refer to administration of a substance occurring in the body other than by the mouth or alimentary canal. For example, the term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques.

The term "pattern recognition receptors" or "PRRs" as used herein, is meant to refer to receptors that are present at the cell surface to recognize extracellular pathogens; in the endosomes where they sense intracellular invaders, and finally in the cytoplasm. They recognize conserved molecular structures of pathogens, called pathogen associated molecular patterns (PAMPs) specific to the microorganism and essential for its viability. PRRs are divided into four families: toll-like receptors (TLR); nucleotide oligomerization receptors (NLR); C-type leptin receptors (CLR), and RIG-1 like receptors (RLR).

The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 14 amino acids in length. The series of amino acids are consider an "oligopeptide" when the amino acid length is greater than about 14 amino acids in length, typically up to about 30 to 40 residues in length. When the amino acid residue length exceeds 40 amino acid residues, the series of amino acid residues is termed "polypeptide".

A peptide, oligopeptide, polypeptide, protein, or polynucleotide coding for such a molecule is "immunogenic" and thus an immunogen within the present disclosure if it is capable of inducing an immune response. In the present disclosure, immunogenicity is more specifically defined as the ability to induce a CTL-mediated response. Thus, an immunogen would be a molecule that is capable of inducing an immune response, and in the present disclosure, a molecule capable of inducing a CTL response. An immunogen may have one or more isoforms or splice variants that have equivalent biological and immunological activity, and are thus also considered for the purposes of this disclosure to be immunogenic equivalents of the original, natural polypeptide.

In accordance with the present disclosure, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity} = 100[1-(C/R)]$$

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

The term "pharmaceutical composition" as used herein is meant to refer to a composition that is employed to prevent, reduce in intensity, cure or otherwise treat a target condition, syndrome, disorder or disease.

The term "pharmaceutically acceptable carrier" as used herein is meant to refer to any substantially non-toxic carrier conventionally useable for administration of pharmaceuticals in which the isolated polypeptide of the present disclosure will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein is meant to refer to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present disclosure or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the disclosure by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The terms "portion," "segment," and "fragment," when used herein in relation to polypeptides, are meant to refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, such terms refer to the products produced by treatment of said polynucleotides with endonucleases.

The term "prevention" as used herein, is meant to refer to a process of prophylaxis in which an animal, especially a mammal, and most especially a human, is exposed to an immunogen of the present disclosure prior to the induction or onset of the disease process. This could be done where an individual is at high risk for any influenza infection based on the living or travel to the influenza pandemic areas. Alternatively, the immunogen could be administered to the general population as is frequently done for any infectious diseases. Alternatively, the term "suppression" is often used to describe a condition wherein the disease process has already begun but obvious symptoms of said condition have yet to be realized. Thus, the cells of an individual may have been infected but no outside signs of the disease have yet been clinically recognized. In either case, the term prophylaxis can be applied to encompass both prevention and suppression.

The term "proliferate" and its various grammatical forms as used herein is meant to refer to the process that results in an increase of the number of cells, and is defined by the balance between cell division and cell loss through cell death or differentiation.

The term "protect" or "protection of" a subject from developing a disease or from becoming susceptible to an infection as referred herein means to partially or fully protect a subject. As used herein, to "fully protect" means that a treated subject does not develop a disease or infection caused by an agent such as a virus, bacterium, fungus, protozoa, helminth, and parasites, or caused by a cancer cell. To "partially protect" as used herein means that a certain subset of subjects may be fully protected from developing a disease or infection after treatment, or that the subject does not develop a disease or infection with the same severity as an untreated subject.

The term "protective immune response" or "protective response" as used herein, is meant to refer to an immune response mediated by antibodies against an infectious agent, which is exhibited by a vertebrate (e.g., a human), that prevents or ameliorates an infection or reduces at least one symptom thereof. Vaccines of the present disclosure can stimulate the production of antibodies that, for example, neutralize infectious agents, blocks infectious agents from entering cells, blocks replication of said infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates a viral infection or reduces at least one symptom thereof.

The term "recombinant" as used herein to describe a nucleic acid molecule is meant to refer to a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The term "recombinant" vector, such as a DNA plasmid, pseudotyped lentiviral or retroviral vector as used herein, is meant to refer to a vector wherein the material (e.g., a nucleic acid or encoded protein) has been artificially or synthetically (non-naturally) altered by human intervention. The alteration can be performed on the material within, or removed from, its natural environment or state. Specifically, e.g., a protein derived from influenza virus is recombinant when it is produced by the expression of a recombinant nucleic acid. For example, a "recombinant nucleic acid" is one that is made by recombining nucleic acids, e.g., during cloning, or other procedures, or by chemical or other mutagenesis; and a "recombinant polypeptide" or "recombinant protein" is a polypeptide or protein which is produced by expression of a recombinant nucleic acid. Some embodiments of a recombinant nucleic acid includes an open reading frame encoding an HA, NA, and/or a protease, and can further include non-coding regulatory sequences, and introns.

The term "reporter gene" ("reporter") or "assay marker" as used herein is meant to refer to a gene and/or peptide that can be detected, or easily identified and measured. The expression of the reporter may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

The term "selectable marker" as used herein is meant to refer to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "subject" as used herein is meant to refer to any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

The phrase "subject in need thereof" as used herein is meant to refer to a patient that (i) will be administered a vaccine according to the described disclosure, (ii) is receiving a vaccine according to the described disclosure; or (iii) has received a vaccine according to the described disclosure, unless the context and usage of the phrase indicates otherwise.

The term "stimulate an immune cell" or "stimulating an immune cell" as used herein is meant to refer to a process (e.g., involving a signaling event or stimulus) causing or resulting in a cellular response, such as activation and/or expansion, of an immune cell, e.g. a CD8+ T cell.

The term "substantially identical" as used herein is meant to refer to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). For example, such a sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

The terms "T lymphocyte" or "T cell" are used interchangeably to refer to cells that mediate a wide range of immunologic functions, including the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines. T cells recognize antigens on the surface of other cells and mediate their functions by interacting with, and altering, the behavior of these antigen-presenting cells (APCs).T cells can also be classified based on their function as helper T cells; T cells involved in inducing cellular immunity; suppressor T cells; and cytotoxic T cells.

The term "T cell antigen" as used herein is meant to refer to a protein or fragment thereof which can be processed into a peptide that can bind to either Class I MHC, Class II MHC, non-classical MHC, or CD1 family molecules (collectively antigen presenting molecules), and in this combination can engage a T cell receptor on a T cell.

The term "T cell epitope" as used herein is meant to refer to a short peptide molecule that binds to a class I or II MHC molecule and that is subsequently recognized by a T cell. T cell epitopes that bind to class I MHC molecules are typically 8-14 amino acids in length, and most typically 9 amino acids in length. T cell epitopes that bind to class II MHC molecules are typically 12-20 amino acids in length. In the case of epitopes that bind to class 11 MHC molecules, the same T cell epitope may share a common core segment, but differ in the length of the carboxy- and amino-terminal flanking sequences due to the fact that ends of the peptide molecule are not buried in the structure of the class II MHC molecule peptide-binding cleft as they are in the class I MHC molecule peptide-binding cleft.

The term "T cell mediated immune response" as used herein is meant to refer to a response that occurs as a result of recognition of a T cell antigen bound to an antigen presenting molecule on the cell surface of an antigen presenting cell, coupled with other interactions between costimulatory molecules on the T cell and APC. This response serves to induce T cell proliferation, migration, and production of effector molecules, including cytokines and other factors that can injure cells.

The term "T cell receptor" (TCR) as used herein, is meant to refer to a complex of integral membrane proteins that participate in the activation of T cells in response to an antigen. The TCR expressed by the majority of T cells consisting of α and β chains. A small group of T cells express receptors made of γ and δ chains. Among the α/β cells are two sublineages: those that express the coreceptor molecule CD4 (CD4+ cells), and those that express CD8 (CD8+ cells). These cells differ in how they recognize antigen and in their effector and regulatory functions. CD4+ T cells are the major regulatory cells of the immune system. Their regulatory function depends both on the expression of their cell-surface molecules, such as CD40 ligand whose expression is induced when the T cells are activated, and the wide array of cytokines they secrete when activated. The cytokines can be directly toxic to target cells and can mobilize potent inflammatory mechanisms.CD8+ T cells, can develop into cytotoxic T-lymphocytes (CTLs) capable of efficiently lysing target cells that express antigens recognized by the CTLs.

The term "treatment" as used herein is meant to refer to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

The terms "therapeutic amount", "therapeutically effective amount", an "amount effective", or "pharmaceutically effective amount" of an active agent are used interchangeably to refer to an amount that is sufficient to provide the intended benefit of treatment. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amounts" and "pharmaceutically effective amounts" include prophylactic or preventative amounts of the compositions of the described disclosure. In prophylactic or preventative applications of the described disclosure, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

The term "therapeutic effect" as used herein is meant to refer to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" as used herein is meant to refer to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

The term "vaccinated" as used herein is meant to refer to being treated with a vaccine.

The term "vaccination" as used herein is meant to refer to treatment with a vaccine.

The term "vaccine" as used herein is meant to refer to a formulation which is in a form that is capable of being administered to a vertebrate and which induces a protective immune response sufficient to induce immunity to prevent and/or ameliorate an infection and/or to reduce at least one symptom of an infection and/or to enhance the efficacy of another dose of a formulation. Typically, the vaccine comprises a conventional saline or buffered aqueous solution medium in which the composition of the present disclosure is suspended or dissolved. In this form, the composition of the present disclosure can be used conveniently to prevent, ameliorate, or otherwise treat a viral infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

The term "vaccine therapy" as used herein is meant to refer to a type of treatment that uses a substance or group of substances to stimulate the immune system to destroy a tumor or infectious microorganisms.

The term "variant" or "derivative" with respect to a peptide or DNA sequence as used herein is meant to refer to a non-identical peptide or DNA sequence that is modified from its original sequence. The differences in the sequences may by the result of changes, by design, in sequence or structure. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence. The terms "variant" or "derivative" with respect to cells as used herein refers to a cell line that has been modified from its cell line of origin (e.g. modified to express recombinant DNA sequences).

The term "vector" as used herein, is meant to refer to a DNA construct that contains a promoter operably linked to a downstream gene or coding region (e.g., a cDNA or genomic DNA fragment, which encodes a polypeptide or polypeptide fragment). Introduction of the vector into a recipient cell (e.g., a prokaryotic or eukaryotic cell, e.g., a bacterium, yeast, insect cell, or mammalian cell, depending upon the promoter within the expression vector) or organism (including, e.g., a human) allows the cell to express mRNA encoded by the vector, which is then translated into the encoded optimized viral polypeptide of the disclosure. Vectors for in vitro transcription/translation are also well known in the art and are described further herein. A vector may be a genetically engineered plasmid, virus, or artificial chromosome derived from, e.g., a bacteriophage, adenovirus, retrovirus, poxvirus, or herpesvirus.

The term "virus-like particle" or "VLP" as used herein, is meant to refer to a nonreplicating, viral shell. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. See, e.g., Baker et al., Biophys. J. (1991) 60:1445-1456; Hagensee et al., J. Virol. (1994) 68:4503-4505. For example, VLPs can be isolated by density gradient centrifugation and/or identified by characteristic density banding (e.g., Examples). Alternatively, cryoelectron microscopy can be performed on vitrified aqueous samples of the VLP preparation in question, and images recorded under appropriate exposure conditions. Additional methods of VLP purification include but are not limited to chromatographic techniques such as affinity, ion exchange, size exclusion, and reverse phase procedures.

The term "wild-type" as used herein is meant to refer to the typical form of an organism, strain, gene, protein, nucleic acid, or characteristic as it occurs in nature. Wild-type refers to the most common phenotype in the natural population. The terms "wild-type" and "naturally occurring" are used interchangeably.

Compositions

According to one aspect, the disclosure provides an immunogen, or an immunogenic portion thereof, that is designed against an internal CD8+ T cell epitope of an infectious agent as described herein, by using the internal conserved proteins of the infectious agent. As described in more detail throughout the description and Examples herein, consensus amino acid sequences can be deduced for example from viral strains available in the Genbank database, and the amino acid having the highest frequency of occurrence at each position of the amino acid sequence can be used as the consensus amino acid at that site. Thus, the resulting protein sequence constitutes the shared amino acid of each site, and can be analyzed using a publicly available online CD8+ T cell epitope prediction software and at tools.immuneepitope.org/main/tcell/ (available online at syfpeithi.de and described in Singh H, et al. (2003) Bioinformatics; 19: 1009-1014 and Moutaftsi M, et al. (2006) Nat Biotechnol. 24: 817-819, the contents of each of which are incorporated by reference in their entireties herein). The sequences can then be modified following optimized mammalian codon usage.

According to some embodiments, the infectious agent is a virus belongs to a virus family selected from, but not limited to the group consisting of Flaviviridae, Paramyxoviridae, Togaviridae, Filoviridae, Orthomyxoviridae, Rhabdoviridae and Retroviridae. According to some embodiments, the virus from the Flaviviridae family is selected from a virus from the genus Flavivirus. According to some embodiments, the virus from the Flaviviridae family is selected from a virus from the genus *Hepacivirus*. According to some embodiments, the virus from the Flaviviridae family is selected from a virus from the genus *Pegivirus*. According to some embodiments, the virus from the Flaviviridae family is selected from a virus from the genus *Pestivirus*. According to some embodiments, the virus from the Paramyxoviridae family is selected from a virus from the Pneumonvirinae subfamily. According to some embodiments, the virus from the Paramyxoviridae family is selected from a virus from the Paramyxovirinae subfamily. According to some embodiments, the virus from the Togaviridae family is from the genus *Alphavirus*. According to some embodiments, the virus from the Togaviridae family is from the genus *Rubivirus*. According to some embodiments, the virus from the Togaviridae family is from the genus *Pestivirus*. According to some embodiments, the virus from the Togaviridae family is from the genus *Arterivirus*. According to some embodiments, the virus from the Filoviridae family is from the genus *Cuevavirus*. According to some embodiments, the virus from the Filoviridae family is from the genus *Ebolavirus* (EBOV). According to some embodiments, the virus from the Filoviridae family is from the genus *Marburgvirus* (MARV). According to some embodiments, the virus from the Orthomyxoviridae family is from the genus *Influenzavirus* A. According to some embodiments, the virus from the Orthomyxoviridae family is from the genus *Influenzavirus* B. According to some embodiments, the virus from the Orthomyxoviridae family is from the genus *Influenzavirus* C. According to some embodiments, the virus from the Orthomyxoviridae family is from the genus *Isavirus*. According to some embodiments, the virus from the Rhabdoviridae family is from the genus *Vesiculovirus*. According to some embodiments, the virus from the Rhabdoviridae family is from the genus *Ephemerovirus*. According to some embodiments, the virus from the Rhabdoviridae family is from the genus *Lyssavirus*. According to some embodiments, the virus from the Retroviridae family is from the genus *Alpharetrovirus*. According to some embodiments, the virus from the Retroviridae family is from the genus *Betaretrovirus*. According to some embodiments, the virus from the Retroviridae family is from the genus *Deltaretrovirus*. According to some embodiments, the virus from the Retroviridae family is from the genus *Epsilonretrovirus*. According to some embodiments, the virus from the Retroviridae family is from the genus *Gammaretrovirus*. According to some embodiments, the virus from the Retroviridae family is from the genus *Lentivirus*. According to some embodiments, the virus from the Retroviridae family is from the genus *Spumavirus*.

Exemplary conserved viral proteins and corresponding RefSeq Nos are shown in Table 1, in Example 1A. It is to be understood that Table 1 is merely exemplary, and any internal conserved protein of any desired virus that is publicly available in GenBank can be used in the methods described herein.

According to some embodiments, nucleic acids are provided that express immunogenic domains rather than the entire protein. These portions (or fragments) may be of any length sufficient to be immunogenic or antigenic. Immunogenicity can be determined using any of the assays described herein. Fragments may be at least four amino acids long, or for example 5-9 amino acids long, but may be longer, such as e.g. 10, 11, 12, 13, 14, 15, 16, 17, 18, 19, 20, 30, 40, 50, 60, 70, 80, 90, 100, 500 amino acids long or more, or any length in between. Epitopes that induce a protective immune response to a pathogen such as bacteria, viruses, fungi or protozoae may be combined with heterologous gene sequences that encode proteins with immunomodulating activities, such as cytokines, interferon type 1, gamma interferon, colony stimulating factors, interleukin-1, -2, -4, -5, -6, -12.

Immunogens as described herein comprise polypeptides with amino acid sequences comprising conserved CD8+ T cell epitopes of internal antigens of the infectious agent generated and selected according to the methods described herein, wherein said immunogens facilitate a cytotoxic T lymphocyte (CTL)-mediated immune response against various strains of cells infected with the agent. Also provided by the present disclosure are nucleic acid molecules that encode polypeptides comprising said epitopic peptide, and which can also be used to facilitate an immune response against the infected cells.

The present disclosure provides compositions comprising the polypeptides and nucleic acid molecules that encode polypeptides described herein whereby the oligopeptides and polypeptides of such immunogens are capable of inducing a CTL response against cells expressing a protein comprising conserved CD8+ T cell epitopes of internal antigens of an infectious agent generated and selected according to the methods described herein, presented in association with Class I MHC protein, which cells are infected with various strains of an infectious agent. Alternatively, the immunogens of the present disclosure can be used to induce a CTL response in vitro. The generated CTL population(s) can then be introduced into a patient with an infection caused by the infectious agent. Alternatively, the ability to generate CTLs in vitro can serve as a diagnostic for infection by the infectious agent.

The immunogens described herein include fragments or portions thereof that maintain the same biological activity as the reference immunogen. For example, the immunogens, or fragment thereof, described herein, comprise infectious agent-specific CD8+epitopes that bind with high affinity to human MHC class I molecules to elicit a CD8+ T cell response.

Immunogens

Using the methods described herein to identify and generate universal vaccines targeting conserved T cell epitopes, it should be possible to immunize against a wide spectrum of infectious agents such as, but not limited to, those described below.

According to some embodiments, an immunogen (i.e., a conserved immunogen as described herein), by inducing an immune response, inhibits an infectious disease, e.g., reduces or alleviates a cause or symptom of an infectious disease, or improves a value for a parameter associated with the infectious disease.

According to some embodiments, the immunogens of the disclosure can be chemically synthesized and purified using methods which are well known to the ordinarily skilled artisan. The immunogens can also be synthesized by well-known recombinant DNA techniques. According to some embodiments, the immunogenic peptides and polypeptides of the disclosure are prepared synthetically, or by any means known in the art, including those techniques involving recombinant DNA technology.

According to some embodiments, the coding sequences for peptides contemplated herein can be synthesized on commercially available automated DNA synthesizers or modified to a desired amino acid substitution. The coding sequence can be transformed or transfected into suitable hosts to produce the desired fusion protein.

Genetic modifications including codon optimization, RNA optimization, and/or the addition of a high efficient immunoglobin leader sequence to increase the immunogenicity of constructs are contemplated.

Viral Immunogens

According to some embodiments, the vaccine of the present disclosure immunizes against an Orthomyxoviridae virus. For example, the Orthomyxoviridae virus is Influenzavirus A, Influenzavirus B, Influenzavirus C, or Influenzavirus D. According to some embodiments, the Influenzavirus A is H1N1, H2N2, H3N2, H5N1, H7N7, H1N2, H9N2, H7N2, H7N3, or H10N7. According to some embodiments, the Orthomyxoviridae virus is a causative agent for avian influenza, swine influenza, bovine influenza, and the like.

According to some embodiments, the vaccine of the present disclosure immunizes against an Adenoviridae virus. According to some embodiments, the adenoviridae virus is mastadenovirus aviadenovirus, human adenovirus types HAdV-1 to 57 in human adenovirus species HAdV-A to G, and the like.

According to some embodiments, the vaccine of the present disclosure immunizes against a Paramyxoviridae or a Pneumoviridae virus. For example, the Paramyxoviridae or Pneumoviridae virus is measles virus, mumps virus, human respiratory syncytial virus, respiratory syncytial virus, virulent Newcastle disease, paramyxovirus, parainfluenza virus 1, metapneumovirus, avian pneumovirus and human metapneumovirus, and the like.

According to some embodiments, the vaccine of the present disclosure immunizes against a Flaviviridae virus. For example, the Flaviviridae virus is hepatitis C virus, dengue virus, yellow fever virus, St. Louis encephalitis virus, Japanese encephalitis virus, West Nile virus, zika virus, La Crosse virus, and the like.

According to some embodiments, the vaccine of the present disclosure immunizes against a Pappilomarviridae or a Polymaviridae virus. For example, the Papilomarviridae or Polymaviridae virus is human papillomavirus 1-18, human polyomavirus 1-14, and the like.

According to some embodiments, the vaccine of the present disclosure immunizes against a Herpesviridae virus. According to some embodiments, the Herpesviridae virus is an alphaherpesvirinae virus, betaherpesvirinaevirus, or a gammaherpesvirinae virus. For example, the alphaherpesvirinae virus is a varicellovirus, simplexvirus, infectious laryngotracheitis virus, and the like. For example the varicellovirus is varicella-zoster virus, bovine herpesvirus, equid herpesvirus, pseudorabies virus, and the like. For example, the simplexvirus is herpes simplex virus 1-6 and the like. For example, the gammaherpesvirinae virus is the epstin-barr virus.

According to some embodiments, the vaccine of the present disclosure immunizes against a Retroviridae virus. For example, the Retroviridae virus is a Lentivirus, a Retrovirus, a Spumaretrovirinae virus, and the like. For example, the Lentivirus is human immunodeficiency virus 1 and human immunodeficiency virus 2. For example, the Retrovirus is mammalian type B retroviruses, mammalian type C retroviruses, avian type C retroviruses, type D retrovirus group, BLV-HTLV retroviruses, and the like. For example, the Spumaretrovirinae virius is a spumavirus, and the like.

According to some embodiments, the vaccine of the present disclosure immunizes against a Rhabdoviridae virus. For example, the Rhabdoviridae virus is vesiculovirus, lyssavirus, ephemerovirus, cytorhabdovirus, and necleorhabdovirus, and the like. For example, the lyssavirus is rabies virus.

According to some embodiments, the vaccine of the present disclosure immunizes against a Picornaviridae virus. For example, the Picornaviridae virus is an apthovirus, cardiovirus, enterovirus, rhinovirus, hepatovirus and the like. For example, the apthovirus is bovine rhibitis virus, equine rhinitis virus, foot-and-mouth-disease virus and the like. For example, the hepatovirus is hepatovirus A. For example, the enterovirus is the poliovirus.

According to some embodiments, the vaccine of the present disclosure immunizes against a Reoviridae virus. For example, the Reoviridae virus is orthoreovirus, orbivirus, rotavirus, cypovirus, fijivirus, phytoreovirus, oryzavirus and the like. For example, the rotavirus is a rotavirus gastroenteritis.

According to some embodiments, the vaccine of the present disclosure immunizes against a Poxyviridae virus. For example, (e.g., chordopoxyirinae, parapoxvirus, avipoxvirus, capripoxvirus, leporipoxvirus, suipoxvirus, molluscipoxvirus, and entomopoxyirinae)

According to some embodiments, the vaccine of the present disclosure immunizes against a Hepadnaviridae virus. For example, the hepadnaviridae virus is hepatitis B.

According to some embodiments, the vaccine of the present disclosure immunizes against a Togaviridae or Matonaviridae virus. For example, the Togaviridae virus is an alphavirus or a rubivirus. For example, the alphavirus is a sindbis virus, Venezuelan equine encephalitis virus, and the like. For example, the rubivirus is chikungunya virus, rubella virus, and the like.

According to some embodiments, the vaccine of the present disclosure immunizes against an Arenaviridae virus. For example, the Arenaviridae virus is renavirus, lymphocytic choriomeningitis virus, ippy virus, lassa virus, and the like.

According to some embodiments, the vaccine of the present disclosure immunizes against a Coronaviridae virus. For example, the coronaviridae virus is a coronavirus, torovirus, SARs-like coronavirus, and the like.

According to some embodiments, the vaccine of the present disclosure immunizes against a Filoviridae virus. For example, the Filoviridae fivus is ebolavirus, Marburg marburgvirus, and the like.

According to some embodiments, the vaccine of the present disclosure immunizes against a Hantaviridae virus. For example, the Hantaviridae virus is a hanta virus.

According to some embodiments, the vaccine of the present disclosure immunizes against a Leviviridae virus. For example, the Leviviridae virus is levivirus, allolevirus, and the like.

According to some embodiments, the vaccine of the present disclosure immunizes against swine viruses. For example, swine viruses include swine rotavirus, swine parvovirus, bovine viral diarrhea, neonatal calf diarrhea virus, hog cholera virus, African swine fever virus, swine influenza, and the like.

According to some embodiments, the vaccine of the present disclosure immunizes against equine viruses. For example, equine viruses include equine influenza virus, equine herpesvirus, Venezuelan equine encephalomyelitis virus, and the like.

According to some embodiments, the vaccine of the present disclosure immunizes against cattle or bovine viruses. For example, bovine viruses include bovine respiratory syncytial virus, bovine parainfluenza virus, bovine viral diarrhea virus, infectious bovine rhinotracheitis virus, foot and mouth disease virus, punta toro virus, and the like.

According to an aspect of the present disclosure, an anti-influenza virus recombinant vector vaccine is provided which is expressed and constructed by using an anti-influenza vaccine immunogen or an immunogenic fragment thereof or a combination thereof in a plurality of different vectors.

According to some embodiments, the immunogen of the present disclosure comprises at least one conserved protein of an Orthomyxoviridae virus or an immunogenic fragment thereof. For example, the Orthomyxoviridae virus is Influenzavirus A, Influenzavirus B, Influenzavirus C, or Influenzavirus D. According to some embodiments, the Influenzavirus A is H1N1, H2N2, H3N2, H5N1, H7N7, H1N2, H9N2, H7N2, H7N3, or H10N7. According to some embodiments, the Orthomyxoviridae virus is the causative agent of avian influenza, swine influenza, bovine influenza, and the like. According to some embodiments, the immunogen of the present disclosure comprises at least one influenza virus internal conserved protein selected from matrix protein (M1, M2), a nuclear protein (NP), an alkaline polymerase (PB1, PB2), and an acidic polymerase (PA) or an immunogenic fragment thereof. According to some embodiments, the present disclosure provides a broad-spectrum anti-influenza virus immunogen or an immunogenic fragment thereof, or a combination thereof, and an immunization method, characterized in that the immunogen comprises at least one influenza virus internal conserved protein selected from matrix protein (M1, M2), a nuclear protein (NP), an alkaline polymerase (PB1, PB2), and an acidic polymerase (PA) or an immunogenic fragment thereof. According to one embodiment, consensus sequence(s) for the immunogen of the present disclosure can be found through methods known in the art and in publicly available literature, for example, at in the Genbank Database, Genbank accession no. J02132; in Air, 1981, Proc. Natl. Acad. Sci. USA 78:7639-7643; Newton et al., 1983, Virology 128:495-501; in ZHAO, CHEN, AND JIANQING XU. Towards Universal Influenza Virus Vaccines: from Natural Infection to Vaccination Strategy. Vol. 53, no. 1, 2018, pp. 1-6; or in Dalrymple et al., 1981, in Replication of Negative Strand Viruses, Bishop and Compans (eds.), Elsevier, N.Y., p. 167.

According to some embodiments, the immunogen of the present disclosure comprises at least one conserved protein of an Adenoviridae virus. For example, the adenoviridae virus is mastadenovirus aviadenovirus, human adenovirus types HAdV-1 to 57 in human adenovirus species HAdV-A to G, and the like. According to some embodiments, the immunogen of the present disclosure comprises at least one adenoviridae virus conserved E1A, E1B, E2, E3, E4, E5, L1, L2, L3, L4, L5 protein.

According to some embodiments, the immunogen of the present disclosure comprises at least one conserved protein of a Flaviviridae virus, or an immunogenic fragment thereof. For example, the Flavivirus is zika virus, dengue virus, and the like. According to some embodiments, the immunogen of the present disclosure comprises at least one zika virus conserved capsid protein (C), membrane protein (prM/M), envelope protein (E), polymerase (NS5) or nonstructural protein(s) (NS1, NS2A-B, NS3, NS4A-4B), or an immunogenic fragment thereof. Consensus sequences for conserved protein(s) in the Flaviviridae virus family, for example, the zika virus, are known in the prior art. Consensus sequences can also be generated as discussed en supra or found in the literature, for example, in Shrivastava et al., "Whole genome sequencing, variant analysis, phylogenetics, and deep sequencing of Zika virus strains." Nature: Scientific Reports (2018) 8:15843 the entirety of which is incorporated herein by reference.

According to some embodiments, the immunogen of the present disclosure comprises at least one dengue virus conserved protein, for example a conserved capsid protein (C), matrix protein (M), and the like. Consensus sequences for conserved protein(s) in the Flaviviridae virus family, for example, the dengue virus, are known in the prior art. Consensus sequences can also be generated as discussed en supra or found in the literature, for example, in Genbank accession no. M19197; or in Hahn et al., (1988), Virology 162:167-180.

According to some embodiments, the immunogen of the present disclosure comprises at least one conserved protein of a Paramyxoviridae or Pneumoviridae virus, or an immunogenic fragment thereof. For example, the paramyxovirus or pneumovirus is measles virus. According to some embodiments, the immunogen of the present disclosure comprises at least one measles virus conserved internal matrix protein (M), nucleocapsid protein (N), large protein (L), orphosphorous-protein (P), humagglutinin (HA), or an immunogenic fragment thereof. According to one embodiment, a consensus sequence for the immunogen of the present disclosure can be found through methods known in the art and in publicly available literature, for example, at in RADECKE F., BILLETER M. A. (1995) Appendix: Measles Virus Antigenome and Protein Consensus Sequences. In: V. ter Meulen et al (eds) Measles Virus. Current Topics in Microbiology and Immunology, vol 191. 181-192 Springer, Berlin, Heidelberg; (HA) Genbank accession no. M81899; or in Rota et al. (1992), Virology 188:135-142.

In another example, the paramyxovirus or pneumovirus is human respiratory syncytial virus. According to some embodiments, the immunogen of the present disclosure comprises at least one conserved glycoprotein (G), viral protein (VP), F glycoprotein (FG), or an immunogenic fragment thereof. According to one embodiment, a consensus sequence for the immunogen of the present disclosure can be found through methods known in the art and in publicly available literature, for example, at in Genbank ((G): accession no. Z33429); and in Garcia et al. (1994) J. Virol.; Collins et al., (1984) Proc. Natl. Acad. Sci. USA 81:7683), which are incorporated herein by reference.

According to some embodiments, the immunogen of the present disclosure comprises at least one conserved protein of a Papilomarviridae or a Polymaviridae virus or an immunogenic fragment thereof. For example, the Papilomarviridae or Polymaviridae virus is human papillomavirus 1-18, or human polyomavirus 1-14. According to some embodiments, the immunogen of the present disclosure comprises at least one conserved E1, E2, E3, E4, E5a, E5b, E6, E7, E8, L1, L2 protein.

According to some embodiments, the immunogen of the present disclosure comprises at least one conserved protein of a Togaviridae virus, or an immunogenic fragment thereof. For example, the togavirus is rubivirus or rubella virus. According to some embodiments, the immunogen of the present disclosure comprises at least one rubella virus conserved capsid protein (C), envelope proteins (E1, E2), and nonstructural proteins (p90 and p150), or an immunogenic fragment thereof.

According to some embodiments, the immunogen of the present disclosure comprises at least one conserved protein of a Filoviridae virus or an immunogenic fragment thereof. For example, the filovirus is ebolavirus or marburgvirus. According to some embodiments, the immunogen off the present disclosure comprises at least one ebola virus conserved nucleoprotein (NP), viral proteins (VP35, VP24), surface glycoprotein (GP), and large polymerase (L) or an immunogenic fragment thereof. According to one embodiment, consensus sequence for the immunogen of the present disclosure can be found through methods known in the art and in publicly available literature, for example, at in JUN, SE-RAN, et al. Ussery (2015) Ebolavirus comparative genomics. FEMS Microbiology Reviews, Volume 39, Issue 5, Pages 764-778; or in HARDICK, J., et al., (2016) Sequencing Ebola and Marburg Viruses Genomes Using Microarrays. J. Med. Virol. 88:1303-1308.

According to some embodiments, the immunogen of the present disclosure comprises at least one Marburg virus conserved protein for example, at least one conserved nucleoprotein (NP), viral proteins (VP), surface glycoprotein (GP), and large polymerase (L) or an immunogenic fragment thereof. According to one embodiment, consensus sequences for the immunogen of the present disclosure can be found through methods known in the art and in publicly available literature, for example, at in HARDICK, J., et al., (2016) Sequencing Ebola and Marburg Viruses Genomes Using Microarrays. J. Med. Virol. 88:1303-1308.

According to some embodiments, the immunogen of the present disclosure comprises at least one conserved protein of a Poxviridae virus or an immunogenic fragment thereof. For example, the poxvirus is variola virus. According to some embodiments, the immunogen of the present disclosure comprises at least one variola virus conserved membrane protein (A13, A17, A27, A28, A33, B5, D8, H3, L1) or an immunogenic fragment thereof. According to one embodiment, consensus sequences for the immunogen of the present disclosure can be found through methods known in the art and in publicly available literature, for example, in MORIKAWA, S., et al. (2005) An Attenuated LC16m8 Smallpox Vaccine: Analysis of Full-Genome Sequence and Induction of Immune Protection. Journal Of Virology, Vol. 79, No. 18. 11873-11891.

According to some embodiments, the immunogen of the present disclosure comprises at least one conserved protein of a rhabdoviridae virus or an immunogenic fragment thereof. For example, the rhabdovirus is rabies virus. According to some embodiments, the immunogen of the present disclosure comprises at least one rabies virus conserved nucleoprotein (N), phosphoprotein (P), matrix protein (M), glycoprotein (G), large polymerase (L) or an immunogenic fragment thereof. According to one embodiment, consensus sequences for the immunogen of the present disclosure can be found through methods known in the art and in publicly available literature, for example, in TORDO, N. & KOUKNETZOFF, A. (1993) The rabies virus genome: an overview. Onderstepoort Journal of Veterinary Research, 60:263-269; or in BORUCKI M K, et al. (2013) Ultra-Deep Sequencing of Intra-host Rabies Virus Populations during Cross-species Transmission. PLoS Negl Trop Dis 7(11): e2555.

According to some embodiments, the immunogen of the present disclosure comprises at least one conserved protein of a Herpesviridae virus or an immunogenic fragment thereof. For example, the herpesvirus is the herpes simplex virus. According to some embodiments, the immunogen of the present disclosure comprises at least one herpes simplex virus conserved capsid protein (MCP, SCP), portal protein (PORT), and triplex monomer or dimer protein (TRI1, TRI2), or an immunogenic fragment thereof. In another example, according to some embodiments, the immunogen of the present disclosure comprises at least one conserved herpes simplex virus type 2 glycoprotein gB, gB, gC, gD, and gE, HIV (GP-120, p17, GP-160, gag, pol, qp41, gp120, vif, tat, rev, nef, vpr, vpu, vpx antigens), ribonucleotide reductase, α-TIF, ICP4, ICP8, ICP35, LAT-related proteins, gB, gC, gD, gE, gH, gI, gJ, and dD antigens, and the like. According to one embodiment, consensus sequences for the immunogen of the present disclosure can be found through methods known in the art and in publicly available literature, for example, in Genbank accession no. M14923; and in Bzik et al. (1986), Virology 155:322-333.

In another example, the herpesvirus is pseudorabies virus. According to some embodiments, the immunogen of the present disclosure comprises at least one pseudorabies virus conserved g50 protein (gpD), gpB, gI11 protein (gpC), glycoprotein H, glycoprotein E, or an immunogeneic fragment thereof.

In another example, the herpesvirus is infectious laryngotracheitis virus. According to some embodiments, the immunogen of the present disclosure comprises at least one infectious laryngotracheitis virus conserved glycoprotein G or glycoprotein 1 protein or an immunogeneic fragment thereof.

According to some embodiments, the immunogen of the present disclosure comprises at least one conserved protein of a Reoviridae virus. For example, the Reoviridae virus is a rotavirus, for example, rotavirus gastroenteritis. According to some embodiments, the immunogen of the present disclosure comprises at least one conserved rotavirus gastroenteritis glycoprotein, matrix protein, or an immunogeneic fragment thereof.

According to some embodiments, the immunogen of the present disclosure comprises at least one conserved protein of a Picornaviridae virus or an immunogenic fragment thereof. For example, the picornavirus is foot-and-mouth-disease virus. According to some embodiments, the immunogen of the present disclosure comprises at least one foot-and-mouth-disease virus conserved capsid protein (P1), membrane protein (2B), helicase (2C), protease (3C), and polymerase (3D) or an immunogenic fragment thereof.

In another example, the picornavirus is poliovirus. According to some embodiments, the immunogen of the present disclosure comprises at least one poliovirus conserved viral protein (VP1) or an immunogeneic fragment thereof. According to one embodiment, consensus sequences for the immunogen of the present disclosure can be found through methods known in the art and in publicly available literature, for example, in Emini et al. (1983) Nature 304:699.

According to some embodiments, the immunogen of the present disclosure comprises at least one conserved protein of a Hepadnaviridae virus or an immunogenic fragment thereof. For example, the hepadnavirus is the hepatitis B virus. According to some embodiments, the immunogen of the present disclosure comprises at least one hepatitis B virus conserved envelope or surface protein (L,M,S), core protein (C), X protein (X), and polymerase (P) or an immunogenic fragment thereof. In another embodiment, the immunogen of the present disclosure comprises at least one hepatitis B virus conserved hepatitis B surface antigen (gp27S, gp36S, gp42S, p22c, pol, x), hepatitis B virus core protein and/or hepatitis B virus surface antigen or an immunogenetic fragment thereof. According to one embodiment, consensus sequences for the immunogen of the present disclosure can be found through methods known in the art and in publicly available literature, for example, in U.K. Patent Publication No. GB 2034323A published Jun. 4, 1980; in Ganem and Varmus (1987) Ann. Rev. Biochem. 56:651-693; Tiollais et al., (1985) Nature 317:489-495; and in Itoh et al., (1986) Nature 308:19; Neurath et al. (1986) Vaccine 4:34.

According to some embodiments, the immunogen of the present disclosure comprises at least one conserved protein of a Retroviridae virus or an immunogenic fragment thereof. For example, the retrovirus is the human immunodeficiency virus. According to some embodiments, the immunogen of the present disclosure comprises at least one human immunodeficiency virus conserved capsid protein (gag), envelope protein (env), polymerase protein (pol), or protease protein (pro) or an immunogenic fragment thereof.

According to some embodiments, the immunogen of the present disclosure comprises at least one conserved protein of at least one swine virus. For example, swine viruses include swine rotavirus, swine parvovirus, bovine viral diarrhea, neonatal calf diarrhea virus, hog cholera virus, African swine fever virus, swine influenza, and the like. According to some embodiments, the immunogen of the present disclosure comprises at least one conserved protein of a swine virus, such as swine rotavirus or swine parvovirus conserved glycoprotein 38, swine capsid protein, serpulina hydrodysenteriae protective antigen, bovine viral diarrhea glycoprotein 55, neonatal calf diarrhea virus (Matsuno and Inouye (1983) Infection and Immunity 39:155), hog cholera virus, African swine fever virus, swine influenza: swine flu hemagglutinin and swine flu neuraminidase, or an immunogeneic fragment thereof.

According to some embodiments, the immunogen of the present disclosure comprises at least one conserved protein of at least one equine virus. For example, equine viruses include equine influenza virus, equine herpesvirus, Venezuelan equine encephalomyelitis virus, and the like. According to some embodiments, the immunogen of the present disclosure comprises at least one equine conserved protein of an equine virus such as equine influenza virus or equine herpesvirus: equine influenza virus type A/Alaska 91 neuraminidase, equine influenza virus type A/Miami 63 neuraminidase, equine influenza virus type A/Kentucky 81 neuraminidase, equine herpesvirus type 1 glycoprotein B, and equine herpesvirus type 1 glycoprotein D, or an immunogeneic fragment thereof.

According to some embodiments, the immunogen of the present disclosure comprises at least one conserved protein of at least one bovine virus. For example, bovine viruses include bovine respiratory syncytial virus, bovine parainfluenza virus, bovine viral diarrhea virus, infectious bovine rhinotracheitis virus, foot and mouth disease virus, punta toro virus, and the like. According to some embodiments, the immunogen of the present disclosure comprises at least at least one bovine conserved protein of a bovine virus such asbovine respiratory syncytial virus or bovine parainfluenza virus: bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and bovine parainfluenza virus type 3 hemagglutinin neuraminidase), bovine viral diarrhea virus glycoprotein 48 or glycoprotein 53, infectious bovine rhinotracheitis virus: infectious bovine rhinotracheitis virus glycoprotein E or glycoprotein G, foot and mouth disease virus, punta toro virus (Dalrymple et al., 1981, in Replication of Negative Strand Viruses, Bishop and Compans (eds.), Elsevier, N.Y., p. 167), or an immunogeneic fragment thereof.

As discussed herein, according to some embodiments, the conserved proteins of the present disclosure are represented as conserved sequences comprising pathogen antigen sequences, which are selected by achieving the highest degree of protection that avoids the concomitant administration of neutralizing antibody epitopes. Furthermore, such sequences must be able to withstand the high mutation rates and new genetic variants that are resistant to immune responses generated against earlier pathogen subtypes and subvert the immune response generated by altered peptide-ligand phenomena as described herein. Therefore, according to some embodiments, the conserved protein sequences utilized herein will be generated to overcome pathogen genomic variation. Moreover, according to some embodiments, the conserved protein sequences utilized herein will also be generated to achieve cross-protection against pathogens with multiple strains, variants, groups (clades, serotypes or subtypes), and against related pathogeneic species, related pathogenic genera, and/or related pathogenic families.

According to some embodiments, conserved sequences are represented as consensus sequences as utilized in the invention of the present disclosure, are generated through multiple sequence alignments of pathogen conserved proteins derived from different strains, variants, groups, clades, serotypes, subtypes, species, genera, and/or families.

Bacterial Immunogens

According to some embodiments, the antigenic or immunogenic protein fragment or epitope may be derived from a pathogenic bacteria including, but not limited to:

Anthrax,

Chlamydia: Chlamydia protease-like activity factor (CPAF), major outer membrane protein (MOMP)

Mycobacteria,

Legioniella: Legionella peptidoglycan-associated lipoprotein (PAL), mip, flagella, OmpS, hsp60, major secretory protein (MSP)

Diptheria: diptheria toxin (Audibert et al., 1981, Nature 289:543)

Streptococcus 24M epitope (Beachey, 1985, Adv. Exp. Med. Biol. 185:193)

Gonococcus: gonococcal pilin (Rothbard and Schoolnik, 1985, Adv. Exp. Med. Biol. 185:247), Mycoplasm: mycoplasma hyopneumoniae.

Mycobacterium tuberculosis: M. tuberculosis antigen 85A, 85B, MPT51, PPE44, mycobacterial 65-kDa heat shock protein (DNA-hsp65), 6-kDa early secretary antigenic target (ESAT-6)

Salmonella typhi

Bacillus anthracis B. anthracis protective antigen (PA)

*Yersinia perstis: Y. pestis* low calcium response protein V (LcrV), F1 and F1-V fusion protein

*Francisella tularensis*

*Rickettsia typhi*

*Treponema pallidum.*

*Salmonella*: SpaO and H1a, outer membrane proteins (OMPs);

*Pseudomonas: P. aeruginosa* OMPs, PcrV, OprF, OprI, PilA and mutated ToxA

According to some embodiments, the immunogen of the present disclosure comprises at least one conserved protein of a Cornebacteriaceae bacterium or an immunogenic fragment thereof. For example, the cornebacteria is cornebacterium diphtheria. According to some embodiments, the immunogen of the present disclosure comprises at least one Cornebacterium diphtheriae conserved diphtheria toxin (tox), diphtheria toxin repressor (dtxR), pilin protein(s) (spaA, spaB, spaC) or an immunogenic fragment thereof.

According to some embodiments, the immunogen of the present disclosure comprises at least one conserved protein of a mycobacteriaceae bacterium or an immunogenic fragment thereof. For example, the mycobacteriaceae bacterium is *Mycobacterium tuberculosis*. According to some embodiments, the immunogen of the present disclosure comprises at least one Se protein (secA).

According to some embodiments, the immunogen of the present disclosure comprises at least one conserved protein of a bacillaceae bacterium or an immunogenic fragment thereof. For example, the bacillabacteria is *Bacillus anthracis*. According to some embodiments, the immunogen of the present disclosure comprises at least one *Bacillus anthracis* conserved capsule protein (capA), an s layer protein (e.g., sap or EA1), virulence proteins (e.g., pX01, px02), and sigma proteins (e.g., PA, ECF) or an immunogenic fragment thereof.

According to some embodiments, the immunogen of the present disclosure comprises at least one conserved protein of a yersineaceae bacterium or an immunogenic fragment thereof. For example, the *Yersinia* bacterium is *Yersinia pestis*. According to some embodiments, the immunogen of the present disclosure comprises at least one *Yersinia pestis* conserved outer membrane protein (bamA, Yops), inner rod protein (Yscl), virulence protein (Lcru), or needle protein (YscF) or an immunogenic fragment thereof.

According to some embodiments, the immunogen of the present disclosure comprises at least one conserved protein of an Enterobacteriaceae bacterium or an immunogenic fragment thereof. For example, the Enterobacteriae bacterium is *Salmonella enterica* serovar *Typhi*. According to some embodiments, the immunogen of the present disclosure comprises at least one conserved outer membrane protein (e.g., STIV, Tolc), virulence protein (e.g., Vi), phage protein, occluden toxin family protein (e.g., Zot), or an immunogenic fragment thereof.

According to some embodiments, the immunogen of the present disclosure comprises at least one conserved protein of a rickettsiae bacterium or an immunogenic fragment thereof. For example, the rickettsiae bacteriam is *Rickettsia prowazekii.*

Fungal Immunogens

According to some embodiments, the antigenic or immunogenic protein fragment or epitope may be derived from a pathogenic fungus, including but not limited to:

*Coccidioides immitis: Coccidioides* Ag2/Pra106, Prp2, phospholipase (P1b), alpha-mannosidase (Amn1), aspartyl protease, Gell

*Blastomyces dermatitidis: Blastomyces dermatitidis* surface adhesin WI-1

*Cryptococcus neoformans: Cryptococcus neoformans* GXM and its Peptide mimotopes, and mannoproteins, Cryptosporidiums surface proteins gp15 and gp40, Cp23 antigen, p23

*Candida albicans,*

*Aspergillus* species: *Aspergillus* Asp f 16, Asp f 2, Der p 1, and Fel d 1, rodlet A, PEP2, *Aspergillus* HSP90, 90-kDa catalase Protozoan Immunogens According to some embodiments, the antigenic or immunogenic protein fragment or epitope may be derived from a pathogenic protozoan, including, but not limited to:

*Plasmodium falciparum, Plasmodium vivax, Plasmodium ovale, Plasmodium malariae, Plasmodium* apical membrane antigen 1 (AMA1), 25-kDa sexual-stage protein (Pfs25), erythrocyte membrane protein 1 (PfEMP1) circumsporozoite protein (CSP), Merozoite Surface Protein-1 (MSP 1)

*Leishmania* species: *Leishmania* cysteine proteinase type III (CPC)

Trypanosome species (African and American): *T. pallidum* outer membrane lipoproteins, Trypanosome beta-tubulin (STIB 806), microtubule-associate protein (MAP p15), cysteine proteases (CPs)

cryptosporidiums,

*isospora* species,

*Naegleria fowleri,*

*Acanthamoeba* species,

*Balamuthia mandrillaris,*

*Toxoplasma gondii*, or

*Pneumocystis carinii: Pneumocystis carinii* major surface glycoprotein (MSG), p55 antigen

*Babesia*

Schistosomiasis: Schistosomiasis *mansoni* Sm4, 21.7 and SmFim antigen, Tegument Protein Sm29, 26 kDa GST, *Schistosoma japonicum*, SjCTPI, SjC23, Sj22.7, or SjGST-32

Toxoplasmosis: *gondii* surface antigen 1 (TgSAG1), protease inhibitor-1 (TgPI-1), surface-associated proteins MIC2, MIC3, ROP2, GRA1-GRA7.

According to some embodiments, the immunogen of the present disclosure comprises at least one conserved protein of a plasmodiidae parasite. For example, the *plasmodium* is *plasmodium falciparum*. According to some embodiments, the immunogen of the present disclosure comprises at least one conserved circumsporozoite protein (CS) protein and thrombospondin-related adhesion protein (TRAP) or an immunogenic fragment thereof.

T Cell Epitope Prediction

T cells recognize an epitope comprised of a self portion (Class I MHC) and a foreign portion (a short peptide). It is known that the foreign peptide part of T cell epitopes consists of peptides of between 8 and 11 residues in length. Briefly, T cell epitopes can be derived from either breaking down a sample of the pathogen to test for T-cell activation against various peptides, or through bioinformatics tools that predict T cell epitopes for pathogens.

Bioinformatics Tools

As described supra and as known in the art (for example in Khan et al., "A systematic bioinformatics approach for selection of epitope based vaccine targets." *Cell Immunol.* (2006) December; 244(2): 141-147; and Soriera-Guerra, et al., (2015) "An overview of bioinformatics tools for epitope prediction: Implications on vaccine development." *Journal of Biomedical Informatics* 53: 405-414; the entireties of which are incorporated herein by reference) T-cell immune responses are triggered by the recognition of foreign peptide antigens bound to cell membrane-expressed MHC molecules. Because T-cell recognition is limited to those peptides presented by MHC molecules, prediction of peptides that can bind to MHC molecules is the basis for the anticipation of T-cell epitopes binding to MHC molecules that must fit into a specific chemical and physical environment conditioned by polymorphic residues in the MHC molecule. Consequently, distinct MHC molecules have distinct peptide-binding specificities. In addition, the peptides that bind to the same MHC molecule are related by sequence similarity. Sequence patterns reflecting amino acid preferences in peptide-MHC binders (anchor residues) are routinely used for defining peptide-MHC binding motifs and prediction of peptide-MHC binding. This data is known in the art and has been collected into databases that contain MHC peptide motifs, MHC ligands, T-cell epitopes, as well as, amino acid sequences of MHC molecules.

Databases can be used as prediction tools that predict the outcome of experiments, such as MHC class I or class II binding, and MHC class I processing and immunogenicity. T cell processing predictions combine MHC binding with other parts of the MHC class I cellular pathway, namely proteasomal cleavage and TAP transport, and are generated from independent experimental datasets. There are also predictors trained on eluted MHC ligands that provide an overlay of the signals from MHC binding and MHC processing presentation pathway. The processing prediction tools offer a relatively small but statistically significant increase in accuracy compared to using the MHC binding prediction alone.

Binding prediction methods facilitate the selection of potential epitopes. The methods available in the art were developed using experimental peptide binding data for different MHC alleles to train machine learning algorithms that in turn can be used to predict the binding likelihood or binding affinity for any arbitrary peptide.

The prediction and measure of affinity binding for a given peptide sequence can analysed through for example, the calculation of a scoring matrix. In general, matrices are constructed using amino acid frequencies at different position of known binders or quantitative MHC-binding data. The former indicates the binding likelihood of a peptide sequence to the MHC molecule, while the later provides means of quantifying the peptide binding affinity. In a binding affinity scoring matrix, the binding affinity for the sequence is computed based on the amino acid and its position in the binding groove. The values for each residue in the sequence are summed to yield the overall binding for the entire sequence. A position-specific scoring matrix is derived by varying the values of the matrix until the sums for known, measured peptides approximate the measured affinities. Consensus scores are obtained by summing, multiplying or averaging the matrix coefficients and compared against a predetermined threshold. Thresholds are predetermined and calibrated into the prediction tools to enable machine learning.

MHC Class I Binding Prediction Generation

Peptide binding datasets can be searched with either single or multiple different prediction algorithms, including a number of publicly available prediction websites, such as SYFPEITHI and BIMAS, where the correlation between the measured binding affinity score and each algorithm's predicted score (heuristic score for SYFPEITHI or a half-life of binding score for BIMAS) is computed. The binding affinity score is the affinity between an MHC and isolated peptides, usually expressed as IC50 concentration with low IC50 value implying a high affinity binder.

Binding Affinity Threshold Calibration

The threshold will allow for the computation of the number of true negatives, true positives, false negatives, and false positives. By systematically varying the predicted score threshold from low to high, the rate of true positives and false positives will be calculated as a function of the threshold to derive a ROC (receiver operating characteristic) curve. The area under this ROC curve is the AUC value. The AUC value is independent of the predicted scale because it compares the rank of the matrices and it is independent of the composition of the dataset, such as having different proportions of binders and non-binders. The AUC value is essentially capturing the probability that given two peptides, one a binder and the other a non-binder, the predicted score will be higher for the binder compared to the non-binder. An AUC value of 0.5 is equivalent to a random prediction and a value of 1.0 is equivalent to a perfect prediction.

Epitope Selection

There are three main strategies for selecting potential binders. The first involves selecting all peptides with IC50 value (meaning half maximal inhibitory concentration, which is a measure of potency, (i.e., amount required to produce an inhibitory effect of given intensity, compared to a reference standard) less than 500 nM, a threshold previously associated with immunogenicity. A second strategy is to pick the top 1% of peptides for each allele/length combination. The third strategy is to pick peptides with percentile ranks below 1%.

Vaccines

According to some aspects, the disclosure provides vaccines generated by providing proteins and genetic constructs that encode proteins with conserved, internal CD8+ T cell epitopes that make them particularly effective as immunogens against which immune responses against a broad range of viruses can be induced. According to some embodiments, the vaccines can be provided to induce a therapeutic or prophylactic immune response.

According to some embodiments, the means to deliver the immunogen is a DNA vaccine, a recombinant vaccine, a protein subunit vaccine, a composition comprising the immunogen, an attenuated vaccine or a killed vaccine. According to some embodiments, the vaccine comprises a combination selected from one or more DNA vaccines, one or more recombinant vaccines, one or more protein subunit vaccines, one or more compositions comprising the immunogen, one or more attenuated vaccines and one or more killed vaccines.

According to some embodiments, a vaccine according to the disclosure can be delivered to an individual to modulate the activity of the individual's immune system and thereby enhance the immune response against a viral, bacterial, fungal, or protozoan infection. When a nucleic acid molecule that encodes the protein is taken up by cells of the individual the nucleotide sequence is expressed in the cells and the protein are thereby delivered to the individual.

According to some embodiments, the recombinant vaccine is constructed by using a plurality of different vaccine vectors with the above-mentioned immunogens, and each immunization is sequentially vaccinated with different recombinant vector vaccines. Each recombinant vaccine is inoculated at least once, and the vaccination program includes at least one respiratory immunization and one systemic immunization. The combination of the recombinant vector vaccine and the inoculation method can achieve high levels of T cell immune responses in the respiratory and systemic systems, thereby enabling vaccine recipients to obtain immunity against different subtypes of virus.

According to some embodiments, compositions and methods are provided which prophylactically and/or therapeutically immunize an individual against a virus family selected from, but not limited to the group consisting of Flaviviridae, Paramyxoviridae, Togaviridae, Filoviridae, Orthomyxoviridae, Rhabdoviridae and Retroviridae.

Viral Vector Vaccines

According to some embodiments, attenuated, replication-deficient viruses such as vaccinia viruses are used to deliver an exogenous viral, bacterial, fungal or protozoan immunogen as described herein, in an amount effective to elicit or stimulate a cell mediated immune response. Any one or more immunogens of interest, as described herein, can be inserted into a viral vector as described herein.

Poxvirus Vectors

Because poxviruses have a large genome, they can readily be used to deliver a wide range of genetic material including multiple genes (i.e., act as a multivalent vector). The sizes of the poxvirus genome range from about 130 kbp to about 300 kbp, inclusive, with up to 300 genes, depending on the strain of the virus. Therefore, it is possible to insert large fragments of foreign DNA into these viruses and yet maintain stability of the viral genome.

Poxviruses are useful vectors for a range of uses, for example vaccines to generate immune responses, for the development of new vaccines, for delivery of desired proteins and for gene therapy. The advantages of poxvirus vectors include: (i) ease of generation and production, (ii) the large size of the genome permitting insertion of multiple genes (i.e., as a multivalent vector), (iii) efficient delivery of genes to multiple cell types, including antigen-presenting cells, (iv) high levels of protein expression, (v) optimal presentation of antigens to the immune system, (vi) the ability to elicit cell-mediated immune responses as well as antibody responses, (vii) the ability to use combinations of poxviruses from different genera, as they are not immunologically cross-reactive and (viii) the long-term experience gained with using this vector in humans as a smallpox vaccine.

Poxviruses are well known cytoplasmic viruses. The genetic material expressed by such viral vectors typically remains in the cytoplasm and does not have the potential for inadvertent integration of the genetic material into host cell genes, unless specific steps are taken. As a result of the non-integrative cytoplasmic nature of the poxvirus, the poxvirus vector system will not result in having long term persistence in other cells. Thus, the vector and the transformed cells will not adversely affect cells in the host animal at locations distant from the target cell. Further, the large genome of poxviruses enables large genes to be inserted into pox-based vectors.

Poxviruses can be genetically engineered to contain and express heterologous DNA with or without impairing the ability of the virus to replicate. According to some embodiments, the DNA encodes one or more immunogens determined using the methods described herein. According to some embodiments, such heterologous DNA can encode a wide range of proteins, such as antigens that induce protection against one or more infectious agents, immune modulating proteins such as co-stimulatory molecules, or enzymatic proteins.

According to some embodiments, vaccine compositions described herein are based on poxvirus vectors.

A number of poxviruses have been developed as live viral vectors for the expression of heterologous proteins, e.g. attenuated vaccinia virus strains Modified Vaccinia Ankara (MVA) and Wyeth (Cepko et al., (1984) Cell 37:1053 1062; Morin et al. (1987) Proc. Natl. Acad. Sci. USA 84:4626 4630; Lowe et al., (1987) Proc. Natl. Acad. Sci. USA, 84:3896 3900; Panicali & Paoletti, (1982) Proc. Natl. Acad. Sci. USA, 79:4927 4931; Mackett et al., (1982) Proc. Natl. Acad. Sci. USA, 79:7415 7419). Other attenuated vaccinia virus strains include WR strain, NYCBH strain, ACAM2000, Lister strain, LC16 m8, Elstree-BNm, Copenhagen strain, and Tiantan strain.

Vaccinia virus is the prototype of the genus *Orthopoxvirus*. It is a double-stranded DNA (deoxyribonucleic acid) virus that has a broad host range under experimental conditions (Fenner et al. 1989 Orthopoxviruses. San Diego, Calif.: Academic Press, Inc.; Damaso et al., (2000) Virology 277:439-49). Modified vaccinia virus Ankara (MVA) or derivatives thereof have been generated by long-term serial passage of the Ankara strain of vaccinia virus (CVA) on chicken embryo fibroblasts (for review see Mayr, A., et al., (1975) Infection, 3:6-14. The MVA virus itself may be obtained from a number of public repository sources. For example, MVA was deposited in compliance with the requirements of the Budapest Treaty at CNCM (Institut Pasteur, Collection Nationale de Cultures Microorganisms, 25, rue du Docteur Roux, 75724 Paris Cedex 15) on Dec. 15, 1987 under Depositary No. 1-721 (U.S. Pat. No. 5,185,146); MVA virus was deposited in compliance with the Budapest Treaty at the European Collection of Cell Cultures (ECACC) (CAMR, Porton Down, Salisbury, SP4 OJG, UK) on Jan. 27, 1994, under Depository No. V94012707) (U.S. Pat. No. 6,440,422 and United States patent publication number 2003/0013190). Also, United States patent publication number 2003/0013190 further discloses particular MVA strains deposited at the ECACC under Depository No. 99101431, and ECACC provisional accession number 01021411. Commercially available vectors include THERION-MVA, THE- RION PRIFREE vectors and THERION M-SERIES vectors (Therion Biologics Corporation, M A).

MVA was generated by 516 serial passages on chicken embryo fibroblasts of the Ankara strain of vaccinia virus (CVA) (Mayr, A., et al. [1975] Infection 3, 6-14). As a consequence of these long-term passages, about 31 kilobases of the genomic sequence were deleted from the virus (deletion I, II, III, IV, V, and VI) and, therefore, the resulting MVA virus was described as being highly host cell restricted to avian cells (Meyer, H. et al., [1991] J. Gen. Virol. 72, 1031-1038). It was shown in a variety of animal models that the resulting MVA was significantly avirulent (Mayr, A. & Danner, K. [1978] Dev. Biol. Stand. 41: 225-34). Additionally, this MVA strain has been tested in clinical trials as a vaccine to immunize against the human smallpox disease (Mayr et al., [1987]Zbl. Bakt. Hyg. I, Abt. Org. B 167, 375-390, Stickl et al., [1974] Dtsch. med. Wschr. 99, 2386-2392). These studies involved over 120,000 humans, including high-risk patients, and proved that compared to vaccinia based vaccines, MVA had diminished virulence or infectiousness while it induced a good specific immune response. Generally, a virus strain is regarded as attenuated if it has lost its capacity or only has reduced capacity to reproductively replicate in host cells.

Because the genome of both wild type VV and MVA have been sequenced, it is possible to clone viruses that bear some resemblence to MVA with regard to replication properties, but that are genetically distinct from MVA. These may serve the same purpose, or may be more immunogenic than MVA while being just as safe by virtue of their replication deficiency.

According to some embodiments, the virus has a replication capability 5% or less, or 1% or less compared to wild-type virus. Non-replicating viruses are 100% replication deficient in normal primary human cells.

Viral replication assays are known in the art, and can be performed for vaccinia viruses on e.g. primary keratinocytes, and are described in Liu et al. J. Virol. 2005, 79:12, 7363-70. Viruses which are non-replicating or replication-impaired may have become so naturally (i.e. they may be isolated as such from nature) or artificially e.g. by breeding in vitro or by genetic manipulation, for example deletion of a gene which is critical for replication. There will generally be one or a few cell types in which the viruses can be grown, such as CEF cells for MVA.

According to some embodiments, changes in the virus include, for example, alterations in the gene expression profile of the virus. According to some embodiments, the modified virus may express genes or portions of genes that encode peptides or polypeptides that are foreign to the poxvirus, i.e. they would not be found in a wild-type virus. These foreign, heterologous or exogenous peptides or polypeptides can include sequences that are immunogenic such as, for example, bacterial, viral, fungal, and protozoal antigens, or antigenic sequences derived from viruses other than the viral vector. The genetic material may be inserted at an appropriate site within the virus genome for the recombinant virus to remain viable, i.e. the genetic material may be inserted at a site in the viral DNA (e.g., non-essential site in the viral DNA) to ensure that the recombinant virus retains the ability to infect foreign cells and to express DNA, while maintaining the desired immunogenicity and diminished virulence. For example, as described above, MVA contains 6 natural deletion sites which have been demonstrated to serve as insertion sites. See, for example, U.S. Pat. Nos. 5,185,146, and 6,440,422, incorporated by reference herein. According to some embodiments, genes that code for desired antigens are inserted into the genome of a poxvirus in such a manner as to allow them to be expressed by that virus along with the expression of the normal complement of parent virus proteins.

The modified poxviruses have a low replicative efficiency in the target cell, which prevents sustained replication and infection of other cells. According to some embodiments, the modified poxvirus may also have altered characteristics concerning aspects of the viral life cycle, such as target cell specificity, route of infection, rate of infection, rate of replication, rate of virion assembly and/or rate of viral spreading.

According to some embodiments, the inserted gene(s) encoding immunogens determined using the methods described herein may be operably linked to a promoter to express the inserted gene. Promoters are well known in the art and can readily be selected depending on the host and the cell type one wishes to target. For example in poxviruses, poxviral promoters may be used, such as the vaccinia 7.5K, 40K, fowlpox. In certain embodiments, enhancer elements can also be used in combination to increase the level of expression. In certain embodiments, inducible promoters, which are also well known in the art, may be used. Representative poxvirus promoters include an entomopox promoter, an avipox promoter, or an orthopox promoter such as a vaccinia promoter, e.g., HH, 11K or Pi. For example, the Pi promoter, from the Ava I H region of vaccinia, is described in Wachsman et al., J. of Inf. Dis. 155, 1188-1197 (1987). This promoter is derived from the Ava I H (Xho I G) fragment of the L-variant WR vaccinia strain, in which the promoter directs transcription from right to left. The map location of the promoter is approximately 1.3 Kbp (kilobase pair) from the 5' end of Ava IH, approximately 12.5 Kbp from the 5' end of the vaccinia genome, and about 8.5 Kbp 5' of the Hind III C/N junction. The Hind III H promoter (also "HH" and "H6" herein) sequence is an up-stream of open reading frame H6 by Rosel et al., (1986) J. Virol. 60, 436-449. The 11K promoter is as described by Wittek, (1984) J. Virol. 49, 371-378) and Bertholet, C. et al., (1985) Proc. Natl. Acad. Sci. USA 82, 2096-2100). One can take advantage of whether the promoter is an early or late promoter to time expression of particular genes.

According to some embodiments, vaccine compositions described herein are based on vaccinia virus vectors. According to some embodiments, the vaccinia virus vector is a vaccinia virus Tiantan strain (vaccine virus TianTan strain, VTT). The vaccinia virus Tiantan strain was widely inoculated in China as a smallpox vaccine since it was isolated by Chinese scientists in the 1920s, and eventually destroyed smallpox in China. The number of inoculations of Tiantan strains reached more than one billion, and its safety has been long-term and fully verified in practice. The incidence of side effects of the Tiantan strain vaccine is significantly lower than that of other smallpox vaccine strains used internationally, including the New York strain used in bioterrorism in the United States in recent years. TianTan vaccinia vector has a wide host range, high reproductive titer, induced immune response is very long-lasting, and the capacity of inserting foreign genes is extremely large, theoretically up to 25-50 kb. The Tiantan strain carrier has high safety and good immunogenicity, and can induce strong humoral immunity and cellular immunity in vivo, and the duration of the immune reaction is much longer than that of the non-replicating vector.

According to some embodiments, the promoter is modulated by an external factor or cue, allowing control of the level of polypeptide being produced by the vectors by activating that external factor or cue. For example, heat shock proteins are proteins encoded by genes in which the promoter is regulated by temperature. The promoter of the gene which encodes the metal-containing protein metallothionine is responsive to Cd+ ions. Incorporation of this promoter or another promoter influenced by external cues also makes it possible to regulate the production of the polypeptides comprising antigen.

According to some embodiments, the nucleic acid encoding at least one gene of interest encoding, e.g. an immunogen as described herein, is operably linked to an "inducible" promoter. Inducible systems allow careful regulation of gene expression. See, Miller and Whelan, Human Gene Therapy, 8:803-815 (1997). The phrase "inducible promoter" or "inducible system" as used herein includes systems wherein promoter activity can be regulated using an externally delivered agent. Such systems include, for example, systems using the lac repressor from *E. coli* as a transcription modulator to regulate transcription from lac operator-bearing mammalian cell promoters (Brown et al. Cell, 49:603-612, 1987); systems using the tetracycline repressor (tetR) (Gossen and Bujard, 1992 Proc. Natl. Acad. Sci. USA 89: 5547-5551; Yao et al., 1998 Human Gene Ther. 9:1939-1950; Shokelt et al., 1995 Proc. Natl. Acad. Sci. USA 92.6522-6526). Other such systems include FK506 dimer, Vβ16 or p65 using castradiol, RU486/mifepristone, diphenol muristerone or rapamycin. Another example is an ecdysone inducible system (see, e.g. Karns et al, 2001 MBC Biotechnology 1:11). Inducible systems are available, e.g., from Invitrogen, Clontech, and Ariad. Systems using a repressor with the operon are preferred. These promoters may be adapted by substituting portions of pox promoters for the mammalian promoter.

According to some embodiments, a "transcriptional regulatory element" or "TRE" is introduced for regulation of the gene of interest. A TRE is a polynucleotide sequence, preferably a DNA sequence, that regulates transcription of an operably-linked polynucleotide sequence by an RNA polymerase to form RNA. A TRE increases transcription of an operably linked polynucleotide sequence in a host cell that allows the TRE to function. The TRE comprises an enhancer element and/or viral promoter element, which may or may not be derived from the same gene. The promoter and enhancer components of a TRE may be in any orientation and/or distance from the coding sequence of interest, and comprise multimers of the foregoing, as long as the desired, transcriptional activity is obtained.

According to some embodiments, an "enhancer" for regulation of the gene of interest is provided. An enhancer is a polynucleotide sequence derived from a gene which increases transcription of a gene which is operably-linked to a promoter to an extent which is greater than the transcription activation effected by the promoter itself when operably-linked to the gene, i.e. it increases transcription from the promoter.

The activity of a regulatory element such as a TRE or an enhancer generally depends upon the presence of transcriptional regulatory factors and/or the absence of transcriptional regulatory inhibitors. Transcriptional activation can be measured in a number of ways known in the art, but is generally measured by detection and/or quantification of mRNA or the protein product of the coding sequence under control of (i.e., operatively linked to) the regulatory element. The regulatory element can be of varying lengths, and of varying sequence composition. By transcriptional activation, it is intended that transcription will be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably, at least about 1000-fold. Basal levels are generally the level of activity, if any, in a non-target cell, or the level of activity (if any) of a reporter construct lacking the TRE or enhancer of interest as tested in a target cell type.

Certain point mutations within sequences of TREs decrease transcription factor binding and gene activation. One of skill in the art would recognize that some alterations of bases in and around known the transcription factor binding sites are more likely to negatively affect gene activation and cell-specificity, while alterations in bases which are not involved in transcription factor binding are not as likely to have such effects. Certain mutations also increase TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

Adenoviral Vectors

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., (1983) J. Virol., 45: 555-564 as corrected by Ruffing et al., (1994) J. Gen. Virol., 75: 3385-3392. Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (Rep 78, Rep 68, Rep 52, and Rep 40) from the rep gene. Rep 78 and Rep 68, are respectively expressed from unspliced and spliced transcripts initiating at the p5 promoter, while Rep 52 and Rep 40, are respectively expressed from unspliced and spliced transcripts initiating at the p19 promoter. Rep proteins possess multiple enzymatic properties which are ultimately responsible for replicating the viral genome. Rep 78 and 68 appear to be involved in AAV DNA replication and in regulating AAV promoters, while Rep 52 and 40 appear to be involved in formation of single-stranded AAV DNA. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, (1992) Current Topics in Microbiology and Immunology, 158: 97-129.

When wild type AAV infects a human cell, the viral genome can integrate into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive for delivering DNA to cells in a clinical application, for example, as a gene therapy vector or an immunization vector. AAV infection of cells in culture is noncytopathic, and natural infection of humans and other animals is silent and asymptomatic. Moreover, AAV infects many mammalian cells allowing the possibility of targeting many different tissues in vivo. The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56 to 65° C. for several hours), making cold preservation of AAV-vectors less critical. AAV may even be lyophilized. Finally, AAV-infected cells are not resistant to superinfection.

Production of rAAV requires the AAV rep78/68 and rep52/40 genes and expression of their gene products, a DNA of interest flanked by AAV ITRs, helper functions provided by an AAV helper virus, and a cell line comprising these components that is permissive for AAV replication. Examples of helper virus functions are adenovirus genes E1, E2A, E4 and VA (Carter, Adeno-associated virus helper functions. (1989) In "Handbook of Parvoviruses" Vol I (P. Tjissen, ed.) CRC Press, Boca Raton, pp 255-282). Wild type AAV (wt AAV) has one of the largest burst sizes of any virus following infection of cells with AAV and adenovirus. This may be well in excess of 100,000 particles per cell (Aitken et al., 2001 Hum Gene Therapy, 12:1907-1916), while some rAAV production systems have been reported to achieve 10e3 or 10e4 particles per cell. Rep proteins are absolutely required for both wt AAV and rAAV replication and assembly of intact infectious particles, as summarized in Carter et al., AAV vectors for gene therapy. (2004) In "Gene and Cell Therapy: Therapeutic Mechanisms and Strategies", Second Edition (Ed. N. Templeton-Smith), pp 53-101, Marcel Dekker, New York). Expression of the rep proteins during the replicative phase of AAV production is both autoregulated and highly coordinated at the transcription level exhibiting both positive and negative regulatory activities. The relative ratio of the rep proteins necessary to achieve rAAV vector production levels equivalent to WT AAV has not been fully understood. See Li et al., (1997) J Virol., 71:5236-5243; Xiao et al., (1998) J Virol, 72:2224-2232; Matushita et al., (1998) Gene Therapy, 5:938-945; and Carter et al., AAV vectors for gene therapy, in "Gene and Cell Therapy: Therapeutic Mechanisms and Strategies", Second Edition (Ed. N. Templeton-Smith), pp 53-101, Marcel Dekker, New York. Numerous vector production methods have been described which have altered the relative ratios of rep 52/40 and rep 78/68 by decoupling regulation of their respective promoters. See, e.g., Natsoulis, U.S. Pat. No. 5,622,856; Natsoulis et al., U.S. Pat. No. 6,365,403; Allen et al., U.S. Pat. No. 6,541,258; Trempe et al., U.S. Pat. No. 5,837,484; Flotte et al., U.S. Pat. No. 5,658,776; Wilson et al. U.S. Pat. No. 6,475,769; Fan and Dong, (1997) Human Gene Therapy, 8:87-98; and Vincent et al., (1997) J Virol, 71:1897-1905. This decoupling of the large and small rep proteins at the transcriptional has been achieved by a number of methods including, replacing the native p5, p19, and p40 native AAV promoters either completely or in some combination with heterologous promoters, inducible promoters; or by physical means of either placing the components on separate genetic elements including without limitation separate plasmids; or by utilizing separate genetic construct for transducing or transfecting the permissive cell line including carrier viruses such as adenovirus or herpes virus; inserting additional spacer elements, or physically rearranging the rep gene or its regulatory sequences within a single genetic construct. These strategies have been employed both for transient production systems where one or more of the components are introduced to the permissive cell line via plasmid transfection; hybrid viral infection such as recombinant adenoviruses, herpes virus, or baculovirus; or in stable cell line approaches utilizing production from transformed cancerous cells permissive for AAV production such as HELA and 293 cells.

According to some embodiments, vaccine compositions described herein are based on adenovirus (Ad) vectors.

According to some embodiments, vaccine compositions described herein are based on Ad serotype 5 (AdHu5). AdHu5-based vectors, have been extensively studied in laboratories and clinical trials over the past decades (Alonso-Padilla et al. 2016 Mol Ther.; 24: 6-16). It has been demonstrated that the AdHu5 vector can elicit potent antigen-specific immune responses in both preclinical and clinical studies (Alonso-Padilla 2016 Mol Ther.; 24: 6-16; Abbink et al. 2007 J Virol.; 81:4654-4663). However, although the AdHu5 vector has been shown to be very efficient, AdHu5 infection is endemic in humans. Thus, adenoviral vectors isolated from different species have been tested. In particular, chimpanzee adenoviruses (AdCs) are attractive for use because they can be cultured in human cell lines such as human embryonic kidney 293 cells (HEK293), and have a low seroprevalence in the human population as they rarely circulate in humans. Moreover, some AdCs can induce T- and B-cell immune responses comparable to those of commonly used human Ad serotypes like AdHu5 (Quinn et al. 2013 J Immunol.; 190:2720-2735; Ledgerwood et al. 2017 N Engl J Med.; 376:928-938).

According to some embodiments, vaccine compositions described herein are based on adenovirus (Ad) vectors that are derived from a chimpanzee. According to some embodiments, the adenoviral vector is based on a chimpanzee adenoviral isolate Y25 (Hillis et al. (1969) J Immunol 103: 1089-109). According to some embodiments, the adenoviral vector is based on AdC68 (also called Sad-V25; Farina S F, et al. (2001) Journal of Virology 75: 11603-11613, incorporated by reference in its entirety herein).

The chimpanzee adenovirus isolate Y25 was first described by Hillis et al. ((1969) J Immunol 103: 1089-1095). The viral genome is represented in GenBank accession no. JN254802, incorporated by reference in its entirety herein. The genome sequence data has confirmed early serological indications that this adenovirus is related to the Human adenovirus E virus, HAdV-4 (Wigand R, et al. (1989) Intervirology 30: 1-9). Simian adenoviruses (SAdV) isolated from great apes are not phylogenetically distinct from human adenoviruses (HAdV), and group together into the same viral species (Human adenovirus B, C and E) (Roy S, et al. (2009) PLoS pathogens 5: e1000503). Although HAdV-4 is the sole representative of Human adenovirus E derived from humans, many of the chimpanzee adenoviruses group phylogenetically within species E, including vaccine vector candidates ChAd63, AdC68 (SAdV-25), AdC7 (SAdV-24) and AdC6 (SAdV-23) (Farina S F, et al. (2001) Journal of virology 75: 11603-11613; Roy S. et al. (2004) Virology 324: 361-372; Roy S., et al. (2004) Human gene therapy 15: 519-530; Reyes-Sandoval et al. (2010) Infection and immunity 78: 145-153; the contents of all the foregoing are incorporated by reference in their entireties herein). Phylogenetic analysis indicates that chimpanzee adenovirus Y25 also groups with Human adenovirus E viruses.

Exemplary sequences from the Y25 genome are set forth below by GenBank Accession Number:

ChAd3 CS479276; ChAd63 CS479277; HAdV-5 AC_000008; SAdV-22 AY530876; SAdV-25 AF394196; HAdV-1 AF534906; HAdV-2 J01917; HAdV-4 AY458656; HAdV-6 FJ349096; HAdV-12 X73487; HAdV-16 AY601636; HAdV-30 DQ149628; HAdV-10 AB369368, AB330091; HAdV-17 HQ910407; HAdV-9 AJ854486; HAdV-37 AB448776; HAdV-8 AB448767; HAdV-7 AB243119, AB243118; HAdV-11 AC 000015; HAdV-21 AY601633; HAdV-34 AY737797; HAdV-35 AC_000019; HAdV-40 NC_001454; HAdV-41 DQ315364; SAdV-21 AC_000010; SAdV-23 AY530877; SAdV-24 AY530878; HAdV-3 DQ086466; HAdV-18 GU191019; HAdV-31 AM749299; HAdV-19 AB448774; SAdV-25.2 FJ025918; SAdV-30 FJ025920; SAdV-26 FJ025923; SAdV-38 FJ025922; SAdV-39 FJ025924; SAdV-36 FJ025917; SAdV-37.1 FJ025921; HAdV-14 AY803294; SAdV-27.1 FJ025909; SAdV-28.1 FJ025914; SAdV-33 FJ025908; SAdV-35.1 FJ025912; SAdV-31.1 FJ025906; SAdV-34 FJ025905; SAdV-40.1 FJ025907; SAdV-3 NC_006144; Y25 JN254802

Very few antibodies exist in the human body against chimpanzee adenovirus type 68, and this adenovirus can infect both dividing cells and non-dividing cells, including lung cells, liver cells, bone cells, cells in blood vessels, muscles, brain and central nervous, etc. Moreover, it has good gene stability and excellent ability to express foreign genes. It can be produced by HEK293 cells and has been widely used in research on vaccines such as AIDS, Ebola, influenza, malaria, and hepatitis C.

Production, purification and quality control procedures for Ad vectors are well established (Tatsis & Ertl, 2004 Mol Ther 10: 616-29). Ad vectors induce innate immune responses ameliorating the need for addition of adjuvants. They also induce very potent B and CD8 T cell responses, which, due to low-level persistence of the vectors, are remarkably sustained (Tatsis et al., 2007, Blood 110: 1916-23). Pre-existing neutralizing antibodies to common human serotypes of Ad viruses such as serotype 5, which impact vaccine efficacy, can readily be avoided by the use of by serotypes from other species such as chimpanzees, which typically neither circulate in humans nor cross-react with human serotypes (Xiang et al., 2006 Emerg Infect Dis 12: 1596-99). In cases where prime-boost regimens are needed to achieve immune responses of sufficient potency, vectors based on distinct Ad serotypes are available (Tatsis & Ertl, 2004 Mol Ther 10: 616-29). Ad viruses and Ad vectors have been used extensively in the clinic where they were well tolerated. They can be applied through a variety of routes including mucosal routes such as the airways (Xiang et al., 2003 J Virol 77: 10780-89) or even orally upon encapsidation as was shown with vaccine to Ad viruses 4 and 7 used by the US military (Lyons et al., 2008 Vaccine 26: 2890-98).

Herpes Simplex Virus Vectors

According to some embodiments, vaccine compositions described herein are based on herpes simplex virus (HSV) vectors.

For the production of an HSV vector strain, combinations of essential and non-essential genes can be removed from the genome so that the virus is nonpathogenic and minimally cytotoxic. Vector viruses are often produced by the deletion of one or other or both of the two essential immediate early genes ICP4 and ICP27. These require growth on cell lines expressing the deleted genes. Further deletions can be made to reduce cytotoxicity. For the production of viruses which allow gene expression during latency, promoters must be designed which allow gene expression to continue during this time, and this has proved to be a considerable challenge in the field of HSV vector development. However, a number of different promoter systems, each incorporating different elements of the HSV latency associated transcript (LAT) region, do give gene expression during latency to various levels of efficiency. These either use one or other of the LAT promoters (LAP1 or LAP2; Goins et al., 1994. J of Virology. 68(4): 2239-2252) to drive directly gene expression during latency, or DNA fragments derived from the LAT region to confer a long term activity on individual or pairs of promoters. This element, referred to herein as LAT P2 (including LAP2 and other upstream sequences; (nts 118866-112019-GenBank HE1CG)), has been shown subsequently to act not as a true promoter but instead to confer long term activity on heterologous promoters placed near to it, these promoters not being active during latency when used on their own.

According to some embodiments, the herpes simplex viruses of the disclosure may be derived from, for example, HSV1 or HSV2 strains, or derivatives thereof, such as HSV1. Derivatives include inter-type recombinants containing DNA from HSV1 and HSV2 strains. Derivatives for example have at least 70% sequence homology to either the HSV1 or HSV2 genomes, for example at least 80%, for example at least 90 or 95%. Other derivatives which may be used to obtain the viruses of the present disclosure include strains that already have mutations in either ICP4 and/or ICP27, for example strain d120 which has a deletion in ICP4 (DeLuca et al., 1985 J. Virol. 56 (2): 558-70). HSV strains have also been produced with deletions in ICP27, for example Reef Hardy and Sandri-Goldin, 1994 J. Virol. 68(12): 7790-99 and Rice and Knipe, 1990 J. Virol. 64(4): 1704-15 (strain d27-1). Strains with deletions in both ICP4 and ICP27 are described in U.S. Pat. No. 5,658,724, and Samaniego et al. 1995 J. Virol. 69: 5705-15 (strain d92).

Cytomegalovirus Vectors

According to some embodiments, vaccine compositions described herein are based on cytomegalovirus virus (CMV) vectors.

CMV is a member of the beta subclass of the herpesvirus family. It is a large (containing a 230 kilobase genome), double stranded DNA virus that establishes life-long latent or persistent infection. In developed countries such as the United States, approximately 70% of the population is infected by CMV. In contrast to gamma herpesviruses such as Epstein-Barr Virus and Kaposi's Sarcoma-associated Herpesvirus, CMV is non-transforming and non-oncogenic.

The ability of live, recombinant CMV to generate immune responses against recombinant antigens has been demonstrated in several reports (Hansen et al, 2009 Nat. Med. 15:293-299; Karrer et al, 2004 J. Virol. 78:2255-2264). Moreover, it has been demonstrated that a recombinant, replication-competent CMV that is engineered to express a self protein will generate long-lasting, CD8+ T cell-based immunity against cells expressing the self protein (Lloyd et al, 2003 Biol. Reprod. 68:2024-2032). Hanson et al. used recombinant rhesus CMV expressing SIV antigens to immunize rhesus macaques against SIV (Hansen et al., 2009 Nat. Med. 15:293-299). The immunization induced large numbers of activated effector memory CD8+ T cells specific for SIV in peripheral tissues, which persisted for the entire multi-year duration of the study. The immunized monkeys were substantially protected from SIV challenge, which was attributed to the presence of activated effector-memory T cells. The study also demonstrated that pre-existing immunity to CMV did not prevent the ability of recombinant CMV to induce a new immune response.

According to some embodiments, vaccine compositions disclosed herein comprise a recombinant, replication-deficient cytomegalovirus comprising a heterologous nucleic acid encoding the immunogens of the present disclosure. According to some embodiments, viral latency is established in the subject, which latency results in the repeatedly stimulated immune response against the antigen. In particular embodiments, the repeatedly stimulated immune response comprises a CD8+ T cell immune response. According to some embodiments, the heterologous immunogen comprises a viral or tumor-derived polypeptide.

According to some embodiments, the recombinant replication-deficient cytomegalovirus comprises an inactivated gB, gD, gH, or gL glycoprotein gene, such as a gL glycoprotein that is inactivated by a knock out mutation. According to some embodiments, the nucleic acid encoding the immunogen is operably linked to a constitutive promoter. According to some embodiments, the nucleic acid encoding the immunogen is operably linked to an inducible promoter. According to some embodiments, the recombinant replication-deficient cytomegalovirus is a murine cytomegalovirus. In other embodiments, the recombinant replication-deficient cytomegalovirus is a human cytomegalovirus, such as an AD 169, Davis, Toledo or Towne strain of CMV.

Virus-Like Particle (VLP) Vectors

According to some embodiments, the present disclosure provides virus-like particles (VLPs) from the plasma membrane of eukaryotic cells, which VLPs carry on their surfaces immunogenic viral proteins, as described herein. The VLPs, alone or in combination with one or more additional VLPs and/or adjuvants, stimulate an immune response that protects against viral infection.

According to some embodiments, the VLP comprises viral proteins produced from naturally occurring and/or mutated nucleic acid sequences of genes coding for matrix protein M (also known as M1) and, optionally, M2 protein. The matrix protein M is a universal component for the formation of all possible polyvalent sub-viral structure vaccine combinations. The M1 and M2 proteins may be derived from any virus. For example, according to some embodiments, the M1 and/or M2 protein of the VLP is derived from an influenza matrix protein. In other embodiments, the M1 and/or M2 protein of the VLP is derived from RSV or thogoto-virus. The M1 and/or M2 proteins may be modified (mutated), for example as disclosed herein or in U.S. Patent Publications 2008/0031895 and 2009/0022762, incorporated by reference in their entireties herein.

VLPs can be prepared using standard recombinant techniques. Polynucleotides encoding the VLP-forming protein(s) are introduced into a host cell and, when the proteins are expressed in the cell, they assemble into VLPs. Polynucleotide sequences coding for molecules (structural and/or antigen polypeptides, including modified antigenic polypeptides) that form and/or are incorporated into the VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

According to some embodiments, the matrix-encoding sequences are RSV matrix proteins. In other embodiments, the matrix-encoding sequences are influenza matrix proteins. It will also be apparent that the matrix-encoding sequences can contain one or more mutations (modifications), for example the modified matrix proteins as described in U.S. Patent Publications 2008/0031895 and 2009/0022762. The VLPs described herein may further comprise additional influenza proteins (wild-type, modified (mutants) and/or hybrids of wild-type or mutants).

Any of the proteins used in the VLPs described herein may be hybrid (or chimeric) proteins. It will be apparent that all or parts of the polypeptides may be replaced with sequences from other viruses and/or sequences from other influenza strains. According to some exemplary embodiment, any of the proteins of the VLP may be hybrids in that they include heterologous sequences encoding the transmembrane and/or cytoplasmic tail domains, for example domains from influenza proteins such as HA or NA. See, e.g., U.S. Patent Publication Nos. 2008/0031895 and 2009/0022762.

In exemplary embodiments, the sequences employed to form influenza VLPs exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring viral polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring polynucleotide sequence.

Any of the sequences described herein may further include additional sequences. For example, to further enhance vaccine potency, hybrid molecules are expressed and incorporated into the sub-viral structure. These hybrid molecules are generated by linking, at the DNA level, the sequences coding for the matrix protein genes with sequences coding for an adjuvant or immuno-regulatory moiety. During sub-viral structure formation, these hybrid proteins are incorporated into or onto the particle depending on whether M1 or optional M2 carries the adjuvant molecule. The incorporation of one or more polypeptide immunomodulatory polypeptides (e.g., adjuvants) into the sequences described herein to form the VLP may enhance potency and therefore reduces the amount of antigen required for stimulating a protective immune response. Alternatively, one or more additional molecules (polypeptide or small molecules) may be included in the VLP-containing compositions after production of the VLP from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors.

Expression Vectors

Once the constructs comprising the sequences encoding the polypeptide(s) desired to be incorporated into the VLP have been synthesized, they can be cloned into any suitable vector or replicon for expression. Numerous cloning vectors are known to those of skill in the art, and one having ordinary skill in the art can readily select appropriate vectors and control elements for any given host cell type in view of the teachings of the present specification and information known in the art about expression. See, generally, Ausubel et al, supra or Sambrook et al, supra.

Non-limiting examples of vectors that can be used to express sequences that assembly into VLPs as described herein include viral-based vectors (e.g., retrovirus, adenovirus, adeno-associated virus, lentivirus, baculovirus vectors (see, Examples), plasmid vectors, non-viral vectors, mammalians vectors, mammalian artificial chromosomes (e.g., liposomes, particulate carriers, etc.) and combinations thereof.

The expression vector(s) typically contain(s) coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9): 815-821, 1994; Kozak, M., J Cell Biol 108(2):229-241, 1989; Kozak, M., and Shatkin, A. J., Methods Enzymol 60:360-375, 1979).

For example, typical promoters for mammalian cell expression include the SV40 early promoter, a CMV promoter such as the CMV immediate early promoter (a CMV promoter can include intron A), RSV, HIV-LTR, the mouse mammary tumor virus LTR promoter (MMLV-LTR), FIV-LTR, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs as described herein (Chapman et al., Nuc. Acids Res. (1991) 19:3979-3986).

Enhancer elements may also be used herein to increase expression levels of the mammalian constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence (Chapman et al., Nuc. Acids Res. (1991) 19:3979-3986).

According to some embodiments, one or more vectors may contain one or more sequences encoding proteins to be incorporated into the VLP. For example, a single vector may carry sequences encoding all the proteins found in the VLP. Alternatively, multiple vectors may be used (e.g., multiple constructs, each encoding a single polypeptide-encoding sequence or multiple constructs, each encoding one or more polypeptide-encoding sequences). In embodiments in which a single vector comprises multiple polypeptide-encoding sequences, the sequences may be operably linked to the same or different transcriptional control elements (e.g., promoters) within the same vector. Furthermore, vectors may contain additional gene expression controlling sequences including chromatin opening elements which prevent transgene silencing and confer consistent, stable and high level of gene expression, irrespective of the chromosomal integration site. These are DNA sequence motifs located in proximity of house-keeping genes, which in the vectors create a transcriptionally active open chromatin environment around the integrated transgene, maximizing transcription and protein expression, irrespective of the position of the transgene in the chromosome.

In addition, one or more sequences encoding non-viral immunogens, e.g., non-influenza proteins, may be expressed and incorporated into the VLP, including, but not limited to, sequences comprising and/or encoding immunomodulatory molecules (e.g., adjuvants described below), for example, immunomodulating oligonucleotides (e.g., CpGs), cytokines, detoxified bacterial toxins and the like.

VLP Production

The sequences and/or vectors described herein are then used to transform an appropriate host cell. The construct(s) encoding the proteins that form the VLPs described herein provide efficient means for the production of influenza VLPs using a variety of different cell types, including, but not limited to, insect, fungal (yeast) and mammalian cells.

According to some embodiments, the sub-viral structure vaccines are produced in eukaryotic cells following transfection, establishment of continuous cell lines (using standard protocols) and/or infection with DNA constructs that carry the immunogenic genes of interest (e.g., influenza genes) as known to one skilled in the art. The level of expression of the proteins required for sub-viral structure formation is maximized by sequence optimization of the eukaryotic or viral promoters that drive transcription of the selected genes. The sub-viral structure vaccine is released into the culture media, from where it is purified and subsequently formulated as a vaccine. The sub-viral structures are not infectious and therefore inactivation of the VLP is not required as it is for some killed viral vaccines The ability of the immunogenic polypeptides expressed from sequences as described herein to self-assemble into VLPs with antigenic glycoproteins presented on the surface allows these VLPs to be produced in many host cell by co-introduction of the desired sequences. The sequence(s) (e.g., in one or more expression vectors) may be stably and/or transiently integrated in various combinations into a host cell.

Suitable host cells include, but are not limited to, bacterial, mammalian, baculovirus/insect, yeast, plant and Xenopus cells.

For example, a number of mammalian cell lines are known in the art and include primary cells as well as immortalized cell lines available from the American Type Culture Collection (A.T.C.C.), such as, but not limited to, MDCK, BHK, VERO, MRC-5, WI-38, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 (such cell lines are available, for example, from the A.T.C.C.).

Similarly, bacterial hosts such as *E. coli, Bacillus subtilis*, and *Streptococcus* spp., will find use with the present expression constructs.

Yeast hosts useful in the present disclosure include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Fungal hosts include, for example, *Aspergillus*.

Insect cells for use with baculovirus expression vectors include, inter alia, *Aedes aegypti, Autographa californica, Bombyx mori, Drosophila melanogaster, Spodoptera frugiperda*, and *Trichoplusia ni*. See, Latham & Galarza (2001) J. Virol. 75(13):6154-6165; Galarza et al. (2005) Viral. Immunol. 18(1):244-51; and U.S. Patent Publications 200550186621 and 20060263804.

Cell lines expressing one or more of the sequences described above can readily be generated given the disclosure provided herein by stably integrating one or more expression vector constructs encoding the proteins of the VLP. The promoter regulating expression of the stably integrated influenza sequences (s) may be constitutive or inducible. Thus, a cell line can be generated in which one or more both of the matrix proteins are stably integrated such that, upon introduction of the sequences described herein (e.g., hybrid proteins) into a host cell and expression of the proteins encoded by the polynucleotides, non-replicating viral particles that present antigenic glycoproteins are formed.

The parent cell line from which a VLP-producer cell line is derived can be selected from any cell described above, including for example, mammalian, insect, yeast, bacterial cell lines. In an exemplary embodiment, the cell line is a mammalian cell line (e.g., 293, RD, COS-7, CHO, BHK, MDCK, MDBK, MRC-5, VERO, HT1080, and myeloma cells). Production of influenza VLPs using mammalian cells provides (i) VLP formation; (ii) correct post translation modifications (glycosylation, palmitylation) and budding; (iii) absence of non-mammalian cell contaminants and (iv) ease of purification.

In addition to creating cell lines, immunogen-encoding sequences may also be transiently expressed in host cells. Suitable recombinant expression host cell systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, insect and yeast systems.

Many suitable expression systems are commercially available, including, for example, the following: baculovirus expression (Reilly, P. R., et al., (1992) BACULOVIRUS EXPRESSION VECTORS: A LABORATORY MANUAL; Beames, et al., (1991) Biotechniques 11:378; Pharmingen; Clontech, Palo Alto, Calif.)), vaccinia expression systems (Earl, P. L., et al., "Expression of proteins in mammalian cells using vaccinia" (1991) In Current Protocols in Molecular Biology (F. M. Ausubel, et al. Eds.), Greene Publishing Associates & Wiley Interscience, New York; Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media Pa.; Clontech), expression in yeast (Rosenberg, S. and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., (1992) Antonie Van Leeuwenhoek, 62(1-2):79-93; Romanos, M. A., et al., (1992) Yeast 8(6):423-488; Goeddel, D. V., (1990) Methods in Enzymology 185; Guthrie, C., and G. R. Fink, (1991) Methods in Enzymology 194), expression in mammalian cells (Clontech; Gibco-BRL, Ground Island, N.Y.; e.g., Chinese hamster ovary (CHO) cell lines (Haynes, J., et al., (1983) Nuc. Acid. Res. 1983 11:687-706; Lau, Y. F., et al., (1984) Mol. Cell. Biol. 4:1469-1475; Kaufman, R. J., "Selection and coamplification of heterologous genes in mammalian cells," (1991) in Methods in Enzymology, vol. 185, pp 537-566. Academic Press, Inc., San Diego Calif.), and expression in plant cells (plant cloning vectors, Clontech Laboratories, Inc., Palo-Alto, Calif., and Pharmacia LKB Biotechnology, Inc., Pistcataway, N.J.; Hood, E., et al., (1986) J. Bacteriol. 168:1291-1301; Nagel, R., et al., (1990) FEMS Microbiol. Lett. 67:325; An, et al., "Binary Vectors", and others (1988) in Plant Molecular Biology Manual A3:1-19; Miki, B. L. A., et al., pp. 249-265, and others (1987) in Plant DNA Infectious Agents (Hohn, T., et al., eds.) Springer-Verlag, Wien, Austria; 1997 Pant Molecular Biology: Essential Techniques, P. G. Jones and J. M. Sutton, New York, J. Wiley; Miglani, 1998 Gurbachan Dictionary of Plant Genetics and Molecular Biology, New York, Food Products Press; Henry, R. J., 1997 Practical Applications of Plant Molecular Biology, New York, Chapman & Hall).

Depending on the expression system and host selected, the VLPs are produced by growing host cells transformed by an expression vector under conditions whereby the particle-forming polypeptide(s) is(are) expressed and VLPs can be formed. The selection of the appropriate growth conditions is within the skill of the art. If the VLPs are formed and retained intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990). Alternatively, VLPs may be secreted and harvested from the surrounding culture media.

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. (1993) J. Virol. 67:6929-6936), as well as standard purification techniques including, e.g., ion exchange and gel filtration chromatography.

Bacterial Vector Vaccines

According to some embodiments, vaccine compositions described herein are based on bacterial vectors.

Genetic engineering techniques have made it possible to identify and delete important virulence genes, enabling the attenuation of pathogenic bacteria and creating vectors unable to revert to their virulent forms. Several mutations have been described for different serotypes of *Salmonella enterica* (serovars *Typhi* and *Typhimurium*, referred to as *S. typhi* and *S. typhimurium*, respectively), with the most frequently used being the aroA mutation (as well as aroC and aroD), which blocks the ability of the microorganism to synthesize aromatic compounds. This renders the bacteria unable to reproduce in the host, while retaining the capacity to invade the small intestine and to persist in infecting long enough to produce the antigen and elicit an effective immune response (Cárdenas and Clements, 1992 Clin Microbiol Rev 5:328-342). Other useful mutations that can attenuate pathogenicity affect biosynthesis of the nucleotides adenine (pur) and guanine (guaBA), and outer membrane proteins C and F (ompC, ompF), as well as expression of the cAMP receptor (cya/crp), the conversion of UDP-galactose to UDP-glucose (galE), DNA recombination and repair (recA, recBC), and regulation of virulence genes (phoP, phoQ) (Mastroeni et al., 2001 Vet J 161:132-164).

*Listeria monocytogenes* infection (listeriosis) is a rare and preventable foodborne illness that can cause bacteremia, meningitis, fetal loss, and death, with the risk being greatest for older adults, pregnant women, and persons with immunocompromising conditions. Attenuation of *Listeria monocytogenes* for vaccine purposes has been achieved using auxotrophic mutants (Zhao et al., 2005 Infect Immun 73:5789-5798) or deletion of virulence factors such as the genes actA and internalin B (inlB) (Brockstedt et al., 2004 Proc Natl Acad Sci USA 101:13832-13837).

Among other bacterial species that have been studied for heterologous antigen delivery include *Streptococcus gordonii* (Lee 2003, Curr Opin Infect Dis. 2003; 16:231-235; Oggioni et al., 1995, Vaccine 13:775-779), *Vibrio cholerae* (Kaper and Levine 1990, Res Microbiol. 1990; 141:901-906; Silva et al., 2008 Biotechnol Lett 30:571-579), *Mycobacterium bovis* (BCG) (Bastos et al., 2009 Vaccine. 2009; 27:6495-6503; Nasser Eddine and Kaufmann, 2005, Microbes Infect 7:939-946), *Yersinia enterocolitica* (Leibiger et al., 2008, Vaccine 26:6664-6670), and *Shigella flexnery* (Barry et al., 2006, Vaccine 24:3727-3734). Other species that have been investigated for use as vaccine vectors include *Pseudomonas aeruginosa* (Epaulard et al., 2006 Mol Ther. 2006; 14:656-661), *Bacillus subtilis* (Duc et al., 2003, Infect Immun 71:2810-2818; Isticato et al., 2001, J Bacteriol 183:6294-6301), and *Mycobacterium smegmatis* (Lü et al., 2009 Vaccine. 2009; 27:972-978). In the veterinary field, other bacteria have been used to develop a double protective immune response, against a heterologous antigen and against the vector itself, these include *Erysipelothrix rhusiopathiae* (Ogawa et al., 2009, Vaccine 27:4543-4550), *Mycoplasma gallisepticum* (Muneta et al., 2008, Vaccine. 2008; 26:5449-5454), and *Corynebacterium pseudotuberculosis* (Moore et al., 1999, Vaccine. 1999; 18:487-497). A number of live attenuated bacterial vaccines are licensed for veterinary use, including *Lawsonia intracellularis, Streptococcus equi* (deleted in the aroA gene), *Chlamydophila abortus, Mycoplasma synoviae, Mycoplasma gallisepticum* (temperature-sensitive mutants), and *Bordetella avium*. Most of the strains were selected as attenuated, but were not precisely mutated to promote the attenuation and do not carry heterologous antigens (Meeusen et al., 2007, Clin Microbiol Rev 20:489-510).

Genetic Vaccines

According to some embodiments, the disclosure relates to compositions for delivering nucleic acid molecules that comprise a nucleotide sequence that encodes a conserved immunogenic protein as described herein operably linked to regulatory elements. Aspects of the present disclosure relate to compositions for delivering a recombinant vaccine comprising a nucleotide sequence that encodes that encodes a protein of the disclosure; a live attenuated pathogen that encodes a protein of the disclosure and/or includes a protein of the disclosure; a killed pathogen includes a protein of the disclosure; or a composition such as a liposome or subunit vaccine that comprises a protein of the disclosure. The present disclosure further relates to injectable pharmaceutical compositions that comprise compositions.

As described herein, a vaccine according to the disclosure is delivered to an individual to modulate the activity of the individual's immune system and thereby enhance the immune response. When a nucleic acid molecule that encodes the protein is taken up by cells of the individual the nucleotide sequence is expressed in the cells and the protein are thereby delivered to the individual. Also described herein are methods of delivering the coding sequences of the protein on nucleic acid molecule such as plasmid, as part of recombinant vaccines and as part of attenuated vaccines, as isolated proteins or proteins part of a vector.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, all of which are incorporated by reference in their entireties herein. In addition to the delivery protocols described in those applications, alternative methods of delivering DNA are described in U.S. Pat. Nos. 4,945,050 and 5,036,006, incorporated by reference in their entireties herein.

Genetic immunization according to some embodiments of the present disclosure elicits an effective immune response without the use of infective agents or infective vectors. Vaccination techniques which usually do produce a CTL response do so through the use of an infective agent. A complete, broad based immune response is not generally exhibited in individuals immunized with killed, inactivated or subunit vaccines. Some embodiments of the present disclosure achieve the full complement of immune responses in a safe manner without the risks and problems associated with vaccinations that use infectious agents.

According to some embodiments of the present disclosure, DNA or RNA that encodes a conserved immunogenic protein as described herein is introduced into the cells of an individual, or subject, where it is expressed, thus producing the target protein. The DNA or RNA is linked to regulatory elements necessary for expression in the cells of the individual. Regulatory elements for DNA include a promoter and a polyadenylation signal. In addition, other elements, such as a Kozak region, may also be included in the genetic construct.

The genetic constructs of genetic vaccines comprise a nucleotide sequence that encodes a conserved immunogenic protein as described herein operably linked to regulatory elements needed for gene expression. Accordingly, incorporation of the DNA or RNA molecule into a living cell results in the expression of the DNA or RNA encoding the target protein and thus, production of the target protein.

When taken up by a cell, the genetic construct, which includes the nucleotide sequence encoding the conserved immunogenic protein as described herein operably linked to the regulatory elements, may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Since integration into the chromosomal DNA necessarily requires manipulation of the chromosome, it is preferred to maintain the DNA construct as a replicating or non-replicating extrachromosomal molecule. This reduces the risk of damaging the cell by splicing into the chromosome without affecting the effectiveness of the vaccine. Alternatively, RNA may be administered to the cell. It is also contemplated to provide the genetic construct as a linear minichromosome including a centromere, telomeres and an origin of replication.

The necessary elements of a genetic construct of a genetic vaccine include a nucleotide sequence that encodes a conserved immunogenic protein as described herein and the regulatory elements necessary for expression of that sequence in the cells of the vaccinated individual. The regulatory elements are operably linked to the DNA sequence that encodes the target protein to enable expression.

The molecule that encodes a conserved immunogenic protein as described herein is a protein-encoding molecule which is translated into protein. Such molecules include DNA or RNA which comprise a nucleotide sequence that encodes the target protein. These molecules may be cDNA, genomic DNA, synthesized DNA or a hybrid thereof or an RNA molecule such as mRNA. Accordingly, as used herein, the terms "DNA construct", "genetic construct" "nucleic acid molecule", "nucleic acid" and "nucleotide sequence" are meant to refer to both DNA and RNA molecules.

Nucleic acids encoding the immunogens of the disclosure can be used as components of, for example, a DNA vaccine wherein the encoding sequence is administered as naked DNA or, for example, a minigene encoding the immunogen can be present in a viral vector. The encoding sequences can be expressed, for example, in *mycobacterium*, in a recombinant chimeric adenovirus, or in a recombinant attenuated vesicular stomatitis virus. The encoding sequence can also be present, for example, in a replicating or non-replicating adenoviral vector, an adeno-associated virus vector, an attenuated *Mycobacterium tuberculosis* vector, a *Bacillus* Calmette Guerin (BCG) vector, a vaccinia or Modified Vaccinia Ankara (MVA) vector, another pox virus vector, recombinant polio and other enteric virus vector, *Salmonella* species bacterial vector, *Shigella* species bacterial vector, Venezuelan Equine Encephalitis Virus (VEE) vector, a Semliki Forest Virus vector, or a Tobacco Mosaic Virus vector. The encoding sequence, can also be expressed as a DNA plasmid with, for example, an active promoter such as a CMV promoter. Other live vectors can also be used to express the sequences of the disclosure. Expression of the immunogen of the disclosure can be induced in a patient's own cells, by introduction into those cells of nucleic acids that encode the immunogen, preferably using codons and promoters that optimize expression in human cells. Examples of methods of making and using DNA vaccines are disclosed in U.S. Pat. Nos. 5,580,859, 5,589,466, and 5,703,055

The regulatory elements necessary for gene expression of a DNA molecule include: a promoter, an initiation codon, a stop codon, and a polyadenylation signal. In addition, enhancers are often required for gene expression. It is necessary that these elements be operable in the vaccinated individual. Moreover, it is necessary that these elements be operably linked to the nucleotide sequence that encodes the target protein such that the nucleotide sequence can be expressed in the cells of a vaccinated individual and thus the target protein can be produced.

Initiation codons and stop codons are generally considered to be part of a nucleotide sequence that encodes the target protein. However, it is necessary that these elements are functional in the vaccinated individual.

Similarly, promoters and polyadenylation signals used must be functional within the cells of the vaccinated individual.

Examples of promoters useful to practice some embodiments of the present disclosure, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter (CMV IE), Epstein Barr Virus (EBV), Rous Sarcoma Virus (RSV) as well as promoters from human genes such as human actin, human myosin, human hemoglobin, human muscle creatine and human metalothionein.

Examples of polyadenylation signals useful to practice some embodiments of the present disclosure, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, can be used. Additionally, the bovine growth hormone (bgh) polyadenylation signal can serve this purpose.

In addition to the regulatory elements required for DNA expression, other elements may also be included in the DNA molecule. Such additional elements include enhancers. The enhancer may be selected from the group including but not limited to: human actin, human myosin, human hemoglobin, human muscle creatine and viral enhancers such as those from CMV, RSV and EBV, such as a CMV IE enhancer.

Genetic constructs can be provided with a mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

An additional element may be added which serves as a target for cell destruction if it is desirable to eliminate cells receiving the genetic construct for any reason. A herpes thymidine kinase (tk) gene in an expressible form can be included in the genetic construct. When the construct is introduced into the cell, tk will be produced. The drug gangcyclovir can be administered to the individual and that drug will cause the selective killing of any cell producing tk. Thus, a system can be provided which allows for the selective destruction of vaccinated cells.

In order to be a functional genetic construct, the regulatory elements must be operably linked to the nucleotide sequence that encodes the target protein. Accordingly, it is necessary for the initiation and termination codons to be in frame with the coding sequence.

Open reading frames (ORFs) encoding the protein of interest and another or other proteins of interest may be introduced into the cell on the same vector or on different vectors. ORFs on a vector may be controlled by separate promoters or by a single promoter. In the latter arrangement, which gives rise to a polycistronic message, the ORFs will be separated by translational stop and start signals. The presence of an internal ribosome entry site (IRES) site between these ORFs permits the production of the expression product originating from the second ORF of interest, or third, etc. by internal initiation of the translation of the bicistronic or polycistronic mRNA.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

According to some embodiments, in order to maximize protein production, regulatory sequences may be selected which are well suited for gene expression in the cells into which the construct is administered. Moreover, codons may be selected which are most efficiently transcribed in the cell. One having ordinary skill in the art can produce DNA constructs that are functional in the cells.

According to some embodiments for which protein is used, for example, one having ordinary skill in the art can produce and isolate proteins of the disclosure using well known techniques. According to some embodiments for which protein is used, for example, one having ordinary skill in the art can, using well known techniques, inserts DNA molecules that encode a protein of the disclosure into a commercially available expression vector for use in well-known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., (1989) Molecular Cloning a Laboratory Manual, Second Ed. Cold Spring Harbor Press.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the disclosure from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or if secreted from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

According to some embodiments of the disclosure, the genetic vaccine may be administered directly into the individual to be immunized or ex vivo into removed cells of the individual which are reimplanted after administration. By either route, the genetic material is introduced into cells which are present in the body of the individual.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration of the genetic vaccine include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, or "microprojectile bombardment gene guns".

According to some embodiments, the nucleic acid molecule is delivered to the cells in conjunction with administration of a polynucleotide function enhancer or a genetic vaccine facilitator ("GVF") agent. Polynucleotide function enhancers are described in U.S. Pat. Nos. 5,593,972, 5,962,428 and International Application Serial Number PCT/US94/00899 filed Jan. 26, 1994. Genetic vaccine facilitator agents are described in US. Ser. No. 021,579 filed Apr. 1, 1994. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct According to some embodiments, an immunomodulating protein may be used as a GVF. According to some embodiments, the nucleic acid molecule is provided in association with PLG to enhance delivery/uptake.

The genetic vaccines according to some embodiments of the present disclosure comprise about 1 nanogram to about 1000 micrograms of DNA. According to some exemplary embodiments, the vaccines contain about 10 nanograms to about 800 micrograms of DNA. According to some exemplary embodiments, the vaccines contain about 0.1 to about 500 micrograms of DNA. According to some exemplary embodiments, the vaccines contain about 1 to about 350 micrograms of DNA. According to some exemplary embodiments, the vaccines contain about 25 to about 250 micrograms of DNA. According to some exemplary embodiments, the vaccines contain about 100 micrograms DNA.

Genetic constructs may optionally be formulated with one or more response enhancing agents such as: compounds which enhance transfection, i.e., transfecting agents; compounds which stimulate cell division, i.e., replication agents; compounds which stimulate immune cell migration to the site of administration, i.e., inflammatory agents; compounds which enhance an immune response, i.e., adjuvants or compounds having two or more of these activities.

According to some embodiment, bupivacaine, a well known and commercially available pharmaceutical compound, is administered prior to, simultaneously with or subsequent to the genetic construct. Bupivacaine and the genetic construct may be formulated in the same composition. Bupivacaine is particularly useful as a cell stimulating agent in view of its many properties and activities when administered to tissue. Bupivacaine promotes and facilitates the uptake of genetic material by the cell. As such, it is a transfecting agent. Administration of genetic constructs in conjunction with bupivacaine facilitates entry of the genetic constructs into cells. Bupivacaine is believed to disrupt or otherwise render the cell membrane more permeable. Cell division and replication is stimulated by bupivacaine. Accordingly, bupivacaine acts as a replicating agent. Administration of bupivacaine also irritates and damages the tissue. As such, it acts as an inflammatory agent which elicits migration and chemotaxis of immune cells to the site of administration. In addition to the cells normally present at the site of administration, the cells of the immune system which migrate to the site in response to the inflammatory agent can come into contact with the administered genetic material and the bupivacaine. Bupivacaine, acting as a transfection agent, is available to promote uptake of genetic material by such cells of the immune system as well.

In addition to bupivacaine, mepivacaine, lidocaine, procains, carbocaine, methyl bupivacaine, and other similarly acting compounds may be used as response enhancing agents. Such agents act as cell stimulating agents which promote the uptake of genetic constructs into the cell and stimulate cell replication as well as initiate an inflammatory response at the site of administration.

Other contemplated response enhancing agents which may function as transfecting agents and/or replicating agents and/or inflammatory agents and which may be administered include lectins, growth factors, cytokines and lymphokines such as alpha-interferon, gamma-interferon, platelet derived growth factor (PDGF), gCSF, gMCSF, TNF, epidermal growth factor (EGF), IL-1, IL-2, IL-4, IL-6, IL-8, IL-10 and IL-12 as well as collagenase, fibroblast growth factor, estrogen, dexamethasone, saponins, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalane, hyaluronic acid and hyaluronidase may also be administered in conjunction with the genetic construct. According to some embodiments, combinations of these agents are co-administered in conjunction with the genetic construct. In other embodiments, genes encoding these agents are included in the same or different genetic construct(s) for co-expression of the agents.

Lipid Immunogens

The immunogens (e.g., conserved immunogens) disclosed herein may also be linked directly to, or through a spacer or linker to: an immunogenic carrier such as serum albumin, tetanus toxoid, keyhole limpet hemocyanin, dextran, or a recombinant virus particle; an immunogenic peptide known to stimulate a T helper cell type immune response; a cytokine such as interferon gamma or GMCSF; a targeting agent such as an antibody or receptor ligand; a stabilizing agent such as a lipid; or a conjugate of a plurality of epitopes to a branched lysine core structure, such as the so-called "multiple antigenic peptide" described by Posenett et. al., incorporated by reference in its entirety herein; a compound such as polyethylene glycol to increase the half-life of the peptide; or additional amino acids such as a leader or secretory sequence, or a sequence employed for the purification of the mature sequence. Spacers and linkers typically comprise relatively small, neutral molecules. In addition, such linkers need not be composed of amino acids but any oligomeric structures will do as well so long as they provide the correct spacing so as to optimize the desired level of immunogenic activity of the immunogens of the present disclosure. The immunogen may therefore take any form that is capable of eliciting a CTL response.

The skilled artisan would appreciate, once armed with the teachings provided herein, that the vaccine compositions described herein encompass numerous molecules, some either expressed under the control of a single promoter/regulatory sequence or under the control of more than one such sequence. Moreover, the disclosure encompasses administration of one or more vaccines of the disclosure where the various vaccines encode different molecules. That is, the various molecules (e.g., conserved immunogens, costimulatory ligands, cytokines, and the like) can work in cis (i.e., in the same vaccine vector and/or encoded by the same contiguous nucleic acid or on separate nucleic acid molecules within the same vaccine vector) or in trans (i.e., the various molecules are expressed by different vaccines).

Methods for Determining Immune Response

Most immune responses associated with vaccination are controlled by specific T cells of a CD4+ helper phenotype which mediate the generation of effector antibodies, cytotoxic T lymphocytes (CTLs), or the activation of innate immune effector cells. The resulting antigen-specific T cell responses need to be of the appropriate type involving: helper T cells ($T_H$ cells, expressing cytokines and co-stimulatory molecules), and/or cytotoxic T lymphocytes (CTL), and with memory and homing capacity, and should not be exhausted or anergized via negative feedback or immune checkpoints. A formulation (antigen, vehicle, adjuvants; proportions thereof) and regimen (including the number and interval between immunizations, and route of vaccination) that generates the appropriate T cell response is required. The measurement and characterization of these T cells provides useful markers of immunogenicity and efficacy, and informs on mechanisms for further vaccine development.

Methods for determining immune responses are known in the art. According to some embodiments, viral lesions can be examined to determine the occurrence of an immune response to the virus and/or the antigen. According to some embodiments, in vitro assays may be used to determine the occurrence of an immune response. Examples of such in vitro assays include ELISA assays and cytotoxic T cell (CTL) assays. According to some embodiments, the immune response is measured by detecting and/or quantifying the relative amount of an antibody, which specifically recognizes an antigen in the sera of a subject who has been treated by administering the live, modified, non-replicating or replication-impaired poxvirus comprising the antigen, relative to the amount of the antibody in an untreated subject.

Techniques for assaying antibodies in a sample are known in the art and include, for example, sandwich assays, ELISA and ELISpot. Polyclonal sera are relatively easily prepared by injection of a suitable laboratory animal with an effective amount of the immune effector, or antigenic part thereof, collecting serum from the animal and isolating specific sera by any of the known immunoadsorbent techniques. Antibodies produced by this method are utilizable in virtually any type of immunoassay.

The use of monoclonal antibodies in an immunoassay is preferred because of the ability to produce them in large quantities and the homogeneity of the product. The preparation of hybridoma cell lines for monoclonal antibody production derived by fusing an immortal cell line and lymphocytes sensitized against the immunogenic preparation can be achieved by techniques which are well known to those who are skilled in the art. In other embodiments, ELISA assays may be used to determine the level of isotype specific antibodies using methods known in the art.

CTL assays can be used to determine the lytic activity of CTLs, measuring specific lysis of target cells expressing a certain antigen. Immune-assays may be used to measure the activation (e.g., degree of activation) of sample immune cells. "Sample immune cells" refer to immune cells contained in samples from any source, including from a human patient, human donor, animal, or tissue cultured cell line. The immune cell sample can be derived from peripheral blood, lymph nodes, bone marrow, thymus, any other tissue source including in situ or excised tumor, or from tissue or organ cultures. The sample may be fractionated or purified to generate or enrich a particular immune cell subset before analysis. The immune cells can be separated and isolated from their source by standard techniques.

Immune cells include both non-resting and resting cells, and cells of the immune system that may be assayed, including, but not limited to, B lymphocytes, T lymphocytes, natural killer (NK) cells, invariant NKT (iNKT) cells, lymphokine-activated killer (LAK) cells, monocytes, macrophages, neutrophils, granulocytes, mast cells, platelets, Langerhans cells, stem cells, dendritic cells, and peripheral blood mononuclear cells.

Immune cell activity that may be measured includes, but is not limited to (1) cell proliferation by measuring the cell or DNA replication; (2) enhanced cytokine production, including specific measurements for cytokines, such as γIFN, GM-CSF, or TNF-alpha, IFN-alpha, IL-6, IL-10, IL-12; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; (9) chemokine secretion such as IP-10; (10) expression of costimulatory molecules (e.g., CD80, CD86) and maturation molecules (e.g., CD83), (12) upregulation of class II MHC expression; and (13) apoptosis, which refers to fragmentation of activated immune cells under certain circumstances, as an indication of abnormal activation.

Reporter molecules may be used for many of the immune assays described. A reporter molecule is a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest.

The ability to measure memory T cells in association with vaccination is important to establish a vaccine's immunogenicity and may be a biomarker of efficacy by having a positive association with protection from infection and/or disease. Important factors in the measurement of T cell responses are the methods of measurement, when to make these measurements, and in which locations. T cell responses measured in the circulating PBMCs during a vaccination regimen tend to follow the typical pattern of adaptive immune response, i.e., an initial exposure is followed by a lag phase, then a peak in the response (such as an antigen-specific IFNγ response) at about one to two weeks, that eventually settles back down to a response raised over the naïve response. Due to memory generated by the priming, a second exposure through boosting gives a more rapid, greater response. Through effector T cell ($T_E$) attrition, this response then settles to a level higher than it was before the boost. Thus, the aim of boosting is to cause the T cells to reach a putative "protective" level. To date, few direct correlations between T cell responses and degrees of protection from infection and disease have been established for clinical use. "Quantiferon™" and ELIspot tests have been able to detect latent *Mycobacterium tuberculosis* infection in at-risk individuals through the detection of IFNγ secretion by peripheral T cells reactive to particular TB antigens. However, such responses following vaccination for TB have not been associated with protection from infection. Even if the PBMC may not be the ideal location to detect the reactive T cells that need to act in specific tissues (such as the mucosa), precursors in transit (such as $T_{EM}$ and $T_{CM}$) are measurable with specialized or modified techniques. Ex vivo techniques on whole blood or PBMC involve the exposure to the vaccine antigen and the measurement of responses, which typically occur within one day. The most common of such tests involves bulk cytokine secretion from blood cells (whole blood assay/ELISA) and cytokine measurement by flow cytometry and enzyme-linked immunospot (ELISpot). This is done to identify responding cells at the single cell level. The expansion in the number of available flow cytometry parameters means that cells can be identified as secreting or expressing a multitude of molecules using single-cell mass cytometry and RNA sequencing, thus allowing their characterization within effector phenotypes, memory phenotypes, and beyond. Molecular signatures in blood that are associated with vaccination continue to implicate T cells in protection. Although it is more cumbersome, incorporating a period of culture of blood cells with antigens and other factors allows specific memory cells like $T_{CM}$ to be revealed, as the culture promotes differentiation to $T_{EM}$ and/or $T_E$. One approach with whole blood that was cultured together with a precise vaccine formulation (antigen in adjuvant+ TLR ligand) (Hakimi J. et al., 2017 Hum Vaccin Immunother. September 2; 13(9):2130-2134) revealed significantly higher T cell cytokine secretion. These results suggest that components of the whole blood interact with components of the vaccine to promote T cell reactivation in a way that might emulate in vivo events. Such an assay is capable of monitoring vaccine formulations for potency as well as testing vaccine recipients for their potential to respond to a vaccine in vivo. Being able to emulate ectopic lymphoid structures (memory depots) may provide one method of recreating and studying vaccine responses in vitro.

Other exemplary immune assays are described herein below.

Cell Proliferation Assay: Activated immune cell proliferation is intended to include increase in cell number, cell growth, cell division, or cell expansion, as measured by cell number, cell weight, or by incorporation of radiolabelled nucleic acids, amino acids, proteins, or other precursor molecules. As one example, DNA replication is measured by incorporation of radioisotope labels. According to some embodiments, cultures of stimulated immune cells can be measured by DNA synthesis by pulse-labeling the cultures with tritiated thymidine (3H-Tdr), a nucleoside precursor that is incorporated into newly synthesized DNA. Thymidine incorporation provides a quantitative measure of the rate of DNA synthesis, which is usually directly proportional to the rate of cell division. The amount of 3H-labeled thymidine incorporated into the replicating DNA of cultured cells is determined by scintillation counting in a liquid scintillation spectrophotometer. Scintillation counting yields data in counts per minute (cpm) which may then be used as a standard measure of immune cell responsiveness. The cpm in resting immune cell cultures may be either subtracted from or divided into cpm of the primed immune cells, which will yield a stimulation index ratio.

Flow cytometry can also be used to measure proliferation by measuring DNA with light scatter, Coulter volume and fluorescence, all of which are techniques that are well known in the art.

Enhanced Cytokine Production Assay: A measure of immune cell stimulation is the ability of the cells to secrete cytokines, lymphokines, or other growth factors. Cytokine production, including specific measurements for cytokines, such as γIFN, GM-CSF, or TNF-alpha, may be made by radioimmunoassay (RIA), enzyme-linked immunoabsorbent assay (ELISA), bioassay, or measurement of messenger RNA levels. In general, with these immunoassays, a monoclonal antibody to the cytokine to be measured is used to specifically bind to and thus identify the cytokine. Immunoassays are well known in the art and can include both competitive assays and immunometric assays, such as forward sandwich immunoassays, reverse sandwich immunoassays and simultaneous immunoassays.

In each of the above assays, the sample-containing cytokine is incubated with the cytokine-specific monoclonal antibody under conditions and for a period of time sufficient to allow the cytokines to bind to the monoclonal antibodies. In general, it is desirable to provide incubation conditions sufficient to bind as much cytokine and antibody as possible, since this will maximize the signal. Of course, the specific concentrations of antibodies, the temperature and time of incubation, as well as other such assay conditions, can be varied, depending upon various factors including the concentration of cytokine in the sample, the nature of the sample, and the like. Those skilled in the art will be able to determine operative and optimal assay conditions for each determination by employing routine experimentation.

Cell-Mediated Target Cell Lysis Assay: Another type of indicator for degree of immune cell activation is immune cell-mediated target cell lysis, which is meant to encompass any type of cell killing, including cytotoxic T lymphocyte activity, apoptosis, and the induction of target lysis by molecules secreted from non-resting immune cells stimulated to activity. Cell-mediated lympholysis techniques typically measure the ability of the stimulated immune cells to lyse $^{51}$Cr-labeled target cells. Cytotoxicity is measured as a percentage of $^{51}$Cr released in specific target cells compared to percentage of $^{51}$Cr released from control target cells. Cell killing may also be measured by counting the number of target cells, or by quantifying an inhibition of target cell growth.

Cell Differentiation Assay: Another indicator of immune cell activity is immune cell differentiation and maturation. Cell differentiation may be assessed in several different ways. One such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation.

Immune cells express a variety of cell surface molecules which can be detected with either monoclonal antibodies or polyclonal antisera. Immune cells that have undergone differentiation or activation can also be enumerated by staining for the presence of characteristic cell surface proteins by direct immunofluorescence in fixed smears of cultured cells.

Mature B cells can be measured in immunoassays, for example, by cell surface antigens including CD19 and CD20 with monoclonal antibodies labeled with fluorochromes or enzymes may be used to these antigens. B cells that have differentiated into plasma cells can be enumerated by staining for intracellular immunoglobulins by direct immunofluorescence in fixed smears of cultured cells.

Immunoglobulin Production Assay: B cell activation results in small, but detectable, quantities of polyclonal immunoglobulins. Following several days of culture, these immunoglobulins may be measured by radioimmunoassay or by enzyme-linked immunosorbent assay (ELISA) methods.

B cells that produce immunoglobulins can also be quantified by the reversed hemolytic plaque assay. In this assay, erythrocytes are coated with goat or rabbit anti-human immunoglobulins. These immunoglobulins are mixed with the activated immunoglobulin-producing lymphocytes and semisolid agar, and complement is added. The presence of hemolytic plaques indicates that there are immunoglobulin-producing cells.

Chemotactic Factor Assay: Chemotactic factors are molecules which induce or inhibit immune cell migration into or out of blood vessels, tissues or organs, including cell migration factors. The chemotactic factors of immune cells can be assayed by flow cytometry using labeled monoclonal antibodies to the chemotactic factor or factors being assayed. Chemotactic factors may also be assayed by ELISA or other immunoassays, bioassays, messenger RNA levels, and by direct measurements, such as cell counting, of immune cell movements in specialized migration chambers.

Addback Assays: When added to fresh peripheral blood mononuclear cells, autologous ex vivo activated cells exhibit an enhanced response to a "recall" antigen, which is an antigen to which the peripheral blood mononuclear cells had previously been exposed. Primed or stimulated immune cells should enhance other immune cells response to a "recall" antigen when cultured together. These assays are termed "helper" or "addback" assays. In this assay, primed or stimulated immune cells are added to untreated, usually autologous immune cells to determine the response of the untreated cells. The added primed cells may be irradiated to prevent their proliferation, simplifying the measurement of the activity of the untreated cells. These assays may be particularly useful in evaluating cells for blood exposed to virus. The addback assays can measure proliferation, cytokine production, and target cell lysis as described herein.

The above-described methods and other additional methods to determine an immune response are well known in the art.

Methods of Use

In accordance with further embodiments of the disclosure, methods for reducing risk of an infection with an infectious agent amenable to vaccination according to the present disclosure are provided. According to some embodiments, a method includes administering to a subject in need thereof an amount of immunogen, or protein thereof, sufficient to reduce the risk of infection.

In accordance with further embodiments of the disclosure, there are provided prophylactic methods including methods of vaccinating and immunizing a subject against a viral infection, e.g., influenza infection such as, but not limited to, protecting a subject against influenza infection to decrease or reduce the probability of an influenza infection or pathology in a subject or to decrease or reduce susceptibility of a subject to an influenza infection or pathology or to inhibit or prevent influenza infection in a subject or to reduce risk of spread in a susceptible population.

According to another embodiment, the method includes a process for inducing a cellular immune response in vitro that is specific to viral antigens expressed by a virus infected cell, comprises contacting a CTL precursor lymphocyte with an antigen presenting cell that is expressing a polynucleotide coding for a viral polypeptide of the disclosure, wherein said polynucleotide is operably linked to a promoter. The foreign viral antigen bound to MHC molecules expressed on the stimulator APCs can serve as the activating stimulus to responding T lymphocytes comprising a population of cells that exhibit an ability to kill pathogen-infected cells, while showing resistance to such killing action. The ability to kill pathogen-infected cells may be direct, though cytolytic or cytotoxic activities, or indirect, through the immunoregulation of other cells and proteins that target pathogenic cells. There are multiple kinds of cells that can display this effector function, e.g., NK cells, NKT cells, LAK cells, CIK cells, MAIT cells, CD8+ CTLs, CD4+ CTLs (collectively "CTLs"). Proliferation of the responding T lymphocytes then can be measured.

A variety of techniques exist for assaying the activity of activated CTL, and are described infra.

After expansion of the antigen-specific CTLs, the activated CTLs are then adoptively transferred back into the patient, where they will destroy their specific target cell. Methodologies for reinfusing T cells into a patient are well known and exemplified in U.S. Pat. No. 4,844,893 to Honski, et al., and U.S. Pat. No. 4,690,915 to Rosenberg.

The peptide-specific activated CTL can be purified from the stimulator cells prior to infusion into the patient. For example, monoclonal antibodies directed toward the cell surface protein CD8, present on CTL, can be used in conjunction with a variety of isolation techniques such as antibody panning, flow cytometric sorting, and magnetic bead separation to purify the peptide-specific CTL away from any remaining non-peptide specific lymphocytes or from the stimulator cells.

Thus, according to some embodiments of the present disclosure, a process for reducing risk of infection with a pathogen, reducing risk of spread of infection in a population, or both comprises administering, activated CTLs produced in vitro in an amount sufficient to effect the destruction of the pathogen infected cells either directly or indirectly through the elaboration of cytokines.

Another embodiment of the present disclosure is directed to a process for treating a subject at risk for infection with a pathogen, reducing risk of spread of infection in a population, or both, where the infection is characterized by pathogen-infected cells expressing any class I MHC molecule and an internal CD8+ T cell epitope as determined using methods described herein, comprising producing activated CTLs specific for the epitope or original protein in vitro, and administering the activated CTLs in an amount sufficient to destroy the infected cells through direct lysis or to effect the destruction of the infected cells indirectly through the elaboration of cytokines.

According to some embodiments, the ex vivo generated activated CTLs can be used to identify and isolate the T cell receptor molecules specific for the peptide. The genes encoding the alpha and beta chains of the T cell receptor can be cloned into an expression vector system and transferred and expressed in naive T cells from peripheral blood, T cells from lymph nodes, or T lymphocyte progenitor cells from bone marrow. These T cells, which would then be expressing a peptide-specific T cell receptor, would then have anti-viral reactivity and could be used in adoptive therapy of infection, against multiple heterologous subtypes of virus.

In addition to their use for therapeutic or prophylactic purposes, the immunogenic peptides of the present disclosure are useful as screening and diagnostic agents. Thus, the immunogenic peptides of the present disclosure, together with modern techniques of CTL screening, make it possible to screen patients for the presence of T cells specific for these peptides as a test for viral infection, exposure and immune response. The results of such screening may help determine the efficacy of proceeding with the regimen of treatment disclosed herein using the immunogens of the present disclosure.

The therapeutically effective amount of a composition containing one or more of the immunogens of this disclosure is an amount sufficient to induce an effective CTL response to prevent, cure or arrest disease progression in a population. Thus, this dose will depend, among other things, on the identity of the immunogens used, the nature of the disease condition, the severity of the disease condition, the extent of any need to prevent such a condition where it has not already been detected, the manner of administration dictated by the situation requiring such administration, the weight and state of health of individuals receiving such administration, and the sound judgment of the clinician or researcher.

Pharmaceutical Compositions

Generally, vaccines are prepared as injectables, in the form of aqueous solutions or suspensions. Pharmaceutical carriers, diluents and excipients can be generally added that are compatible with the active ingredients and acceptable for pharmaceutical use.

While any suitable carrier known to those of ordinary skill in the art may be employed in the vaccine compositions of this disclosure, the type of carrier will vary depending on the mode of administration. Compositions of the present disclosure may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this disclosure. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. Modified hepatitis B core protein carrier systems are also suitable, such as those described in WO/99 40934, and references cited therein, all incorporated herein by reference. One may also employ a carrier comprising the particulate-protein complexes described in U.S. Pat. No. 5,928,647, which are capable of inducing a class I-restricted cytotoxic T lymphocyte response in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present disclosure may be formulated as a lyophilizate. Compounds may also be encapsulated within liposomes using well known technology.

Any of a variety of immunostimulants may optionally be employed in the vaccines of this disclosure. For example, an adjuvant may be included. Most adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. Exemplary adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants. Within the context of the HCMV-based and RhCMV-based vaccine vectors provided herein, the adjuvant composition is optional, but if included, is designed to induce an immune response predominantly of the $T_{H1}$ type. High levels of $T_{H1}$-type cytokines {e.g., IFN-γ, TNFα, IL-2 and IL-12) tend to favor the induction of cell mediated immune responses to an administered antigen. In contrast, high levels of $T_{H2}$-type cytokines {e.g., IL-4, IL-5, IL-6 and IL-10) tend to favor the induction of humoral immune responses. Following application of a vaccine as provided herein, a patient will support an immune response that includes $T_{H1}$- and $T_{H2}$-type responses. For example, in an embodiment in which a response is predominantly $T_{H1}$-type, the level of $T_{H1}$-type cytokines will increase to a greater extent than the level of $T_{H2}$-type cytokines. The levels of these cytokines may be readily assessed using standard assays. For a review of the families of cytokines, see Mosmann and Coffman, Ann. Rev. Immunol. 7:145-173, 1989.

According to some embodiments, adjuvants for use in eliciting a predominantly $T_{H1}$-type response are employed. Such adjuvants include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly $T_{H1}$ response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another exemplary adjuvant is a saponin, for example QS21 (Aquila Biopharaiaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other exemplary formulations comprise an oil-in-water emulsion and tocopherol. A particularly potent adjuvant formulation involving QS21, 3D-MPL and tocopherol in an oil-in-water emulsion is described in WO 95/17210. Other exemplary adjuvants include Montanide ISA 720 (Seppic, France), SAF (Chiron, California, United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties. Other exemplary adjuvants comprise polyoxyethylene ethers, such as those described in WO 99/52549 A1.

Any vaccine provided herein may be prepared using well known methods that result in a combination of vector, optional immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., Vaccine 74:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Regardless of the nature of the composition given, additional vaccine compositions may also accompany the immunogens of the present disclosure. Thus, for purposes of preventing or treating infection (e.g., prophylactic or therapeutic vaccine), compositions containing the immunogens disclosed herein may, in addition, contain other vaccine pharmaceuticals. The use of such compositions with multiple active ingredients is left to the discretion of the clinician.

According to some embodiments, the concentration of the immunogenic polypeptides of the disclosure in pharmaceutical formulations are subject to wide variation, including anywhere from less than 0.01% by weight to as much as 50% or more. Factors such as volume and viscosity of the resulting composition must also be considered. The solvents, or diluents, used for such compositions include water, dimethylsulfoxide, PBS (phosphate buffered saline), or saline itself, or other possible carriers or excipients.

According to some embodiments, the pharmaceutical compositions according to the present disclosure comprise about 1 nanogram to about 2000 micrograms of DNA. According to some preferred embodiments, pharmaceutical compositions according to the present disclosure comprise about 5 nanogram to about 1000 micrograms of DNA. According to some preferred embodiments, the pharmaceutical compositions contain about 10 nanograms to about 800 micrograms of DNA. According to some preferred embodiments, the pharmaceutical compositions contain about 0.1 to about 500 micrograms of DNA. According to some preferred embodiments, the pharmaceutical compositions contain about 1 to about 350 micrograms of DNA. According to some preferred embodiments, the pharmaceutical compositions contain about 25 to about 250 micrograms of DNA. According to some preferred embodiments, the pharmaceutical compositions contain about 100 to about 200 microgram DNA.

The peptides and polypeptides of the disclosure can also be added to professional antigen presenting cells such as dendritic cells that have been prepared ex vivo.

Administration

The immunogenic compositions according to the present disclosure may be used against an infectious agent by administration to an individual or to a population by a variety of routes. The composition may be administered parenterally or orally, and, if parenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time.

According to some embodiments, the disclosure provides a vaccine in which an immunogen of the present disclosure is delivered or administered in the form of a polynucleotide encoding a polypeptide or active fragment as disclosed herein, whereby the peptide or polypeptide or active fragment is produced in vivo. The polynucleotide may be included in a suitable expression vector and combined with a pharmaceutically acceptable carrier. A wide variety of vectors are available and apparent to those skilled in the art. Vaccinia vectors and methods useful in immunization protocols are described in U.S. Pat. No. 4,722,848, the disclosure of which is incorporated herein by reference in its entirety.

The compositions described herein can be administered prior to, concurrent with, or subsequent to delivery of other vaccines. Also, the site of administration may be the same or different as other vaccine compositions that are being administered.

Dosage treatment with the composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least impart, be determined by the potency of the modality, the vaccine delivery employed, the need of the subject and be dependent on the judgment of the practitioner.

In a specific embodiment of the disclosure, each injection contains a recombinant vaccine from a different vector source during the immunization of the vaccine described above.

Prime-Boost

According to some embodiments of the present disclosure, in the above vaccine immunization process, the vaccine is immunized with a "prime and boost" immunization strategy, and each recombinant vaccine is inoculated at least once. According to some embodiments, the disclosure relates to "prime and boost" immunization regimes in which the immune response induced by administration of a priming composition is boosted by administration of a boosting composition. For example, effective boosting can be achieved using subunit or protein vaccine, following priming with genetic or DNA plasmid vaccine. Some embodiments of the present disclosure employ a subunit or protein vaccine for providing a boost to an immune response primed to antigen using the genetic or DNA plasmid vaccine.

Use of embodiments of the present disclosure allows for a subunit or protein vaccine to boost an immune response primed by a DNA vaccine. Monovalent or other multivalent vaccines can also be used.

Advantageously, a vaccination regime using intramuscular immunization for both prime and boost can be employed, constituting a general immunization regime suitable for inducing an immune response, e.g., in humans.

Some embodiments of the present disclosure in various aspects and embodiments employ a subunit or protein vaccine for boosting an immune response to the antigen primed by previous administration of the nucleic acid encoding the antigen.

According to some embodiments, the present disclosure provides for the use of a subunit or protein vaccine for boosting an immune response to an antigen.

According to some embodiments, the present disclosure provides a method of inducing an immune response to an antigen in an individual, the method comprising administering to the individual a priming composition comprising the DNA vaccine encoding the antigen such as HA and then administering a boosting composition which comprises a subunit or protein vaccine.

According to some embodiments, the present disclosure provides for use of a genetic vaccine to prime and subunit or protein vaccine to boost.

The priming composition may comprise DNA encoding the antigen, such DNA for example being in the form of a circular plasmid that is not capable of replicating in mammalian cells. Any selectable marker should not be resistant to an antibiotic used clinically, so for example kanamycin resistance is preferred to ampicillin resistance. Antigen expression should be driven by a promoter which is active in mammalian cells, for instance the cytomegalovirus immediate early (CMV IE) promoter.

According to some embodiments of the present disclosure, administration of a priming composition is followed by boosting with first and second boosting compositions, the first and second boosting compositions being the same or different from one another, e.g., as exemplified below. Still further, boosting compositions may be employed without departing from some embodiments of the present disclosure.

Either or both of the priming and boosting compositions may include an adjuvant or cytokine, such as alpha-interferon, gamma-interferon, platelet-derived growth factor (PDGF), granulocyte macrophage-colony stimulating factor (gM-CSF) granulocyte-colony stimulating factor (gCSF), tumor necrosis factor (TNF), epidermal growth factor (EGF), IL-1, IL-2, IL-4, IL-6, IL-8, IL-10 and IL-12, or encoding nucleic acid therefor.

Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. According to some embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition.

Regardless of the nature of the composition given, additional vaccine compositions may also accompany the immunogens of the present disclosure. Thus, for purposes of preventing or treating viral infection (e.g., prophylactic or therapeutic vaccine), compositions containing the immunogens disclosed herein may, in addition, contain other vaccine pharmaceuticals. The use of such compositions with multiple active ingredients is left to the discretion of the clinician.

Subjects

According to some embodiments, a subject in need of treatment is a subject having or at risk of having an infection (e.g., a subject having or at risk of contracting a viral, bacterial, fungal or protozoal infection).

Viral infection during immunosuppression is a major complication in transplantation, rheumatologic, and other immune-deficient conditions (e.g., HIV). Accordingly, subjects that may be treated according to adoptive immunity-based embodiments of the present disclosure include immunocompromised subjects.

According to some embodiments, a "subject having an infection" is a subject that has been exposed to an infectious microorganism with acute or chronic detectable levels of the microorganism in his/her body or has signs and symptoms of the infectious microorganism. Methods of assessing and detecting infections in a subject are known by those of ordinary skill in the art. A "subject at risk of an infection" is a subject that may be expected to come in contact with an infectious microorganism. Examples of such subjects are medical workers or those traveling to parts of the world where the incidence of infection is high. According to some embodiments, the subject is at an elevated risk of an infection because the subject has one or more risk factors to have an infection. Examples of risk factors to have an infection include, for example, immunosuppression, immunocompromise, age, trauma, burns (e.g., thermal burns), surgery, foreign bodies, cancer, newborns especially newborns born prematurely. The degree of risk of an infection depends on the multitude and the severity or the magnitude of the risk factors that the subject has. Risk charts and prediction algorithms are available for assessing the risk of an infection in a subject based on the presence and severity of risk factors. Other methods of assessing the risk of an infection in a subject are known by those of ordinary skill in the art. According to some embodiments, the subject who is at an elevated risk of an infection may be an apparently healthy subject. An "apparently healthy subject" is a subject who has no signs or symptoms of disease.

According to some embodiments, factors other than age associated with the target population for vaccination are considered. These factors include, but are not limited to, comorbidities, geographic factors (including microbial endemicity), nutritional status, and iatrogenic immune suppression.

Kits

To facilitate use of the methods and compositions of the disclosure, any of the vaccine components and/or compositions, e.g., virus in various formulations, etc., and additional components, such as, buffer, cells, culture medium, useful for packaging for experimental or therapeutic vaccine purposes, can be packaged in the form of a kit. Typically, the kit contains, in addition to the above components, additional materials which can include, e.g., instructions for performing the methods of the disclosure, packaging material, and a container.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited. It is also to be understood that throughout this disclosure where the singular is used, the plural may be inferred and vice versa and use of either is not to be considered limiting.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Generation of Consensus Sequences for Conserved Proteins

Example 1A

By way of example only, the use of consensus sequences for conserved protein(s) can be attained through performing multiple sequence alignments from a prepared Pathogeneic Library of conserved sequences, and attaining consensus sequences identified thereof.

Pathogen Library Preparation

According to some embodiments, the Pathogen Library will contain a reference genome or conserved protein sequence, and similar genomic or conserved protein sequences.

The preparation of a DNA Library containing the reference genome or protein sequence can be generated through methods known in the art.

For example, reference genomic/protein sequences can be found as described herein. Briefly, databases such as the National Center of Biotechnology Information (NCBI) specifically, for example, NCBI's GenBank, EMBL's Nucleotide Sequence Database, Universal Protein Resource (UniProt), and Protein Data Bank (PDB), can be searched for the reference genome of the selected pathogen, and then can be filtered to specify coding gene sequences for expressed conserved proteins. Once at the NCBI database, "Genome" will be selected under the all databases drop down box. The targeted pathogen's species name will be entered into the search field and submitted. The reference genome option will be selected. Next, Gene option will be chosen under the Related Topics header. The results will then be filtered to produce Protein-coding sequences. Then, a custom filter will be created to filter for Gene records associated with gene records associated with protein sequence, with variation information, with homology data, and/or with proteins calculated to contain conserved domains. Alternatively, from the Genome Overview table, Protein Details may be selected to display conserved expressed proteins. Selection of each desired record will generate the identification number or sequence to be used in multiple sequence alignment.

Similar genomic or protein sequences can be generated through methods known in the art. For example, selection of "Other Genomes" under the Related Topics header on the reference Genome record for the pathogen under investigation will produce other related genomes for various different strains, variants, groups, clades, serotypes, and subtypes. Alternatively genomic and protein sequences for various different strains, variants, groups, clades, serotypes, and subtypes of the pathogen species can be attained from the Genome Assembly and Annotation Report from the reference Genome Record through the selection of the Organism or the Protein record.

Alternatively, a search for similar conserved protein sequences can be generated through algorithms known in the art, such as FASTA, ClustalW, HMMER, MMseqs2, and Basic Local Alignment Search Tool (BLAST) can be utilized to generate similar genomic or protein sequences. BLAST performs and scores sequence alignment to find similar nucleotide or protein sequences for a given query sequence. The search will be executed against a large database (typically the nr database) and the algorithm will also quantify statistical significance of the scored output matches.

The search will maximize a score that quantifies similarity between sequences, given a particular scoring matrix and gap penalty. The widely used scoring matrices are known in the art and include Point Accepted Mutation (PAM) matrices and BLOcks SUbstitution Matrices (BLOSUM). These matrices will quantify similarities between all pairs of amino acids, such that pairs of the same or similar amino acids have high scores while pairs of dissimilar amino acids are associated with low scores. The gap penalty is for gaps (openings) and will be inserted into one of the aligned sequences to maximize the similarity score. The gap penalty is larger for a new gap when compared to an extension of an already existing gap. BLAST can be parametrized to use different scoring matrices and gap penalties, resulting in different alignments for the same sequences. For example, parameters can restrict the maximal number of aligned (similar) target sequences and can set the maximal E-value. The E-value will quantify statistical significance of the similarity where lower value corresponds to more significant similarity. Parameter filters also include finding word matches between the query and database sequences where the use of smaller word sizes makes the search more sensitive. The "maximal matches in a query range" parameter limits the number of matches.

Once submitted, the search will produce similar proteins, the identification of conserved proteins can be filtered by selecting a limited identify match indicating the percent the found similar sequence matches with the reference sequence, for example by 50-100%, 70-100%, 80-100%, or 90-100%. The Pathogen Library can then be prepared by selecting the desired sequences or identification number, in plain text or in FASTA format.

Sequence Alignment

Once a library containing the sequences for the genome/protein reference and similar sequences thereof, the sequences will be aligned. For example, see Table 1 below.

TABLE 1

| Pathogen | Reference Genome RefSeq No. (Variant(s) Accession No(s).) | Example Conserved Proteins RefSeq No(s). (location) |
| --- | --- | --- |
| human immunodeficiency virus 1 (HIV-1) | NC_001802.1 (MN124512.1, MN187303.1, MN187302.1, MN187301.1, MN187300.1, MN202472.1, MN202471.1, MK984160.1, MK984159.1, MN090935.1, . . . ) | Env: NC_001802.1 (5771 . . . 8341); Gag: NC_001802.1 (336 . . . 1838); Gag-Pol: NC_001802.1 (336 . . . 4642); Nef: NC_001802.1 (8343 . . . 8963); Asp: NC_001802.1 (6919 . . . 7488); Vpu: NC_001802.1 (5608 . . . 5856); Rev: NC_001802.1 (5516 . . . 8199); Tat: NC_001802.1 (5377 . . . 7970); Vpr: NC_001802.1 (5105 . . . 5396); Vif: NC_001802.1 (4587 . . . 5165) |
| zika virus | NC_012532 (MN124091.1, MN124090.1, MN100039.1, MN025403.1, MK713748.1, MH882548.1, MH882547.1, MH882546.1, MH882545.1, MH882544.1, . . . ) | ancC: YP_009227206.1 C: YP_009227196.1 prM: YP_009227197.1 M: YP_009227208.1 E: YP_009227198.1 NS1: YP_009227199.1 NS2A: YP_009227200.1 NS2B: YP_009227201.1 NS3: YP_009227202.1 NS4A: YP_009227203.1 NS4B: YP_009227204.1 NS5 (polymerase): YP_009227205.1 |
| Measles morbillivirus | NC_001498 (MH631016.1, MH631015.1, MK161348.1, MK142916.1, MK142915.1, MK142914.1, LC420351.1, MH356255.1, MH356254.1, MH356253.1, . . . ) | V: YP_003873249.2 Large polymerase protein: NP_056924.1 HA: NP_056923.1 Fusion: NP_056922.1 Matrix: NP_056921.1 C: NP_056920.1 Phosphoprotein: NP_056919.1 Nucleocapsid protein: NP_056918.1 |
| rubella virus | NC_001545.2 (MK787191.1, MK787190.1, MK787189.1, MK787188.1, MK780812.1, MK780811.1, MK780810.1, MK780809.1, MK780808.1, MK780807.1, . . . ) | NP: NP_062883.2 P150(protease): YP_004617077.1 NTPase/Helicase & polymerase: YP_004617078.1 Structural protein: NP_062884.1 Capsid protein: NP_740662.1 E1: NP_740663.1 E2: NP_740664.1 |

TABLE 1-continued

| Pathogen | Reference Genome RefSeq No. (Variant(s) Accession No(s).) | Example Conserved Proteins RefSeq No(s). (location) |
| --- | --- | --- |
| influenza vims | NC_026422.1-NC_026428.1 | PB2: NC_026422.1<br>PB1: NC_026423.1<br>PB1-F2: NC_026423.1<br>PA: NC_026424.1<br>PA-X: NC_026424.1<br>HA: NC_026425.1<br>NP: NC_026426.1<br>NA: NC_026429.1<br>M1: NC_026427.1<br>M2: NC_026427.1<br>NSP1: NC_026428.1<br>NEP: NC_026428.1 |
| Ebola vims | NC_002549.1 (MK731994.1, MK731993.1. MK731992.1, MK731990.1. MK731989.1, MK731988.1, MK731987.1, MK731986.1, MK731985.1, MK088515.1, . . . ) | Polymerase: SCD11539.1, NP_066251.1, NP_066244.1<br>VP24: SCD11538.1<br>VP30: SCD11537.1<br>VP35: SCD11532.1<br>Matrix: SCD11533.1<br>Membrane: NP_066250.1<br>Matrix: NP_066245.1<br>Virion spike: SCD 11534.1<br>Spike glycoprotein: NP_066246.1<br>s(s)GP: SCD11536.1, SCD11535.1<br>minor nuclear protein: NP_066249.1 |
| variola vims | NC_001611.1 (BK010317.1, KY358055.1, DQ437592.1, DQ437591.1, DQ437590.1, DQ437589.1, DQ437588.1, DQ437587.1, DQ437586.1, DQ437585.1, . . . .) | IEV and EEV membrane protein: NC_001611.1 (134714 . . . 135220)<br>EEV membrane protein(B7R): NC_001611.1(157183 . . . 158136)<br>EEV mature protein (C16L): NC_001611.1(29746 . . . 31653, complement)<br>Major membrane protein (C9L): NC_001611.1<br>EEV membrane protein (C17L): NC_001611.1(31694 . . . 32812, complement)<br>Core protein (C21R): NC_001611.1(34561 . . . 34866)<br>IMV membrane protein (K2L): NC_001611.1 (51624 . . . 51845, complement),<br>IMV membrane protein (A20L): NC_001611.1 (118684 . . . 119037, complement)<br>dUTPase(C6L): NC_001611.1 (21874 . . . 22317, complement)<br>F6L: NC_001611.1 (87298 . . . 87738, complement)<br>C7L: NC_001611.1 (22403 . . . 22942, complement)<br>N1L: NC_001611.1 (51624 . . . 51845, complement) |

As described herein, there are multiple publicly available tools that align multiple sequences. ClustalOmega will be used to create multiple sequence alignments (MSAs). This is a procedure for aligning more than two homologous nucleotide or amino acid sequences together such that the homologous residues from the different sequences line up as much as possible in columns. Sequence alignment can be of two types i.e., comparing two (pair-wise) or more sequences (multiple) for a series of characters or patterns. The sequences will be aligned step-wise (first two sequences then one by one) by the program. When a sequence is aligned to a group or when there is alignment in between the two groups of sequences, the alignment is performed that had the highest alignment score. The gap symbols in the alignment will be replaced with a neutral character, such as an asterisk.

Consensus Sequence Identification

Consensus sequence(s) will be identified by analyzing the data and recognizing regions that are largely or entirely uniform across all of the sequences. The most conserved consensus sequences will be selected for epitope prediction.

By way of example only, consensus sequences for conserved protein(s) in the Retroviridae virus family, for example, the human immunodeficiency virus, are known in the prior art and can be found by researching databases such as GenBank®, DNA DataBank of Japan (DDBJ), or the European Nucleotide Archive (ENA) for the virus and resolving for consensus sequences from the sequences provided for each virus variant therein. For example, the genome for Human Immunodeficiency Virus and serotypes thereof have been mapped and submitted to GenBank. A search of the genome database of the National Center for Biotechnology Information (NCBI) provides representative genome information for example, for HIV-1. The main page provides the record of each mRNA, and protein sequence encoded by the genome, and significantly, recorded will be the conserved protein sequences such as those listed in Table 1 above.

Selection of the list for all reference or representative genomes for the species (499 at the time of this submission) or the Genome Assembly and Annotation Report displays all genome variants and a list of either a GenBank Accession Number or RefSeq Accession Number for each genome variant (Assembly column).

Selection of a first GenBank Accession Number will display the record of each mRNA, and protein sequence encoded by the first genome variant. Selection of a second GenBank Accession Number will display the record of each mRNA, and protein sequence encoded by the second genome variant. Selection of the entire genome variant or protein sequence variant can be repeated until all or all desired variants are found.

Next sequence alignment of the genome or protein sequence variants can be found by inputting all variants into any publicly available software that contains sequence alignment database with the ability to align multiple sequences, such as ClustalW2. Importation in the sequences with the selection of DNA as the sequence type will produce the alignment of the sequence that displays any homology across the variants with an asterisk.

Next, identification of regions that are largely or entirely uniform across all of the variants will provide consensus sequence identity. If any single nucleotide polymorphisms exist, then point mutations can be replaced with appropriate IUB Wobble base code which can be retrieved from the Bioinformatics website.

Alternatively, tools such as Galaxy may be used, found at usegalaxy.org, and upon data download and selection of appropriate filters, consensus sequences may be attained.

In another alternative, virus specific sequence databases exist, for example, for HIV-1 which can be retrieved from the HIV Sequence Database website. Consensus sequences can be attained by the selection of the appropriate download format, computer type, region, and aligned proteins options. In this case, the input alignments are the HIV Sequence Database Web Alignments retrieved from the HIV Sequence Database website. These sequences have undergone additional annotation after retrieval. Specifically, question marks in consensus sequences have been resolved, and glycosylation sites have been aligned. From the input, consensus sequences were built using the consensus website. The consensus sequences were calculated according to the default values on the consensus website except that they were computed for all subtype groups having 3 or more (rather than 4 or more) sequences in the alignment. If a column in a subtype group contained equal numbers of two different letters, the tie was resolved by looking at the same column throughout the M group and using the most common letter as the consensus. An upper case letter in a DNA consensus sequence indicates that the nucleotide is preserved unanimously in that position in all sequences used to make the consensus. In cases of nonunanimity the most common nucleotide is shown in lowercase. Regions spanned by multiple insertions and deletions are difficult to align. Accordingly, alignments are anchored in such regions on glycosylation sites, and to preserve the minimal elements which span such regions. Protein consensus sequences are always upper case letters indicating most common amino acid at that position.

Example 1B

There are multiple publicly available databanks to derive protein, DNA, and/or RNA sequences, for example, NCBI's GenBank, EMBL's Nucleotide Sequence Database, Universal Protein Resource (UniProt;), and Protein Data Bank (PDB).

Pathogen Library Preparation

The preparation of a DNA Library containing the reference genome or protein and similar sequences of known conserved proteins can be generated through methods known in the art. For example, NCBI was searched for the "influenza A virus", and the reference genome "Influenza A virus (A/Shanghai/02/2013(H7N9))" (RefSeq No. NC_026422.1) was selected; protein sequences or identification number for the conserved proteins were selected thereof.

The protein sequences for a second reference genome will also be selected to obtain multiple sequence alignments where NCBI was searched for the reference genome "Influenza A virus (A/Puerto Rico/8/1934(H1N1))" (RefSeq Accession No. NC_002018).

TABLE 2

| Locus/Protein | Influenza A virus (A/Shanghai/02/2013(H7N9)) Protein Accession No. | Influenza A virus (A/Puerto Rico/8/1934(H1N1)) Protein Accession No. |
|---|---|---|
| NA/neuraminidase | NC_026429.1 | NC_002018.1 |
| M1/matrix protein 1 | NC_026427.1 | NC_002016.1 |
| M2/matrix protein 2 | NC_026427.1 | NC_002016.1 |
| NP/nucleoprotein | NC_026426.1 | NC_002019.1 |
| HA/haemagglutinin | NC_026425.1 | NC_002017.1 |
| NEP/nonstructural protein 2 | NC_026428.1 | NC_002020.1 |
| NS1/non structural protein 1 | NC_026428.1 | NC_002020.1 |
| PB1/polymerase protein 1 | NC_026423.1 | NC_002021.1 |
| PB1-F2/PB1-F2 protein | NC_026423.1 | NC_002021.1 |
| PB2/polymerase PB2 | NC_026422.1 | NC_002023.1 |
| PA-X/PA-X protein | NC_026424.1 | NC_002022.1 |
| PA/PA-polymerase | NC_026424.1 | NC_002022.1 |

Alternatively, BLASTP, which is a generic purpose protein sequence alignment program that compares a query protein sequence to sequences in a specific protein database, will be searched for consensus sequences similar to the selected conserved proteins. In the "Enter Query Sequence" box, the selected protein reference sequence(s) will be inputted (either directly in the text box or uploaded via a file). The sequence(s) will be provided either in the FASTA format or the query protein will be identified with either accession number or NCBI gi number as found in the NCBI databases. In the "Choose Search Set" box the target organism (pathogen) will be selected (databases are currently available includenr, RefSeq, PDB, and SWISS-PROT). The "Program Selection" box will be ensured to select BLASTP. The BLAST parameters will be set to the pre-selected default parameters. The default value for the maximal number of aligned target sequences will be used (value=100). The default E-value is 10, which means that about 10 of the similar sequences are expected to be found by chance. The default word size for proteins will be used (value=6). The "maximal matches in a query range" parameter will be set to the default value of 0, which means that there is no limit. The default scoring matrix and default set up of gap penalties will be used as BLOSUM62 and 11 for opening the gap and 1 for the extension of the gap. Once submitted, similar sequences or identification numbers for conserved protein(s) will be searched and generated, upon which the DNA library will be prepared.

Sequence Alignment

Sequences to be aligned will be inputted either directly into the text box or uploaded as a file. Sequences will either be inputted in plain text or in FASTA format. ClustalW2 will be run and a graphical representation of regions that have uniformity across the sequences will be produced.

Consensus Sequence Identification

Consensus sequence(s) will be identified by analyzing the data and recognizing regions that are largely or entirely uniform across all of the sequences. The most conserved consensus sequences will be selected for epitope prediction.

Example 2: Epitope Prediction

T cell epitopes for pathogens can be predicted through the use of a number of publicly available databases. Immune Epitope Database and Analysis Resource (IEDB) which will utilize SYFPEITHI (found at http://syfpeithi.de/BMI-AInfos.html) to predict T-cell epitopes.

MHC Class I Binding Prediction Generation

To perform class I binding predictions, the at least one consensus sequence(s) for a given conserved protein will be inputted (sequences will be inputted in as plain text, separating the sequences with blanks, in FASTA format, or by specifying a file containing the proteins) into IEDB. Consensus method(s) of search will be chosen. MHC species as a human will be specified with the selected option of comprising multiple alleles and epitope lengths (e.g., 9, 10, 11, 12, 13, 14).

Binding Affinity Threshold Calibration

To ensure the quality of the data for binding affinity, searches will be calibrated to predict peptides bind with an IC50 value less than 500 nM, an established threshold associated with immunogenicity for 80-90% of all epitopes.

Once the search is submitted, the protein sequence will be parsed into all possible peptides for the specified length and the predicted binding affinity for each will be calculated. The tool will compare the predicted affinity to that of a large set of randomly selected peptides and assigns a percentile rank (lower percentile rank corresponds to higher binding affinity). The prediction tool will produce a table of results including columns for the allele, peptide start and end positions, the peptide length, the peptide sequence, the method(s) used, and the percentile rank. Results will be presented by default sorted by predicted percentile rank, but results can also be sorted by sequence position.

Epitope Selection

The top 1% of peptides will be selected for each allele/length combination.

Example 3

The following examples were carried out with, but not limited to, the following materials and methods.

Immunogen Sequence Design and Optimization

Consensus amino acid sequences were deduced from approximately 40,000 strains of influenza A virus available in Genbank database. Briefly, the amino acid sequences of M1, M2, NP, PB1, PB2, and PA proteins of about 40,000 strains of influenza virus were calculated and analyzed. The amino acid having the highest frequency of occurrence at each position of the amino acid sequence was used as the consensus amino acid at that site. The protein sequence constitutes the shared amino acid of each site, thereby obtaining the consensus amino acid sequence of the M1, M2, NP, PB1, PB2, and PA proteins.

The consensus amino acid sequences of PB1, PB2 and PA obtained as described above were analyzed using the online CD8+ T cell epitope prediction software (available online at syfpeithi.de/ (Singh H, Raghava G P. ProPredl: prediction of promiscuous MHC Class-I binding sites. Bioinformatics. 2003; 19: 1009-1014) and tools.immuneepitope.org/main/tcell/ (Moutaftsi M, et al. A consensus epitope prediction approach identifies the breadth of murine T (CD8+)-cell responses to vaccinia virus. Nat Biotechnol. 2006; 24: 817-819). The sequences were modified following optimized mammalian codon usage.

Vaccine Construction

Two concatenated immunogen sequences were generated. One, called PAPB1M1 (SEQ ID NO: 1) was composed of partial PA and PB1 sequences and full length M1 sequence. The other, called NPPB2M2 (SEQ ID NO: 2) was composed of partial PB2 sequence and full length of NP and M2 sequences. The two immunogen sequences were cloned into three types of vectors for vaccine construction. For the DNA vaccine, pSV1.0 vector was used as the backbone vector. For adenovirus-based vaccine, the immunogen sequences were first cloned into p-Shuttle vector and subsequently subcloned into the E1/E3 deleted AdC68 vector. The resulting vectors were named as AdC68-SEQ ID NO:1 and AdC68-SEQ ID NO:2, respectively. AdC68-SEQ ID NO:1 and AdC68-SEQ ID NO:2 were linearized and transfected into HEK293 cells to generate adenoviruses which were purified from the supernatant by CsCl gradient centrifugation followed by determination of virus particle number by UV absorbance. For TTV vaccinia-based vaccines, the peptide p2a was used to link the immunogens SEQ ID NO:1 and SEQ ID NO:2, and cloned into pSC65 shuffle vector and transfected into TK143 cells (referred to herein as TTV-SEQ ID NO: 1/2). The transfected cells were subsequently infected with recombinant wild-type Tiantan virus followed by BrdU screening, yielding recombinant virus which was amplified using Vero cells.

Validation of Vaccines in Immunogen Expression

The DNA-based vaccine vectors were transfected into HEK293 cells. The AdC68-based and TTV vaccinia-based virus vaccines were used to infect HEK293 cells and Vero cells respectively. The transfected or infected cells were harvested 24 hours or 48 hours later. Western blot was used to analyze the expression of vaccine-encoded immunogens, using anti-M1 monoclonal antibody (abcam, ab22396) or anti-M2 monoclonal antibody (Santa Cruz, sc-52026).

The specific steps of western blotting assay to detect the expression of anti-influenza vaccine immunogens were as follows:

Preparation of Experimental Samples pSV1.0-SEQ ID NO:1 and pSV1.0-SEQ ID NO:2 were transfected into 293T cells (purchased from the Cell Resource Center of Shanghai Institutes for Biological Sciences, Chinese Academy of Sciences), and 293T cells were collected 48 hours later. The cells were resuspended in 75 μl of cell lysate, and added 25 μl of protein loading buffer, then incubated at 100° C. for 10 minutes.

293A cells were infected with AdC68-SEQ ID NO:1 and AdC68-SEQ ID NO:2 and were collected 24 hours later. The cells were resuspended in 75 μl of cell lysate, and added 25 μl of protein loading buffer, then incubated at 100° C. for 10 minutes.

TK143 cells were infected with TTV-SEQ ID NO: 1/2 and were collected 48 hours later. The cells were resuspended in 75 μl of cell lysate, and added 25 μl of protein loading buffer, then incubated at 100° C. for 10 minutes.

(2) Western blotting experiments were performed with 8% polyacrylamide separation gel. After standing at room temperature for 30 minutes, 10% polyacrylamide concentrated gel was added, and the comb was gently inserted into the gel, allowing 30 minutes for the gel to solidify. Pour the electrophoresis buffer, slowly remove the comb, then add the prepared sample in order. The electrophoresis was performed at 70 volts for 30 minutes, then voltage was adjusted to 90 volts and continued for 1.5 hours. After the polyvinylidene fluoride (PVDF) membrane was activated in methanol for 30 seconds, the sponge, filter paper and PVDF membrane were soaked in the protein transfer liquid, and then put in the order. The transfer device and the ice bag were placed in the transfer tank. The transfer process was maintained at constant flow 200 mA for 2.5 hours. After protein transferring, the membrane was taken out and blocked with 5% skim milk for 1 hour. The influenza matrix protein 1 antibody (purchased from Shanghai Aibo Kang Trading Co., Ltd.) and the influenza matrix protein 2 antibody (from Santa Cruz Biotechnology (Shanghai) Co., Ltd.), was added at 1:1000 and 1:250, respectively. After incubation with primary antibodies for 2 hours at room temperature on a shaker, the membrane was washed with phosphate buffer containing Tween-20 for 3 times at 5 minutes each time. Horseradish peroxidase-labeled goat anti-mouse IgG secondary antibody was added to the membrane at 1:5000 and incubated for 1 hour at room temperature. After incubation, the membrane was washed 5 times, for 5 minutes each wash. Luminescence was detected after incubated with substrate solution.

DNA Vaccine Prime-Viral Vector Boost Strategies in Mouse Model by Intramuscular Immunization 6-8 week-old female C57BL/6 mice were purchased from the B&K Universal Group Limited (Shanghai, China) and housed under specific pathogen-free (SPF) conditions at the animal facilities of Shanghai Public Health Clinical Center, Fudan University (Shanghai, China). Mice were divided into two control groups and two experimental groups. Mice were immunized intramuscularly with indicated vector combinations. For the two experimental groups, (1) DNA+AdC68 group and (2) DNA+ TTV group, the animals received two doses of pSV1.0-PAPB1M1 (50 μg) and pSV1.0-NPPB2M2 (50 μg) as prime and two weeks later AdC68-PAPB1M1 ($5 \times 10^{10}$ vp)/AdC68-NPPB2M2 ($5 \times 10^{10}$ vp) or TTV-2a ($1 \times 10^7$ pfu) as boost respectively. For the two control groups, either only the priming vector was substituted by empty vector, or both the priming and boosting vectors were replaced with empty vectors. Four weeks after vaccination, three mice from each group were sacrificed for immunogenicity evaluation using IFN-γ ELISpot assay and intracellular staining of cytokines.

Combinatorial Immunizations of DNA, AdC68 and TTV Vaccines with AdC68 Administered Via Either Intramuscular or Intranasal Route 6-8 week-old female C57BL/6 mice were divided into five groups. The control group was the same as described as above; the four experimental groups were immunized with different sequence of the three types of vaccines with AdC68 vaccine administered via either intramuscular (i.m.) or intranasal (i.n.) routes. The group name denoted the sequential order with vaccine type being followed by route (intranasal route was abbreviated as "i.n." and the default intramuscular route was left undenoted). Four weeks after vaccination, three mice in each group were sacrificed for immunogenicity evaluation using IFN-γ ELISpot assay and intracellular staining of cytokines.

IFN-γ ELISpot Assay

Enzyme-linked immunosorbent spot (ELISpot) assays were conducted using mouse IFN-γ ELISpot kit (BD Bioscience, Cat #551083). Control or vaccinated mice were sacrificed and bronchoalveolar lavage cells and splenocytes were isolated. $2 \times 10^5$ splenocytes were plated in triplicate in 96-well plates pre-coated with 5 μg/ml of purified anti-mouse IFN-γ and subsequently stimulated with a peptide specific for one of the six viral immunogens (M2, M1, NP, PA, PB1, PB2) at a final 5 μg/ml concentration [Table 1]. A total of sixteen peptides were used with one for M2 and three each for the rest five immunogens. After 24 hours of stimulation, the cells were washed with deionized water and exposed to 100 μl biotinylated anti-mouse IFN-γ (2 μg/ml) for 2 hours at room temperature, followed by extensive washing prior to the addition of 100 μl Streptavidin-HRP. After 1 hour incubation at room temperature, the cells were washed and 100 μl of substrate solution was added to develop spots. The reaction was stopped with water and the number of spot forming cells (SFCs) was determined using an automated ELISPOT software (Saizhi, Beijing, China).

Intracellular Staining of Cytokines

Splenocytes were prepared as described above. $2 \times 10^6$ splenocytes were stimulated for 1 hour with a peptide pool consisting of equal amount of all the sixteen peptides described above in the presence of anti-mouse CD107α-PE (BioLegend) antibody, followed by exposure to 1 μl/ml Brefeldin (BD Bioscience) for 6 hours. The cells were then washed, and stained with the surface-specific mouse antibodies, LIVE/DEAD-AmyCan, CD3-PerCP-cy5.5, CD8-PB (BioLegend). Cells were subsequently permeabilized using the BD Cytofix/Cytoperm Kit and stained for the intracellular cytokines by FITC anti-mouse IFN-γ antibody and PECy7 anti-mouse TNFa antibody (BioLegend). Samples were measured using Fortessa Flow cytometer (BD Bioscience), and the data were analyzed with FlowJo 10.0.6 software (Tree Star).

Infectious Challenge with Influenza a Viruses

Four weeks after vaccination, mice were challenged with either influenza A/PR8(H1N1) virus or influenza A/Shanghai/4664T/2013(H7N9) virus. The body weights and survival rates were monitored for fourteen days after challenge; five mice in each group were sacrificed on the fifth day post challenge to determine viral titers and assess pathological changes in the lungs. During the whole process of challenge, half mice in control and two intranasal groups were exposed ad libitum to drinking water containing dissolved FTY720 at a concentration of 2 µl/ml. All experiments related to the H7N9 virus were conducted in a biosafety level 3 laboratory following the standard operation protocols approved by the Institutional Biosafety Committee at Shanghai Public Health Clinical Center, Fudan University.

Determination of Lung Viral Loads

Total RNA was extracted from lung tissues and subjected to TaqMan real-time reverse transcription-PCR (RT-PCR) using influenza virus-specific primers for determination of relative levels of viral loads. For normalization, glyceraldehyde phosphate dehydrogenase (GAPDH) was used as the reference gene. The thermocycling conditions used were as follows: 42° C. for 10 min, 95° C. for 1 min, 45 cycles of 95° C. for 15 s and 60° C. for 45 s (Keskin D B, et al. Proc Natl Acad Sci US A. 2015; 112(7): 2151-2156). Data was analyzed using the REALPLE32.2 software (Eppendorf). The sequences of the primers were as follows:

For H7N9 virus detection:

```
                                            (SEQ ID NO: 3)
    F-5'-GAAGAGGCAATGCAAAATAGAATACA-3', (SEQ ID NO: 4)
    R-5'-CCCGAAGCT AAACCARAGT ATCA-3', (SEQ ID NO: 5)
    Probe-5'-CCAGTCAAACTAAGCAGYGGCTACAAA-3';
```

For PR8 virus detection:

```
                                            (SEQ ID NO: 6)
    F-5'-GACCGATCCTGTCACCTCTGA-3', (SEQ ID NO: 7)
    R-5'-AGGGCATTCTGGACAAAGCGTCTA-3';

(SEQ ID NO: 8)
    Probe-5'-TGCAGTCCTCGCTCACTGGGCACG-3';
```

For GAPDH reference detection:

```
                                            (SEQ ID NO: 9)
    F-5'-CAATGTGTCCGTCGTGGATCT-3', (SEQ ID NO: 10)
    R-5'-GTCCTCAGTGT AGCCCAAGA TG-3', (SEQ ID NO: 11)
    Probe-5'-CGTGCCGCCTGGAGAAACCTGCC-3'.
```

Statistical Analysis

All statistical analyses were performed using GraphPad Prism 6.0 (GraphPad Software, Inc). Comparisons between two groups were analyzed by either t test or Mann-Whitney test. Comparisons among three or more groups were analyzed by One-way ANOVA. Significant difference was defined as $p<0.05$.

Example 4. Construction of Influenza Internal Gene Based Vaccines

A universal influenza vaccine was designed to contain conserved CD8+ T cell epitopes of viral internal antigens. The consensus amino acid sequences of influenza M1, M2, NP, PA, PB1, PB2 immunogens were deduced from approximately 40,000 strains of influenza A virus available in the Genebank database. To be more efficient in immunogen design, only sequences enriched with CD8+ T cell epitopes in PA, PB1 and PB2 were included, based on online prediction tools found at syfpeithi.de/ (score≥:29) and at tools.immuneepitope.org/main/tcell/ (percentile rank≤0.1). Consequently, two immunogen sequences were generated. One, denoted as PAPB1M1 immunogen (SEQ ID NO: 1), comprises full length M1 sequence and the selected PA and PB1 sequences; the other, denoted as PB2NPM2 immunogen (SEQ ID NO: 2) comprises the selected PB2 segment and full-length NP, M2 sequences (FIG. 1A).

Vaccines were constructed to express the two immunogens in three platforms including DNA vector, E1/E3-deleted replication-deficient chimpanzee Adenovirus (AdC68), and recombinant Tiantan vaccinia virus (TTV). For the first two platforms, two immunogens were expressed separately, resulting in two DNA-based vaccines (pSV1.0-PAPBIM1 (SEQ ID NO:1) and pSV1.0-PB2NPM2 (SEQ ID NO:2)) and two AdC68-based vaccines (AdC68-PAPB1M1 (SEQ ID NO:1) and AdC68-PB2NPM2 (SEQ ID NO:2)); for TTV platform, two immunogens were expressed from a single vaccinia vaccine, namely TTV-2α. The resulting vaccines were introduced into cultured cells by either transfection or infection, and their expressions of encoded immunogens in the cell lysates was determined by western blotting using monoclonal antibodies specific for influenza A M1 or M2 antigen.

Figure 1B:
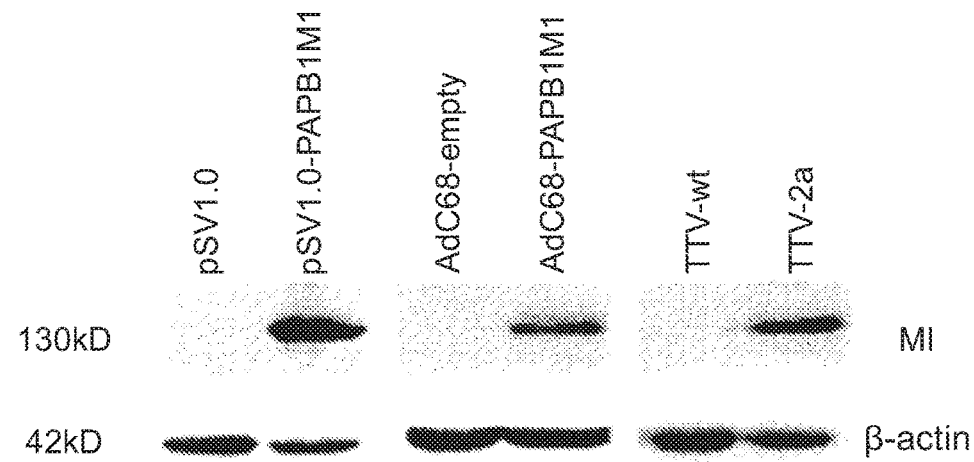
Figure 1C:
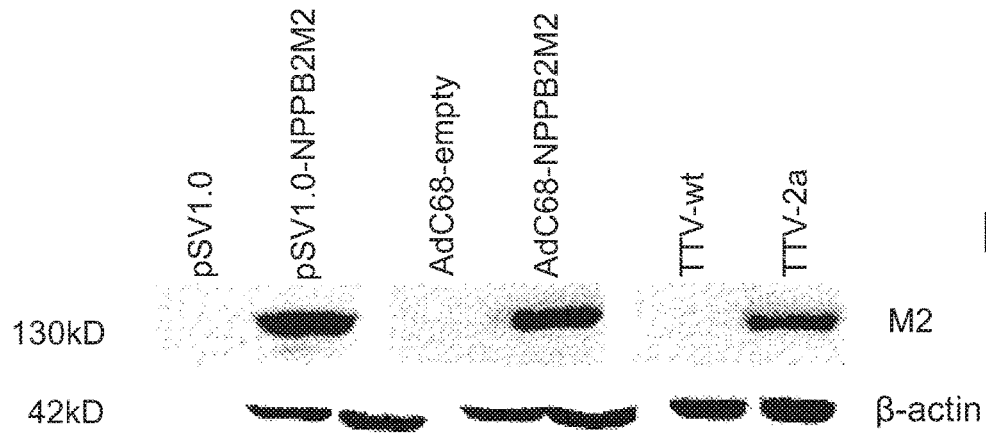

The results of the western blotting assay for immunogen expression is shown in FIG. 1B and FIG. 1C. The DNA vector pSV1.0, the adenoviral vector AdC68 and the vaccinia vector TTV all efficiently expressed the immunogen PAPBIM1 (SEQ ID NO: 1). After incubation with the influenza matrix protein 1 antibody, no specific bands were found in the empty vectors pSV1.0, AdC68, and TTV which did not contain the sequence of the immunogen SEQ ID NO: 1, while a significant ~130 kD band was found in the vectors containing the sequence of immunogen SEQ ID NO: 1, demonstrating the DNA vector pSV1.0, the adenoviral vector AdC68 and the vaccinia vector TTV can effectively express the immunogen SEQ ID NO: 1. After incubation with the influenza matrix protein 2 antibody no specific bands were found in the empty vectors pSV1.0, AdC68, and TTV which did not contain the sequence of the immunogen PB2NPM2 (SEQ ID NO: 2), while a significant ~130 kD band was found in the vectors containing the sequence of immunogen SEQ ID NO: 2, demonstrating the DNA vector pSV1.0, the adenoviral vector AdC68 and the vaccinia vector TTV can effectively express the immunogen SEQ ID NO: 2. After incubation with the β-actin antibody, a significant band with a protein size of ~42 kD was observed, which further proves that the steps of the experiment are accurate, and the results are reliable.

Example 5. Vaccine Immunogenicity Detection Based on Anti-Influenza Vaccine Immunogen A DNA vector vaccine, an adenoviral vector vaccine, and a vaccinia vector vaccine were constructed using the immunogen in the present disclosure as described in Example 1. The mice were immunized with the recombinant influenza vaccine, and the immunogenicity evaluation of the recombinant influenza vaccine was performed four weeks after the completion of the immunization.

Six-week-old C57BL/6 mice were randomly divided into three groups: control group, adenovirus group and vaccinia group. The specific immunization procedure is shown in Table 3, below. Immunization was by intramuscular injection, with a dose of pSV1.0 100 µg, a dose of AdC68 $10^{11}$ virus particles, pSV1.0-SEQ ID NO:1 and pSV1.0-SEQ ID NO:2 inoculation dose 50 μg each, AdC68-SEQ ID NO: 1 and AdC68-SEQ ID NO: 2 inoculation dose $5\times10^{10}$ virus particles each, and TTV-SEQ ID NO: 1/2 inoculation dose $10^7$ of plaque forming units. The vaccine was inoculated once every two weeks.

TABLE 3

Mouse experiments based on anti-influenza vaccine immunogen

| Group/week | Week 0 | Week 2 | Week 4 |
|---|---|---|---|
| Control group | pSV1.0 | pSV1.0 | AdC68 |
| Adenovirus group | pSV1.0-SEQ ID No.: 1<br>pSV1.0-SEQ ID No.: 2 | pSV1.0-SEQ ID No.: 1<br>pSV1.0-SEQ ID No.: 2 | AdC68-SEQ ID No.: 1<br>AdC68-SEQ ID No.: 2 |
| Vaccinia group | pSV1.0-SEQ ID No.: 1<br>pSV1.0-SEQ ID No.: 2 | pSV1.0-SEQ ID No.: 1<br>pSV1.0-SEQ ID No.: 2 | TTV-SEQ ID No.: 1/2 |

ELISpot and intracellular staining of cytokines (ICS) were used to detect the immunogenicity of recombinant influenza vaccine in the spleen cells of mice.

Based on epitope predictions for SEQ ID NO:1 and SEQ ID NO:2, and reported commonly used influenza T cell epitopes, 16 epitope single peptides were selected for stimulation of mouse T cell immune responses, named as: M1-1, M1-2, M1-3, M2, NP-1, NP-2, NP-3, PB1-1, PB1-2, PB1-3, PB2-1, PB2-2, PB2-3, PA-1, PA-2, PA-3 respectively.

Figure 9B:
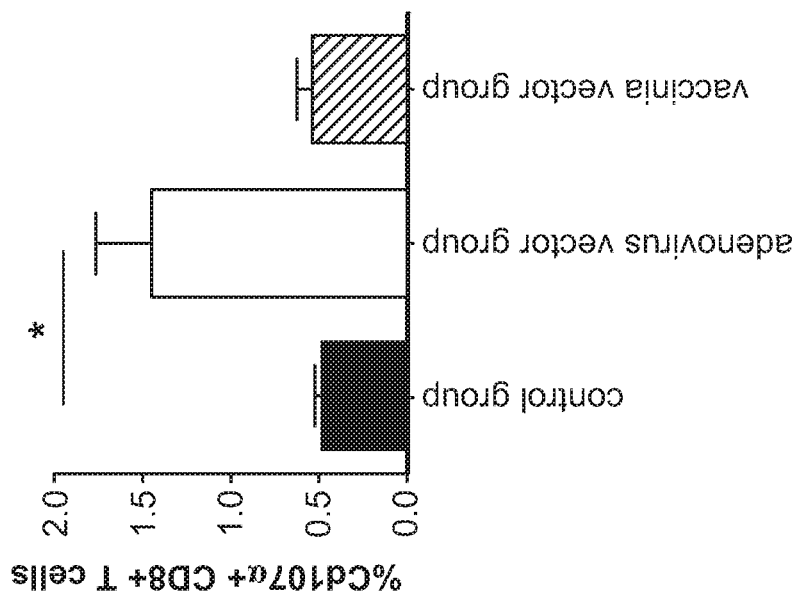
Figure 9C:
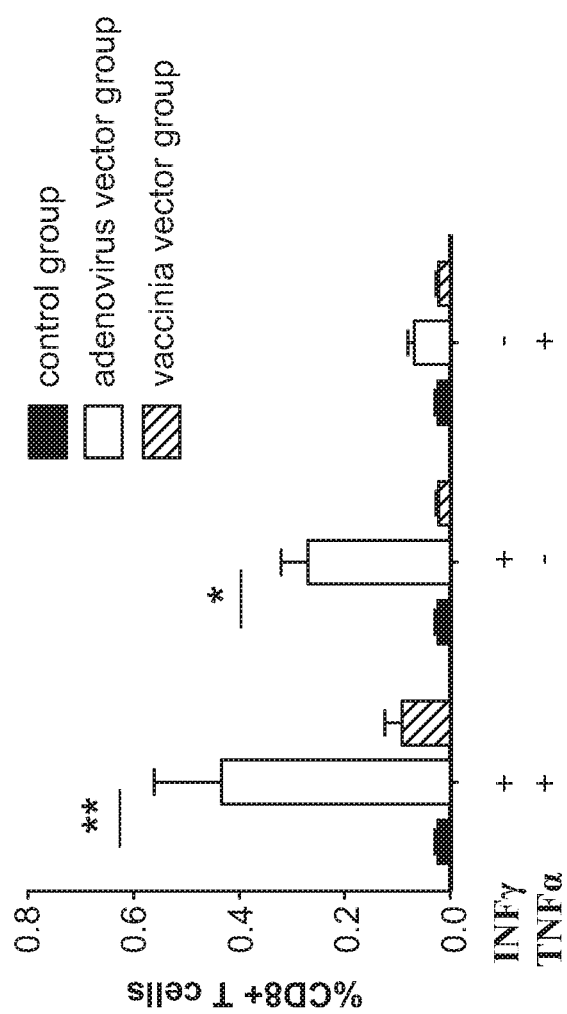
Figure 10A:
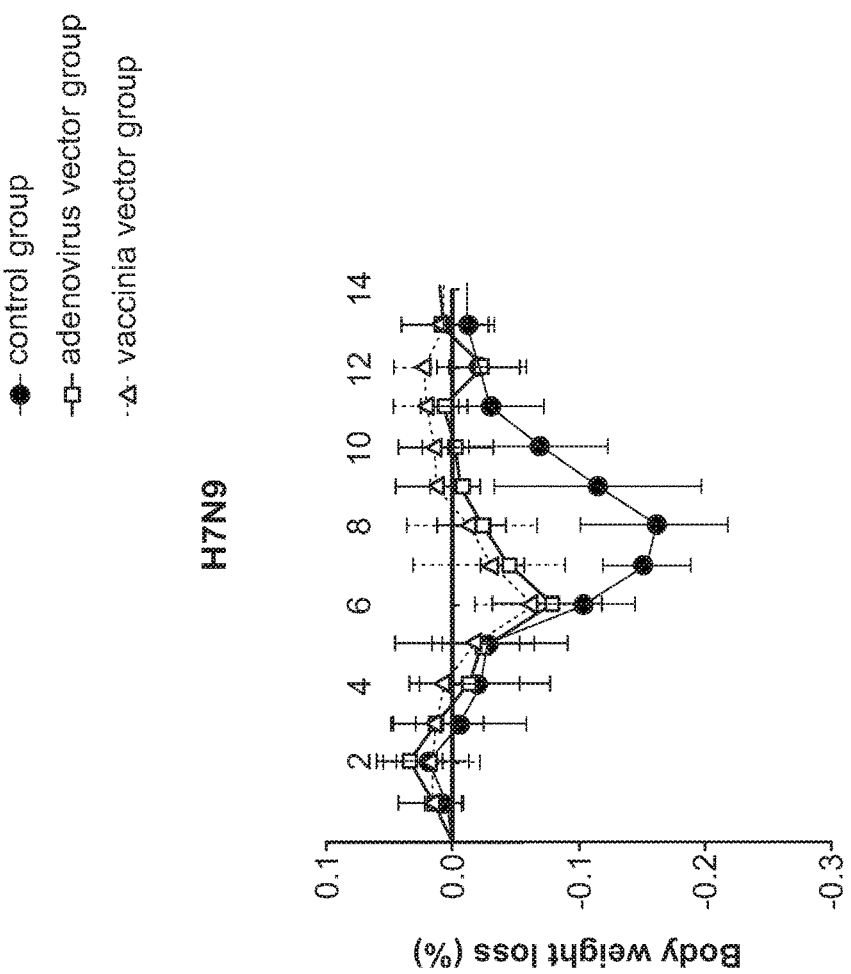
FIG. 10A-FIG. OF show the evaluation of the protective effects against H1N1 and H7N9 influenza viruses based on immunogens.
Figure 10B:
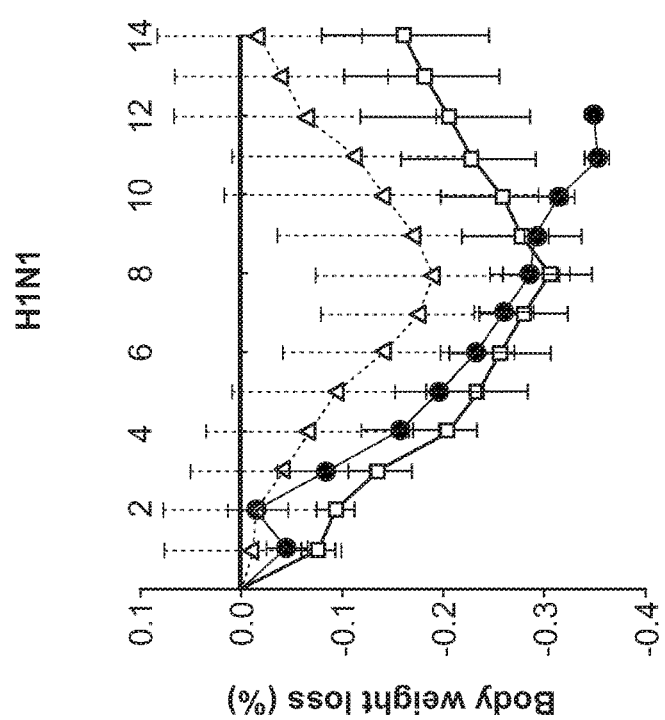
Figure 10E:
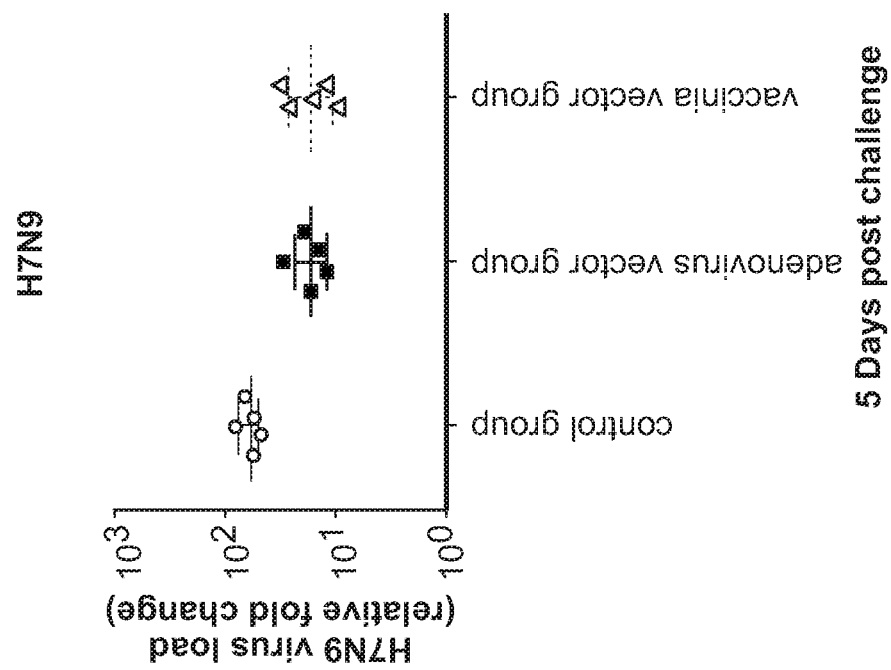
FIG. 10E and FIG. 10F show the detection of the viral load in the lungs of mice on the 5th day after infection. After infection with the H1N1 and H7N9 influenza viruses, the lung viral load of the adenovirus group and the vaccinia group was lower than that of the control group.
Figure 10F:
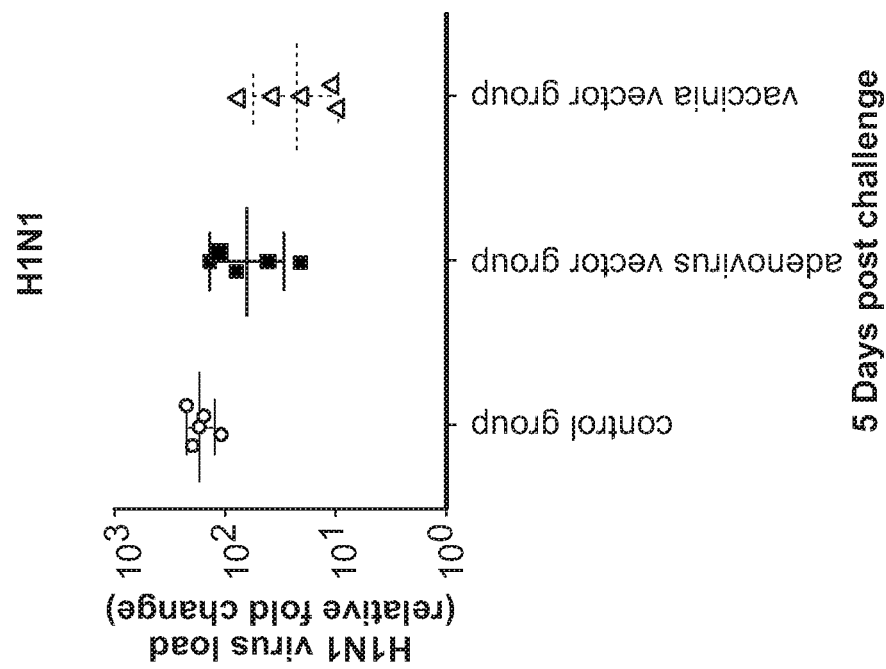
Figure 11A:
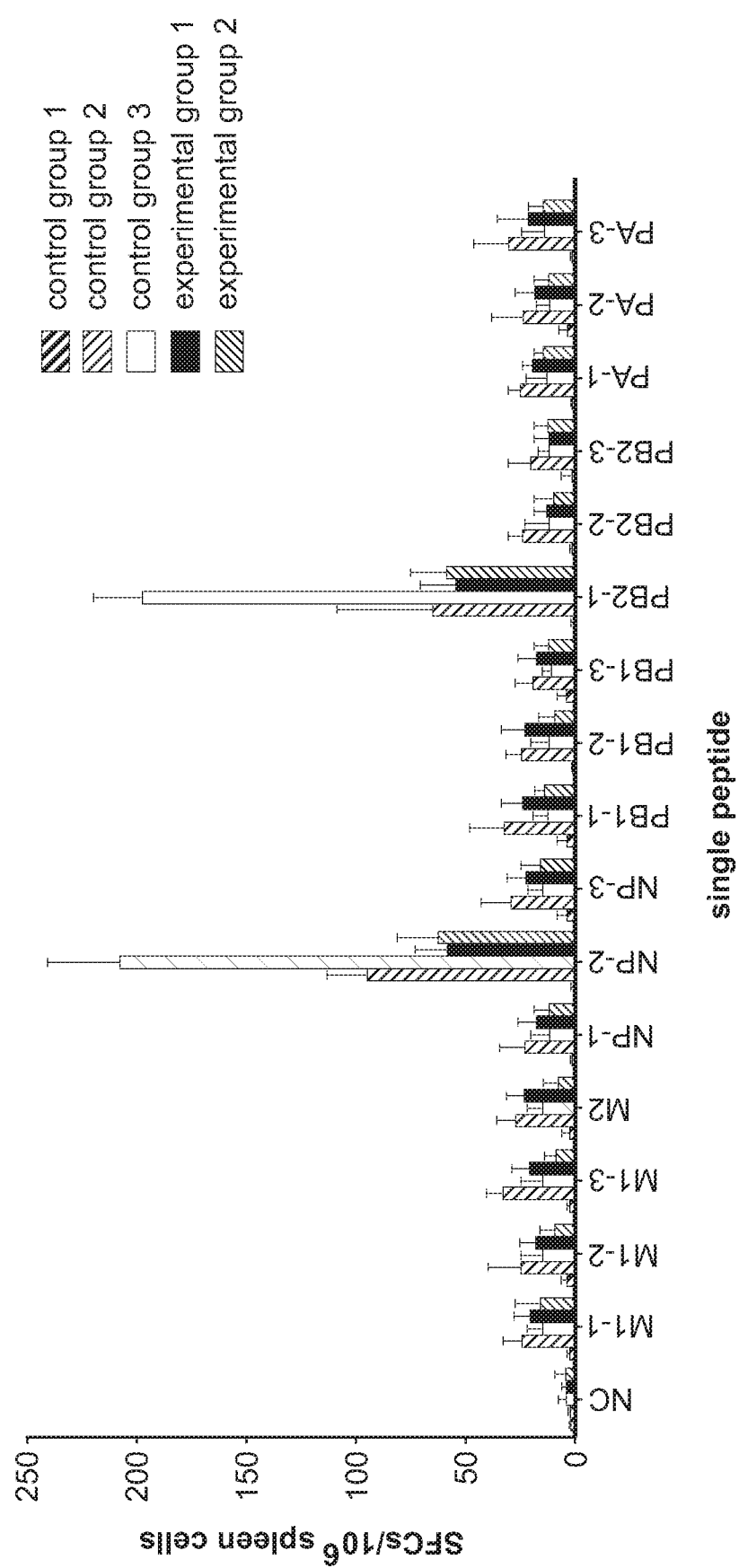
FIG. 11A-FIG. 11D show the detection of influenza-specific T cell immune responses induced by different immunization methods.
Figure 11B:
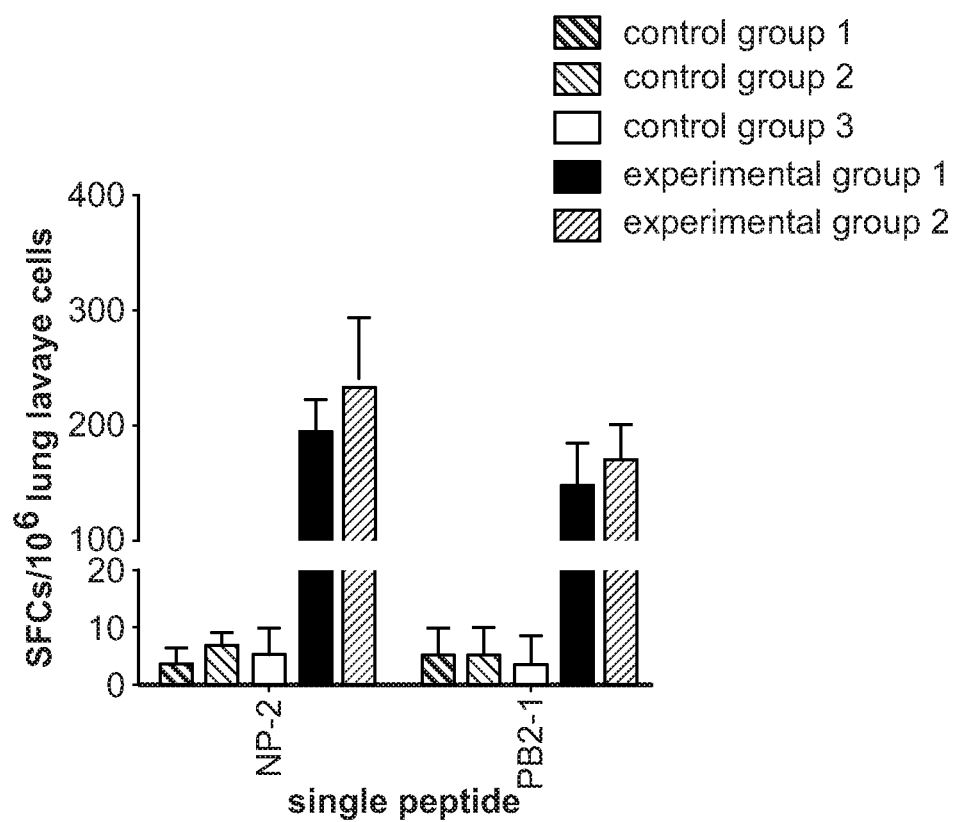
Figure 11D:
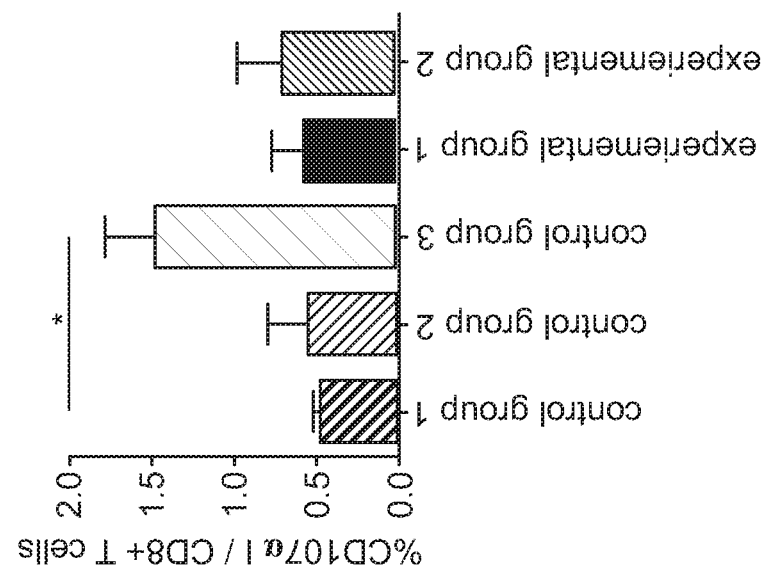
Figure 11C:
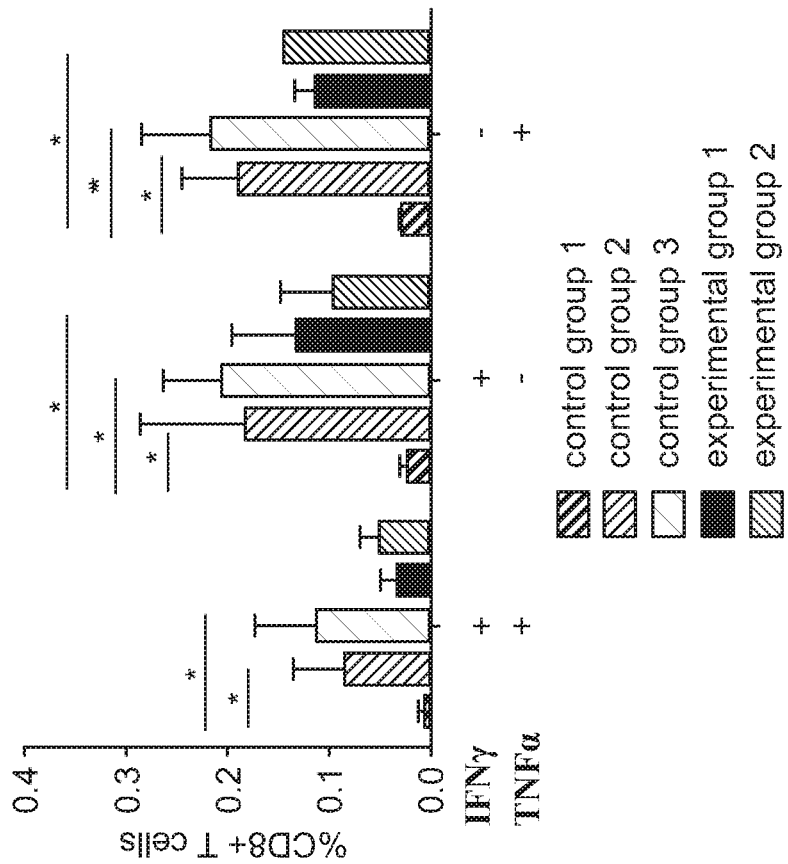
Figures 12A, 12B:
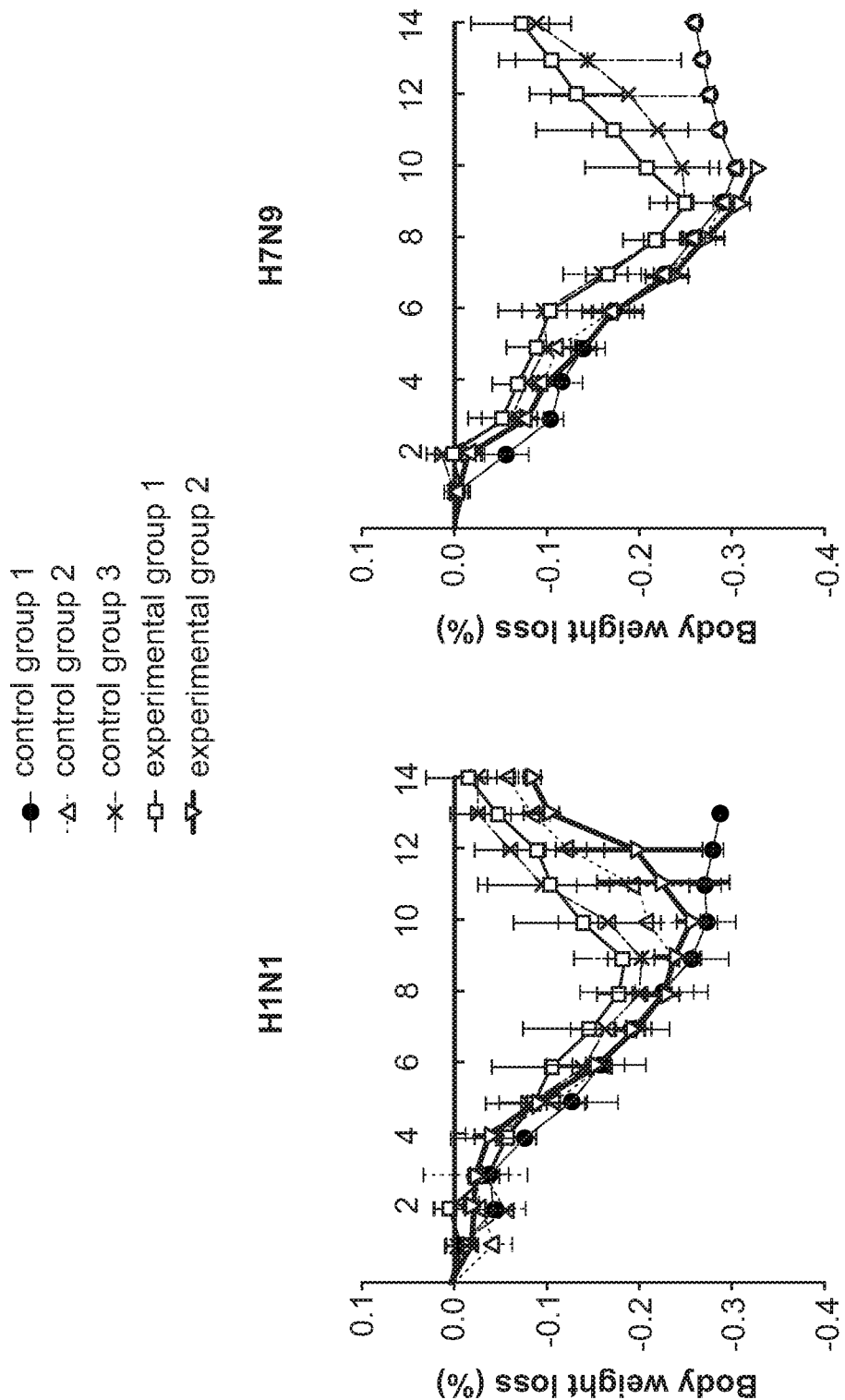
Figure 12D:
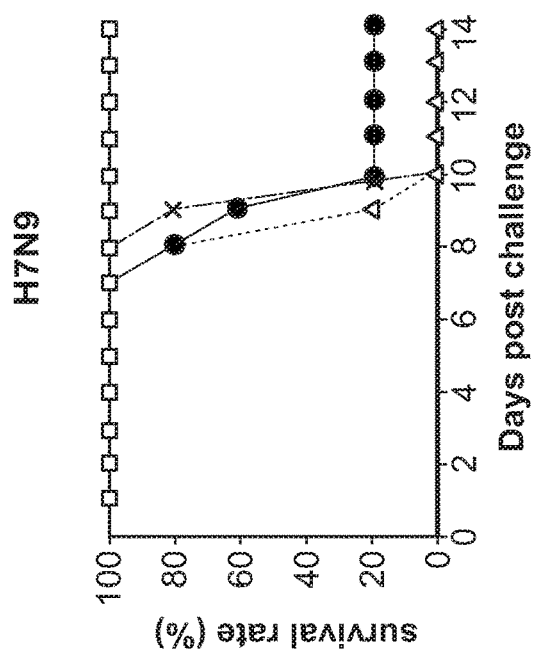
Figure 12C:
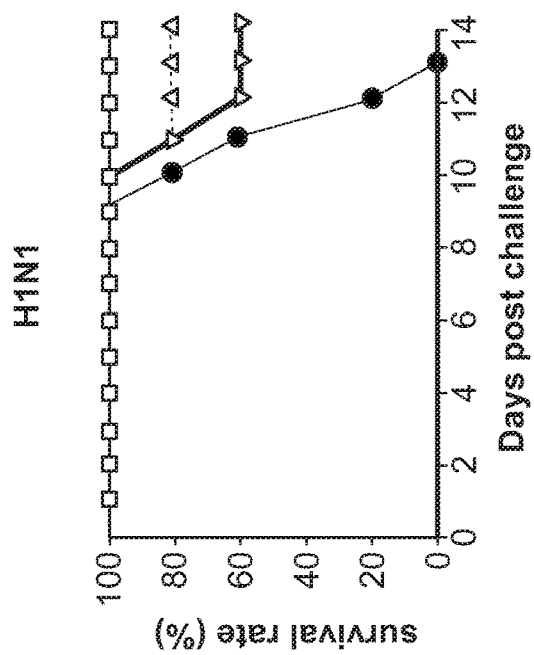
Figures 13A, 13B:
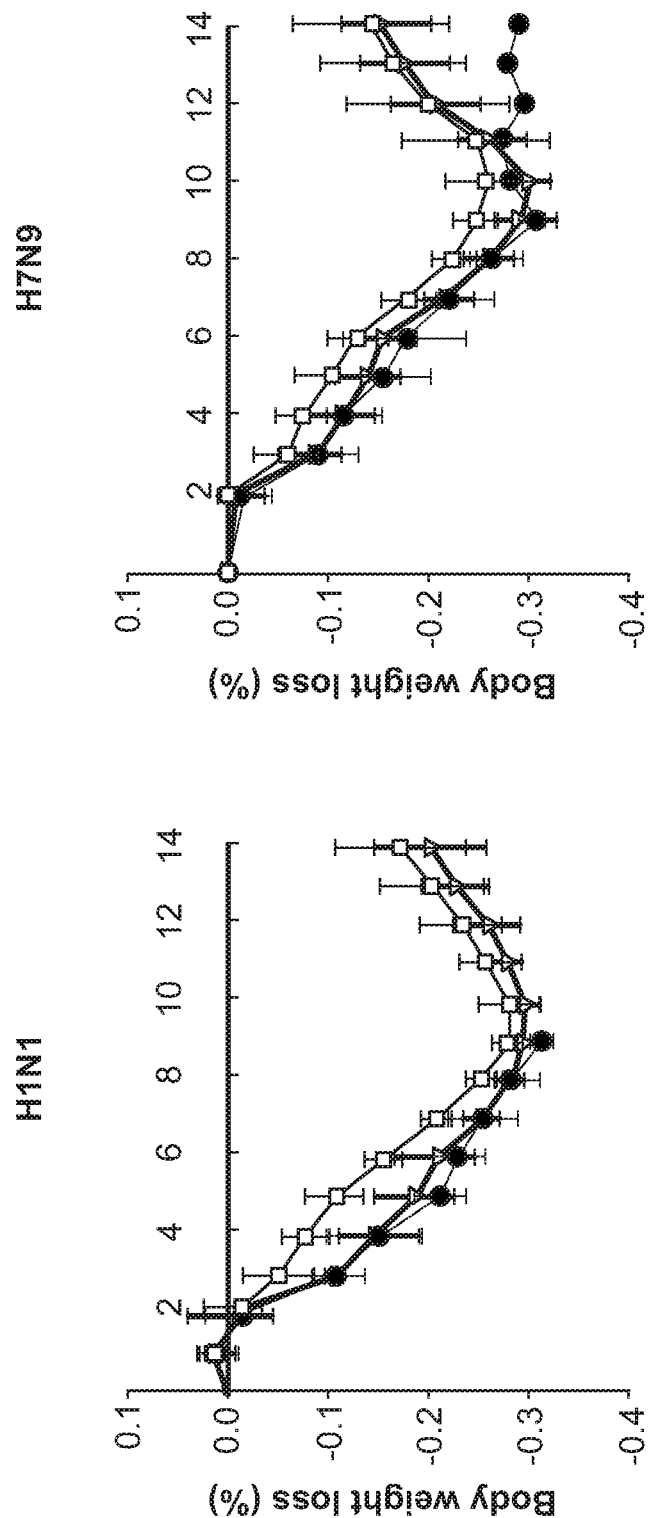
Figure 13E:
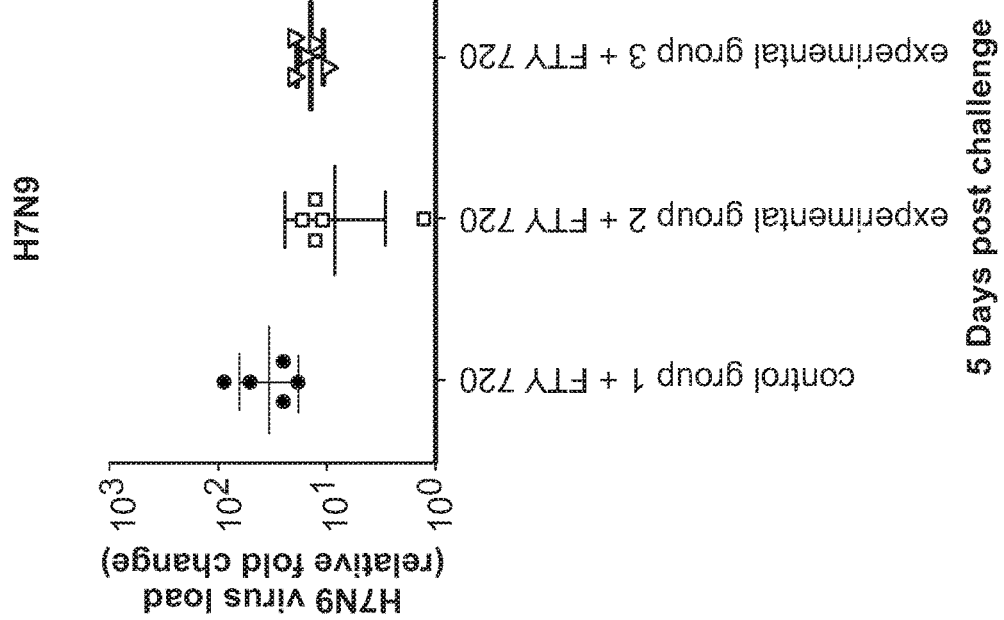
Figure 13F:
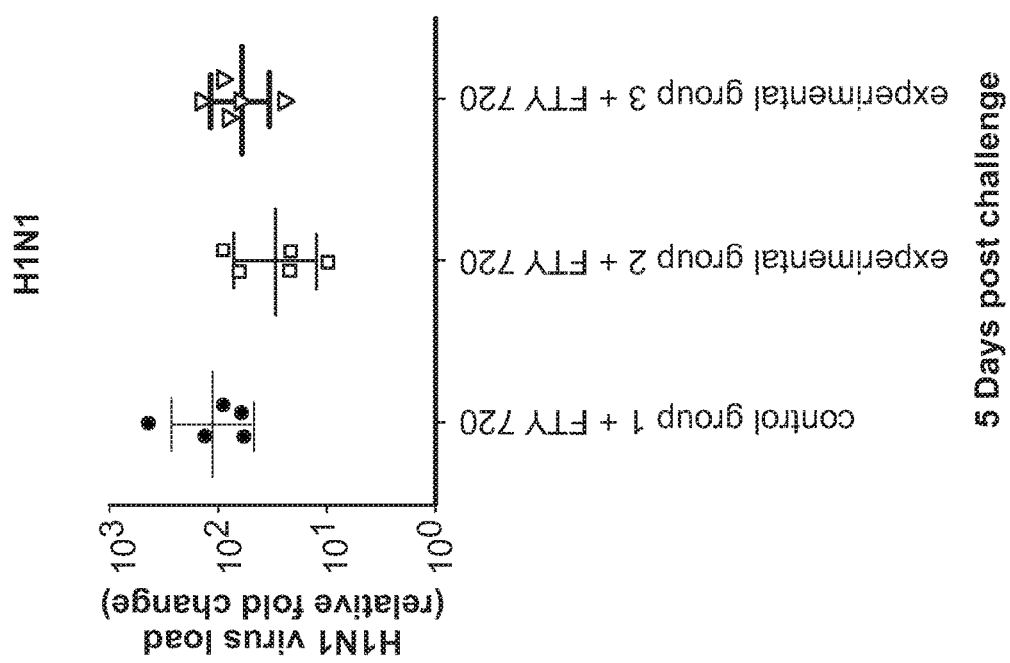

The vaccine immunogenicity test results are shown in FIG. 9A-9C. The results of ELISpot assay showed that the control mice showed no spot-forming cells and showed no influenza-specific T cell immune response; the adenovirus group exhibited higher level cellular response for both NP-2 and PB2-1 epitopes; vaccinia group mice have a higher T cell immune response for NP-2, NP-3, PB1-1, PB1-3, PA-3 and other epitopes.

Intracellular cytokine staining, including IFNγ, TNFα and CD107a, was used to detect the level of influenza-specific immune responses in mouse spleen cells. T cells expressing IFNγ, TNFα and CD107a were not observed in the control group, while they were observed in the adenovirus group and the vaccinia group, thus showing a T cell immune response with influenza characteristics.

Taken together, this experiment confirmed that expression of the anti-influenza vaccine immunogens SEQ ID NO: 1 and SEQ ID NO:2 by different vaccine vectors all induced a significant T cell immune response.

Figure 2A:
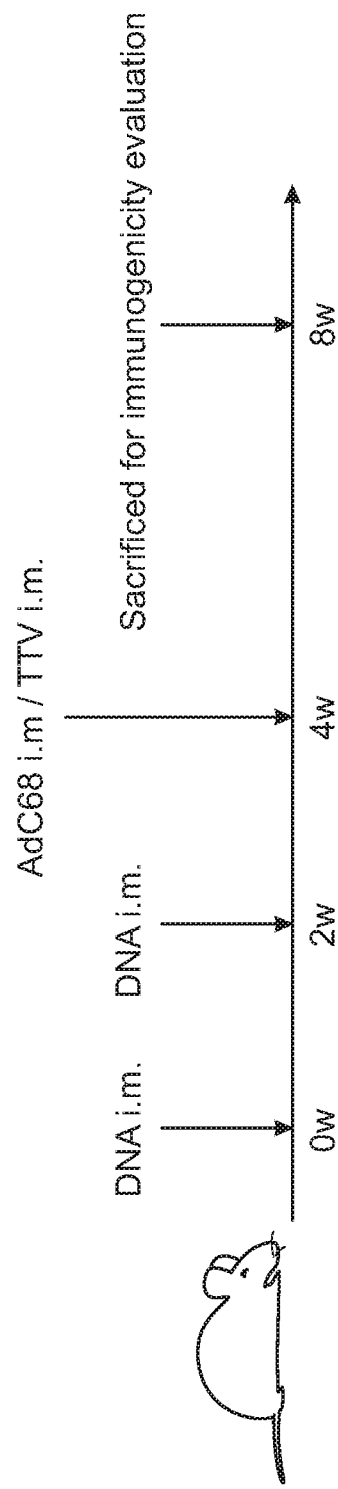
FIG. 2A-FIG. 2D show influenza-specific T-cell immune responses raised by DNA prime-viral vectored vaccine boost.
Figure 2B:
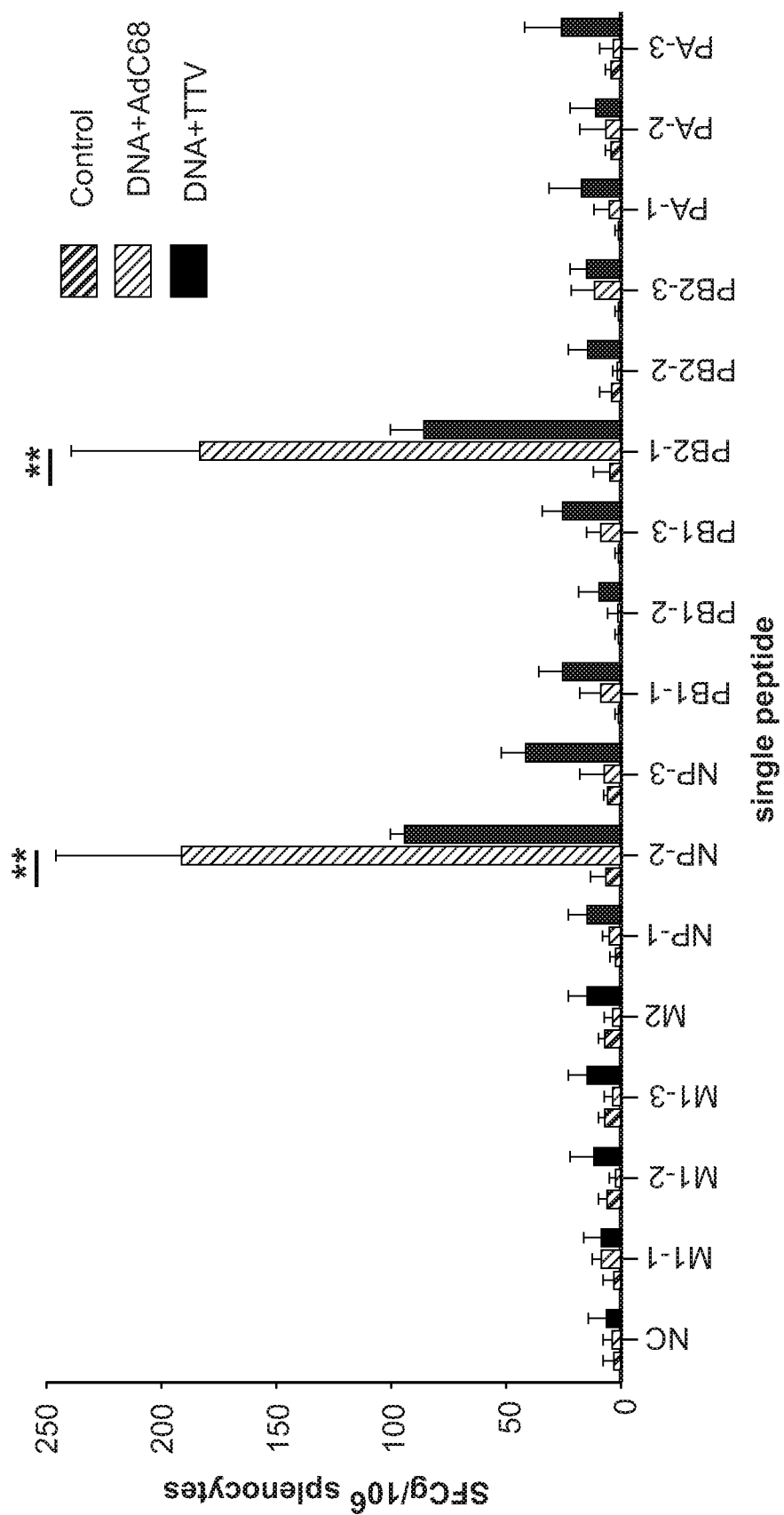
Figure 2C:
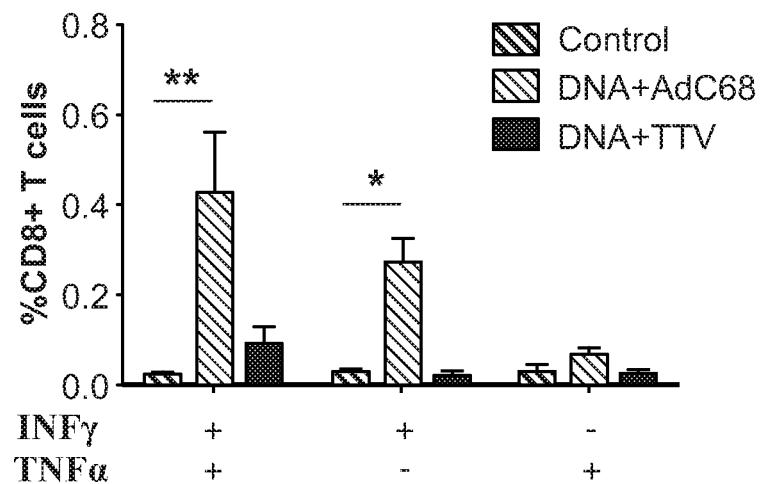
Figure 2D:
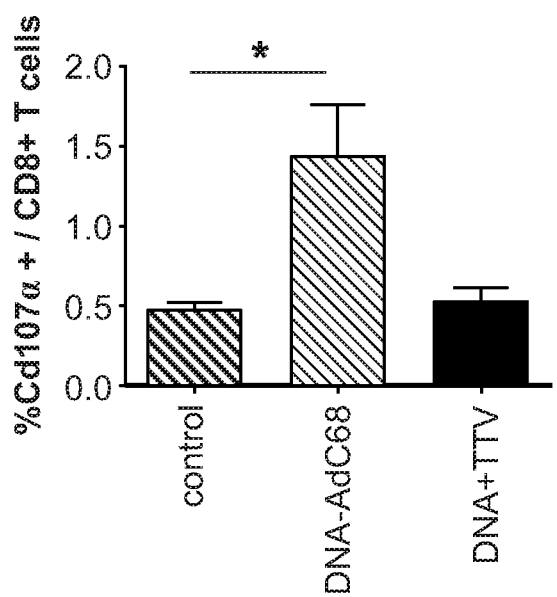

Example 6. DNA Prime and Viral Vectored Vaccine Boost Efficiently Mounts Influenza-Specific CD8+ T Cell Responses Next, the capability of the newly developed vaccines to induce influenza-specific cellular immune responses was examined in mice. The mice were divided into three groups: the control group was immunized intramuscularly with two doses of control vector pSV1.0 (100 ug) and one dose of control vector AdC68-empty ($1\times10^{11}$ vp). The two experimental groups, named as DNA+AdC68 group and DNA+ TTV group, were immunized intramuscularly with two doses of pSV1.0-PAPB1M1 (50 μg)/pSV1.0-NPPB2M2 (50 μg), followed by intramuscularly boosting with one dose of AdC68-PAPB1M1 ($5\times10^{10}$ vp)/AdC68-NPPB2M2 ($5\times10^{10}$ vp) or TTV-2a ($1\times10^7$ pfu) respectively (FIG. 2A). Four weeks after vaccination, three mice in each group were euthanized and splenocytes were isolated for measuring influenza-specific CD8+ T cell response by IFN-γ ELISpot assay (FIG. 2B) and intracellular cytokine staining (ICS) assay (FIG. 2C & FIG. 2D).

The data showed that, among all the sixteen influenza-specific epitope peptides tested (Table 4) NP-2 and PB2-1 peptides were dominant in inducing IFN-γ-producing immune cells for both experimental groups. However, DNA+AdC68 group exhibited a noticeably higher cellular response to either of these two peptides (p=0.006 for NP-2 peptide and p=0.007 for PB2-1 peptide) than the DNA+ TTV group (FIG. 2B). In addition, significantly more IFN-γ+/TNF-a+, IFN-γ+ cells and CD107a+ cells appeared in DNA+AdC68 group (p=0.007 for IFN-γ+/TNF-a,+ cells, p=0.029 for IFN-γ+ cells and p=0.049 for CD107a+ cells) as compared to DNA+ TTV group after stimulation with a peptide pool composed of the all sixteen peptides (FIG. 2C & FIG. 2D). In contrast, DNA+ TTV group exhibited a broader cellular response, as was indicated by the fact that many more peptides, e.g., M2, NP-3, PB1-1, PB1-3, PA-1, PA-3, were able to elicit modest but detectable IFN-γ induction in immune cells from this group (FIG. 2B). Thus, these results show that the DNA+AdC68 regimen was more effective in raising immunodominant T-cell responses whereas DNA+ TTV regimen appeared to perform better in eliciting sub-immunodominant T-cell responses.

TABLE 4

Influenza A virus-specific peptides employed to stimulate splenocytes for the quantification of T cell responses

| Protein | Amino acid sequence of peptides | SEQ ID NO: |
|---|---|---|
| M1 | 58-66: GILGFVFTL [31] | 12 |
|  | 128-135: MGLIYNRM [32] | 13 |
|  | 99-107: LYRKLKREI | 14 |
| M2 | 2-24: SLLTEVETPIRNEWGCRCNDSSD | 15 |
| NP | 146-155: ATYQRTRALV [33] | 16 |
|  | 366-374: ASNENMDTM [34] | 17 |
|  | 383-391: SRYWAIRTR [35] | 18 |
| PB1 | 703-711: SSYRRVPGI [36] | 19 |
|  | 415-424: VSGVNESADM | 20 |
|  | 494-502: DGGPNLYNI | 21 |
| PB2 | 198-206: ISPLMVAYM [37] | 22 |
|  | 342-354: VLTGNLQTL | 23 |
|  | 544-553: SVLVNTYQWI | 24 |
| PA | 509-518: SHLRNDTDVV | 25 |
|  | 515-523: TDVVNFVSM | 26 |
|  | 601-609: VEEGSIGKV | 27 |

Example 7. DNA Prime/Viral Vectored Boost Regimens in Murine Model Afforded Protection Against Heterologous Influenza Virus Challenges Next, aiming to determine the protective efficacy of the DNA prime/viral vectored boost regimens, a murine model of influenza challenge was used. Mice were immunized with sham control or vaccines as described above, split into two groups, and four weeks later challenged with either 500 50% tissue culture-infective dose (TCID50) of A/PRS(H1N1) or 100 TCID50 A/Shanghai/4664T/2013(H7N9) influenza virus. Body weights were then monitored for fourteen days and survival rates were also calculated. Five mice from each group were euthanized on day five after challenge for lung viral load determination.

Figure 3A:
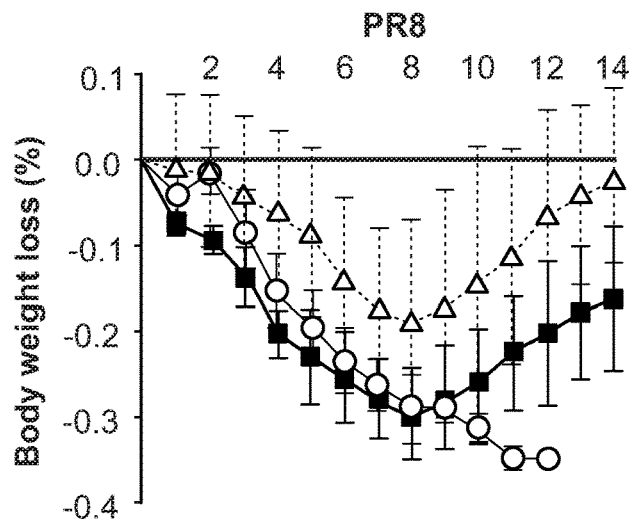
FIG. 3A-FIG. 3E show DNA prime-viral vectored vaccine boost strategies conferred protection against PR8/(H1N1) and H7N9 viruses in vaccinated mice. Mice were immunized following the schedule outlined in FIG. 2A, and four weeks later challenged with either 500 50% tissue culture-infective dose (TCID50) of A/PR8(H1N1) or 100 TCID50 A/Shanghai/4664T/2013(H7N9) influenza virus. After infection, mice (n=5 in each group) were monitored daily for body weight (FIG. 3A, FIG. 3D) survival (FIG. 3B, FIG. 3E) or RNA expression (FIG. 3C, FIG. 3F). Five mice in each group were sacrificed on day 5 post infection to isolate lung tissues for RNA extraction, followed by RT-PCR quantification of viral RNA to determine the relative viral loads. The error bars represent the SDs; where * indicates p<0.001; where  indicates p<0.01; and where * indicates p<0.05.
Figure 3B:
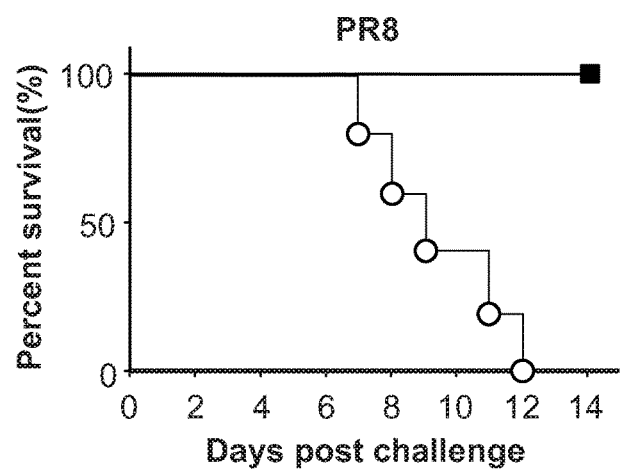
Figure 3C:
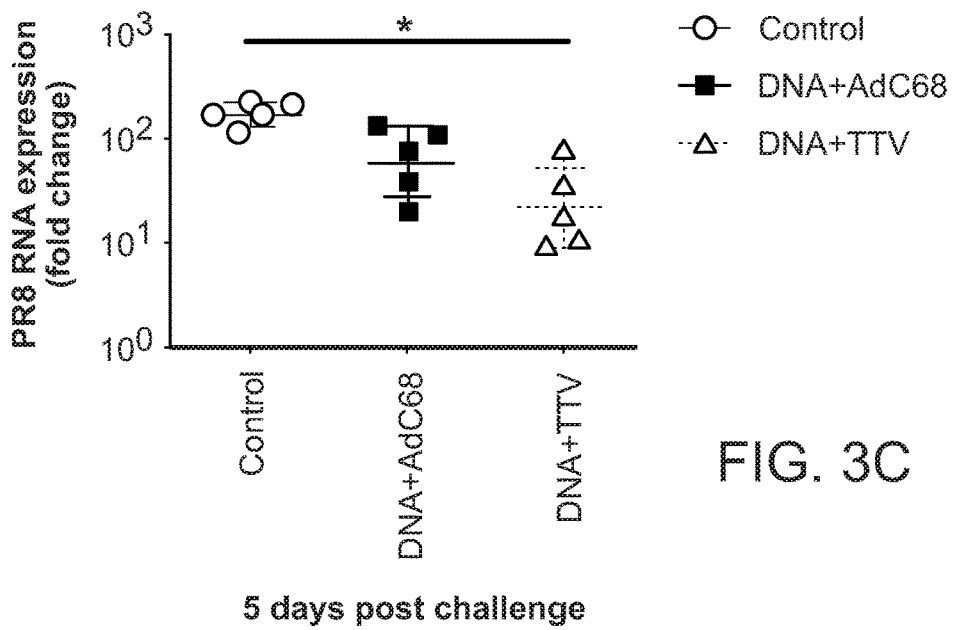

After a fatal challenge with A/PR8 (H1N1) virus, mice in the sham control group rapidly and continuously lost weight (FIG. 3A). Consequently, these mice died between day 7 and 12 (FIG. 3B). In contrast, although the body weights of the two vaccinated groups also experienced an initial decrease after PR8 challenge, they reached a nadir on day 8 and then rebound afterwards (FIG. 3A). Accordingly, all the mice survived (FIG. 3B). The protection of vaccinated mice from PR8 challenge was further affirmed by reduced lung viral loads ($p=0.07$ for DNA-AdC68 group and $p=0.04$ for DNA-TTV group) as compared to control group (FIG. 3C). Interestingly, mice in DNA+ TTV group underwent a slower and less decrease in their body weights in comparison with DNA-AdC68 group (FIG. 3A), which was in line with slightly lower viral loads (FIG. 3C), suggesting that DNA+ TTV regimen may provide a better protection against PR8 challenge. Taken together, these data demonstrated that a well-designed T-cell vaccine is capable of affording protection against the fatal challenge of PR8 (H1N1) influenza A virus.

Figure 3D:
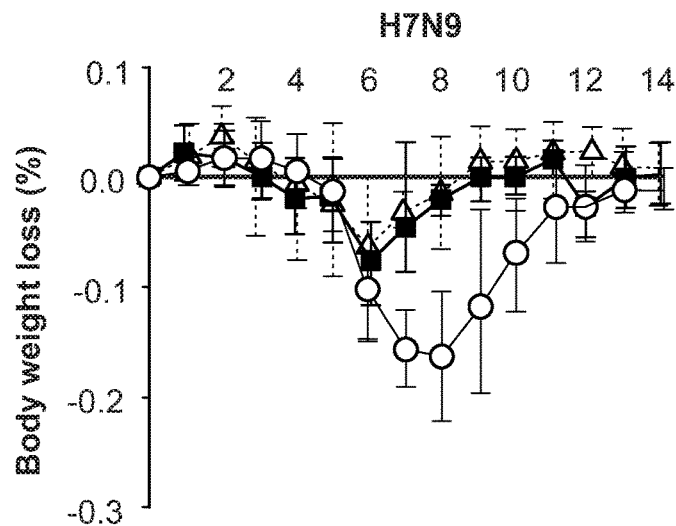
Figure 3E:
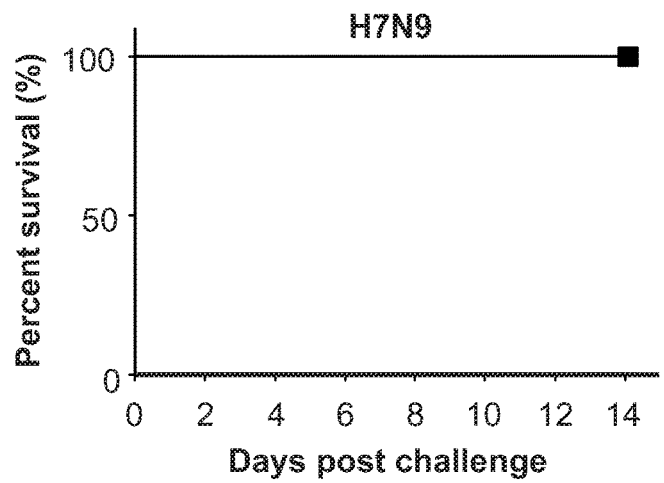
Figure 3F:
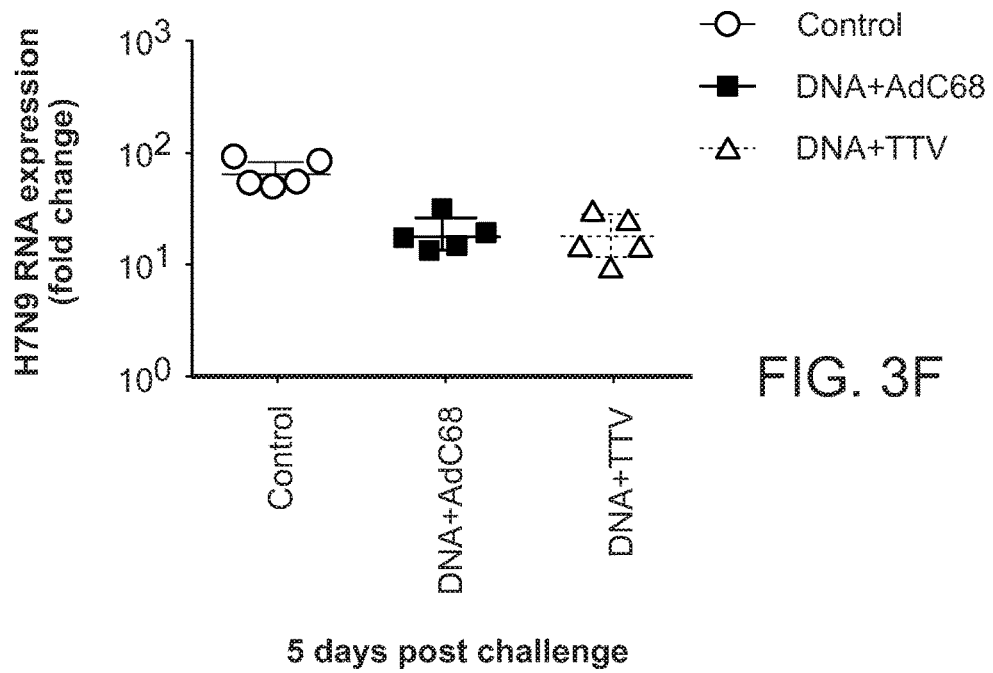

Next, a non-lethal H7N9 challenge model was used (FIG. 3E) as both regimens failed to protect from a lethal challenge with H7N9 (data not shown). Interestingly, both vaccinated groups showed less initial loss and earlier recovery of body weight as compared to control group (FIG. 3D), which was in agreement with inhibited viral replication in lung ($p=0.4$ for DNA-AdC68 group and $p=0.16$ for DNA-TTV group) (FIG. 3F). Thus, by delivering conserved influenza-specific CD8+ T cell epitopes, both DNA+AdC68 and DNA+ TTV regimens were able to mount cross-group protection in murine models.

Figure 4A:
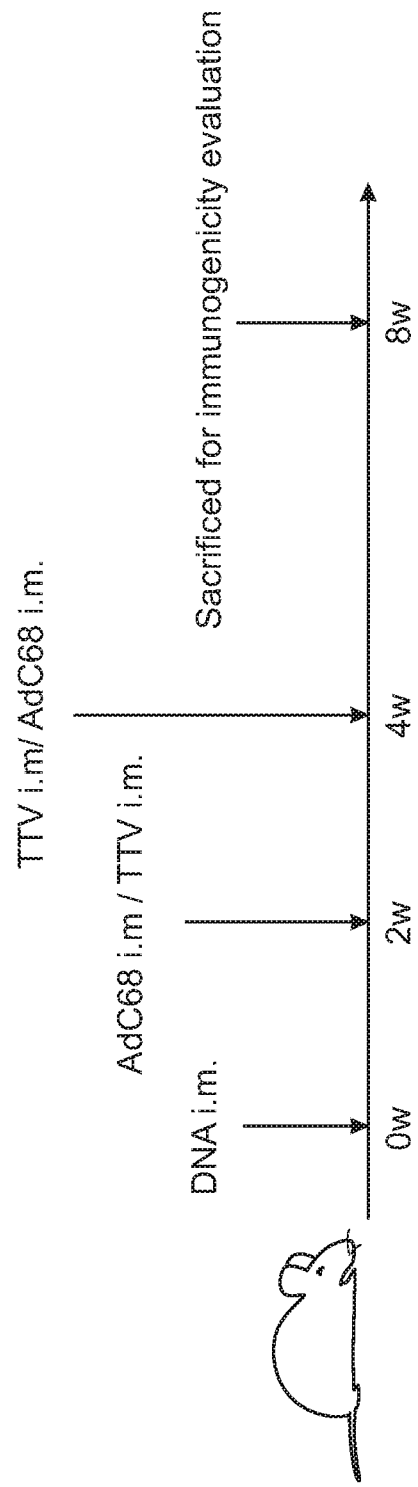
FIG. 4A-FIG. 4E show intranasal administration of AdC68 elicits significantly more potent respiratory residential and less systemic memory T cell responses.
Figure 4B:
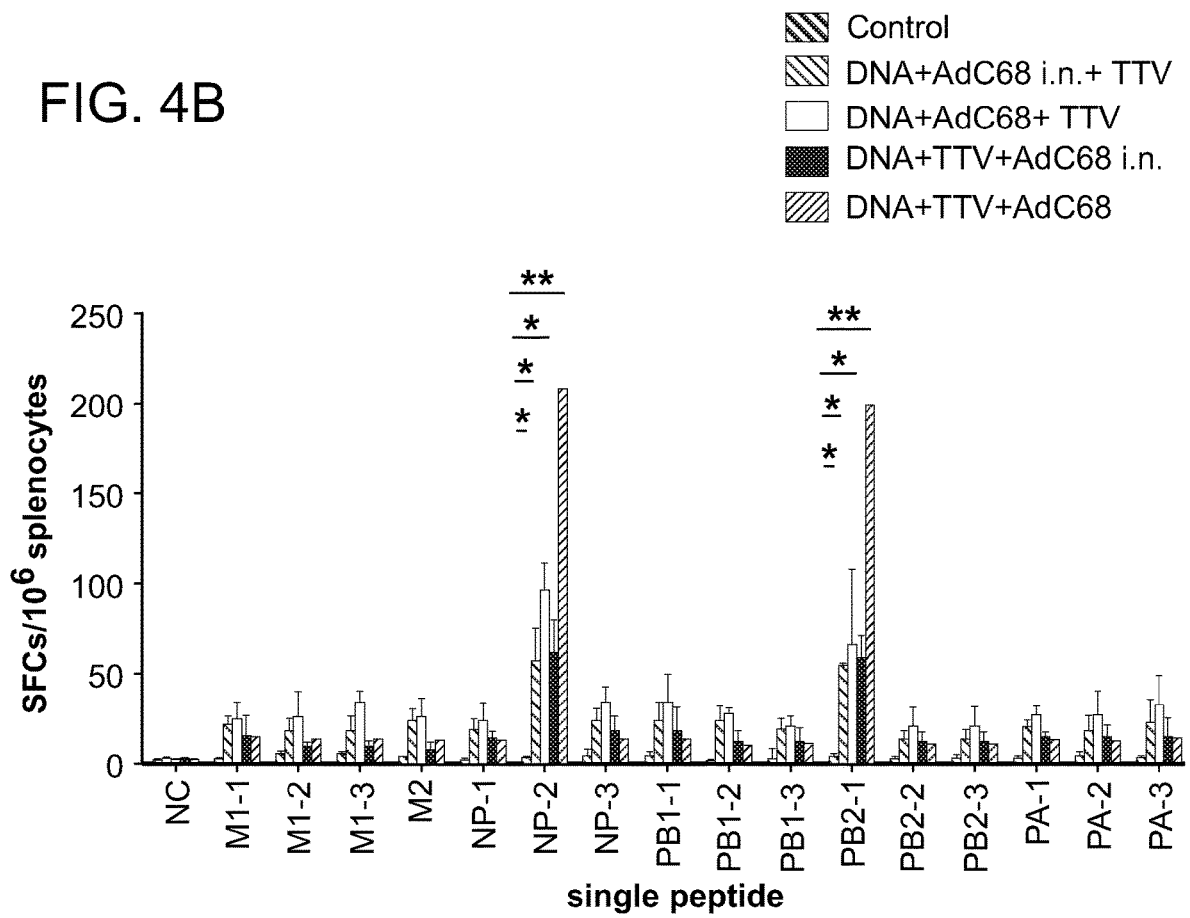
Figure 4C:
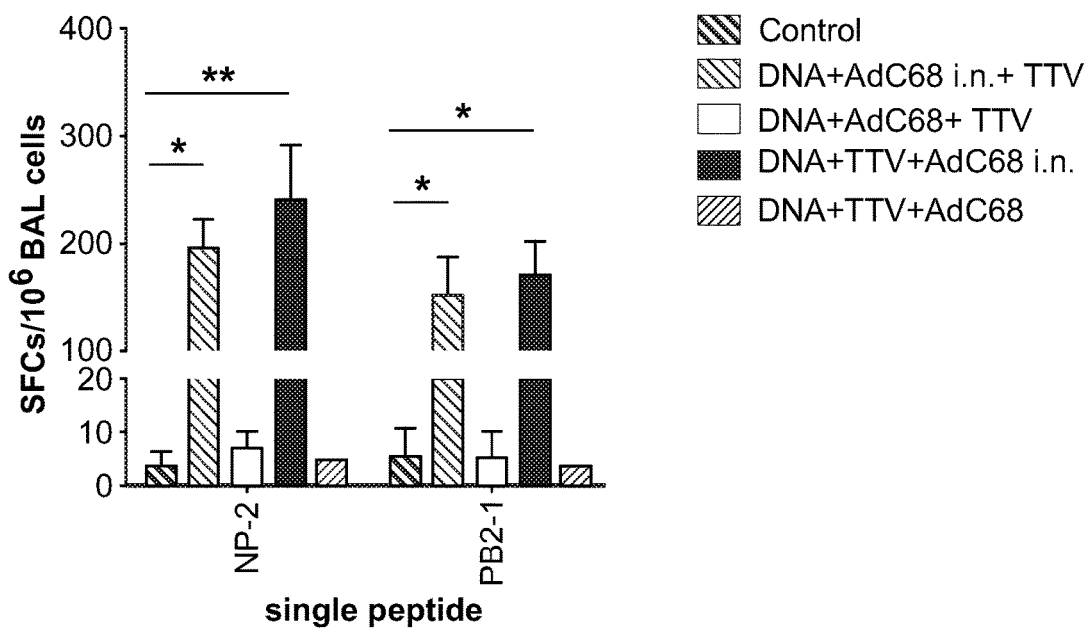
Figure 4D:
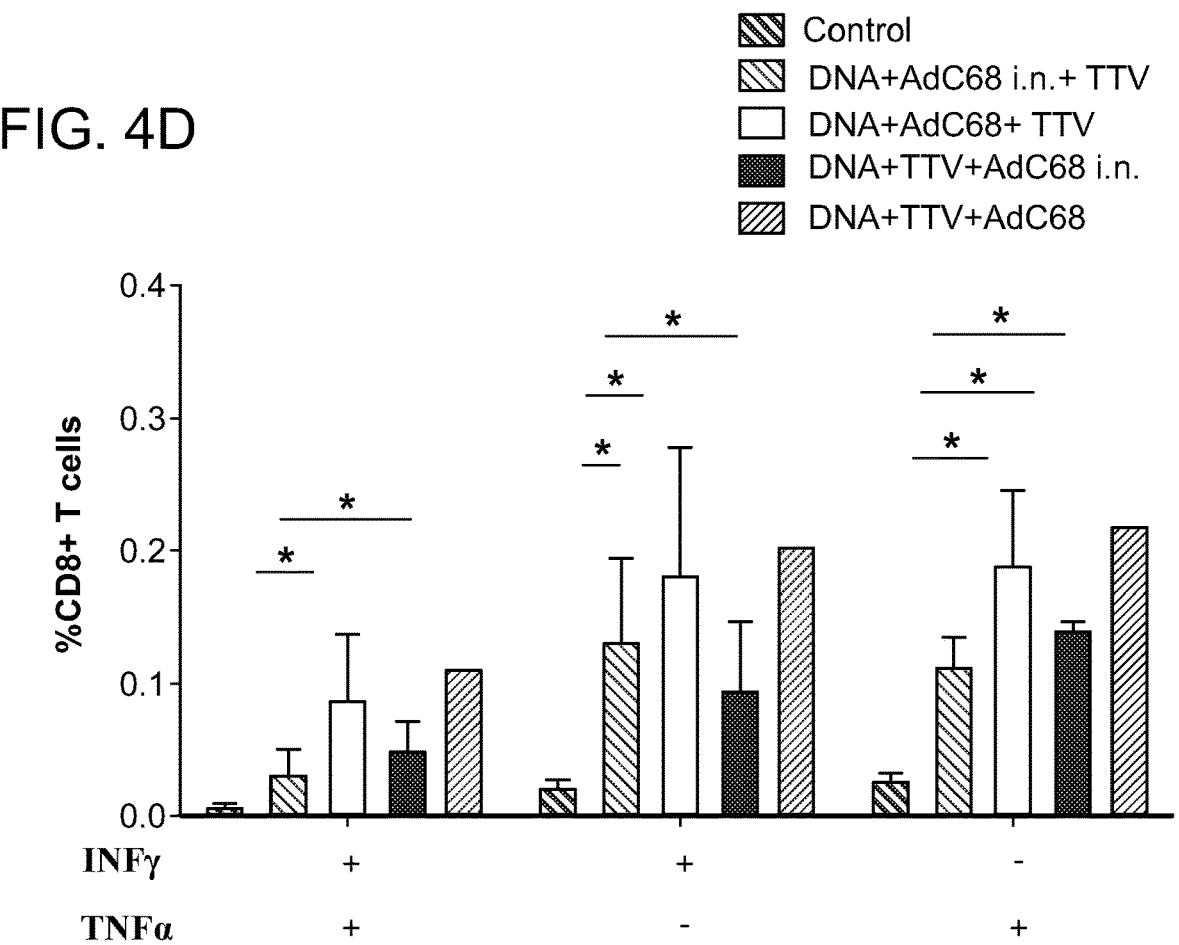
Figure 4E:
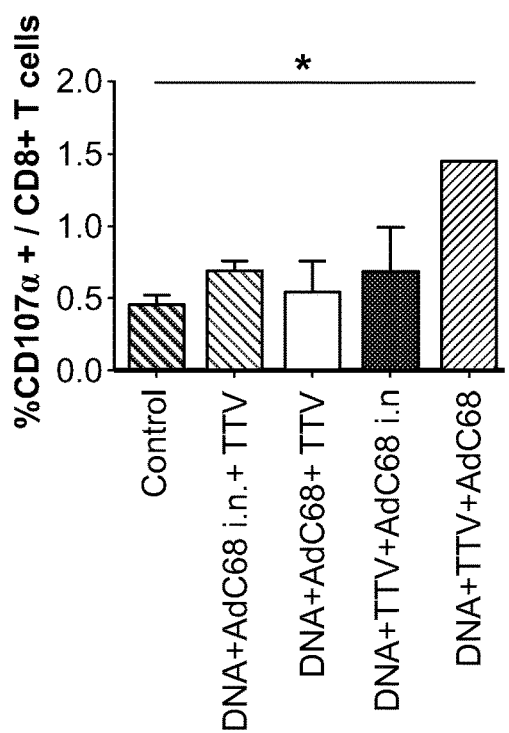

Example 8. Intranasal Administration of Adenoviral Vectored Vaccine Elicits Vigorous Respiratory Residential T-Cell Responses in a Combinatory Regimen To further enhance respiratory tract and lung residential memory T cells in order to improve the protection from influenza challenge, the intranasal inoculation of AdC68 before or after TTV intramuscular immunization was tested in a combinatorial regimen with a DNA intramuscular priming. The intramuscular administration of AdC68 was employed as control. All groups were immunized as scheduled in FIG. 4A, three mice in each group were sacrificed four weeks after vaccination for immunogenicity assessment using IFN-γ ELISpot assay and intracellular IFN-γ staining based flow-cytometry assay. The systemic T-cell responses in splenocytes isolated from vaccinated mice was first analyzed. IFN-γ ELISpot assay results showed that, among the four tested groups, DNA+ TTV+AdC68 group mounted significantly higher cellular responses to immunodominant NP-2 and PB21 epitope peptides than the other three groups which showed comparable responses ($p=0.002$ for NP-2 peptide and $p=0.008$ for PB2-1 peptide) (FIG. 4B and FIG. 4E). In contrast, the regimens of DNA+AdC68+ TTV and DNA+AdC68 i.n.+ TTV raised more potent T-cell immune responses against subdominant epitopes than those of the other two regimens (FIG. 4B). The functionalities were further analyzed with intracellular cytokine staining based flow-cytometry assay in the splenocytes after stimulation with the peptide pool. As shown in FIG. 4D, the intramuscular administration of AdC68 mounted more influenza-specific IFN-γ+, TNF-α+ and IFN-γ+ TNF-α+ double positive T cells than their intranasal counterparts. In addition, among all four groups, DNA+ TTV+AdC68 group exhibited the highest induction of CD107α+ cells ($p=0.049$) (FIG. 4E). Taken together, these results led to the conclusion that intramuscular route is a better route for triggering systemic immune response in both the magnitude and functionality.

Next, the IFN-γ ELISpot analysis was extended to bronchoalveolar lavage (BAL) lymphocytes. Strikingly, only DNA+AdC68 i.n.+ TTV and DNA+ TTV+AdC68 i.n. groups showed robust BAL T-cell immune cells in response to stimulation by NP-2 ($p=0.02$ for DNA+AdC68 i.n.+ TTV and $p=0.006$ for DNA+ TTV+AdC68 i.n group) and PB2-1 epitope peptides ($p=0.034$ for DNA+AdC68 i.n.+ TTV group and $p=0.047$ for DNA+ TTV+AdC68 i.n group) (FIG. 4C). Thus, intranasal administration of AdC68 had a pronounced advantage over intramuscular administration in the induction of respiratory tract and lung resident T cells.

Example 9. Intranasal Administration of AdC68 Afforded Better Protection from Lethal Challenge of Influenza Next, the protective efficacy of combinatorial immunization regimens from PR8 and H7N9 challenges was evaluated. Mice that received vaccination as described for FIG. 4 were subjected to challenges either with 500 TCID50 of PR8 influenza virus or 500 TCID50 of H7N9 influenza virus four weeks after the last inoculation.

Figure 5A:
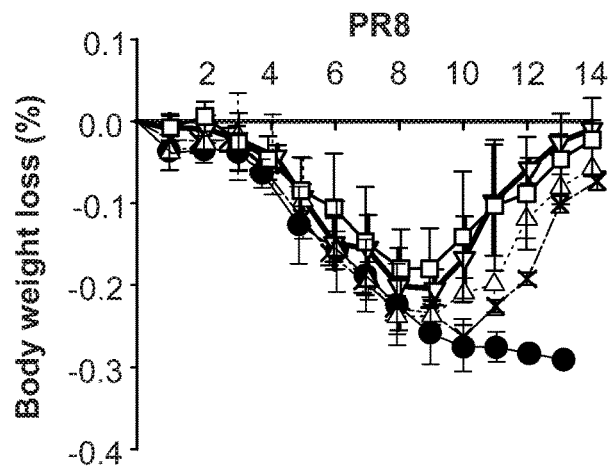
FIG. 5A-5F show intranasal administration of AdC68 afforded better protection from lethal challenge of influenza. Mice were subjected to different combinatorial immunizations following schemes outlined in FIG. 4A, and four weeks later challenged with lethal doses of PRS or H7N9 influenza A virus. Shown are.
Figure 5B:
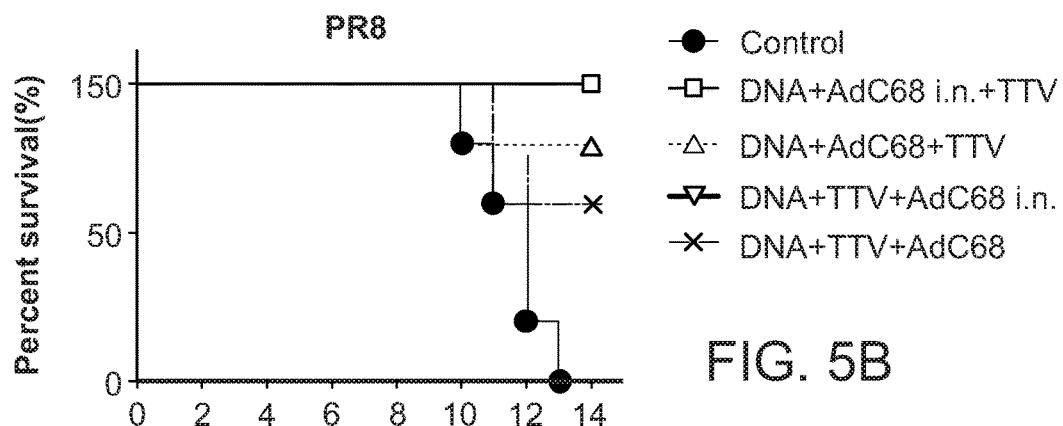
Figure 5C:
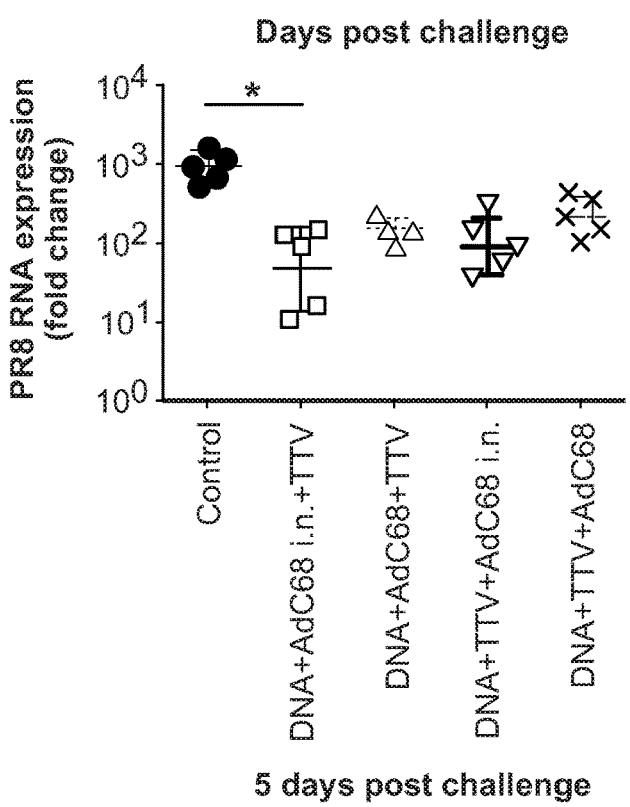

In response to PR8 challenge, the two AdC68 intranasal immunization groups experienced similar weight loss that was less severe than the two intramuscular immunization groups (FIG. 5A). This was marked by a slower initial loss and an earlier rebound of weight on day 9 as compared to that on day 10 in the later groups, resulting in a higher nadir weight before rebounding. The survival rate corroborated the body weight curve with 100% for the two intranasal immunization groups versus 60-80% for the two intramuscular immunization groups (FIG. 5B). In contrast, all the mice in the sham control group died between day 10 and day 13, consistent with earlier experiments as described above (FIG. 5B). Further, it was found that intranasal administration appeared to result in more reduced lung vial loads, which was especially obvious with the DNA+Adc68 i.n.+ TTV group ($p=0.046$) (FIG. 5C). Thus, although all the four combinatorial immunization regimens were able to confer protection against PR8 infection, the two regimens with intranasal AdC68 vaccination were more effective.

Figure 5D:
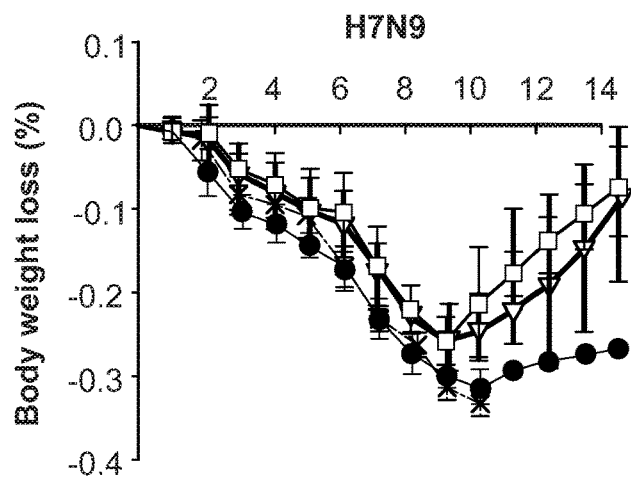
Figure 5E:
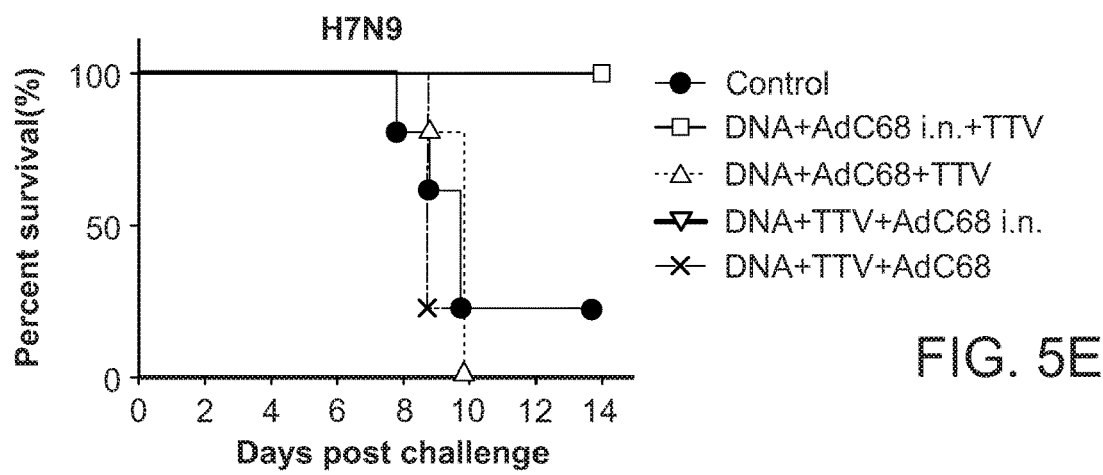

Studies on lethal H7N9 challenge models further supported the observation above. The intranasal route was endowed with superior protective efficacy as compared to intramuscular route. This superiority was first reflected by changes in body weight, as both DNA+Adc68 i.n.+ TTV and DNA+ TTV+Adc68 i.n. groups exhibited a body weight loss curve similar to that observed in PR8 challenge, with the body weight reaching a nadir at day 9 and then rebounding afterwards. In contrast, both DNA+Adc68+TTV and DNA+TTV+Adc68 groups suffered more rapidly and continuously lost weight without recovery, resembling the sham control group (FIG. 5D). Consequently, all the animals of the two intranasal immunization groups survived, whereas most, if not all, of the two intramuscular immunization groups died (FIG. 5E).

Figure 5F:
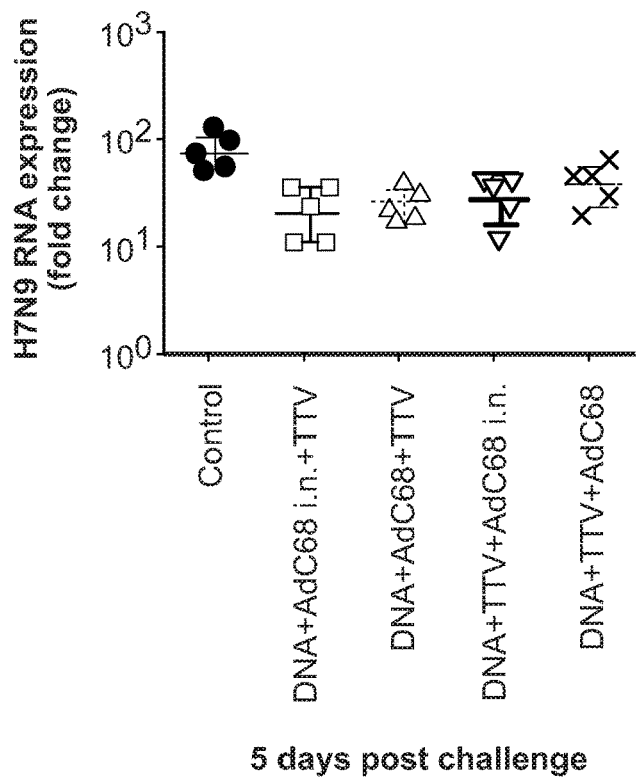

Measurements of lung viral load at day 5 after challenge revealed only modest advantage of intranasal vaccination over intramuscular vaccination (FIG. 5F). Without being bound by theory, it is plausible to speculate that the induced cellular immunity might exert additional mechanisms to attenuate the pathogenicity in addition to suppression of viral replication, for example to reduce the lung inflammation. Altogether, the H7N9 challenge studies further highlight the advantage of intranasal immunization over intramuscular immunization in improving protective efficacy of T cell-based influenza vaccine(s).

Example 10. Both Respiratory Residential and Systemic Memory T Cells are Essential for Full Protection As both DNA+AdC68 i.n.+ TTV and DNA+ TTV+Adc68 i.n. regimens were capable of raising both respiratory residential and systemic memory T cells, in order to dissect the contributions of these two T cell subpopulations to the protective immunity, Fingolimod (FTY720), an immunomodulating drug targeting sphingosine-1-phosphate was used to prevent T cell egress from lymph nodes or spleen, but that would not affect the respiratory residential memory T cells T cells (Masopust D, et al. J Exp Med. 201'0; 207(3): 553-64).

Figure 6A:
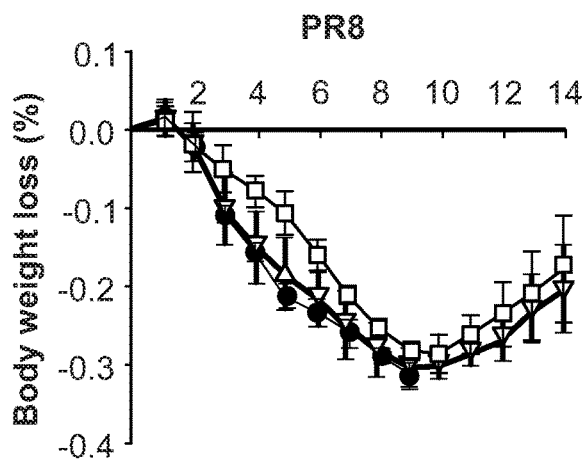
FIG. 6A-FIG. 6F show both respiratory residential and systemic memory T cells are essential for full protection. The sequential immunizations and virus challenges of mice were essentially performed as described in FIG. 5A, except that all mice were exposed ad libitum to drinking water containing 2 µl/ml of dissolved FTY720 during challenge. Shown are.
Figure 6B:
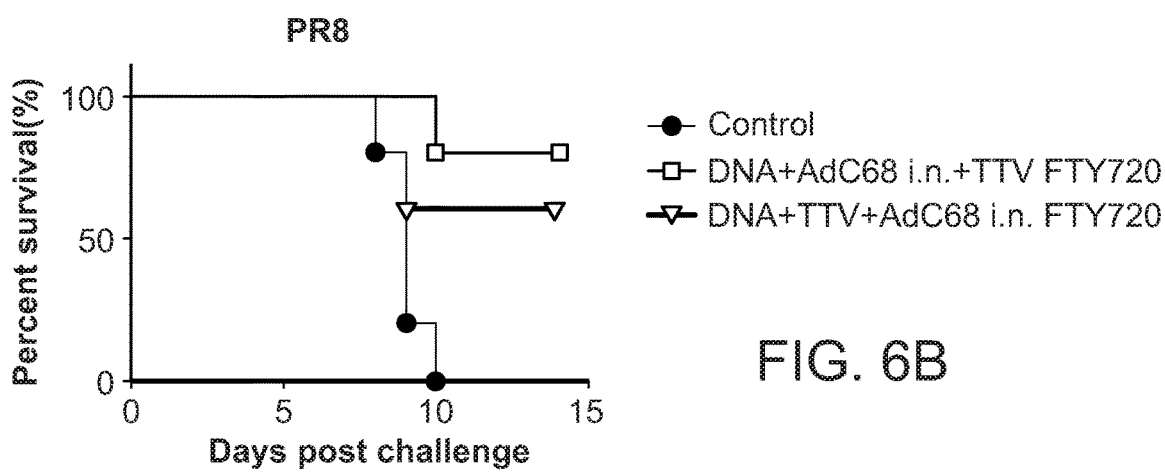
Figure 6C:
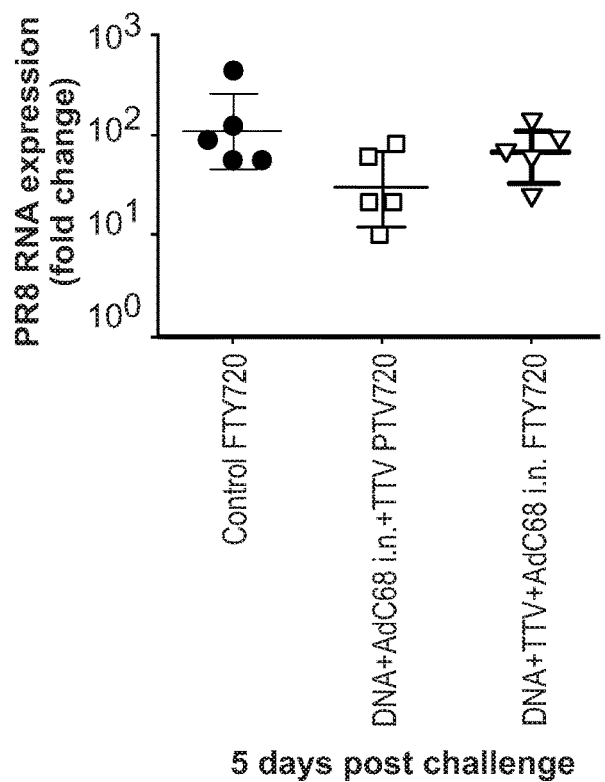
Figure 6D:
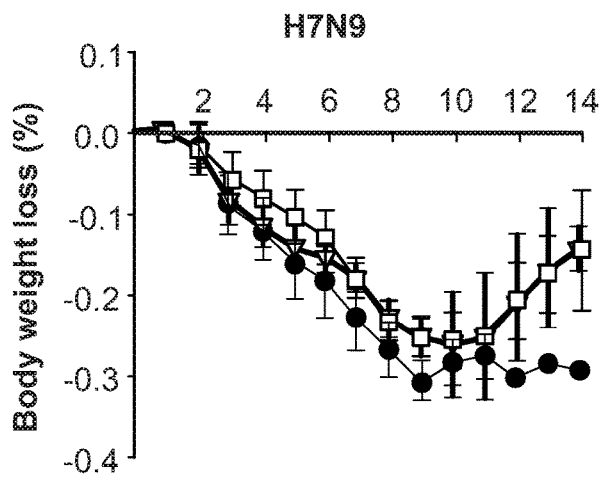
Figure 6E:
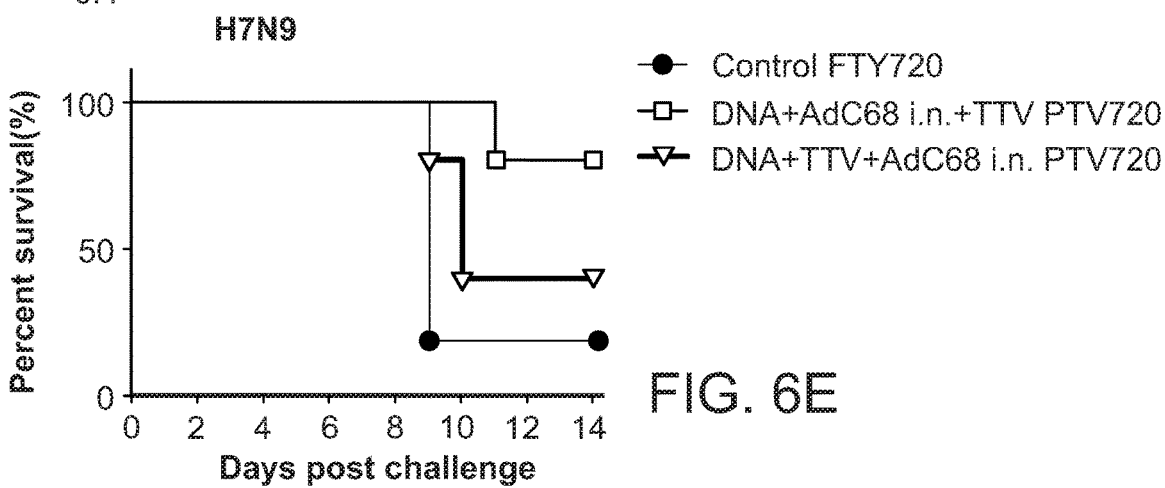
Figure 6F:
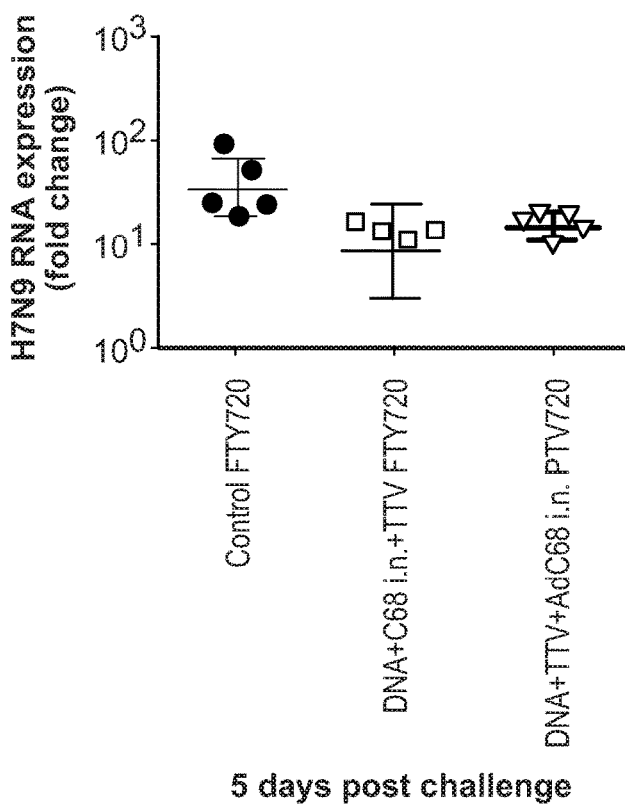
Figure 7:
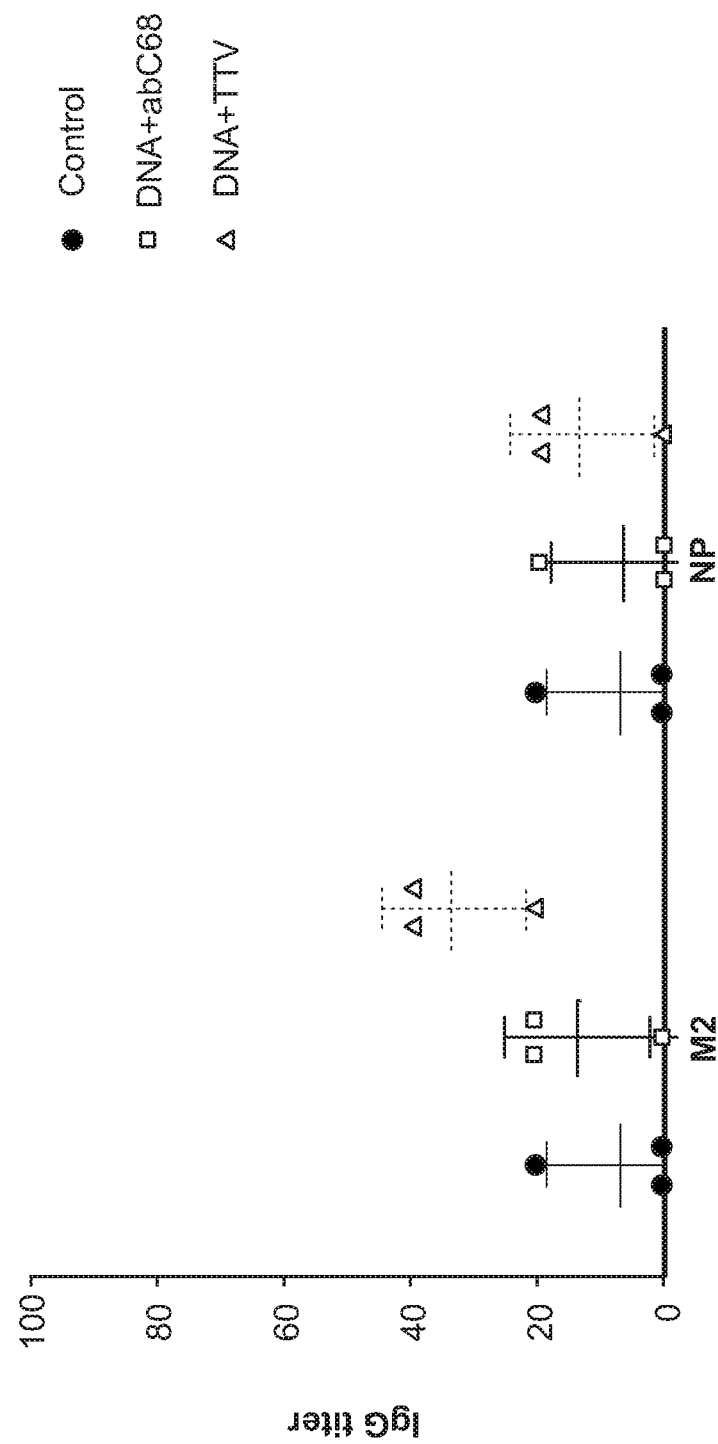
FIG. 7 shows a comparison of DNA prime-AdC68 boost and DNA prime-TTV boost strategies in delivering conserved influenza epitopes to raise influenza virus-specific antibody immune responses. Anti-M2 and anti-NP IgG levels in the serum of immunized mice following immunization. Control group was immunized with three doses of control vector pSV1.0 i.m. (100 ug). The experimental group was immunized with two doses of DNA vaccine and one dose of AdC68 or TTV vaccine. Serum was obtained at 4 weeks post-vaccination and tested for anti-M2 and anti-NP IgG titers using ELISA. The error bars represent the SDs; where * indicates p<0.001; where  indicates p<0.01; and where * indicates p<0.05.
Figure 8:
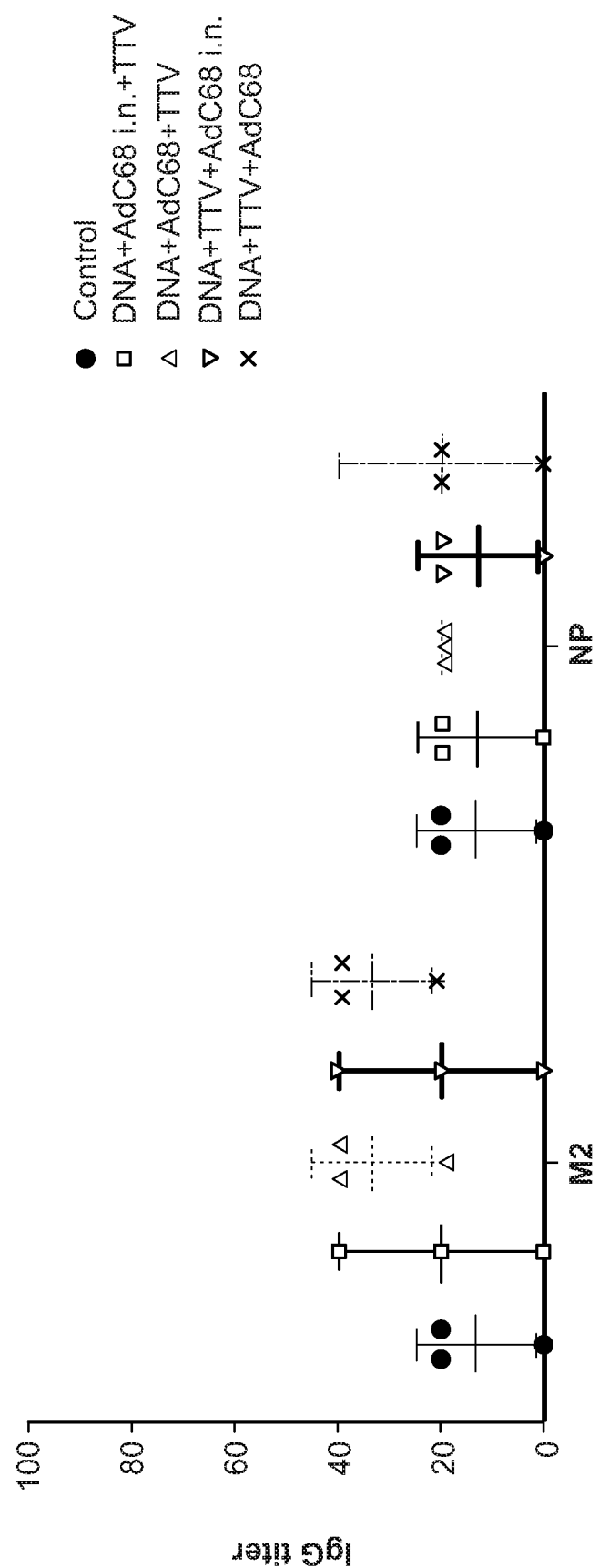
FIG. 8 shows an evaluation of influenza virus-specific antibody immune responses induced by combinatorial immunization with DNA, AdC68 and TTV vaccines through both intramuscular and intranasal routes. Anti-M2 and anti-NP IgG levels were determined in the serum of immunized mice following immunization. Control group was immunized with one dose of control vector pSV1.0 i.m (100 µg) and two doses of control vector AdC68-empty i.n./i.m. ($1 \times 10^{11}$vp); experimental group was sequentially immunized with DNA, AdC68 and TTV with the indicated order; for the two AdC68 administration routes, only intranasal route was denoted as i.n., while the intramuscular route was treated as default, and left undenoted. Serum was obtained at 4 weeks post-vaccination and tested for anti-M2 and anti-NP IgG titers using ELISA. The error bars represent the SDs; where * indicates p<0.001; where indicates p<0.01; and where * indicates p<0.05.

When exposed to FTY720 during lethal PR8 challenge, both DNA+AdC68 i.n.+ TTV and DNA+ TTV+Adc68 i.n. groups conferred partial protections as compared to the control group, as evidenced by both body weight curve (FIG. 6A) and survival curve (FIG. 6B). The protective efficacies appeared to be lower than that in the absence of FTY720 with a more rapid body weight loss and a later regain of body weight; Importantly, the survival dropped from 100% to 80% and 60% for DNA+AdC68 i.n+ TTV group and DNA+ TTV+AdC68 i.n. respectively (FIG. 6B), and a less potent suppression of viral replication was observed (FIGS. 5C and 6C). Similar partial protections were also observed against H7N9 challenge, despite that DNA+ TTV+AdC68 i.n. group suffered even a bigger drop in survival (FIG. 6D, FIG. 6E & FIG. 6F). It should be noted that when exposure to FTY720 DNA+AdC68 i.n+ TTV regimen conferred a more outstanding survival than DNA+ TTV+AdC68 i.n. from lethal PR8 and H7N9 challenges (FIGS. 6A, B, D and E). Altogether, these data suggest that the respiratory residential T cells induced by intranasal immunization alone was capable of affording remarkable cross-group protection against influenza challenges, as was displayed by DNA+AdC68 i.n.+ TTV+FTY720 group. Further, FTY720 treatment resulted in reduced survival rates, especially for DNA+AdC68 i.n.+ TTV group, arguing that both respiratory residential and systemic T cells are essential for the fully protective efficacy.

Example 11: Evaluation of the Protective Effect Based on Anti-Influenza Immunogen A DNA vaccine, an adenoviral vector vaccine, and a vaccinia vector vaccine were constructed using the immunogen of the present disclosure as described in Example 1, and immunized with the recombinant influenza vaccine as described in Example 1, and the challenge protection effect of the recombinant influenza vaccine was evaluated four weeks after the completion of the immunization.

The H1N1 and H7N9 influenza challenge models were used to evaluate the protective effect of the immunogen. The H1N1 influenza challenge experiment was conducted in the biosafety level 2 laboratory, and the H7N9 influenza challenge experiment was conducted in the biosafety level 3 laboratory.

Each mouse was intraperitoneally injected with 50 μl of 10% chloral hydrate and challenged with 50 μl of influenza virus. Half of the tissue infection dose of H1N1 influenza virus was 500 viruses per mouse. Half of the tissue infection dose of H7N9 influenza virus was 100 virus per mouse. On the 5th day after the challenge, 5 mice were sacrificed in each group, and the lungs were taken for viral load measurement.

The results of the infection challenge experiment are shown in FIG. 10A-10F. After challenge with a lethal dose of H1N1 influenza virus, the mice in the control group continued to lose weight and died on day 12. The weight of the adenovirus mice began to rise on day 9, and all survived to 14 days. The weight loss of the vaccinia group was significantly slowed down, and the body weight began to rise on day 9, and all mice survived to 14 days.

After challenge with a non-lethal dose of H7N9 influenza virus, the weight of the control mice decreased by nearly 20%, and the body weight rose on day 9. The weight loss of mice in the adenovirus group and the vaccinia group was less than 10%, and the body weight was quickly rebounded on day 7.

This experiment demonstrates that expression of the anti-influenza vaccine immunogens SEQ ID NO:1 and SEQ ID NO:2 by different vaccine vectors can have a cross-protective effect on H1N1 and H7N9 influenza viruses, i.e., the two immunogens in the present disclosure have a broad spectrum of protection on different subtypes of influenza viruses.

Example 12: Immunogenicity Detection of Influenza Vaccine Based on Different Immunization Methods A DNA vaccine, an adenoviral vector vaccine, and a vaccinia vector vaccine were constructed using the anti-influenza immunogen of the present disclosure as described in Example 2. The mouse immunization was carried out by the immunization method of the present disclosure. After four weeks of the completion of immunization, the immunogenicity test was carried out as described in Example 3.

Six-week-old C57BL/6 mice were randomly divided into 5 groups: control group 1, control group 2, control group 3, experimental group 1 and experimental group 2, wherein experimental group 1 and experimental group 2 used the immunization method of the present invention. The specific immunization procedure is shown in Table 5. The dose of pSV1.0 is 100 g, the dose of AdC68 is $10^{11}$ virus particles, and the dose of pSV1.0-SEQ ID NO:1 and pSV1.0-SEQ ID NO:2 is 50 μg each, AdC68-SEQ ID NO:1 and AdC68-SEQ ID NO:2 inoculation doses were 5×10 virus particles, TTV and TTV-SEQ ID NO: 1/2 inoculation dose was $10^7$ plaque forming units. The vaccine is inoculated every two weeks.

TABLE 5

Mouse immunization experiments based on different immunization methods

| Group/Week | Week 0 | Week 2 | Week 4 |
|---|---|---|---|
| Control Group 1 | Intramuscular injection pSV1.0 | Intramuscular injection AdC68 | Intramuscular injection TTV |
| Control Group 2 | Intramuscular immunization pSV1.0-SEQ ID No.: 1 pSV1.0-SEQ ID No.: 2 | Intramuscular immunization AdC68-SEQ ID No.: 1 AdC68-SEQ ID No.: 2 | Intramuscular injection TTV-SEQ ID No.: 1/2 |
| Control Group 3 | Intramuscular immunization pSV1.0-SEQ ID No.: 1 pSV1.0-SEQ ID No.: 2 | Intramuscular immunization TTV-SEQ ID No.: 1/2 | Intramuscular injection AdC68-SEQ ID No.: 1 AdC68-SEQ ID No.: 2 |
| Experimental Group 1 | Intramuscular immunization pSV1.0-SEQ ID No.: 1 pSV1.0-SEQ ID No.: 2 | Intranasal immunization AdC68-SEQ ID No.: 1 AdC68-SEQ ID No.: 2 | Intramuscular immunization TTV-SEQ ID No.: 1/2 |
| Experimental Group 2 | Intramuscular immunization pSV1.0-SEQ ID No.: 1 pSV1.0-SEQ ID No.: 2 | Intramuscular immunization TTV-SEQ ID No.: 1/2 | Intranasal immunization AdC68-SEQ ID No.: 1 AdC68-SEQ ID No.: 2 |

The vaccine immunogenicity test results are shown in FIG. 11A-FIG. 11D. The results of ELISpot assay showed that in the mouse spleen cells, there was no influenza-specific T cell immune response was observed in the control group 1 mice; while there was a high level of T cell immune response in the control group 2, 3 and the experimental groups 1,2. In mouse lung lavage fluid, no spotted cells were found in control groups 1, 2 and, and influenza-specific immune responses could no longer be established in the lungs. Experimental groups 1 and 2 showed more spot-forming cells, i.e., experimental group 1 and 2 showed very high levels of influenza-specific T cell immune responses using the vaccination method in the present disclosure.

Intracellular cytokines staining of IFNγ, TNFα and CD107a was used to detect the level of influenza-specific immune responses in mouse spleen cells. The results showed that T cells expressing IFNγ and TNFα were not observed in control group 1, while they were observed in control group 2, 3 and experimental groups 1 and 2, thus showing T cell immune response induced by influenza A.

This experiment confirmed that the sequential immunization method of experimental group 1 and experimental group 2 with different recombinant vector vaccines, combined with respiratory immunization and systemic immunization, can effectively establish high levels of influenza-specific immune response in the whole system and the lungs, that was superior to the control group.

Example 13: Evaluation of the Protective Effect of Influenza Vaccine from Virus Challenge Based on Different Immunization Methods Mice were immunized as described herein, and the H1N1 and H7N9 influenza challenge models were used to evaluate the protective effect of the immunogen four weeks after the last vaccine immunization in the mice. The H1N1 influenza challenge experiment was conducted in the biosafety level 2 laboratory, and the H7N9 influenza challenge experiment was conducted in the biosafety level 3 laboratory.

Each mouse was intraperitoneally injected with 50 µl of 10% chloral hydrate and challenged with 50 µl of influenza virus. Half of the tissue infection dose of H1N1 influenza virus was 500 viruses per mouse. Half of the tissue infection dose of H7N9 influenza virus was 500 viruses per mouse. On day 5 after the challenge, 5 mice were sacrificed in each group, and the lungs were taken for viral load measurement.

The results of the protection from virus challenge experiment are shown in FIG. 12A-FIG. 12D. After the H1N1 influenza virus challenge, the mice in control group 1 all died on day 13, while the mice in control groups 2 and 3 showed the partial protection effect, in which 80% and 60% of the mice survived to the day 14 respectively. The body weight of the experimental group 1 and 2 mice rose on day 10, and all survived to day 14 using the vaccine immunization method in the present disclosure. And the viral load of the experimental group 2 was significantly decreased, showing an excellent protective effect.

After the H7N9 influenza virus challenge, the body weight of the experimental group 1 and 2 using the vaccination method of the present disclosure rapidly rose on day 10, and all the mice survived to day 14, showing excellent protective effect in these 2 experimental groups. There was no significant protective effect in the other groups of mice.

This experiment confirmed that by sequential immunization with different recombinant vector vaccines, combined with respiratory immunization and systemic immunization, experimental group 1 and experimental group 2, using the vaccine immunization method of the present disclosure, showed excellent cross-protection effects against H1N1 and H7N9 influenza viruses. The protective effect found in these two groups is better than that of the control group 2 and 3, which only use an intramuscular injection route. In addition, the vaccine has the best protective effect when the recombinant vaccinia vector vaccine is immunized as the last vaccine.

Example 14: Evaluation of the Protective Effect of Influenza Virus Challenge by Intranasal Immunization in Mice Mice were immunized as described herein, and the protective effect of the immunogen was evaluated by using the H1N1 and H7N9 influenza challenge models four weeks after the last vaccine immunization in mouse. The protection from influenza challenge is as described in Example 6. During the entire challenge, the mice continued to drink water containing 2 µg/ml FTY720, an immunosuppressive agent that effectively reduced the number of peripheral circulating lymphocytes but was unable to affect the respiratory residential memory T cells. FTY720 was used during the challenge of lethal doses of H1N1 and H7N9 influenza viruses to evaluate whether the intranasal immunization method had a potentiating effect.

The experimental results are shown in FIG. 13A-FIG. 13F. After mice were challenged with the H1N1 and H7N9 influenza viruses, the mice in experimental group 1+FTY720 and the experimental group 2+FTY720 all showed partial protection. The body weight of the mice began to rise on day 11 and survived to day 14, and the viral load was decreased. The protective effect was better than the control group 1+FTY720.

This experiment confirmed that the respiratory tract inoculation method of the vaccine effectively enhanced the protective effect of vaccine immunization against H1N1 and H7N9 influenza virus.

Current influenza vaccines function by raising humoral immunity against strain-specific HA and NA glycoproteins. Consequently, they failed to confer cross-protection in human and must be re-formulated every year to match the circulating influenza strains [39]. There has been growing urgency to develop universal influenza A vaccines that are capable of affording cross-protection [40]. The development of cross-reactive influenza vaccines has been explored on both the humoral arm of the immune response directing against the conserved HA stem or M2e, and its cellular arm targeting the internal viral proteins which are much more conserved than surface viral glycoproteins [41]. The potential of T-cell based vaccine was further supported by recent studies of H7N9-infected patients revealing the pivotal role of an effective and timely CD8+ T cell response in overcoming H7N9 infection in human. Provided herein are new vaccination strategies focusing on the effective delivery of cross-conserved influenza-specific epitopes to induce broad spectrum T-cell response capable of cross-group protection.

The first step in this new strategy involved designing immunogens to contain conserved T cell epitopes of viral internal antigens. This was accomplished by deducing the consensus amino acid sequences of all the six internal structural proteins of influenza from approximately 40,000 strains of influenza A virus; for PA, PB1 and PB2, only sequences enriched with predicted CD8+ T cell epitopes were included. Consequently, two universal T-cell epitope ensemble immunogens were generated, namely PAPB1M1 and PB2NPM2 herein. It would be expected that PAPB1M1 and PB2NPM2 immunogens together should provide a close to full coverage of conserved T-cell epitopes internally on influenza A virus. Indeed, the co-introduction of the two immunogens in a modality of DNA prime followed by AdC68 or TTV viral vectored boost elicited not only strong T cell response to immunodominant epitopes but also discernible T cell response to sub-immunodominant epitopes which was more evident when TTV served as the boost. Although it is not known whether such expanded breadth of T cell immunity is underlying the cross-group protection conferred by the DNA prime/viral vector boost vaccination modalities in murine influenza infection models, it is certainly critical for a potential universal human influenza vaccine.

One of the major challenges in the development of T cell-based universal influenza vaccine is that the T cell response to the same influenza infection or vaccine might vary considerably between individuals, primarily owing to the possession of diverse HLA alleles (the alternative nomenclature for MHC inhuman) that restricted the number of viral peptides displayed to T cells for recognition[42]. With HLA restriction, an influenza vaccine incorporating a multitude of conserved viral epitopes would more likely provide better population coverage than that concentrated on specific conserved epitopes. Thus, the new vaccines that were engineered have the potential to overcome the HLA challenge in human settings, fitting one important criterion of universal influenza vaccines. As described herein, the construction of three types of vaccines to express the PAPBIMI and PB2NPM2 immunogens enabled the testing of a sequential immunization strategy combining the three vaccines. It is a rare opportunity as, for viral vectored vaccine, the second boost with the same vaccine was not be beneficial in most cases due to the pre-existing vector immunity raised by the first boost. In light of recent findings that influenza-specific tissue resident memory (Trm), particularly which localized in the lung, is required for cross-protection against influenza challenges [43,44], either intramuscular or intranasal route was used for administering AdC68 based vaccine and analyzed the impact on induction of memory T cells and protective efficacy. The results demonstrated that, although intramuscular immunization was more effective in triggering systemic CD8+ T cell response, only intranasal immunization was capable of evoking efficient lung Trm.

Consequently, full protection from lethal PR8 and H7N9 challenges was only observed in intranasal immunization groups. One interesting observation is that the level of lung viral load at early phase of infection was marginally correlated with the protective efficacy in terms of weight loss and survival rate. Without being limited by theory, this might be explained by the polyfunctionality of Trm, engaged in not only directly clearing virus-infected cells but also secreting cytokines to create a hostile local environment to thwart virus spreading [45]. There is also evidence that Trm may help mobilize circulating immune cells into lesioned tissues [46].

Finally, the results provided herein describe the discovery that systemic T cell response also mediates the protection afforded by intranasal immunization. FTY720 treatment, which prevents homing of circulated T-cells to damaged periphery tissues, compromised the protective efficacy. Interestingly, a number of recent studies revealed that the circulating memory T cells can be recruited into lung and converted to Trm, thus essential for sustained maintenance of Trm. This new revelation implicated that systemic and respiratory residential memory T cell might not act independently, but rather orchestrate together in mounting an effective protection against influenza infection.

In conclusion, the examples described herein show the development and implementation of novel sequential immunization strategy for delivering the cross-protective epitopes embedded in conserved internal viral protein sequences. By demonstrating the capability of this strategy to raise both systemic and lung resident memory T-cells, thus conferring cross-group protection in vaccinated mice against lethal influenza challenges, the candidacy of this strategy as a new avenue toward development of universal influenza vaccine in the future was confirmed.

Example 15. Use of NSG Mice Reconstituted with Human Immune System Components for Evaluation of Vaccine Candidates NSG (NOD-scid 11.2 Rγnull) mice (from The Jackson Laboratory, jax.org/jax-mice-and-services/find-and-order-jax-mice/nsg-portfolio) will be engrafted with human PBMC as follows. Fresh whole blood from healthy adult donors collected with preservative free heparin will be diluted (1:3) with low endotoxin PBS (PBSle) (Biochrom) and the leukocyte fraction enriched using standard ficoll gradient centrifugation. The interface will be harvested and washed twice with PBSle. For a 9 week reconstitution protocol, mice will be irradiated with a sub-lethal dose of 100 cGy one day before intravenous injection of 1×10$^6$ human PBMCs; a 4-week protocol will use a single intravenous injection of 10×10$^6$ PBMC, without irradiation. Mice will be vaccinated first on day 42 or day 14 after reconstitution, respectively as follows. The mice comprising the fully human functional immune system will be immunized by priming the fully human immune system with the PSV1.0 phage DNA vector described in Example 3, and then boosting the fully human immune system by immunizing with the AdV vector or AAV vector followed by the VV vector, or the VV vector followed by the AdV vector or AAV vector.

Example 16. Evaluation of Immune Response and Selective Expansion of Immune Cell Subtypes The quality of the immune response attained in the reconstituted NSG mice in Example 15 will be assessed, followed by selective expansion of CTL cell subsets.

Briefly, PBMCs, splenocytes, or bone marrow cells of human or murine origins will be isolated and stained for 1 h at 4° C. in the dark with the appropriate antibody cocktail. Following washing (1% (v/v) FBS in PBS), cells will be fixed with fixation buffer (1% (v/v) FBS, 4% (w/v) PFA in PBS) for 30 min at 4° C. in the dark. Flowcytometric analysis will be performed, and flow cytometry data will be analyzed using FlowJo software (TreeStar, Ashland, Oreg.). Chimerism of all humanized mice model will be assessed prior each experiment by quantifying the following human populations: Human CD45+, human CD45+ murine CD45−; T-cells, CD45+ CD3+; CD4+ T cells, CD45+ CD3+ CD4+; CD8+ T cells, CD45+ CD3+ CD8+; CD45+ CD16+ leukocytes; B-cells, CD45+ CD19; conventional dendritic cells, CD45+ CD11c+; NK/NKT cells, CD45+ CD56+; Monocytes, CD45+ CD14+. Mouse immune cell subsets will be gated as followed: Murine CD45+, Human CD45− Murine CD45+; Conventional dendritic cells, CD45+ CD3− CD19− NK1.1− TER119− Ly-6G/Grl− CD11c+; Plasmacytoid dendritic cells, CD45+ CD3− CD19− NK1.1− TER119− Ly-6G/Grl− CD317+; Monocytes, CD45+ CD3− CD19− NK1.1− TER119− Ly-6G/Grl− CD11b+ CD11c− F4/80−; Macrophages, CD45+CD3− CD19-NK1.1− TER119− Ly-6G/Grl− CD11b+ F4/80+. Human immune cell subsets will be gated as followed: Human CD45+, human CD45+ murine CD45−; T-cells, CD45+ CD3+; CD4+ T cells, CD45+ CD3+ CD4+; CD8+ T cells, CD45+ CD3+ CD8+; Myeloid cells, CD45+ CD3− CD19− (CD56+) CD33+; Granulocytes, CD45+ CD66b+; B cells, CD45+ CD3− CD19+; Natural Killer cells, CD45+CD3−(CD19−) CD56+; Natural Killer T cells and γδ T cells, CD45+ CD3+ (CD19−) CD56+; Conventional dendritic cells, CD45+ CD3− CD19− (CD56−) (CD33+) CD11c+ (BDCA1/3+); CD45+ CD3− CD19 CD123+, group composed of monocytes, plasmacytoid dendritic cells, basophils and myeloid precursors; Plasmacytoid dendritic cells, CD45+ CD3− CD19− (CD56−) BDCA-2+ CD123+; Monocytes, CD45+ CD3− CD19− (CD56−) CD14+; Macrophages, CD45+ CD3− CD19− (CD56−) CD68+.

Flow cytometry fluorophor compensation for antibodies will be performed using AbC™ Anti-Mouse Bead Kit (Life Technologies, Invitrogen, Foster City, Calif., USA). Counting beads will be added to each sample prior flow-cytometry analysis (AccuCheck Counting Beads, Life Technologies, Invitrogen, Foster City, Calif., USA).

The frequency of each cell fraction will be shown as a percentage of CD45+ cells, with the exception of CD4+ and CD8+ T cells, which will be shown as a percentage of CD3+ T cells. The frequencies of important myeloid subsets (CD14+ monocytes and CD11c+ dendritic cells) and CD56+ NK cells will also be determined.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

REFERENCES

[1] Russell R J, Kerry P S, Stevens D J, Steinhauer D A, Martin S R, Gamblin S J, Skehel J J. Structure of influenza hemagglutinin in complex with an inhibitor of membrane fusion. Proc Natl Acad Sci USA. 2008; 105(46): 17736-17741.
[2] Gostin L O, Phelan A, Stoto M A, Kraemer J D, Reddy K S. Virus sharing, genetic sequencing, and global health security. Science. 2014; 345(6202): 1295-1296.
[3] Horimoto T, Kawaoka Y. Influenza: lessons from past pandemics, warnings from current incidents. Nat Rev Microbiol. 2005; 3(8): 591-601.
[4] Johnson N P, Mueller J. Updating the accounts: globalmortality of the 1918-1920 "Spanish" influenza pandemic. Bull Hist Med. 2002; 76(1): 105-115
[5] Gao R, Gao B, Hu Y, Feng Z, Wang D, Hu W, et al. Human infection with a novel avian-origin influenza A (H7N9) virus. N Engl J Med. 2013; 368(20): 1888-1897.
[6] Houser K, Subbarao K. Influenza Vaccines: Challenges and Solutions. Cell Host Microbe. 2015; 17(3): 295-300.
[7] Hannoun C. The evolving history of influenza viruses and influenza vaccines. Expert Rev Vaccines. 2013; 12(9): 1085-1094.
[8] Wang Z, Wan Y, Qiu C, Quinones-Parra S, Zhu Z, Loh L, et al. Recovery from severe H7N9 disease is associated with diverse response mechanisms dominated by CDS+ T cells. Nat Commun. 2015; 6: 6833.
[9] Sridhar S, Begom S, Bermingham A, Hoschler K, Adamson W, [s} ]Carman W, et al. Cellular immune correlates of protection against symptomatic pandemic influenza. Nat Med. 2013; 19(10): 1305-12.
[10] Fan J, Liang X, Horton M S, Perry H C, Citron M P, Heidecker G J, et al. Preclinical study of influenza virus A M2 peptide conjugate vaccines in mice, ferrets, and rhesus monkeys. Vaccine. 2004; 22(23-24): 2993-3003.
[11] Valkenburg S A, Li O T, Mak P W, Mok C K, Nicholls J M, Guan Y, et al. IL-15 adjuvanted multivalent vaccinia-based universal influenza vaccine requires CD4+ T cells for heterosubtypic protection. Proc Natl Acad Sci USA. 2014; 111(15): 5676-81.
[12] Lamere M W, Moquin A, Lee F E, Misra R S, Blair P J, Haynes L, et al. Regulation of antinucleoprotein IgG by systemic vaccination and its effect on influenza virus clearance. J Virol. 2011; 85(10): 5027-5035.
[13] Pica N, Palese P. Toward a universal influenza virus vaccine: prospects and challenges. Annu Rev Med. 2013; 64: 189-202.
[14] Uddback I E, Steffensen M A, Pedersen S R, Nazerai L, Thomsen A R, Christensen J P. PB1 as a potential target for increasing the breadth of T-cell mediated immunity to Influenza A. Sci Rep. 2016; 6:35033.

[15] Cox A, Dewhurst S. A Single Mutation at PB1 Residue 319 Dramatically Increases the Safety of PR8 Live Attenuated Influenza Vaccine in a Murine Model without Compromising Vaccine Efficacy. J Virol. 2015; 90(5): 2702-5.

[16] Jaiswal V, Chanumolu S K, Sharma P, Chauhan R S, Rout C. EpiCombFlu: exploring known influenza epitopes and their combination to design a universal influenza vaccine. Bioinformatics. 2013; 29(15):1904-7.

[17] Brown L E, Kelso A. Prospects for an influenza vaccine that induces cross-protective cytotoxic T lymphocytes. Immunol Cell Biol. 2009; 87(4):300-8.

[18] Holloway R, Rasmussen S A, Zaza S, Cox N J, Jermigan D B. Updated preparedness and response framework for influenza pandemics. MMWR Recomm Rep. 2014; 63(RR-06): 1-18.

[19] Draper S J, Heeney J L. Viruses as vaccine vectors for infectious diseases and cancer. Nat Rev Microbiol. 2010; 8(1): 62-73.

[20] Stanekova Z, Varecykova E. Conserved epitopes of influenza A virus inducing protective immunity and their prospects for universal vaccine development. Viral J. 2010; 7: 351.

[21] Wang X, Xing M, Zhang C, Yang Y, Chi Y D, Tang X Y, et al. Neutralizing antibody responses to enterovirus and adenovirus in healthy adults in China. Emerg Microbes Infec. 2014; 3(5): e30.

[22] Xing M, Wang X, Chi Y, Zhou, D. Gene therapy for colorectal cancer using adenovirus-mediated full-length antibody, cetuximab. Oncotarget. 2016; 7(19): 28262-72.

[23] Zhang S, Huang W, Zhou X, Zhao Q, Wang Q, Jia B. Seroprevalence of neutralizing antibodies to human adenoviruses type-5 and type-26 and chimpanzee adenovirus type-68 in healthy Chinese adults. J Med Viral. 2013; 85(6): 1077-84.

[24] Barouch D H, Alter G, Broge T, Linde C, Ackerman M E, Brown E P, et al. Protective Efficacy of Adenovirus/Protein Vaccines Against SIV Challenges in Rhesus Monkeys. Science. 2015; 349(6245): 320-324.

[25] Stanley D A, Honko A N, Asiedu C, Trefry J C, Lau-Kilby A W, Johnson J C, et al. Chimpanzee adenovirus vaccine generates acute and durable protective immunity against ebolavirus challenge. Nat Med. 2014; 20(10): 1126-9.

[26] Huang X, Xu J, Qiu C, Ren L, Liu L, Wan Y, et al. Mucosa! priming with PEI/DNA complex and systemic boosting with recombinant TianTan vaccinia stimulate vigorous mucosal and systemic immune responses. Vaccine. 2007; 25(14): 2620-9

[27] Huang X, Liu L, Ren L, Qiu C, Wan Y, Xu J. Mucosal priming with replicative Tiantan vaccinia and systemic boosting with DNA vaccine raised strong mucosa! and systemic HIV-specific immune responses. Vaccine. 2007; 25(52): 8874-84.

[28] Singh H, Raghava G P. ProPredl: prediction of promiscuous MHC Class-I binding sites. Bioinformatics. 2003; 19: 1009-1014.

[29] Moutaftsi M, Peters B, Pasquetto V, Tscharke D C, Sidney J, Bui H H, et al. A consensus epitope prediction approach identifies the breadth of murine T(CD8+)-cell responses to vaccinia virus. Nat Biotechnol. 2006; 24: 817-819.

[30] Keskin D B, Reinhold B B, Zhang G L, Ivanov A R, Karger B L, Reinherz E L. Physical detection of influenza A epitopes identifies a stealth subset on human lung epithelium evading natural CD8 immunity. Proc Natl Acad Sci USA. 2015; 112(7): 2151-2156.

[31] Halstead E S, Mueller Y M, Altman J D, Katsikis P D. In vivo stimulation of CD137 broadens primary antiviral CD8+ T cell responses. Nat Immunol. 2002; 3(6): 536-41.

[32] Lawrence C W, Ream R M, Braciale T J. Frequency, specificity, and sites of expansion of CD8+ T cells during primary pulmonary influenza virus infection. J Immunol. 2005; 174(9): 5332-40.

[33] Turner S J, La Gruta N L, Stambas J, Diaz G, Doherty P C. Differential tumor necrosis factor receptor 2-mediated editing of virus-specific CD8+ effector T cells. Proc Natl Acad Sci USA. 2004; 101(10):3545-3550.

[34] Tussey L G, Rowland-Jones S, Zheng T S, Androlewicz M J, Cresswell P, Frelinger J A, et al. Different MHC class I alleles compete for presentation of overlapping viral epitopes. Immunity. 1995; 3(1): 65-77.

[35] Belz G T, Xie W, Doherty P C. Diversity of Epitope and Cytokine Profiles for Primary and Secondary Influenza A Virus-Specific CD8+ T Cell Responses. J Immunol. 2001; 166(7): 74627-4633.

[36] Chen W, Norbury C C, Cho Y, Yewdell J W, Bennink J R. Immunoproteasomes shape immunodominance hierarchies of antiviral CD8(+) T cells at the levels of T cell repertoire and presentation of viral antigens. J Exp Med. 2001; 193(11): 1319-26.

[37] Zhu Z, Yang Y, Feng Y, Shi B, Chen L, Zheng Y, et al. Infection of inbred BALB/c and C57B L/6 and outbred Institute of Cancer Research mice with the emerging H7N9 avian influenza virus. Emerg Microbes Infect. 2013; 2(8): e50.

[38] Masopust D, Choo D, Vezys V, Wherry E J, Duraiswamy J, Akondy R, et al. Dynamic T cell migration program provides resident memory within intestinal epithelium. J Exp Med. 201'0; 207(3): 553-64

[39] Steel J, Lowen A C, Wang T T, Yondola M, Gao Q, Haye K, et al. Influenza virus vaccine based on the conserved hemagglutinin stalk domain. mBio. 2010; 1(1).

[40] Grant E, Wu C, Chan K F, Eckle S, Bharadwaj M, Zou Q M, et al. Nucleoprotein of influenza A virus is a major target of immunodominant CD8+ T-cell responses. Immunol Cell Biol. 2013; 91(2): 184-94.

[41] Saletti G, Gerlach T, Rimmelzwaan G F. Influenza vaccines: 'tailor-made' or 'one fits all'. 2018; 53: 102-110.

[42] Clemens E B, van de Sandt C, Wong S S, Wakim L M, Valkenburg S A. Harnessing the Power of T Cells: The Promising Hope for a Universal Influenza Vaccine. Vaccines (Basel). 2018; 6(2).

[43] Wu T, Hu Y, Lee Y T, Bouchard K R, Benechet A, Khanna K, et al. Lung-resident memory CD8 T cells ($T_{RM}$) are indispensable for optimal cross-protection against pulmonary virus infection. J Leukoc Biol. 2014; 95(2):215-24.

[44] Zens K D, Chen J K, Farber D L. Vaccine-generated lung tissue-resident memory T cells provide heterosubtypic protection to influenza infection. JCI Insight. 2016; 1(10).

[45] Ariotti S, Hogenbirk M A, Dijkgraaf F E, Visser L L, Hoekstra M E, Song J Y, et al. T cell memory. Skin-resident memory CD8+ T cells trigger a state of tissue-wide pathogen alert. Science. 2014; 346(6205): 101-5.

[46] Schenkel J M, Fraser K A, Vezys V, Masopust D. Sensing and alarm function of resident memory CDS+ T cells. Nat Immunol. 2013; 14(5): 509-13.

[47] Sliitter B, Van Braeckel-Budimir N, Abboud G, Varga S M, Salek-Ardakani S, Harty J T. Dynamics of influenza-induced lung-resident memory T cells underlie waning heterosubtypic immunity. Sci Immunol. 2017; 2(7).

[48] Pizzolla A, Nguyen T H, Sant S, Jaffar J, Loudovaris T, Mannering S I, et al. Influenza-specific lung-resident memory T cells are proliferative and polyfunctional and maintain diverse TCR profiles. J Clin Invest. 2018; 128 (2): 721-733.

The invention claimed is:

1. A universal vaccine against an immunogen of an infectious pathogenic organism selected from a virus, a bacteria, a fungus or a protozoan comprising at least one ribonucleic acid (RNA) polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens,
   (a) wherein a cytotoxic T lymphocyte (CTL) epitope consists of peptides of from 8-11 residues in length, and
   (b) wherein an immune response elicited in response to the vaccine comprises one or more of:
      (i) activation of one or more T cell populations directed to at least one antigen present in the vaccine; or
      (ii) neutralization of infectivity of the pathogen; or
      (iii) an antigen-specific response comprising destruction of the pathogen; lysis of cells infected with the pathogen, or both;
   compared to a control.

2. The universal vaccine according to claim 1, wherein the activated cell populations comprise activated cytotoxic T lymphocytes (CTLs).

3. The universal vaccine according to claim 2, wherein the activated CTLs comprise one or more of an NK cell population, an NKT cell population, an LAK cell population, a CIK cell population, an MAIT cell population, a CD8+ CTL population, or a CD4+ CTL population.

4. The universal vaccine according to claim 1, wherein the conserved immunogenic polypeptide or immunogenic fragment is a viral internal matrix protein, a viral capsid protein, a viral nuclear protein, a viral nucleoprotein, a viral glycoprotein, a viral phosphoprotein, a viral envelope protein, a viral protease, a reverse transcriptase, or a viral polymerase.

5. The universal vaccine of claim 1 prepared by a process comprising:
   a. identifying and selecting from a consensus amino acid sequence a highly conserved internal protein of an infectious pathogen or an immunogenic fragment thereof enriched in CD8+ T cell recognition antigens;
   b. constructing immunogen sequences of the highly conserved internal proteins in (a);
   c. constructing:
      i. a *Streptomyces* phage SV1.0 DNA vector comprising the immunogen sequences of (b);
      ii. an adenovirus-based (AdV) vector comprising the immunogen sequences of (b); and
      iii. an attenuated, replication-competent recombinant vaccinia virus based (VV) vector comprising the immunogen sequences of (b); and
   d. propagating separately each of the recombinant vectors comprising encoded immunogens in (c) for immunizing a subject in vivo in an amount effective to elicit or stimulate a therapeutic or prophylactic cell mediated immune response against an infection with the infectious pathogen by:
      i. priming the fully human immune system by immunizing with the phage DNA vector of (c)(i); and
      ii. boosting the fully human immune system by immunizing with the AdV vector of (c)(ii) followed by the VV vector of (c)(iii), or the VV vector of (c)(iii) followed by the AdV vector of (c)(ii).

6. The universal vaccine prepared by the process according to claim 5, wherein the conserved immunogenic protein or immunogenic fragment is a viral internal matrix protein, a viral capsid protein, a viral nuclear protein, a viral nucleoprotein, a viral glycoprotein, a viral phosphoprotein, a viral envelope protein, a viral protease, a reverse transcriptase, or a viral polymerase.

7. An engineered nucleic acid encoding at least one RNA polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens of the universal vaccine of claim 1.

8. An expression vector comprising engineered nucleic acid encoding at least one RNA polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens of the universal vaccine of claim 1.

9. A host cell comprising an engineered nucleic acid encoding at least one RNA polynucleotide comprising an open reading frame encoding at least one polypeptide antigen or an immunogenic fragment thereof, wherein the polypeptide antigen, or the immunogenic fragment thereof, comprises a conserved internal protein that is enriched in CD8+ T cell recognition antigens of the universal vaccine of claim 1.

10. A method of inducing an immune response in a subject, the method comprising administering to the subject a universal vaccine against an immunogen of an infectious pathogenic organism selected from a virus, a bacteria, a fungus or a protozoan comprising at least one ribonucleic acid (RNA) polynucleotide comprising an open reading frame encoding at least one antigenic polypeptide or an immunogenic fragment thereof, wherein the antigenic peptide, or the immunogenic fragment thereof, comprises a conserved internal protein that is enriched in CD8+ T cell recognition antigens,
   wherein a CD8+ T cell recognition antigen consists of peptides of from 8-11 residues in length, and wherein an immune response produced in response to the vaccine comprises one or more of:

(i) activation of one or more T cell populations directed to an antigen(s) present in the vaccine; or (ii) neutralization of infectivity of the pathogen; or (iii) an antigen-specific response comprising destruction of the infectious pathogenic organism; lysis of cells infected with the infectious pathogenic organism, or both;

compared to a control.

11. The method of claim 10, comprising priming the subject with a *Streptomyces* phage SV1.0 DNA vector comprising a first immunogen sequence encoding a conserved internal protein that is enriched in CD8+ T cell recognition antigens and then boosting the subject with an adenovirus-based (AdV) vector or an attenuated, replication-competent recombinant vaccinia virus based (VV) vector comprising a second immunogen sequence encoding a conserved internal protein that is enriched in CD8+ T cell recognition antigens.

12. The method of claim 10, comprising administering the vaccine to the subject by intradermal injection, intranasally or by intramuscular injection.

13. The method of claim 10, wherein the mode of administration of the priming dose and the mode of administration of the booster dose are different.

14. The method according to claim 10, wherein the subject is a mouse of phenotype NOD-scid γc−/− or BALB/c Rag2−/− γc−/−.

15. The method according to claim 10, comprising reconstituting the mouse of phenotype NOD-scid γc−/− with human C34+CD133+ cord blood cells injected intracardially as newborns into the NOD-scid γc−/− mouse.

16. The method according to claim 10, comprising reconstituting the mouse of phenotype BALB/c Rag2−/− γc−/− comprises CD34+ hematopoietic progenitor cells (HPCs) isolated from human fetal liver transferred intrahepatically into newborn BALB/c Rag2−/− γc−/−.

17. A method for inducing a pan-influenza specific cellular immune response in vivo in an animal model comprising a fully human functional immune system comprising:

(1) Identifying and selecting from a consensus amino acid sequence a plurality of highly conserved internal influenza viral proteins enriched in CD8+ T cell recognition antigens;

(2) constructing concatenated immunogen sequences of the highly conserved internal influenza viral proteins in (1);

(3) constructing:

a. a *Streptomyces* phage SV1.0 DNA vector comprising the concatenated immunogen sequences of (2);

b. an adenovirus-based (AdV) vector comprising the concatenated immunogen sequences of (2); and c. an attenuated, replication-competent recombinant vaccinia virus based (VV) vector comprising the concatenated immunogen sequences of (2);

(4) propagating separately each of the recombinant vectors comprising encoded immunogens in (3);

(5) immunizing the animal model comprising the fully human functional immune system in vivo by:

a. priming the fully human immune system by immunizing with the phage DNA vector of 3(a); and b. boosting the fully human immune system by immunizing with the AdV vector of 3(b) followed by the VV vector of 3(c), or the VV vector of 3(c) followed by the AdV vector of 3(b); and (6) after the immunizing in (5), challenging the animal model comprising the immunized fully human functional immune system with either influenza A/PR8 (H1N1) or Influenza A/Shanghai (H7N9) virus.

18. The method of claim 17, comprising administering the vaccine to the subject by intradermal injection, intranasally, or by intramuscular injection.

19. The method of claim 17, wherein the mode of administration of the single dose and the booster dose are different.

20. The method of claim 17, wherein the animal model is a mouse of phenotype NOD-scid γc−/− or BALB/c Rag2−/− γc−/−.

21. The method of claim 17, comprising reconstituting the mouse of phenotype NOD-scid γc−/− with human C34+ CD133+ cord blood cells injected intracardially as newborns into the NOD-scid γc−/− mouse.

22. The method of claim 17, comprising reconstituting the mouse of phenotype BALB/c Rag2−/− γc−/− comprises CD34+ hematopoietic progenitor cells (HPCs) isolated from human fetal liver transferred intrahepatically into newborn BALB/c Rag2−/− γc−/−.

23. The method of claim 17, wherein the pan-influenza specific cellular immune response in the animal model is effective to reduce spread of infection in a population of unimmunized reconstituted mice.

* * * * *

SEQUENCE LISTING

<160> NUMBER OF SEQ ID NOS: 28

<210> SEQ ID NO 1

<400> SEQUENCE: 1

000

<210> SEQ ID NO 2

<400> SEQUENCE: 2

000

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaagaggcaa tgcaaaatag aataca                                          26

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccgaagcta aaccaragta tca                                             23

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ccagtcaaac taagcagygg ctacaaa                                         27

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaccgatcct gtcacctctg a                                               21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agggcattct ggacaaagcg tcta					24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tgcagtcctc gctcactggg cacg					24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caatgtgtcc gtcgtggatc t						21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcctcagtg tagcccaaga tg					22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cgtgccgcct ggagaaacct gcc					23

<210> SEQ ID NO 12
<211> LENGTH: 9
<212> TYPE: PRT
<213> ORGANISM: Influenza A virus

<400> SEQUENCE: 12

Gly Ile Leu Gly Phe Val Phe Thr Leu
1               5

<210> SEQ ID NO 13
<211> LENGTH: 8
<212> TYPE: PRT
<213> ORGANISM: Influenza A virus

<400> SEQUENCE: 13

Met Gly Leu Ile Tyr Asn Arg Met
1               5

```
<210> SEQ ID NO 14
<211> LENGTH: 9
<212> TYPE: PRT
<213> ORGANISM: Influenza A virus

<400> SEQUENCE: 14

Leu Tyr Arg Lys Leu Lys Arg Glu Ile
1               5

<210> SEQ ID NO 15
<211> LENGTH: 23
<212> TYPE: PRT
<213> ORGANISM: Influenza A virus

<400> SEQUENCE: 15

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 16
<211> LENGTH: 10
<212> TYPE: PRT
<213> ORGANISM: Influenza A virus

<400> SEQUENCE: 16

Ala Thr Tyr Gln Arg Thr Arg Ala Leu Val
1               5                   10

<210> SEQ ID NO 17
<211> LENGTH: 9
<212> TYPE: PRT
<213> ORGANISM: Influenza A virus

<400> SEQUENCE: 17

Ala Ser Asn Glu Asn Met Asp Thr Met
1               5

<210> SEQ ID NO 18
<211> LENGTH: 9
<212> TYPE: PRT
<213> ORGANISM: Influenza A virus

<400> SEQUENCE: 18

Ser Arg Tyr Trp Ala Ile Arg Thr Arg
1               5

<210> SEQ ID NO 19
<211> LENGTH: 9
<212> TYPE: PRT
<213> ORGANISM: Influenza A virus

<400> SEQUENCE: 19

Ser Ser Tyr Arg Arg Val Pro Gly Ile
1               5

<210> SEQ ID NO 20
<211> LENGTH: 10
<212> TYPE: PRT
<213> ORGANISM: Influenza A virus

<400> SEQUENCE: 20

Val Ser Gly Val Asn Glu Ser Ala Asp Met
1               5                   10
```

```
<210> SEQ ID NO 21
<211> LENGTH: 9
<212> TYPE: PRT
<213> ORGANISM: Influenza A virus

<400> SEQUENCE: 21

Asp Gly Gly Pro Asn Leu Tyr Asn Ile
1               5

<210> SEQ ID NO 22
<211> LENGTH: 9
<212> TYPE: PRT
<213> ORGANISM: Influenza A virus

<400> SEQUENCE: 22

Ile Ser Pro Leu Met Val Ala Tyr Met
1               5

<210> SEQ ID NO 23
<211> LENGTH: 9
<212> TYPE: PRT
<213> ORGANISM: Influenza A virus

<400> SEQUENCE: 23

Val Leu Thr Gly Asn Leu Gln Thr Leu
1               5

<210> SEQ ID NO 24
<211> LENGTH: 10
<212> TYPE: PRT
<213> ORGANISM: Influenza A virus

<400> SEQUENCE: 24

Ser Val Leu Val Asn Thr Tyr Gln Trp Ile
1               5                   10

<210> SEQ ID NO 25
<211> LENGTH: 10
<212> TYPE: PRT
<213> ORGANISM: Influenza A virus

<400> SEQUENCE: 25

Ser His Leu Arg Asn Asp Thr Asp Val Val
1               5                   10

<210> SEQ ID NO 26
<211> LENGTH: 9
<212> TYPE: PRT
<213> ORGANISM: Influenza A virus

<400> SEQUENCE: 26

Thr Asp Val Val Asn Phe Val Ser Met
1               5

<210> SEQ ID NO 27
<211> LENGTH: 9
<212> TYPE: PRT
<213> ORGANISM: Influenza A virus

<400> SEQUENCE: 27

Val Glu Glu Gly Ser Ile Gly Lys Val
1               5
```

```
<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Gly Ser Gly Gly Gly Gly Ser
1               5                   10                  15
```